(12) United States Patent
Nacro et al.

(10) Patent No.: US 10,544,149 B2
(45) Date of Patent: *Jan. 28, 2020

(54) BICYCLIC ALKYNE DERIVATIVES AND USES THEREOF

(71) Applicant: Agency for Science, Technology and Research, Singapore (SG)

(72) Inventors: Kassoum Nacro, Singapore (SG); Lohitha Rao Chennamaneni, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/858,733

(22) Filed: Dec. 29, 2017

(65) Prior Publication Data

US 2018/0194771 A1 Jul. 12, 2018

Related U.S. Application Data

(63) Continuation of application No. 15/026,955, filed as application No. PCT/SG2014/000468 on Oct. 3, 2014, now Pat. No. 9,884,867.

(30) Foreign Application Priority Data

Oct. 3, 2013 (GB) .................................. 1317545.0

(51) Int. Cl.
   *C07D 487/04* (2006.01)
   *C07D 471/04* (2006.01)
   *C07D 519/00* (2006.01)

(52) U.S. Cl.
   CPC ......... *C07D 487/04* (2013.01); *C07D 471/04* (2013.01); *C07D 519/00* (2013.01)

(58) Field of Classification Search
   CPC ... C07D 487/04; C07D 471/04; C07D 519/00
   See application file for complete search history.

(56) References Cited

U.S. PATENT DOCUMENTS

| | | | |
|---|---|---|---|
| 9,884,867 B2 | 2/2018 | Nacro et al. | |
| 2016/0229860 A1 | 8/2016 | Nacro et al. | |

FOREIGN PATENT DOCUMENTS

| | | |
|---|---|---|
| CN | 101389338 A | 3/2009 |
| CN | 102584830 A | 7/2012 |
| JP | 2009-502734 A | 1/2009 |
| JP | 2009-521462 A | 6/2009 |
| WO | WO 2006/099972 A1 | 9/2006 |
| WO | WO 2007/013673 A1 | 2/2007 |
| WO | WO 2007/075869 A2 | 7/2007 |
| WO | WO 2009/060197 A1 | 5/2009 |
| WO | WO 2010/017047 A1 | 2/2010 |
| WO | WO 2013/107326 A1 | 7/2013 |
| WO | WO 2013/147711 A1 | 10/2013 |
| WO | WO 2013/170770 A1 | 11/2013 |
| WO | WO 2015/050505 A1 | 4/2015 |

OTHER PUBLICATIONS

Gozgit et al., Mol Cancer Ther, 10(6) Jun. 2011, pp. 1028-1035.*
International Search Report and Written Opinion for International Application No. PCT/SG2014/000468, dated Jan. 15, 2015.
International Preliminary Report on Patentability for International Application No. PCT/SG2014/000468, dated Apr. 14, 2016.
Extended European Search Report for European Application No. 14851209.8, dated Feb. 24, 2017.
Second Office Action for Chinese Application No. 201480065650.2, dated Dec. 7, 2017.
CAS RN 1348255-19-5, 5-[2-[5-(4-chlorophenyl)pyrazolo [1,5-a]pyrimidin-3-yl]ethynyl]-N-(2-hydroxy-1,1-dimethylethyl)-N-methyl-3-Pyridinsulfonamide; STN Entry Date Dec. 4, 2011.
CAS RN 1026243-19-5, 5-[2-[6-[ 4-(trifluoromethyl)phenyl]imidazo[1,2-a ]pyridine-3-yl]ethynyl] -3-Pyridinsulfonamide; STN Entry Date Jun. 8, 2008.
Desai et al., "Rapid Discovery of a Novel Series of Abl Kinase Inhibitors by Application of an Integrated Microfluidic Synthesis and Screening Playform." Journal of Medicinal Chemistry. 2013;56(7):3033-47.
Rajput et al., "Synthesis of Benzaldehyde Substituted Phenyl Carbonyl Hydrazones and their Formylation Using Vilsmeier-Haack Reaction." International Journal of PharmTech Research. 2009;1(4):1605-11.
Australian Examination Report dated Apr. 5, 2018 in connection with Australian Application No. 2014330089.
Chinese Office Action dated May 16, 2018 and English translation thereof in connection with Chinese Application No. 201480065650. 2.
European Examination Report dated Sep. 20, 2018 in connection with European Application No. 14851209.8.
English translation of Japanese Notice of Reasons for Rejection dated Jun. 8, 2018 in connection with Japanese Application No. 2016-520055.
Japanese Notice of Reasons for Rejection dated Sep. 19, 2018 and English translation thereof in connection with Japanese Application No. 2016-520055.
Japanese Decision to Grant a Patent dated Feb. 22, 2019 in connection with Japanese Application No. 2016-520055.

* cited by examiner

*Primary Examiner* — Rebecca L Anderson
(74) *Attorney, Agent, or Firm* — Wolf, Greenfield & Sacks, P.C.

(57) ABSTRACT

The present invention relates to certain compounds (e.g., imidazopyrazine, imidazopyridine, imidazopyridazine and imidazpyrimidine compounds) that act as inhibitors of the MAP kinase interacting kinases MNK2a, MNK2b, MNK1a, and MNK1b. The present invention further relates to pharmaceutical compositions comprising these compounds, and to the use of the compounds for the prevention and treatment of diseases (e.g., proliferative diseases (e.g., cancer), inflammatory diseases, autoimmune diseases, metabolic diseases, and neurodegenerative diseases (e.g. autism, autism spectrum disorders, Alzheimer's disease)), as well as methods of treating these diseases.

21 Claims, 1 Drawing Sheet

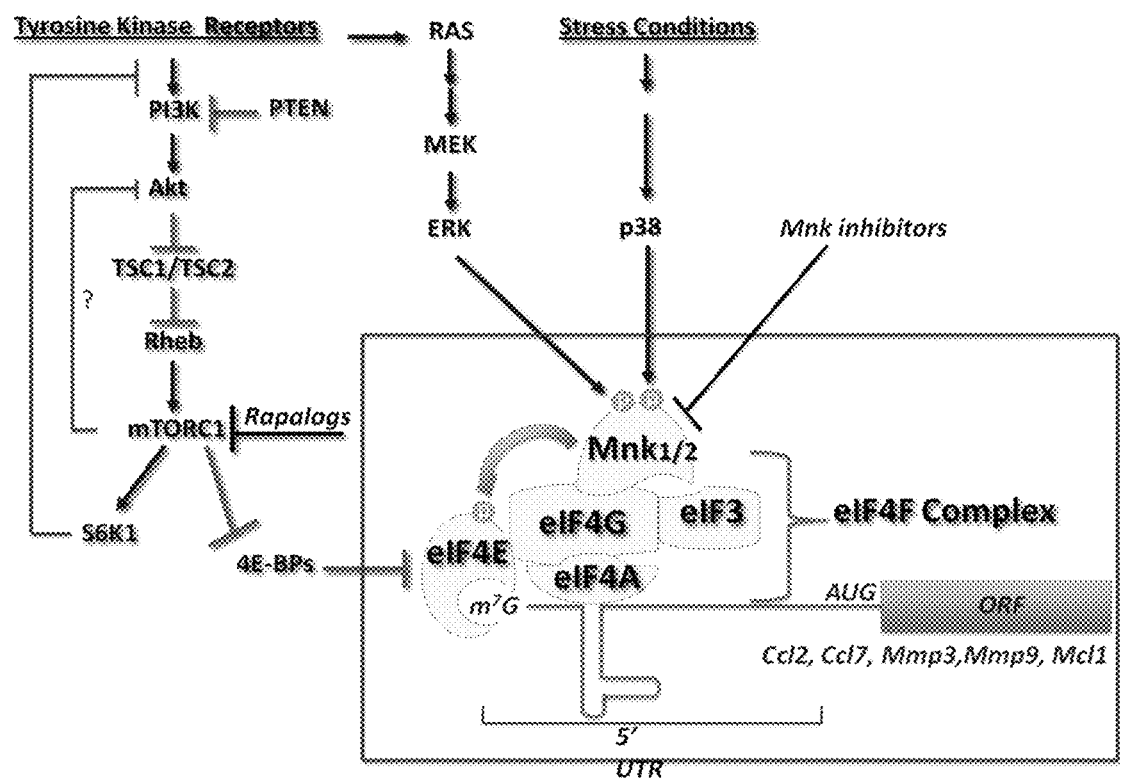

BICYCLIC ALKYNE DERIVATIVES AND USES THEREOF

CROSS-REFERENCE TO RELATED APPLICATIONS

This patent application claims the benefit under 35 U.S.C. § 120 of U.S. application Ser. No. 15/026,955, entitled "BICYCLIC ALKYNE DERIVATIVES AND USES THEREOF" filed on Apr. 1, 2016, which is a U.S. National Phase Application under 35 U.S.C. § 371 of International Application No. PCT/SG2014/000468, filed Oct. 3, 2014, entitled BICYCLIC ALKYNE DERIVATIVES AND USES THEREOF, which claims priority to Great Britain Patent Application No. 1317545.0, filed Oct. 3, 2013.

BACKGROUND OF THE INVENTION

The human MAP Kinase-interacting kinases, also known as MAP Kinase signal-integrating kinases, (MNKs), are ubiquitously expressed protein-serine/threonine kinases that are directly activated by ERK or p38 MAP kinases (Buxade, M.; Parra-Palau, J. L.; Proud, C. G. Front Biosci. 2008, 13, 5359-5373; Fukunaga, R.; Hunter, T. EMBO J. 1997, 16, 1921-1933; Waskiewicz, A. J.; Flynn, A.; Proud, C. G.; Cooper, J. A. EMBO J. 1997, 16, 1909-1920). They comprise a group of four proteins derived from two genes (gene symbols: MKNK1 and MKNK2) by alternative splicing. MNK1a/b and MNK2a/b proteins differ at their C-termini, in each case the a-form has a longer C-terminal region than the b-form which lacks the MAP Kinase-binding region. The N-termini of all forms contains a polybasic region which binds importin α and the translation factor scaffold protein eukaryotic Initiation Factor (eIF4G). The catalytic domains of MNK1a/b and MNK2a/b share three unusual features, two short inserts and a DFD motif instead of the most common DFG tripeptide present found on other kinases. MNK isoforms differ markedly in their activity, regulation and subcellular localization. The best-characterized MNK substrate is Eukaryotic Initiation Factor-4 E (eIF4E). Although the cellular role of eIF4E phosphorylation remains unclear and is thought to promote export of a defined set of mRNAs from the nucleus. Other MNK substrates bind to AU-rich elements that modulate the stability/translation of specific mRNAs. MNK1 is highly expressed in hematological malignancies, and both MNK1 and MNK2 are up-regulated in solid tumors such as gliomas and ovarian cancers (Worch, J.; Tickenbrock, L.; Schwable, J.; Steffen, B.; Cauvet, T.; Mlody, B.; Buerger, H.; Koeffler, H. P.; Berdel, W. E.; Serve, H.; Muller-Tidow, C. Oncogene 2004, 23, 9162-9172; Pellagatti, A.; Esoof, N.; Watkins, F.; Langford, C. F.; Vetrie, D.; Campbell, L. J.; Fidler, C.; Cavenagh, J. D.; Eagleton, H.; Gordon, P.; Woodcock, B.; Pushkaran, B.; Kwan, M.; Wainscoat, J. S.; Boultwood, J. Br. J. Haematol. 2004, 125, 576-583; Bredel, M.; Bredel, C.; Juric, D.; Harsh, G. R.; Vogel, H.; Recht, L. D.; Sikic, B. I. Cancer Res. 2005, 65, 4088-4096; Hendrix, N. D.; Wu, R.; Kuick, R.; Schwartz, D. R.; Fearon, E. R.; Cho, K. R. Cancer Res. 2006, 66, 1354-1362).

eIF4E regulates the expression of genes involved in the proliferation and survival as a cap dependent mRNA translation and mRNA export factor. eIF4E is dysregulated in several human cancers, including breast, prostate, and leukemia, and elevated levels of eIF4E are a marker of poor prognosis (Nathan, C. O.; Carter, P.; Liu, L.; Li, B. D.; Abreo, F.; Tudor, A.; Zimmer, S. G.; De Benedetti, A. Oncogene 1997, 15, 1087-1094; Bianchini, A.; Loiarro, M.; Bielli, P.; Busa, R.; Paronetto, M. P.; Loreni, F.; Geremia, R.; Sette, C. Carcinogenesis 2008, 29, 2279-2288.; Topisirovic, I.; Guzman, M. L.; McConnell, M. J.; Licht, J. D.; Culjkovic, B.; Neering, S. J.; Jordan, C. T.; Borden, K. L. Mol. Cell Biol. 2003, 23, 8992-9002; Graff, J. R.; Zimmer, S. G. Clin. Exp. Metastasis 2003, 20, 265-273). Moreover, overexpression and dysregulation of eIF4E leads to an increased number of tumors, invasion, and metastases in mouse models[13] and transgenic expression of eIF4E leads to a variety of cancers (Graff, J. R.; Zimmer, S. G. Clin. Exp. Metastasis 2003, 20, 265-273; Ruggero, D.; Montanaro, L.; Ma, L.; Xu, W.; Londei, P.; Cordon-Cardo, C.; Pandolfi, P. P. Nat. Med. 2004, 10, 484-486). eIF4E overexpression is believed to increase the translation of weakly competitive mRNAs, many of which encode products that stimulate cell growth and angiogenesis, e.g., fibroblast growth factor 2 and vascular endothelial growth factor, cyclin D1, and ribonucleotide reductase (Kevil, C.; Carter, P.; Hu, B.; DeBenedetti, A. Oncogene 1995, 11, 2339-2348; Kevil, C. G.; De Benedetti, A.; Payne, D. K.; Coe, L. L.; Laroux, F. S.; Alexander, J. S. Int. J. Cancer 1996, 65, 785-790; Scott, P. A.; Smith, K.; Poulsom, R.; De Benedetti, A.; Bicknell, R.; Harris, A. L. Br. J. Cancer 1998, 77, 2120-2128; Rosenwald, I. B.; Lazaris-Karatzas, A.; Sonenberg, N.; Schmidt, E. V. Mol. Cell Biol. 1993, 13, 7358-7363; Abid, M. R.; Li, Y.; Anthony, C.; De Benedetti, A. J. Biol. Chem. 1999, 274, 35991-35998). eIF4E is phosphorylated by the MNK1/2 serine/threonine kinases in response to activation by mitogenic and stress signals downstream of ERK1/2 and p38 MAP kinase respectively (Buxade, M.; Parra-Palau, J. L.; Proud, C. G. Front Biosci. 2008, 13, 5359-5373; Fukunaga, R.; Hunter, T. EMBO J. 1997, 16, 1921-1933; Waskiewicz, A. J.; Flynn, A.; Proud, C. G.; Cooper, J. A. EMBO J. 1997, 16, 1909-1920). Thus, inhibitors of MNK1/2 will prevent eIF4E phosphorylation and therefore could provide a viable therapeutic approach in high-eIF4E dependent cancers.

Studies have shown that overexpression of eIF4E, as well as eIF4E phosphorylation, promote cancer cell survival, at least in part by increasing the level of the anti-apoptotic protein Mcl-1 (Wendel, H. G.; Silva, R. L.; Malina, A.; Mills, J. R.; Zhu, H.; Ueda, T.; Watanabe-Fukunaga, R.; Fukunaga, R.; Teruya-Feldstein, J.; Pelletier, J.; Lowe, S. W. Genes Dev. 2007, 21, 3232-3237; Ueda, T.; Watanabe-Fukunaga, R.; Fukuyama, H.; Nagata, S.; Fukunaga, R. Mol. Cell Biol. 2004, 24, 6539-6549). Mcl-1 is a Bcl2 family member with a very short half-life, and Mcl-1 mRNA translation highly depends on eIF4E. Thus, it is foreseeable that the inhibition of eIF4E phosphorylation by MNK might induce tumor cells death, as shown for Myc-induced lymphoma. (Wendel, H. G.; Silva, R. L.; Malina, A.; Mills, J. R.; Zhu, H.; Ueda, T.; Watanabe-Fukunaga, R.; Fukunaga, R.; Teruya-Feldstein, J.; Pelletier, J.; Lowe, S. W. Genes Dev. 2007, 21, 3232-3237) Blast crisis chronic myeloid leukemia (BC-CML) is characterized by an expansion of a population of granulocyte macrophage progenitor-like cells (GMPs) that have acquired self-renewal capacity, a feature not seen in normal or chronic phase (CP) GMPs and targeting of the MNK-eIF4E axis in blast crisis chronicmyeloid leukemia inhibits leukemia stem cell function. (Sharon Lim, Tzuen Yih Saw, Min Zhang, Matthew R. Janes, Kassoum Nacro, Jeffrey Hill, An Qi Lim, Chia-Tien Chang, David A. Fruman, David A. Rizzieri, Soo Yong Tan, Hung Fan, c, Charles T. H. Chuah, g, and S. Tiong Ong; N. Proc. Natl. Acad. Sci. U.S.A 2013, 110(25), E2298-E2307). The ability to self-renew is thought to be mediated by β-catenin activation, and may contribute to disease persistence, as well as initiate drug resistance. It was found siRNA-mediated knockdown or inhibition of the MNK1/2 kinases (which mediate in vivo eIF4E phosphorylation) with small molecules prevented the increased beta-catenin activity, induced by eIF4E overexpression. These studies suggest that pharmacologic inhibition of the MNK1/2 kinases is a plausible therapeutic mean to treat BC CML.

The level of expression of eIF4E and the degree of eIF4E phosphorylation is regulated by pathways that include the P38 kinase, MAPK kinase and AKT/mTOR pathways (Hay, N. Proc. Natl. Acad. Sci. U.S.A 2010, 107, 13975-13976). Inhibitors of mTOR such as rapamycin, decrease the level of phosphorylated eIF4E (Hay, N. Proc. Natl. Acad. Sci. U.S.A 2010, 107, 13975-13976). The treatment with rapalogs typically leads to the clinically stable disease or partial remission rather than complete tumor regression (Gibbons, J. J.; Abraham, R. T.; Yu, K. Semin. Oncol. 2009, 36 Suppl 3, S3-S17). Combination therapy with MNK1/2 and mTOR kinases inhibitors could be a viable strategy to treat certain types of cancer (Wang, X.; Yue, P.; Chan, C. B.; Ye, K.; Ueda, T.; Watanabe-Fukunaga, R.; Fukunaga, R.; Fu, H.; Khuri, F. R.; Sun, S. Y. Mol. Cell Biol. 2007, 27, 7405-7413). WO 2010/055072 discloses MNK and mTOR combination therapy with small molecules, antibodies and siRNA for the treatment of cancer, and recent findings support that MNK and mTOR combination induces apoptosis in cutaneous T cell lymphoma cells (WO2010055072; Marzec, M.; Liu, X.; Wysocka, M.; Rook, A. H.; Odum, N.; Wasik, M. A. PLoS. One. 2011, 6, e24849).

Macrophages are major effectors of innate immunity, stimulated by a broad variety of bacterial products through specific TLRs on the cell surface to produce pro-inflammatory cytokines, such as TNF. *E. coli* LPS is a potent stimulus to macrophage gene expression, especially TNF, by engaging the TLR4 membrane signaling complex (Hou, L.; Sasaki, H.; Stashenko, P. Infect. Immun. 2000, 68, 4681-4687). It was shown that TLR signaling pathways require MNK expression through the use of a panel of commercial TLR agonist panel on macrophage. TNF production was increased as a response to *Salmonella* LPS (TLR4), ODN2006 (TLR9), HKLM (TLR2), FSL (TLR6/2) and imiquimod (TLR7) stimulation. In each case the production of TNF was inhibited by MNK kinases inhibitor CGP57380 in a dose dependant fashion and the release of multiple innate proinflammatory cytokines were affected, supporting a central role for MNK in inflammation (Rowlett, R. M.; Chrestensen, C. A.; Nyce, M.; Harp, M. G.; Pelo, J. W.; Cominelli, F.; Ernst, P. B.; Pizarro, T. T.; Sturgill, T. W.; Worthington, M. T. Am. J. Physiol Gastrointest. Liver Physiol 2008, 294, G452-G459).

MNK inhibitors can regulate the innate immune response in macrophage. A compound with anti inflammatory properties will inhibit the release of pro-inflammatory cytokines. It has been shown that CGP57380, a MNK inhibitor, inhibits the release of TNF alpha by macrophage (and not eIF4E). According to WO2005/003785 MNK kinases are promising targets for anti-inflammatory therapy.

MNK1/2 were also reported to phosphorylate a number of different proteins in addition to eIF4E. Three of these are hnRNPA1, cPLA2 and Sprouty2 (Guil, S.; Long, J. C.; Caceres, J. F. Mol. Cell Biol. 2006, 26, 5744-5758; Buxade, M.; Morrice, N.; Krebs, D. L.; Proud, C. G. J. Biol. Chem. 2008, 283, 57-65; Hefner, Y.; Borsch-Haubold, A. G.; Murakami, M.; Wilde, J. I.; Pasquet, S.; Schieltz, D.; Ghomashchi, F.; Yates, J. R., III; Armstrong, C. G.; Paterson, A.; Cohen, P.; Fukunaga, R.; Hunter, T.; Kudo, I.; Watson, S. P.; Gelb, M. H. J. Biol. Chem. 2000, 275, 37542-37551; DaSilva, J.; Xu, L.; Kim, H. J.; Miller, W. T.; Bar-Sagi, D. Mol. Cell Biol. 2006, 26, 1898-1907). Their role and function is still being investigated. Among these substrates, hnRNPA1 is overexpressed in colorectal cancer and could contribute to maintenance of telomere repeats in cancer cells with enhanced cell proliferation (Ushigome, M.; Ubagai, T.; Fukuda, H.; Tsuchiya, N.; Sugimura, T.; Takatsuka, J.; Nakagama, H. Int. J. Oncol. 2005, 26, 635-640). It is also reported that the expression levels of hnRNPA/B is deregulated in non small cell lung cancer (Boukakis, G.; Patrinou-Georgoula, M.; Lekarakou, M.; Valavanis, C.; Guialis, A. BMC. Cancer 2010, 10, 434).

MNK inhibitors have a substantial potential for the treatment of cancers including breast, prostate, hematological malignancies (e.g., CML, AML), head and neck, colon, bladder, prostatic adenocarcinoma, lung, cervical, and lymphomas (Soni, A.; Akcakanat, A.; Singh, G.; Luyimbazi, D.; Zheng, Y.; Kim, D.; Gonzalez-Angulo, A.; Meric-Bernstam, F. Mol. Cancer Ther. 2008, 7, 1782-1788; Berkel, H. J.; Turbat-Herrera, E. A.; Shi, R.; De Benedetti, A. Cancer Epidemiol. Biomarkers Prev. 2001, 10, 663-666; Wendel, H. G.; De Stanchina, E.; Fridman, J. S.; Malina, A.; Ray, S.; Kogan, S.; Cordon-Cardo, C.; Pelletier, J.; Lowe, S. W. Nature 2004, 428, 332-337; De Benedetti, A.; Graff, J. R. Oncogene 2004, 23, 3189-3199).

SUMMARY OF THE INVENTION

In one aspect, the present invention relates to compounds that act as kinase inhibitors, in particular as inhibitors of the MAP kinase interacting kinases 1 and 2 (MNK1 and MNK2). These compounds may be useful in the treatment of various disease associated with kinase activity such as proliferative disorders (e.g., cancer), autoimmune disorders, inflammatory-disorders, metabolic disorders, and neurological disorders.

In certain embodiments, a compound of the present invention is of Formula (I):

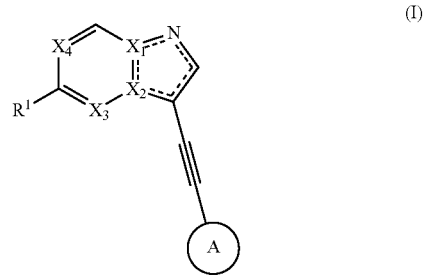

or a pharmaceutically acceptable form (such as pharmaceutically acceptable salt, solvate, hydrate, polymorph, co-crystal, tautomer, stereoisomer, isotopically labeled derivative, and prodrugs thereof thereof, wherein $R^1$, Ring A, $X_1$, $X_2$, $X_3$, and $X_4$ are as described herein. In certain embodiments, the pharmaceutical acceptable form is pharmaceutically acceptable salt. These compound are useful in treating proliferative diseases (e.g. cancer including hematological cancers and solid tumors), inflammatory diseases, neurodegenerative diseases (e.g. Alzheimer's disease, autism, or autism spectrum disorders (e.g. Asperger syndrome or Mendelsohn's Syndrome), and metabolic disorders (e.g. obesity, diabetes).

In certain embodiments, the provided compound is of formula

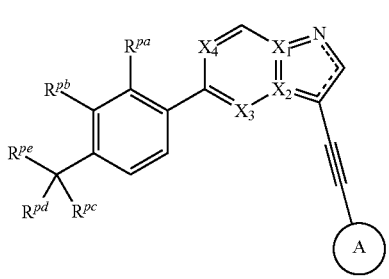

(I-i)

wherein $R^{pa}$, $R^{pb}$, $R^{pc}$, $R^{pd}$, $R^{pe}$, Ring A, $X_1$, $X_2$, $X_3$, and $X_4$ are as described herein.

In another aspect, the present invention relates to pharmaceutical compositions comprising an inventive compound, and optionally a pharmaceutically acceptable excipient, and to their use for treating diseases associated with aberrant MNK1 or MNK2 activity or dysregulation of the MNK1 or MNK2 pathway, where MNK1 and MNK2 play a role (MNK overexpression, eIF4E overexpression, P38 MAPK kinase pathway). Exemplary MNK-related disorders include, but are not limited to, metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, neurodegenerative disorders such as Alzheimer's disease, autism, or autism spectrum disorders (e.g. Asperger syndrome or Mendelsohnn's Syndrome), and cancer such as breast, prostate, hematological malignancies (e.g., CML, AML, lymphomas), head and neck, colon, bladder, prostatic adenocarcinoma, lung, cervical, and lymphomas.

In another aspect, the present invention relates to pharmaceutical compositions comprising an inventive compound, and optionally a pharmaceutically acceptable excipient, and to their use for the prevention and treatment of a PI3-kinase (PI3K)-related disorder. In certain embodiments, the PI3K-related disorder is PI3K α-related disorder. In certain embodiments, the PI3K-related disorder is PI3K β-related disorder. In certain embodiments, the PI3K-related disorder is PI3K γ-related disorder. In certain embodiments, the PI3K-related disorder is PI3K δ-related disorder. Exemplary PI3K-related disorders include, but are not limited to, cancers such as ovarian cancer, cervical cancer, breast cancer, colon cancer, rectal cancer, endometrial cancer, stomach cancer, liver cancer, lung cancer, thyroid cancer, acute myelogenous leukemia (AML), chronic myelogenous leukemia (CML), and glioblastotias.

In another aspect, the present invention relates to pharmaceutical compositions comprising these compounds and to their use for the prevention and treatment of a Janus kinase (JAK)-related disorder. In certain embodiments, the JAK-related disorder is JAK1-related disorder. In certain embodiments, the JAK-related disorder is JAK2-related disorder. In certain embodiments, the JAK-related disorder is JAK3-related disorder. Exemplary JAK-related disorders include, but are not limited to, psoriasis, rheumatoid arthritis, and cancers such as prostate, colon, ovarian and breast cancers, melanoma, leukemia and other hematological malignancies.

In another aspect, the present invention relates to pharmaceutical compositions comprising these compounds and to their use for the prevention and treatment of a Human Epidermal Growth Factor Receptor-related (HER-) disorder. In certain embodiments, the HER-related disorder is HER2-related disorder. In certain embodiments, the HER-related disorder is HER3-related disorder. Exemplary HER-related disorders include, but are not limited to, cancers such as breast, lung, kidney, brain, ovarian, colon, cervical, endometrial, prostate, liver, thyroid, GI tract, blood and lymphoma and other diseases such as multiple sclerosis.

In another aspect, the present invention relates to pharmaceutical compositions comprising these compounds and to their use for the prevention and treatment of an mTOR-related disorder. Exemplary mTOR-related disorders include, but are not limited to, cancers, such as breast, lung, kidney, brain, ovarian, colon, cervical, endometrial, prostate, liver, thyroid, GI tract, hematological cancers, and lymphoma, and other diseases such as hamartoma syndromes, rheumatoid arthritis, and multiple sclerosis.

In another aspect, the present invention relates to pharmaceutical compositions comprising these compounds and to their use for the prevention and treatment of diseases such as, but not limited to, proliferative diseases, cancer (e.g., hematological cancers, non-solid cancers, and solid tumors), inflammatory diseases, neurodegenerative diseases (e.g., Alzheimer's disease, autism, or autism spectrum disorders (e.g. Asperger syndrome or Mendelsohn's Syndrome), metabolic disorders (obesity, diabetes) as well as methods of treating these disorders using compounds described herein as single agents or in combination with one or more additional agents. In some embodiments, the additional agent is a kinase inhibitor. In some embodiments, the additional agent is an mTOR inhibitor (e.g., Sirolimus (rapamycin), Temsirolimus (CCI779), Everolimus (RAD001), AP23573 or other compounds disclosed in U.S. Pat. No. 7,091,213). In some embodiments, the additional agent is a PI3K inhibitor. Exemplary PI3-kinase inhibitors include wortmannin, demethoxyviridin, LY294002, perifosine, CAL101, PX-886, BEZ235, SF1126, INK1117, INK1197, IPI-145, GDC-0941, BKM120, XL147, XL765, palomid 529, GSK1059615, ZSTK474, PWT33597, IC87114, TG100-115, CAL263, PI-103, GNE-477, CUDC-907, GSK 2126458, GDC-0980, PF-46915032, CAL263, SF1126 and PX-886. In some embodiments, the PI3-kinase inhibitor inhibits PI3K-α, PI3K-β, PI3K-γ, and/or PI3K-δ.

In yet another aspect, the present invention describes methods for the synthesis of compounds of Formula (I), such as, for example, (4-methylpiperazin-1-yl)(4-(3-(phenylethynyl)imidazo[1,2-a]pyrazin-6-yl)phenyl)methanone and 4-methyl-2-((6-(4-(piperazine-1-carbonyl)phenyl)imidazo[1,2-a]pyrazin-3-yl)ethynyl)benzonitrile.

In another aspect, the present invention provides kits comprising a compound as described herein, or a pharmaceutically acceptable salt thereof, or a pharmaceutical composition thereof. The provided kits may be useful for the treatment of proliferative diseases, cancer (e.g., hematological cancers, non-solid cancers, and solid tumors), inflammatory diseases, neurodegenerative diseases (e.g., Alzheimer's disease, autism, or autism spectrum disorders (e.g. Asperger syndrome or Mendelsohn's Syndrome)), and metabolic disorders (e.g., obesity, diabetes). In certain embodiments, the kits described herein further include instructions for administering the compound as described herein, or a pharmaceutically acceptable salt thereof, or a pharmaceutical composition thereof. The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a syringe for parenteral administration.

BRIEF DESCRIPTION OF THE DRAWING

FIG. 1 illustrates the cellular pathways that lead to eIF4E activation and phosphorylation by MNK1/2 (PNAS, 2010, 107(32): 13975-6).

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR)R$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, aa, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{614}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{aa}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, N(R$^{ff}$)$_2$, —N(R$^{ff}$)$_3$$^+$X$^-$, —N(OR$^{cc}$)R$^{ff}$, —SH, —SR$^{ee}$, —SSR$^{ee}$, —C(=O)R$^{ee}$, —CO$_2$H, —CO$_2$R, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$Re, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ee}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl; C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —OC(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{aa}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(Re)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(0,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate. (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamnide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)R^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The present invention is not intended to be limited in any manner by the above exemplary listing of substituents.

Other Definitions

The term "pharmaceutically acceptable form thereof" as used herein refers to pharmaceutically acceptable salts, solvates, hydrates, prodrugs, tautomers, isomers, enantiomers, diastereomers, and/or polymorphs of a compound of the present invention.

In certain embodiments, the pharmaceutically acceptable form is a pharmaceutically acceptable salt. The term "pharmaceutically acceptable salt" as used herein refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In certain embodiments, the pharmaceutically acceptable form is a hydrate or solvate. The term "hydrate" as used herein refers to a compound non-covalently associated with one or more molecules of water. Likewise, the term "solvate" refers to a compound non-covalently associated with one or more molecules of an organic solvent.

In certain embodiments, the pharmaceutically acceptable form is a prodrug. The term "prodrug" as used herein refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage. In recent years several types of bioreversible derivatives have been exploited for utilization in designing prodrugs. Using esters as a prodrug type for compounds containing a carboxyl or hydroxyl functionality is known in the art as described, for example, in *The Organic Chemistry of Drug Design and Drug Interaction* by Richard Silverman, published by Academic Press (1992).

In certain embodiments, the pharmaceutically acceptable form is a tautomer. The term "tautomer" as used herein includes two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

In certain embodiments, the pharmaceutically acceptable form is an isomer. The term "isomer" as used herein includes any and all geometric isomers and stereoisomers (e.g., enantiomers, diastereomers, etc.). For example, "isomer" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., Tetrahedron 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

In certain embodiments, the pharmaceutically acceptable form is a polymorph. The term "polymorph" as used herein refers to a crystalline compound existing in more than one crystalline form/structure. When polymorphism exists as a result of difference in crystal packing it is called packing polymorphism. Polymorphism can also result from the existence of different conformers of the same molecule in conformational polymorphism. In pseudopolymorphism the different crystal types are the result of hydration or solvation.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, and/or turkeys. In certain embodiments, the subject is an animal. The animal may be of either sex and may be of any stage of development. In certain embodiments, the animal is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

"Treat," "treating" and "treatment" encompasses an action that occurs while a subject is suffering from a condition (e.g., a "MNK1- or MNK2-related" disease, disorder, or condition, e.g., a disease, disorder, or condition in which MNK1 and/or MNK2 is known to play role) which reduces the severity of the condition or retards or slows the progression of the condition ("therapeutic treatment").

As used herein "inhibition," "inhibiting," and "inhibit", refer to the ability of a compound to reduce, slow, halt, or prevent the activity of a particular biological process relative to a control. In certain embodiments, the biological process is in vitro (e.g., a biochemical or cellular assay). In certain embodiments, the biological process is in vivo.

An "effective amount" of a compound refers to an amount sufficient to elicit the desired biological response, e.g., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent. In some embodiments, a therapeutically effective amount is an amount effective to inhibit cell growth or induce cell death.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "kinase" represent a class of enzymes that are able to transfer a phosphate group from a donor molecule to an acceptor molecule, e.g., an amino acid residue of a protein or a lipid molecule. Representative, non-limiting examples of kinases include Abl, ACK, Akt1/PKBα, Akt2/PKBPβ, Akt3/PKBγ, ALK1, ALK2, Alk4, AMPKα1/β1/γ1, AMPKα1/β1/γ2, AMPKα1/β1/γ3, AMPKα1/β2/γ1, AMPKα2/β1/γ1, AMPKα2/P32/γ2, Abl2, ARKS, Ask1, Aurora A, Aurora B, Aurora C, Axl, BARK1, Blk, Bmx, B-Raf, Brk, BrSK1, BrSK2, Btk, CaMK1α, CaMK1β, CaMK1γ, CaMK1δ, CAMK2α, CaMK2β, CAMK2δ, CAMK2γ, CAMK4, CAMKK1, CAMKK2, CDK1, CDK2, CDK3, CDK4, CDK5, CDK6, CDK7, CDK9, CDK1/cyclin B, CDK2/cyclin A, CDK2/cyclin E, CDK3/cyclin E, CDK5/p25, CDK5/p35, CDK6/cyclinD3, CDK7/cyclin H/MAT1, CDK9/cyclin T1, CHK1, CHK2, CK1(γ), CK1δ, CK2α1, CK2α2, cKit, c-RAF, CLK1, CLK2, CLK3, COT, Csk, DAPK1, DAPK2, DAPK3, DCAMLK2, DDR2, DMPK, DRAK1, DYRK1A, DYRK2, DYRK3, eEF2K, EGFR, EPHA1, EPHA2, EPHA3, EPHA4, EPHA5, EPHA6, EPHA7, EPHA8, EphB1, EphB2, EphB3, EphB4, ErbB4, Erk1, Erk2, FAK, Fer, Fes, FGFR1, Flt2, Flt4, FLT3 D835Y, FGFR2, FGFR3, FGFR4, Fgr, Flt1, Flt3, Fms, FRK, FynA, GCK, GPRK5, GRK2, GRK4, GRK6, GRK7, GSK3α, GSK3β, Hck, HER2, HER4, HIPK1, HIPK2, HIPK3, HIPK4, IGF1R, IKKβ, IKKα, IKKε, IR, InsR, IRR, IRAK1, IRAK2, IRAK4, Itk, JAK2, JAK3, JNK1, JNK2, JNK3, KDR, KHS1, Kit, Lck, LIMK1, LKB1, LOK, LRRK2, Lyn A, Lyn B, MAPK1, MAPK2, MAPK12, MAPKAP-K2, MAPKAP-K3, MAPKAPK2, MAPKAPK3, MAPKAPK5, MARK1, MARK2, MARK3, MARK4, MELK, MEK1, MEK2, MEKK2, MEKK3, Mer, Met, MET M1250T, MINK, MKK4, MKK6, MKK73, MLCK, MLK1, MLK3, MNK1, MNK2, MRCKα, MRCKβ, MSK1, MSK2, MSSK1, STK23, STK4, STK3, STK24, MST1, MST2, MST3, MST4, MUSK, mTOR, MYO3β, MYT1, NDR1, NEK11, NEK2, NEK3, NEK6, NEK7, NEK9, NLK, NUAK2, p38α, p38β, p386, p38γ, p70S6K, S6K, SRK, PAK1/CDC42, PAK2, PAK3, PAK4, PAK5, PAK6, PAR-1Bα, PASK, PBK, PDGFRα, PDGFRβ, PDK1, PEK, PHKG2, PI3Kα, PI3Kβ, PI3Kγ, PI3Kδ, Pim1, Pim2, PKAcα, PKAcβ, PKAcγ, PKA(b), PKA, PKBα, PKBβ, PKBγ, PKCα, PKCPβ1, PKCPβ2, PKCβ11, PKCδ, PKCε, PKCγ, PKCµ, PKCη, PKCι, PKCθ, PKCζ, PKD1, PKD2, PKD3, PKG1α, PKG1B, PKN1, PKN2, PKR, PLK1, PLK2, PLK3, PLK4, Polo, PRAK, PRK2, PrKX, PTK5, PYK2, QIK, Raf1, Ret, RIPK2, RIPK5, ROCK1, ROCK2, RON, ROS, Rse, RSK1, RSK2, RSK3, RSK4, SAPK2a, SAPK2b, SAPK3, SAPK4, SGK1, SGK2, SGK3, SIK, MLCK, SLK, Snk, Src, SRPK1, SRPK2, STK33, SYK, TAK1-TAB1, TAK1, TBK1, TAO1, TAO2, TAO3, TBK1, TEC, TESK1, TGFβR1, TGFβR2, Tie2, TLK2, TrkA, TrkB, TrkC, TSSK1, TSSK2, TTK, TXK, TYK2, TYRO3, ULK1, ULK2, WEE1, WNK2, WNK3, Yes1, YSK1, ZAK, ZAP70, ZC3, and ZIPK.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis or diseases associated with angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

As used herein, the term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myclodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostateadenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoina); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and growth of new blood vessels. Normal angiogenesis occurs in the body of a healthy subject during wound healing and for restoring blood flow to tissues after injury. The body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can result in new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyosifis, pemphigus, pemphigoid, diabetes (e.g., Type I), myasthenia gravis, Hashimoto's thyroditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis *nodosa*), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomylitis, optic neuritis, temporal arteritis, transverse myelitis, necrotizing fasciitis, and necrotizing enterocolitis.

As used herein, an "autoimmune disease" refers to a disease arising from an inappropriate immune response in the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppressants, e.g., medications which decrease the immune response. Exemplary autoimmune diseases include, but are not limited to, glomerulonephritis, Goodspature's syndrome, necrotizing vasculitis, lymphadenitis, peri-arteritis *nodosa*, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-associated vasculitis (e.g., Wegener's granulomatosis, microscopic polyangiitis), urveitis; Sjogren's syndrome, Crohn's disease, Reiter's syndrome, ankylosing spondylitis, Lyme arthritis, Guillain-Barre syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behçet's disease.

The term "neurodegenerative disease" as used herein refers to motor neuron diseases represented by amyotrophic lateral sclerosis, Parkinson's syndrome including Parkinson's disease, dementia represented by Alzheimer's disease, progressive supranuclear palsy, Huntington's disease, multiple system atrophy including striatonigral degeneration, Shy-Drager syndrome and olivopontocerebellar atrophy, any type of spinocerebellar ataxia including spinocerebellar ataxia type 1, spinocerebellar ataxia type 2, spinocerebellar ataxia type 3 (Machado-Joseph disease, MJD), spinocerebellar ataxia type 6, spinocerebellar ataxia type 7, spinocerebellar ataxia type 12 and dentatorubral-pallidoluysian atrophy, or multiple sclerosis, as well as autism and autism spectrum disorders (e.g. Asperger syndrome or Mendelsohnn's Syndrome)

DETAILED DESCRIPTION OF CERTAIN EMBODIMENTS

The invention provides bicyclic alkyne derivatives as kinase inhibitors. In particular, the provided compounds act as inhibitors of the MAP kinase interacting kinases 1 and 2 (MNK1 and/or MNK2). The provided compounds and pharmaceutical compositions thereof are useful in treating diseases associated with aberrant MNK1 or MNK2 activity or dysregulation of the MNK1 or MNK2 pathway, where MNK1 and MNK2 play a role (e.g. MNK overexpression, eIF4E overexpression, P38 MAPK kinase pathway). For example, the provided compounds and pharmaceutical compositions can be used to prevent and/or treat cancer (such as solid tumor, non-solid cancers, and hematological cancers), an inflammatory disease, a neurodegenerative disease (such as Alzheimer's. autism, or autism spectrum disorders (e.g. Asperger syndrome or Mendelsohnn's Syndrome), or a metabolic disorder (such as diabetes, hyperlipidemia and obesity).

Compounds

In one aspect, the present invention provides a compound of Formula (I):

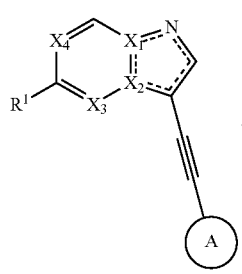

or a pharmaceutically acceptable form thereof (such as pharmaceutically acceptable salt, solvate, hydrate, polymorph, co-crystal, tautomer, stereoisomer, isotopically labeled derivative, and prodrugs thereof), wherein $X_1$ and $X_2$ are independently N or C;
$X_3$ and $X_4$ are independently N or $CR^2$;
provided that at least two of $X_1$, $X_2$, $X_3$, and $X_4$ are N;
═ is a single or double bond, as valency allows;
$R^1$ is independently hydrogen, optionally substituted $C_{1-6}$ alkyl, optionally substituted $C_{3-6}$ carbocyclyl, optionally substituted phenyl, optionally substituted six-membered heteroaryl, optionally substituted six-membered heterocyclyl, optionally substituted $C_{3-6}$ carbocyclylalkyl, optionally substituted arylalkyl, optionally substituted five- or six-membered heteroarylalkyl, optionally substituted five- or six-membered heterocyclylalkyl, —CN, —$OR^A$, or —$N(R^B)_2$;

each instance of $R^2$ is independently hydrogen, halogen, optionally substituted $C_{1-6}$ alkyl, optionally substituted $C_{3-6}$ carbocyclyl, —$OR^A$, or —$N(R^B)_2$, Ring A is optionally substituted phenyl, optionally substituted five-membered heteroaryl, optionally substituted six-membered heteroaryl, or optionally substituted 5,6-bicyclic heteroaryl;

each instance of $R^A$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, or an oxygen protecting group; and each instance of $R^B$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, optionally substituted acyl, or a nitrogen protecting group.

In certain embodiments, the pharmaceutical acceptable form is pharmaceutically acceptable salt.

As generally defined herein, $R^1$ is independently hydrogen, optionally substituted $C_{1-6}$ alkyl, optionally substituted $C_{3-6}$ carbocyclyl, optionally substituted phenyl, optionally substituted six-membered heteroaryl; optionally substituted six-membered heterocyclyl, optionally substituted $C_{3-6}$ carbocyclylalkyl, optionally substituted arylalkyl, optionally substituted five- or six-membered heteroarylalkyl, optionally substituted five- or six-membered heterocyclylalkyl, —CN, —$OR^A$, or —$N(R^B)_2$. In some embodiments, $R^1$ is hydrogen. In some embodiments, $R^1$ is optionally substituted $C_{1-6}$ alkyl. In some embodiments, $R^1$ is substituted $C_{1-6}$ alkyl. In some embodiments, $R^1$ is unsubstituted $C_{1-6}$ alkyl. In some embodiments, $R^1$ is methy, ethyl, n-propyl, or iso-propyl. In some embodiments, $R^1$ is optionally substituted $C_{3-6}$ carbocyclyl. In some embodiments, $R^1$ is cyclopropyl, cyclobutyl, cyclopentyl, or cyclohexyl. In some embodiments, $R^1$ is independently optionally substituted phenyl, optionally substituted six-membered heteroaryl, or optionally substituted six-membered heterocyclyl.

In some embodiments, $R^1$ is optionally substituted phenyl of the formula:

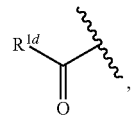

wherein each instance of $R^{1a}$ is independently hydrogen, halogen, optionally substituted $C_{1-6}$ alkyl, optionally substituted $C_{3-6}$ carbocyclyl, optionally substituted phenyl, optionally substituted five- or six-membered heteroaryl, optionally substituted five- or six-membered heterocyclyl, optionally substituted acyl, —CN, —$OR^A$, or —$N(R^B)_2$; and m1 is an integer of 1 to 5, inclusive.

In some embodiments, $R^{1a}$ is of the formula wherein $R^{1d}$ is optionally substituted six-membered heterocyclyl, —$OR^A$, or —$N(R^B)_2$, wherein $R^A$ and $R^B$ are defined herein.

In certain embodiments, $R^1$ is of the formula:

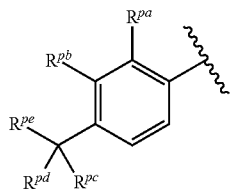

wherein $R^{pa}$ is hydrogen, halogen, CN, optionally substituted $C_{1-6}$ alkyl, —$OR^A$, —$N(R^B)_2$, —NH—CO—$R^C$;

$R^C$ is optionally substituted $C_{1-6}$ alkyl;

$R^{pb}$ is independently hydrogen, halogen, CN, —$OR^A$, —$N(R^B)_2$, optionally substituted $C_{1-6}$ alkyl, optionally substituted $C_{3-6}$ carbocyclyl, optionally substituted aryl, optionally substituted heterocyclyl, or optionally substituted heteroaryl;

each of $R^{pc}$ and $R^{pd}$ is independently hydrogen, halogen, CN, —$OR^A$, or optionally substituted $C_{1-6}$ alkyl;

or $R^{pc}$ and $R^{pd}$ are joined to form =O; and $R^{pe}$ is optionally substituted six-membered heterocyclyl, —$OR^A$, or —$N(R^B)_2$; and each instance of $R^A$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, or an oxygen protecting group; and each instance of $R^B$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, optionally substituted acyl, or a nitrogen protecting group.

In certain embodiments, $R^{pc}$ and $R^{pd}$ are joined to form =O and $R^1$ is of the formula:

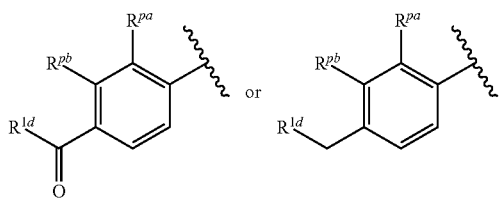

each instance of $R^{1d}$ is optionally substituted six-membered heterocyclyl, —$OR^A$, or —$N(R^B)_2$.

In certain embodiments, $R^{pa}$ is hydrogen and $R^{pb}$ is halogen. In certain embodiments, $R^{pa}$ is hydrogen and $R^{pb}$ is F. In certain embodiments; $R^{pa}$ is hydrogen and $R^{pb}$ is Cl. In certain embodiments, $R^{pa}$ is hydrogen and $R^{pb}$ is Br. In certain embodiments, $R^{pa}$ is hydrogen and $R^{pb}$ is I. In certain embodiments, $R^{pb}$ is hydrogen and $R^{pa}$ is halogen. In certain embodiments, $R^{pb}$ is hydrogen and $R^{pa}$ is F. In certain embodiments, $R^{pb}$ is hydrogen and $R^{pa}$ is Cl. In certain embodiments, $R^{pb}$ is hydrogen and $R^{pa}$ is Br. In certain embodiments, $R^{pb}$ is hydrogen and $R^{pa}$ is I.

In certain embodiments, $R^{pa}$ and $R^{pb}$ are both hydrogen. In certain embodiments, $R^1$ is of the formula:

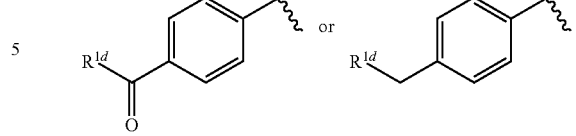

wherein each instance of $R^{1d}$ is optionally substituted six-membered heterocyclyl, —$OR^A$, or —$N(R^B)_2$.

In certain embodiments, $R^1$ is of the formula:

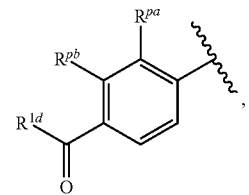

wherein $R^{1d}$ is optionally substituted six-membered heterocyclyl, —$OR^A$, or —$N(R^B)_2$. In certain embodiments, $R^1$ is of the formula:

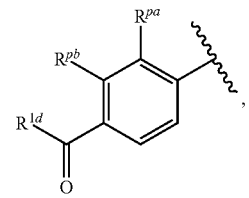

wherein $R^{1d}$ is optionally substituted six-membered heterocyclyl. In certain embodiments, $R^1$ is of the formula:

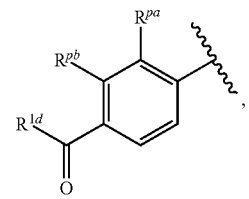

wherein $R^{1d}$ is optionally substituted morpholine or optionally substituted piperazine. In certain embodiments, In certain embodiments, $R^1$ is of the formula:

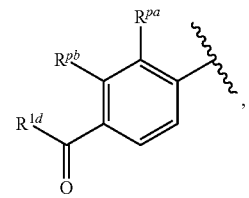

wherein $R^{1d}$ is —$N(R^B)_2$, and each instance of $R^B$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, optionally substituted acyl, or a nitrogen protecting group. In certain embodiments, $R^1$ is of the formula:

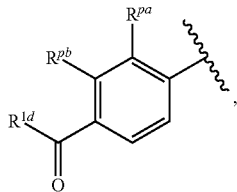

and $R^{1d}$ is hydrogen. In certain embodiments, $R^1$ is one of the following formulae:

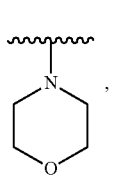 , 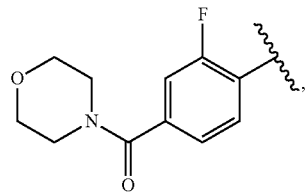 ,

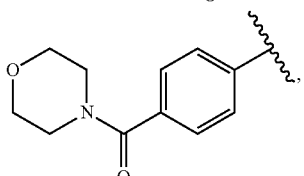 ,

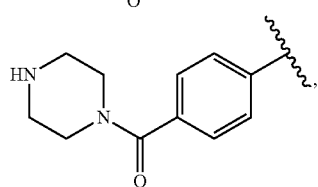 ,

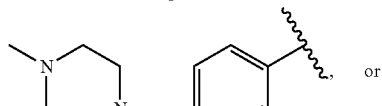 , or

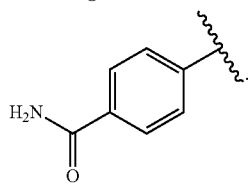 .

In certain embodiments, $R^1$ is of the formula:

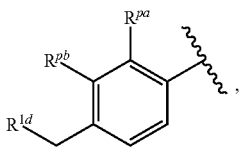

wherein $R^{1d}$ is optionally substituted six-membered heterocyclyl, $-OR^A$, or $-N(R^B)_2$. In certain embodiments, $R^1$ is of the formula:

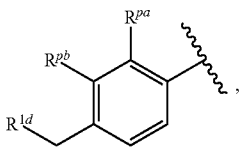 , wherein $R^{1d}$ is optionally substituted six-membered heterocyclyl. In certain embodiments, $R^1$ is of the formula:

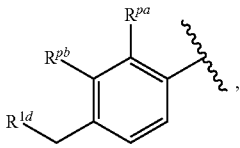 , wherein $R^{1d}$ is optionally substituted morpholine or optionally substituted piperazine. In certain embodiments, $R^1$ is of the formula:

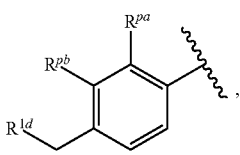 , wherein $R^{1d}$ is $-N(R^B)_2$, and each instance of $R^B$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, optionally substituted acyl, or a nitrogen protecting group. In certain embodiments, $R^1$ is of the formula

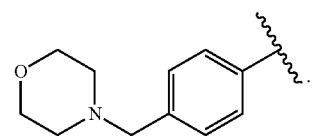 [SMILES: *c1ccc(CN2CCOCC2)cc1] .

In some embodiments, $R^1$ is optionally substituted six-membered heteroaryl. In certain embodiments, $R^1$ is one of the following formulae:

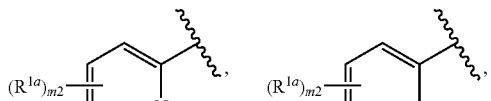 , 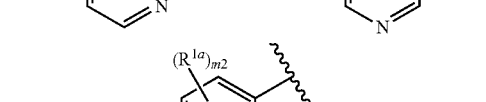 ,

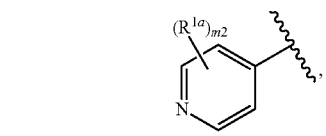 , wherein $R^{1a}$ is as defined herein; and each instance of m2 is independently an integer of 1 to 4, inclusive.

As generally defined herein, m2 is an integer of 1 to 4, inclusive. In certain embodiments, m2 is 1. In certain embodiments, m2 is 2. In certain embodiments, m2 is 3. In certain embodiments, m2 is 4.

In some embodiments, $R^1$ is optionally substituted six-membered heterocyclyl. In some embodiments, $R^1$ is one of the following formulae:

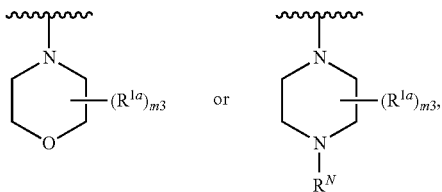

wherein each instance of $R^{1a}$ is as defined herein; each instance of m3 is independently an integer of 1 to 8, inclusive; and $R^N$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, optionally substituted acyl, or a nitrogen protecting group.

In certain embodiments, the provided compound of Formula (I) is of Formula (I-i):

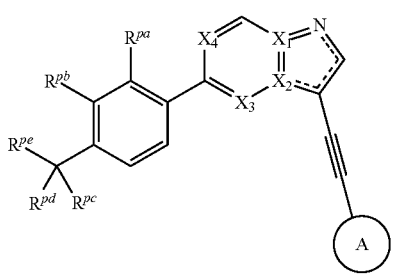

$R^{pa}$ is hydrogen, halogen, CN, optionally substituted $C_{1-6}$ alkyl, —$OR^A$, —$N(R^B)_2$, —NH—CO—$R^C$;

$R^C$ is optionally substituted $C_{1-6}$ alkyl;

$R^{pb}$ is independently hydrogen, halogen, CN, —$OR^A$, —$N(R^B)_2$, optionally substituted $C_{1-6}$ alkyl, optionally substituted $C_{3-6}$ carbocyclyl, optionally substituted aryl, optionally substituted heterocyclyl, or optionally substituted heteroaryl;

each of $R^{pc}$ and $R^{pd}$ is independently hydrogen, halogen, CN, —$OR^A$, or optionally substituted $C_{1-6}$ alkyl;

or $R^{pc}$ and $R^{pd}$ are joined to form =O; and $R^{pe}$ is optionally substituted six-membered heterocyclyl, —$OR^A$, or —$N(R^B)_2$; and each instance of $R^A$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, or an oxygen protecting group; and each instance of $R^B$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, optionally substituted acyl, or a nitrogen protecting group.

As generally defined herein, m3 is an integer of 1 to 8, inclusive. In certain embodiments, m3 is 1. In certain embodiments, m3 is 2. In certain embodiments, m3 is 3. In certain embodiments, m3 is 4. In certain embodiments, m3 is 5. In certain embodiments, m3 is 6. In certain embodiments, m3 is 7. In certain embodiments, m3 is 8.

As generally used herein, $R^N$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, optionally substituted acyl, or a nitrogen protecting group. In certain embodiments, $R^N$ is hydrogen, optionally substituted $C_{1-6}$ alkyl, or an oxygen protecting group. In certain embodiments, $R^N$ is hydrogen. In certain embodiments, $R^N$ is optionally substituted $C_{1-6}$ alkyl. In certain embodiments, $R^N$ is unsubstituted $C_{1-6}$ alkyl. In certain embodiments, $R^N$ is methyl or ethyl. In certain embodiments, $R^N$ is a nitrogen protecting group. In certain embodiments, $R^N$ is Bn; BOC, Cbz, or Fmoc.

In certain embodiments, $R^1$ is of the formula

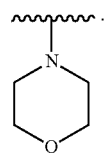

In certain embodiments, $R^1$ is optionally substituted six-membered heterocyclylalkyl. In certain embodiments, $R^1$ is one of the following formulae:

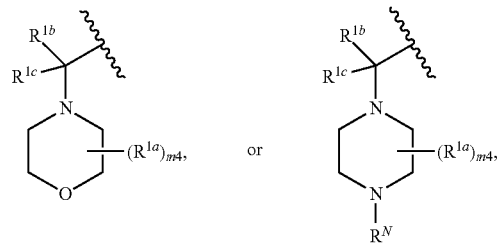

wherein $R^{1a}$ is as define herein; each instanced of $R^{1b}$ and $R^{1c}$ is independently hydrogen, halogen, optionally substituted $C_{1-6}$ alkyl, optionally substituted $C_{3-6}$ carbocyclyl, optionally substituted aryl, optionally substituted heteroaryl, optionally substituted acyl, —CN, —$OR^A$, or —$N(R^B)_2$; each instance of m4 is independently an integer of 1 to 8, inclusive, as valency permits; and $R^N$ is as defined herein.

As generally defined herein, m4 is an integer of 1 to 8, inclusive. In certain embodiments, m4 is 1. In certain embodiments, m4 is 2. In certain embodiments, m4 is 3. In certain embodiments, m4 is 4. In certain embodiments, m4 is 5. In certain embodiments, m4 is 6. In certain embodiments, m4 is 7. In certain embodiments, m4 is 8.

As generally defined herein, each of $R^{1b}$ and $R^{1c}$ is independently hydrogen, halogen, optionally substituted $C_{1-6}$ alkyl, optionally substituted $C_{3-6}$ carbocyclyl, optionally substituted aryl, optionally substituted heteroaryl, optionally substituted acyl, —CN, —$O^{RA}$, or —$N(R^B)_2$, wherein $R^A$ and $R^B$ are as defined herein. In certain embodiments, $R^{1b}$ and $R^{1c}$ are both hydrogen.

In certain embodiments, $R^1$ is one of the following formulae:

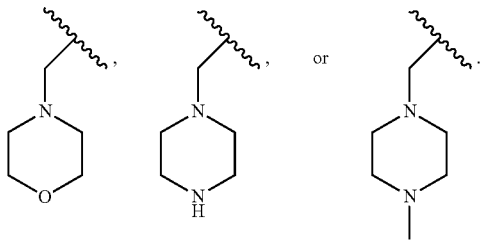

In certain embodiments, $R^1$ is —$N(R^B)_2$, wherein each instance of $R^B$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, optionally substituted acyl, or a nitrogen protecting group. In certain embodiments, $R^1$ is —$N(R^B)_2$, wherein each instance of $R^B$ is independently hydrogen, optionally substituted $C_{1-6}$ alkyl, or optionally substituted acyl. In certain embodiments, $R^1$ is —$NHR^B$, wherein $R^B$ is hydrogen, optionally substituted $C_{1-6}$ alkyl, or optionally substituted acyl. In certain embodiments, $R^1$ is $NH_2$. In certain embodiments, $R^1$ is —$NHR^B$, wherein $R^B$ is optionally substituted $C_{1-6}$ alkyl. In certain embodiments, $R^1$ is —$N(CH_3)_2$. In certain embodiments, $R^1$ is —$NHR^B$, wherein $R^B$ is optionally substituted acyl. In certain embodiments, $R^1$ is —NHAc.

As generally defined herein, Ring A is optionally substituted phenyl, optionally substituted five-membered heteroaryl, optionally substituted six-membered heteroaryl, or optionally substituted 5,6-bicyclic heteroaryl.

In certain embodiments, Ring A is of the formula:

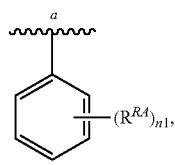

wherein
a indicates the point of attachment to the alkyne;
each instance of $R^{RA}$ is independently hydrogen, halogen, optionally substituted $C_{1-6}$ alkyl, optionally substituted acyl, —CN, —$OR^{AO}$, or —$N(R^{AN})_2$;
each instance of $R^{AO}$ is independently hydrogen, optionally substituted alkyl, optionally substituted carbocyclyl, optionally substituted aryl, optionally substituted heterocyclyl, optionally substituted heteroaryl, or an oxygen protecting group;
each instance of $R^{AN}$ is independently hydrogen, optionally substituted alkyl, optionally substituted carbocyclyl, optionally substituted aryl, optionally substituted heterocyclyl, optionally substituted heteraryl, optionally substituted acyl, or a nitrogen protecting group; and
n1 is an integer of 1 to 5, inclusive.

As generally used herein, n1 is an integer of 1 to 5, inclusive. In certain embodiments, n1 is 1. In certain embodiments, n2 is 2. In certain embodiments, n3 is 3. In certain embodiments, n4 is 4. In certain embodiments, n5 is 5.

In certain embodiments, n1 is 1 and Ring A is one of the formulae:

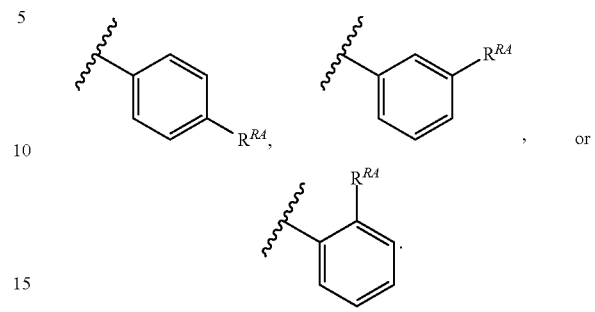

In certain embodiments, n1 is 2, and Ring A is one of the formulae:

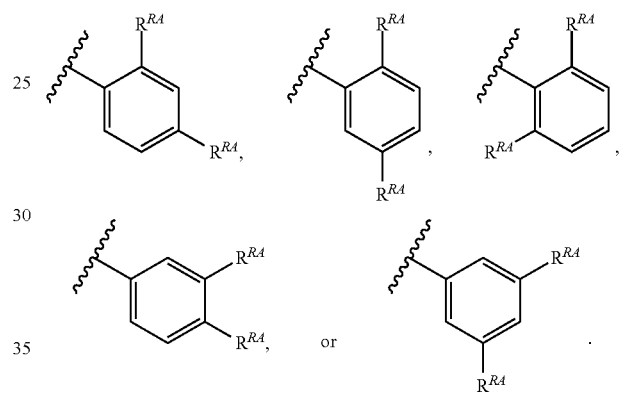

In certain embodiments, n1 is 3 and Ring A is one of the formulae:

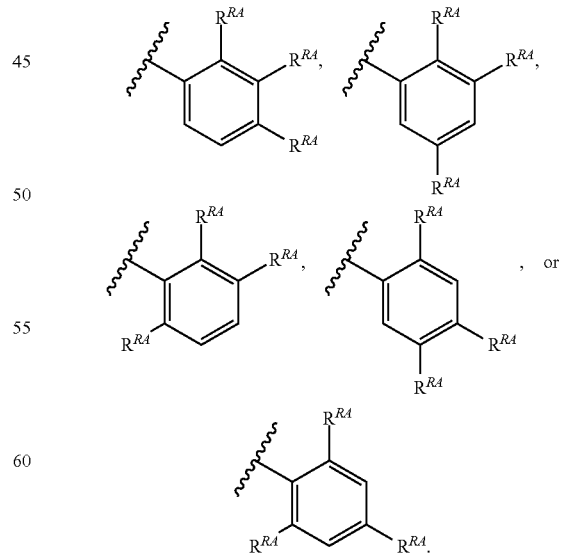

In certain embodiments, n1 is 4, and Ring A is one of the formulae:

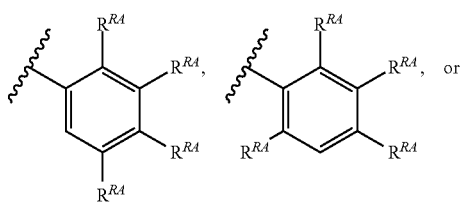

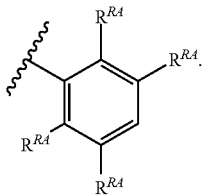

In certain embodiments, n1 is 5, and Ring A is of the formula:

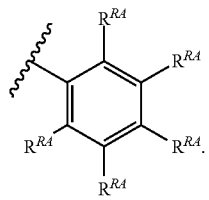

In certain embodiments, Ring A is

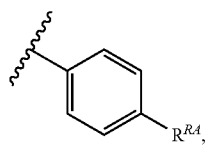

wherein $R^{RA}$ is one of the following formulae:

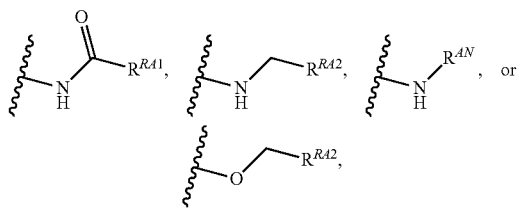

wherein $R^{A1}$, $R^{A2}$, and $R^{AN}$ are as defined herein.

In certain embodiments, Ring A is one of the formulae:

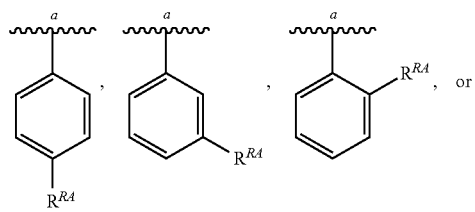

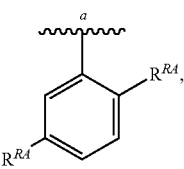

wherein each instance of $R^{RA}$ is independently hydrogen, —CN, —CH$_3$, —OCH$_3$, —NHAc, —NHC(=O)Ph, —NHSO$_2$CH$_3$, or —C(=O)NH$_2$.

In certain embodiments, Ring A is one of the following formulae:

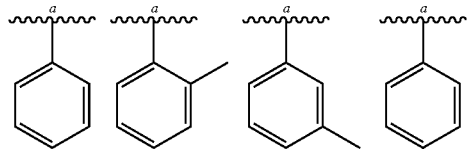

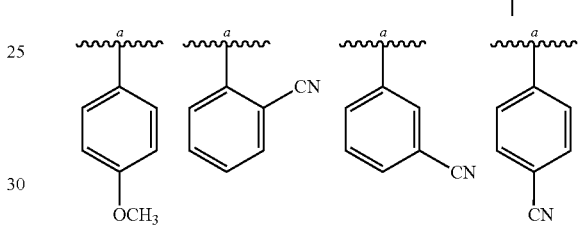

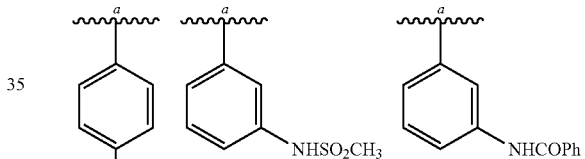

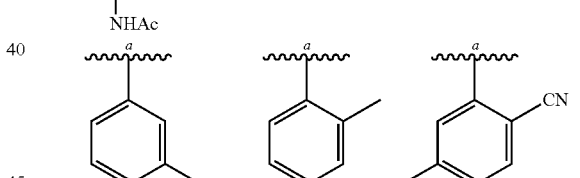

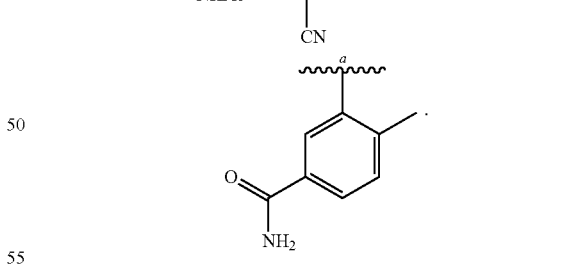

As generally defined herein, $R^{RA}$ is independently hydrogen, halogen, optionally substituted C$_{1-6}$ alkyl, optionally substituted acyl, —CN, —OR$^{AO}$, or —N(R$^{AN}$)$_2$. In certain embodiments, $R^{RA}$ is hydrogen. In certain embodiments, RR is halogen. In certain embodiments, $R^{RA}$ is —F, —Cl, —Br, or —I. In certain embodiments, RR is —CN. In certain embodiments, $R^{RA}$ is optionally substituted C$_{1-6}$ alkyl. In certain embodiments, $R^{RA}$ is unsubstituted C$_{1-6}$ alkyl. In certain embodiments, $R^{RA}$ is methyl, ethyl, n-propyl, or iso-propyl. In certain embodiments, $R^{RA}$ is substituted C$_{1-6}$ alkyl. In certain embodiments, $R^{RA}$ is —CF$_3$, —CHF$_2$, or —CH$_2$F. In certain embodiments, RR is optionally substituted acyl. In certain embodiments, RR is acetyl. In certain embodiments, R$^{RA}$ is —C(=O)NH$_2$.

In certain embodiments, R$^{RA}$ is —OR$^{AO}$, wherein each instance of R$^{AO}$ is independently hydrogen, optionally substituted alkyl, optionally substituted carbocyclyl, optionally substituted aryl, optionally substituted heterocyclyl, optionally substituted heteroaryl, or an oxygen protecting group. In certain embodiments, R$^{RA}$ is —OH. In some embodiments, R$^{RA}$ is —OR$^{AO}$, wherein R$^{AO}$ is independently optionally substituted C$_{1-6}$ alkyl, optionally substituted C$_{3-6}$ carbocyclyl, optionally substituted aryl, optionally substituted heterocyclyl, optionally substituted heteroaryl, or an oxygen protecting group. In certain embodiments, R$^{RA}$ is —OR$^{AO}$, wherein R$^{AO}$ is optionally substituted C$_{1-6}$ alkyl. In certain embodiments, R$^{RA}$ is —OR$^{AO}$, wherein R$^{AO}$ is unsubstituted C$_{1-6}$ alkyl. In certain embodiments, R$^{RA}$ is —O-methyl, —O-ethyl, —O-propyl, or —O-isopropyl. In certain embodiments, R$^{RA}$ is —OR$^{AO}$, wherein R$^{AO}$ is optionally substituted heterocyclyl. In certain embodiments, R$^{RA}$ is —OR$^{AO}$, wherein R$^{AO}$ is optionally substituted aryl. In certain embodiments, RR is —O-phenyl. In certain embodiments, R$^{RA}$ is —OR$^{AO}$, wherein R$^{AO}$ is optionally substituted heteroaryl. In certain embodiments, R$^{RA}$ is —OR$^{AO}$, wherein R$^{AO}$ is an oxygen protecting group. In certain embodiments, R$^{RA}$ is —OR$^{AO}$, wherein R$^{AO}$ is Ac, Boc, TBS, TIPS, Bn, or Bz.

In certain embodiments, R$^{RA}$ is

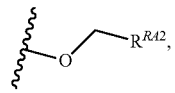

wherein each instance of R$^{RA2}$ is independently optionally substituted C$_{1-6}$ alkyl, optionally substituted C$_{3-6}$ carbocyclyl, optionally substituted phenyl, optionally substituted five- or six-membered heterocyclyl, or optionally substituted heteroaryl. In certain embodiments, R$^{RA}$ is —OBn.

In certain embodiments, R$^{RA}$ is —N(R$^{AN}$)$_2$, each instance of R$^{AN}$ is independently hydrogen, optionally substituted alkyl, optionally substituted carbocyclyl, optionally substituted aryl, optionally substituted heterocyclyl, optionally substituted heteroaryl, optionally substituted acyl, or a nitrogen protecting group. In certain embodiments, RA is —N(R$^{AN}$)$_2$, wherein each instance of R$^{AN}$ is independently hydrogen, optionally substituted alkyl, optionally substituted acyl, or a nitrogen protecting group. In certain embodiments, R$^{RA}$ is —NH$_2$. In some embodiments, R$^{RA}$ is —N(R$^{AN}$)$_2$. In certain embodiments, RR is —NHR$^{AN}$, wherein R$^{AN}$ is optionally substituted alkyl, optionally substituted carbocyclyl, optionally substituted aryl, optionally substituted heterocyclyl, optionally substituted heteroaryl, optionally substituted acyl, or a nitrogen protecting group. In certain embodiments, R$^{RA}$ is —NHR$^{AN}$, wherein R$^{AN}$ is optionally substituted C$_{1-6}$ alkyl. In certain embodiments, R$^{RA}$ is —NHR$^{AN}$, wherein R$^{AN}$ is unsubstituted C$_{1-6}$ alkyl. In certain embodiments, R$^{RA}$ is —NH-methyl, —NH-ethyl, —NH-n-propyl, or —NH-iso-propyl. In certain embodiments, R$^{RA}$ is —NHR$^{AN}$, wherein R$^A$N is a nitrogen protecting group. In certain embodiments, R$^{RA}$ is —NHSO$_2$CH$_3$.

In certain embodiments, R$^{RA}$ is optionally substituted C$_{3-6}$ carbocyclyl. In certain embodiments, R$^{RA}$ is optionally substituted aryl. In certain embodiments, R$^{RA}$ is optionally substituted phenyl. In certain embodiments, R$^{RA}$ is phenyl. In certain embodiments, R$^{RA}$ is substituted phenyl. In certain embodiments, R$^{RA}$ is o-CH$_3$-Ph, m-CH$_3$-Ph, p-CH$_3$-Ph, o-C$_2$H$_5$-Ph, m-C$_2$H$_5$-Ph, p-C$_2$H$_5$-Ph, o-$^i$Pr-Ph, m-$^i$Pr-Ph, p-$^i$Pr-Ph, o-Cl-Ph, m-Cl-Ph, p-Cl-Ph, o-CF$_3$-Ph, m-CF$_3$-Ph, p-CF$_3$-Ph, o-Ph-Ph, m-Ph-Ph, p-Ph-Ph, o-NH$_2$-Ph, m-NH$_2$-Ph, p-NH$_2$-Ph, o-CH$_3$-m-NH$_2$-Ph, o-Cl-m-CF$_3$-Ph, or

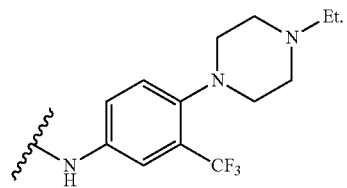 [SMILES: *Nc1ccc(N2CCN(CC)CC2)c(C(F)(F)F)c1]

In certain embodiments, R$^{RA}$ is optionally substituted five- or six-membered heterocyclyl. In certain embodiments, R$^{RA}$ is optionally substituted five-membered heterocyclyl. In certain embodiments, R$^{RA}$ is optionally substituted six-membered heterocyclyl. In certain embodiments, R$^{RA}$ is optionally substituted five- or six-membered heteroaryl. In certain embodiments, R$^{RA}$ is optionally substituted five-membered heteroaryl. In certain embodiments, R$^{RA}$ is optionally substituted six-membered heteroaryl. In certain embodiments, R$^{RA}$ is thiazole, pyridine, or pyrimidine. In certain embodiments, R$^{RA}$ is o-CH$_3$-pyridine, m-CH$_3$-pyridine, or p-CH$_3$-pyridine. In certain embodiments, R$^{RA}$ is —N(R$^{AN}$)$_2$, wherein each R$^{AN}$ is independently optionally substituted C$_{1-6}$ alkyl. In certain embodiments, R$^{RA}$ is —N(R$^{AN}$)$_2$, wherein each R$^{AN}$ is independently unsubstituted C$_{1-6}$ alkyl. In certain embodiments, R$^{RA}$ is —N(CH$_3$)R$^{AN}$, wherein each R$^{AN}$ is independently optionally substituted C$_{1-6}$ alkyl or or a nitrogen protecting group. In certain embodiments, R$^{RA}$ is —N(R$^{AN}$)$_2$, wherein each instance R$^{AN}$ is independently selected from the group consisting of methyl, ethyl, or isopropyl. In some embodiments, R$^{RA}$ is —N(R$^{AN}$)$_2$, wherein each R$^{AN}$ is the same. In some embodiments, R$^{RA}$ is —N(R$^{AN}$)$_2$, wherein each R$^{AN}$ is different. In certain embodiments, R$^{AN}$ is a nitrogen protecting group. In certain embodiments, R$^{AN}$ is Bn, BOC, Cbz, Fmoc, trifluoroacetyl, triphenylmethyl, or Ts.

In certain embodiments, R$^{RA}$ is of the formula

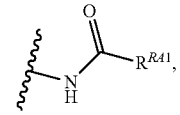

wherein R$^{RA1}$ is independently optionally substituted C$_{1-6}$ alkyl, optionally substituted C$_{3-6}$ carbocyclyl, optionally substituted phenyl, optionally substituted five- or six-membered heterocyclyl, optionally substituted five- or six-membered heteroaryl, —OR$^A$, or —N(R$^B$)$_2$. In certain embodiments, R$^{RA1}$ is independently optionally substituted C$_{1-6}$ alkyl. In certain embodiments, R$^{RA1}$ is unsubstituted C$_{1-6}$ alkyl. In certain embodiments, R$^{RA1}$ is methyl, ethyl, n-propyl, or iso-propyl. In certain embodiments, R$^{RA1}$ is substituted C$_{1-6}$ alkyl. In certain embodiments, R$^{RA1}$ is —CH$_2$Cl, —CHCl$_2$, —CHF$_2$, —CH$_2$F, or —CF$_3$. In certain embodiments, R$^{RA1}$ is optionally substituted C$_{3-6}$ carbocyclyl. In certain embodiments, R$^{RA1}$ is optionally substituted phenyl. In certain embodiments, R$^{RA1}$ is phenyl. In certain embodiments, R$^{RA1}$ is substituted phenyl. In certain embodiments, $R^{RA1}$ is o-CH$_3$-Ph, m-CH$_3$-Ph, p-CH$_3$-Ph, o-Cl-Ph, m-Cl-Ph, p-Cl-Ph, or o-Cl-m-CF$_3$-Ph. In certain embodiments, $R^{RA1}$ is optionally substituted five- or six-membered heterocyclyl. In certain embodiments, $R^{RA1}$ is optionally substituted five-membered heterocyclyl. In certain embodiments, $R^{RA1}$ is optionally substituted six-membered heterocyclyl. In certain embodiments, $R^{RA1}$ is optionally substituted five- or six-membered heteroaryl. In certain embodiments, $R^{RA1}$ is optionally substituted five-membered heteroaryl. In certain embodiments, $R^{RA1}$ is optionally substituted six-membered heteroaryl. In certain embodiments, $R^{RA1}$ is optionally substituted pyridine. In certain embodiments, $R^{RA1}$ is pyridine.

In certain embodiments, $R^{RA}$ is of the formula

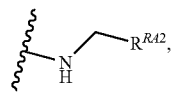

wherein each instance of $R^{RA2}$ is independently optionally substituted C$_{1-6}$ alkyl, optionally substituted C$_{3-6}$ carbocyclyl, optionally substituted phenyl, optionally substituted five- or six-membered heterocyclyl, or optionally substituted five- or six-membered heterocyclyl. In certain embodiments, $R^{RA2}$ is independently optionally substituted C$_{1-6}$ alkyl. In certain embodiments, $R^{RA2}$ is unsubstituted C$_{1-6}$ alkyl. In certain embodiments, $R^{RA2}$ is methyl, ethyl, n-propyl, or iso-propyl. In certain embodiments, $R^{RA2}$ is substituted C$_{1-6}$ alkyl. In certain embodiments, $R^{RA2}$ is —CH$_2$Cl, —CHCl$_2$, —CHF$_2$, —CH$_2$F, or —CF$_3$. In certain embodiments, $R^{RA2}$ is optionally substituted C$_{3-6}$ carbocyclyl. In certain embodiments, $R^{RA2}$ is optionally substituted phenyl. In certain embodiments, $R^{RA2}$ is phenyl. In certain embodiments, $R^{RA2}$ is substituted phenyl. In certain embodiments, $R^{RA2}$ is one the formulae: o-CH$_3$-Ph, m-CH$_3$-Ph, p-CH$_3$-Ph, o-Cl-Ph, m-Cl-Ph, or p-Cl-Ph.

In certain embodiments, $R^{RA}$ is hydrogen, or one of the following formulae: —CN, —Cl, —CF$_3$, —CH$_3$, -Ph, —OH, —OCH$_3$, —OPh, —NH$_2$, —NHAc, —NHSO$_2$CH$_3$,

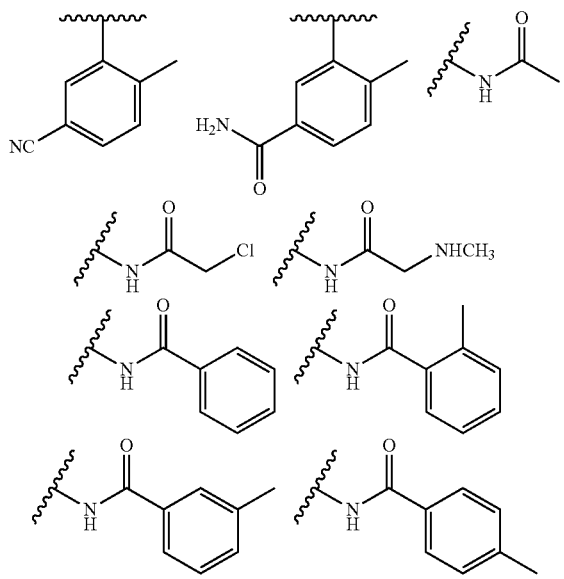

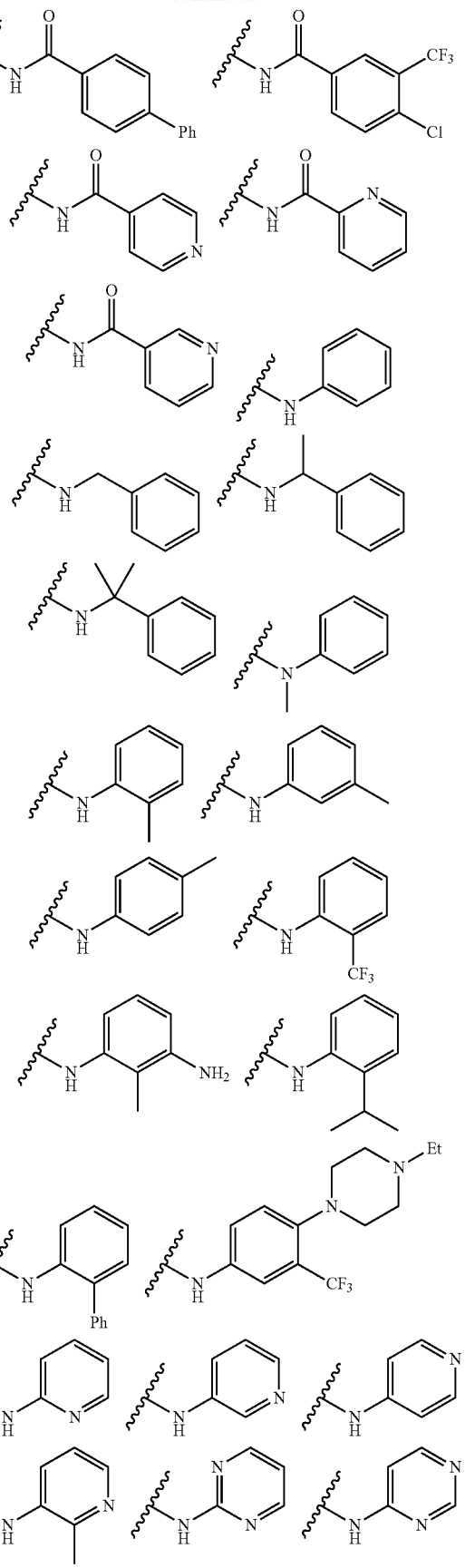

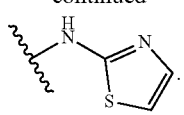

In certain embodiments, Ring A is optionally substituted five-membered heteroaryl with two heteroatoms selected from the group consisting of O, S, and N. In certain embodiments, Ring A is one of the following formulae:

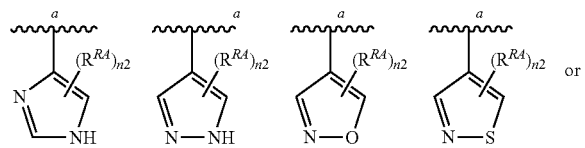

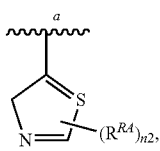

wherein $R^{RA}$ is as defined herein, a indicates the point of attachment to the alkyne; and each instance of n2 is independently an integer of 1 or 2. In certain embodiments, $R^{RA}$ is one of the following formulae:

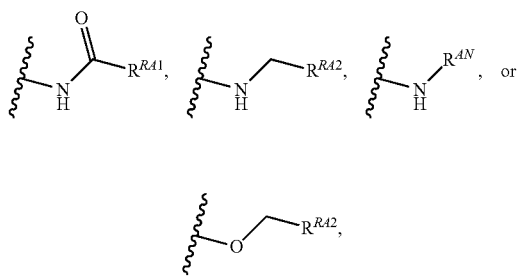

wherein $R^{RA1}$, $R^{RA2}$, and $R^{AN}$ are as defined herein.

In certain embodiments, n2 is 1. In certain embodiments, n2 is 2.

In certain embodiments, Ring A is of the formula:

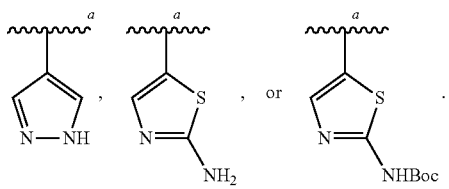

In certain embodiments, Ring A is optionally substituted six-membered heteroaryl with one or two N. In certain embodiments, Ring A is one of the following formulae:

wherein $R^{RA}$ is as defined herein, a indicates the point of attachment to the alkyne; and each instance of n3 is independently an integer of 1 to 4, inclusive. In certain embodiments, $R^{RA}$ is one of the following formulae:

wherein $R^{RA1}$, $R^{RA2}$, and $R^{AN}$ are as defined herein.

As generally used herein, each instance of n3 is independently an integer of 1 to 4, inclusive. In certain embodiments, n3 is 1. In certain embodiments, n3 is 2. In certain embodiments, n3 is 3. In certain embodiments, n3 is 4.

In certain embodiments of Ring A being an optionally substituted pyridine, $R^{RA}$ is one of the following formulae:
Hydrogen, -Ph, —OH, —NH$_2$, —OCH$_3$, —OPh, —Cl, —CF$_3$, —CH$_3$,

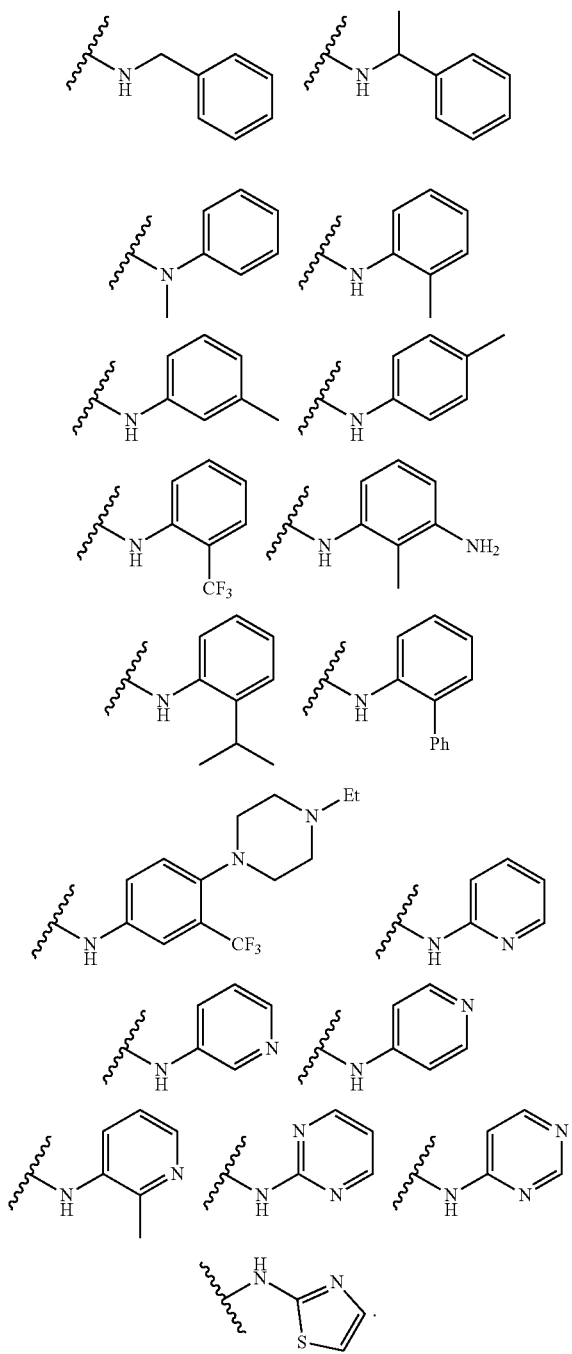

In certain embodiments, Ring A is optionally substituted 5,6-bicyclic heteroaryl with one, two, or three N. In certain embodiments, Ring A is one of the following formulae:

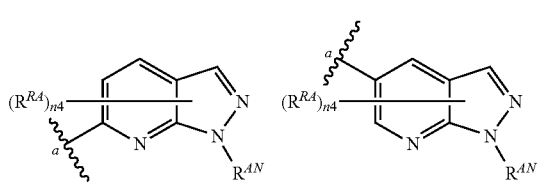

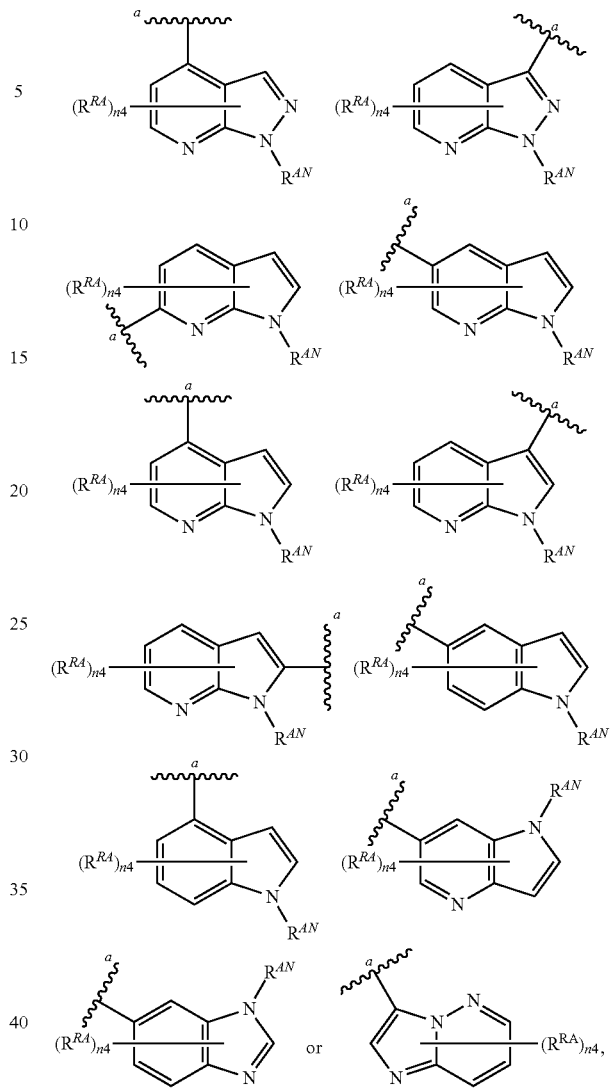

wherein $R^{RA}$ is as defined herein; a indicates the point of attachment to the alkyne; each instance of n4 is independently an integer of 1 to 5, inclusive. In certain embodiments, $R^{RA}$ is one of the following formulae:

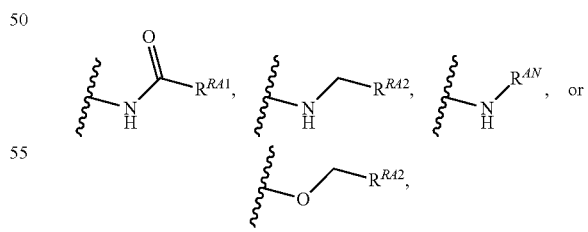

wherein $R^{RA1}$, $R^{RA2}$, and $R^{AN}$ are as defined herein.

As generally used herein, each instance of n4 is independently an integer of 1 to 4, inclusive. In certain embodiments, n4 is 1. In certain embodiments, n4 is 2. In certain embodiments, n4 is 3. In certain embodiments, n4 is 4. In certain embodiments, n4 is 5.

In certain embodiments, when Ring A is optionally substituted 5,6-bicyclic heteroaryl with one, two, or three N atoms, each instance of $R^{RA}$ is selected from the group consisting of —F, —CF$_3$, —CN, and —NHAc.

In certain embodiments, Ring A is one of the following formulae:

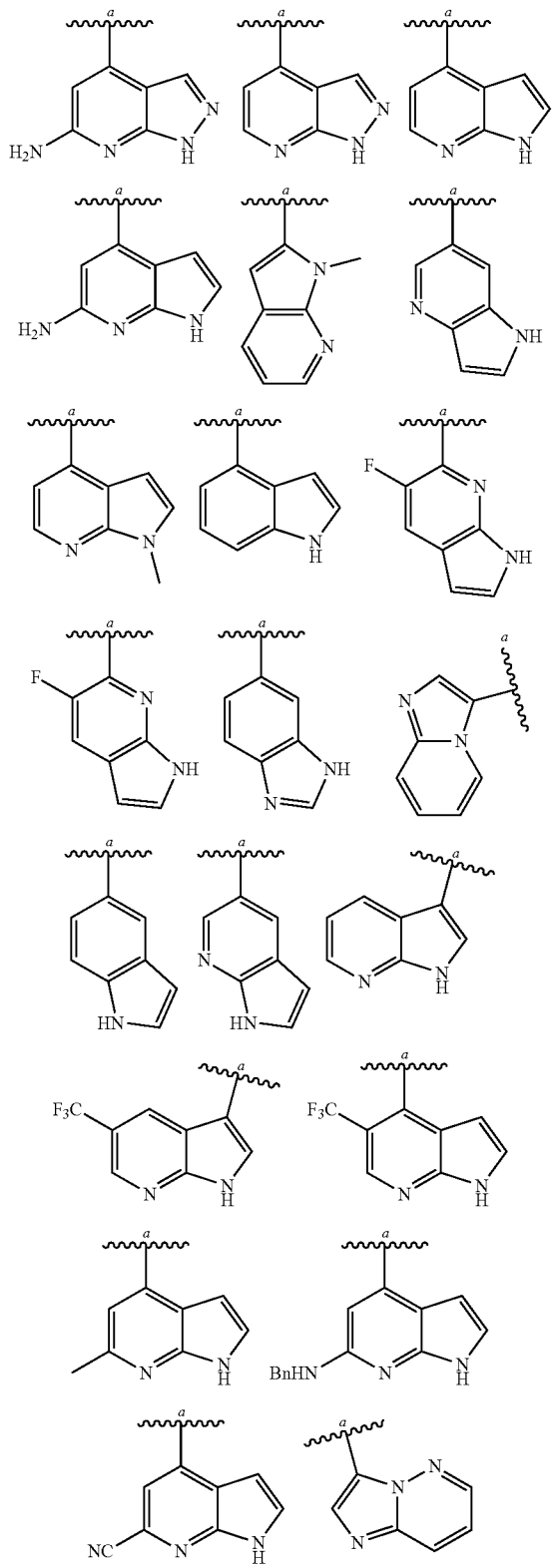

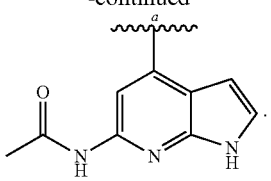

In some embodiments, a compound of the present invention is of one of the following formulae:

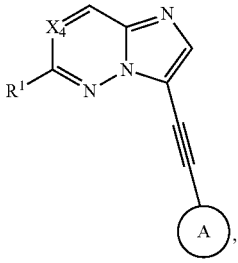

(I-a)

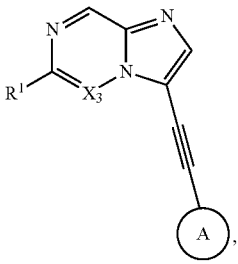

(I-b)

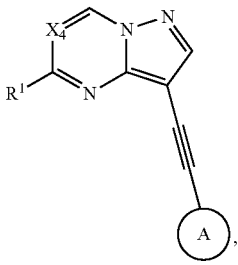

(I-c)

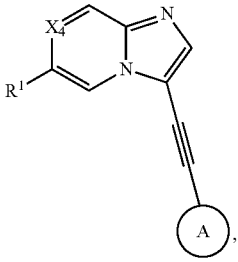

(I-d)

or a pharmaceutically acceptable salt thereof.

In certain embodiments, a provided compound is of one of the following formulae:

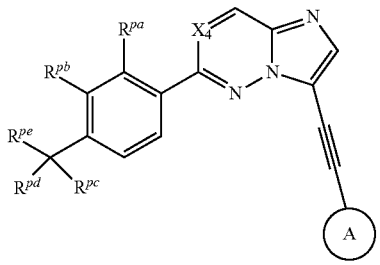
(I-i1)

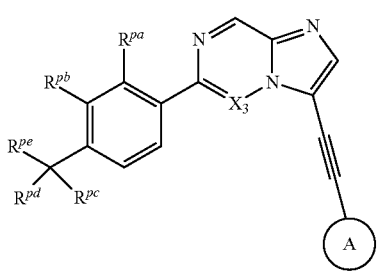
(I-i2)

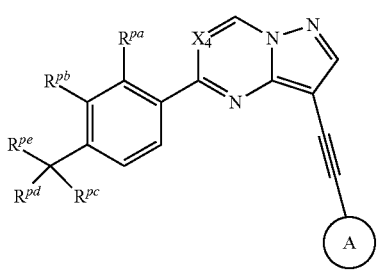
(I-i3)

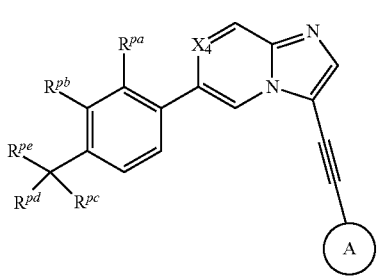
(I-i4)

or a pharmaceutically acceptable salt thereof, $R^{pa}$ is hydrogen, halogen, CN, optionally substituted $C_{1-6}$ alkyl, —$OR^A$, —$N(R^B)_2$, —NH—CO—$R^C$;

$R^C$ is optionally substituted $C_{1-6}$ alkyl;

$R^{pb}$ is independently hydrogen, halogen, CN, —$OR^A$, —$N(R^B)_2$, optionally substituted $C_{1-6}$ alkyl, optionally substituted $C_{3-6}$ carbocyclyl, optionally substituted aryl, optionally substituted heterocyclyl, or optionally substituted heteroaryl;

each of $R^{pc}$ and $R^{pd}$ is independently hydrogen, halogen, CN, —$OR^A$, or optionally substituted $C_{1-6}$ alkyl;

or $R^{pc}$ and $R^{pd}$ are joined to form =O; and $R^{pe}$ is optionally substituted six-membered heterocyclyl, —$OR^A$, or —$N(R^B)_2$; and each instance of $R^A$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, or an oxygen protecting group; and each instance of $R^B$ is independently hydrogen, optionally substituted $C_{1-6}$ alkyl, optionally substituted $C_{3-6}$ carbocyclyl, optionally substituted aryl, optionally substituted heterocyclyl, optionally substituted heteraryl, optionally substituted acyl, or a nitrogen protecting group.

In certain embodiments, a compound of the present invention is of Formula (II):

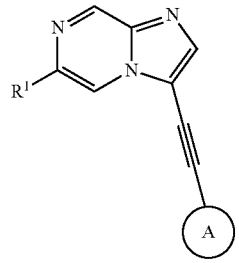
(II)

or a pharmaceutically acceptable salt thereof, wherein $R^1$ and Ring A are as defined herein.

In certain embodiments, a compound of the present invention is of Formula (III):

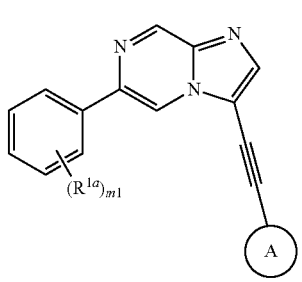
(III)

or a pharmaceutically acceptable salt thereof, wherein Ring A, $R^{1a}$ and m1 are as defined herein.

In certain embodiments, a compound of the present invention is of Formula (III-i):

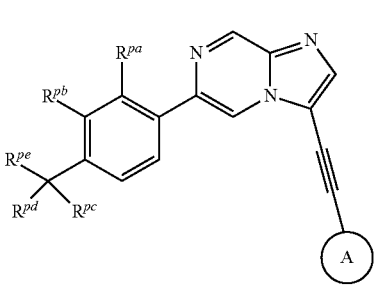
(III-i)

or a pharmaceutically acceptable salt thereof.

In certain embodiments, a compound of the present invention is of Formula (III-a):

(III-a)

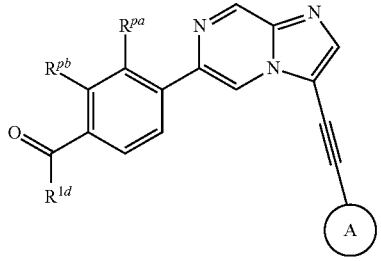

or a pharmaceutically acceptable salt thereof, wherein Ring A and $R^{1d}$ are as define herein.

In certain embodiments, a compound of the present invention is of Formula (III-b):

(III-b)

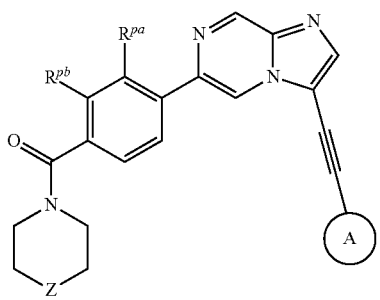

or a pharmaceutically acceptable salt thereof, wherein Z is —O— or —$NR^{NZ}$—; and each instance of $R^{NZ}$ is independently hydrogen, optionally substituted $C_{1-6}$ alkyl, or a nitrogen protecting group; and Ring A is as defined herein. In certain embodiments, Z is —O—. In certain embodiments, Z is —$NR^{NZ}$—; and each instance of $R^{NZ}$ is independently hydrogen, optionally substituted $C_{1-6}$ alkyl, or a nitrogen protecting group. In certain embodiments, Z is —NH—, —$NCH_3$—, or —$NC_2H_5$—.

In certain embodiments, a compound of the present invention is of Formula (IV):

(IV)

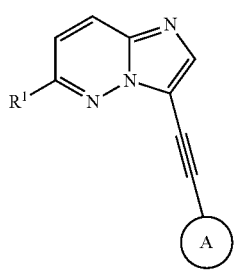

or a pharmaceutically acceptable salt thereof, wherein Ring A and $R^1$ are as defined herein.

In certain embodiments, a compound of the present invention is of Formula (V):

(V)

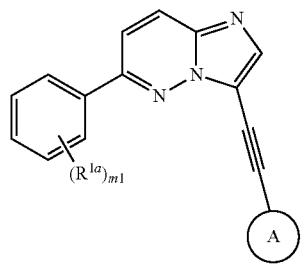

or a pharmaceutically acceptable salt thereof, wherein Ring A, $R^{1a}$ and m1 are as defined herein.

In certain embodiments, a compound of the present invention is of Formula (V-i):

(V-i)

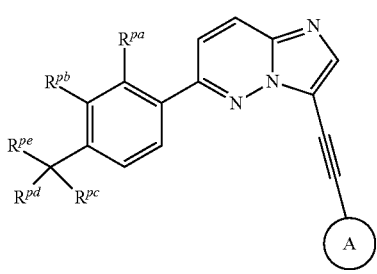

or a pharmaceutically acceptable salt thereof.

In certain embodiments, a compound of the present invention is of Formula (V-a):

(V-a)

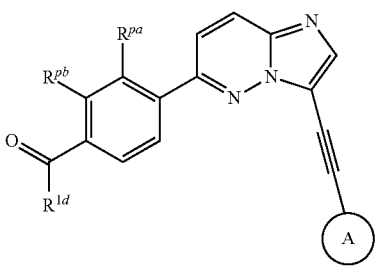

or a pharmaceutically acceptable salt thereof, wherein Ring A and $R^{1d}$ are as defined herein.

In certain embodiments, a compound of the present invention is of Formula (V-b):

(V-b)

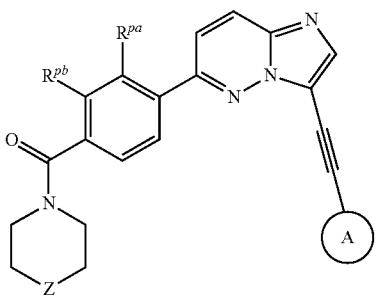

or a pharmaceutically acceptable salt thereof, wherein Ring A is as defined herein; and Z is —O— or —$NR^{NZ}$—; each instance of $R^{NZ}$ is independently hydrogen, optionally substituted $C_{1-6}$ alkyl, or a nitrogen protecting group. In certain embodiments, Z is —O—. In certain embodiments, Z is —$NR^{NZ}$—; and each instance of $R^{NZ}$ is independently hydrogen, optionally substituted $C_{1-6}$ alkyl, or a nitrogen protecting group. In certain embodiments, Z is —NH—, —NCH$_3$—, or —NC$_2$H$_5$—.

In certain embodiments, a compound of the present invention is of Formula (VI):

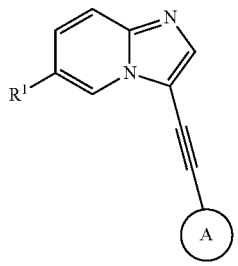

(VI)

or a pharmaceutically acceptable salt thereof.

In certain embodiments, a compound of the present invention is of Formula (VII):

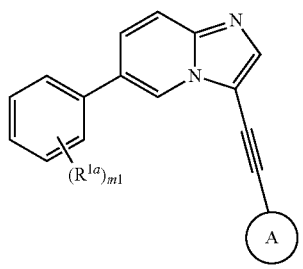

(VII)

or a pharmaceutically acceptable salt thereof, wherein $R^{1a}$, m1; and Ring A are as defined herein.

In certain embodiments, a compound of the present invention is of Formula (VII-i):

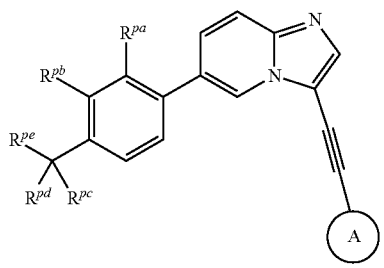

(VII-i)

or a pharmaceutically acceptable salt thereof.

In certain embodiments, a compound of the present invention is of Formula (VII-a):

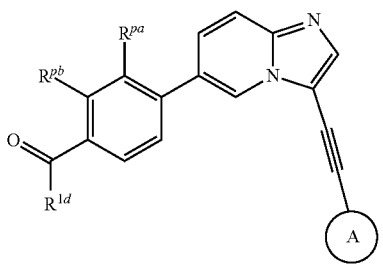

(VII-a)

or a pharmaceutically acceptable salt thereof, wherein $R^{1d}$ and Ring A are as defined herein.

In certain embodiments, a compound of the present invention is of Formula (VII-b):

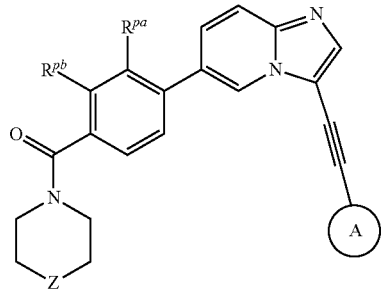

(VII-b)

or a pharmaceutically acceptable salt thereof, wherein Ring A is as defined herein; Z is —O— or —NR$^{NZ}$—; and R$^{NZ}$ is hydrogen, optionally substituted $C_{1-6}$ alkyl, or a nitrogen protecting group. In certain embodiments, Z is —O—. In certain embodiments, Z is —NR$^{NZ}$—; and R$^{NZ}$ is hydrogen, optionally substituted $C_{1-6}$ alkyl, or a nitrogen protecting group. In certain embodiments, Z is —NH—, —NCH$_3$—, or —NC$_2$H$_5$—.

In certain embodiments, a compound of the present invention is of Formula (VIII):

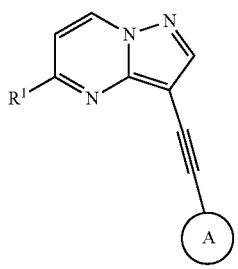

(VIII)

or a pharmaceutically acceptable salt thereof.

In certain embodiments, a compound of the present invention is of Formula (IX):

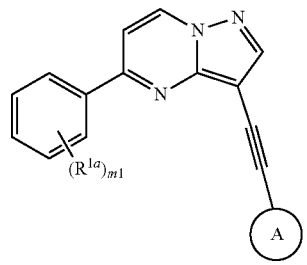

(IX)

or a pharmaceutically acceptable salt thereof, wherein $R^{1a}$, m1, and Ring A are as defined herein.

In certain embodiments, a compound of the present invention is of Formula (IX-i):

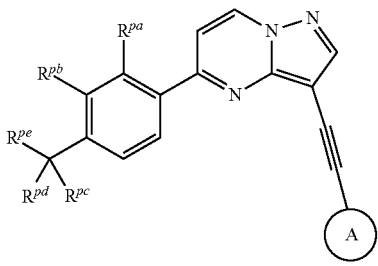

(IX-i)

or a pharmaceutically acceptable salt thereof.

In certain embodiments, a compound of the present invention is of Formula (IX-a):

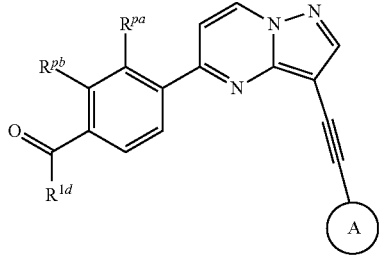

(IX-a)

or a pharmaceutically acceptable salt thereof, wherein $R^{1d}$ and Ring A are as defined herein.

In certain embodiments, a compound of the present invention is of Formula (IX-b):

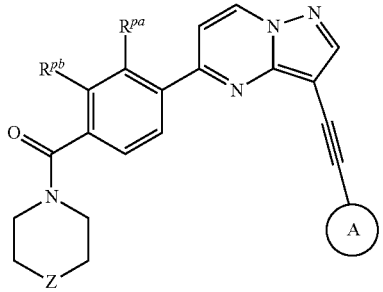

(IX-b)

or a pharmaceutically acceptable salt thereof, wherein Ring A is as defined herein; Z is —O— or —NR$^{NZ}$—; and R$^{NZ}$ is hydrogen, optionally substituted $C_{1-6}$ alkyl, or a nitrogen protecting group. In certain embodiments, Z is —O—. In certain embodiments, Z is —NR$^{NZ}$—; and R$^{NZ}$ is hydrogen, optionally substituted $C_{1-6}$ alkyl, or a nitrogen protecting group. In certain embodiments, Z is —NH—, —NCH$_3$—, or —NC$_2$H$_5$—.

As used in any one of Formulae (I)-(IX), in certain embodiments, R$^{pa}$ is hydrogen. In certain embodiments, R$^{pa}$ is halogen. In certain embodiments, R$^{pa}$ is F. In certain embodiments, R$^{pa}$ is Cl. In certain embodiments, R$^{pa}$ is optionally substituted $C_{1-6}$ alkyl. In certain embodiments, R$^{pa}$ is unsubstituted $C_{1-6}$ alkyl (e.g. methyl). In certain embodiments, R$^{pa}$ is —OR$^A$ and R$^A$ is optionally substituted $C_{1-6}$ alkyl. In certain embodiments, R$^{pa}$ is —N(R$^B$)$_2$ and each instance of R$^B$ is independently hydrogen or optionally substituted $C_{1-6}$ alkyl. In certain embodiments, R$^{pa}$ is —NH$_2$. In certain embodiments, R$^{pa}$ is —NHR$^B$ and R$^B$ is optionally substituted $C_{1-6}$ alkyl. In certain embodiments, R$^{pa}$ is —N(R$^B$)$_2$ and each instance of R$^B$ is independently optionally substituted $C_{1-6}$ alkyl. In certain embodiments, R$^{pa}$ is NH—CO—R$^C$ and R$^C$ is optionally substituted $C_{1-6}$ alkyl.

As used in any one of Formulae (I)-(IX), in certain embodiments, R$^{pb}$ is hydrogen. In certain embodiments, R$^{pb}$ is halogen. In certain embodiments, R$^{pb}$ is F. In certain embodiments, R$^{pb}$ is Cl. In certain embodiments, R$^{pb}$ is optionally substituted $C_{1-6}$ alkyl. In certain embodiments, R$^{pb}$ is unsubstituted $C_{1-6}$ alkyl (e.g. methyl). In certain embodiments, R$^{pb}$ is —OR$^A$ and R$^A$ is optionally substituted $C_{1-6}$ alkyl. In certain embodiments, R$^{pb}$ is —N(R$^B$)$_2$ and each instance of R$^B$ is independently hydrogen or optionally substituted $C_{1-6}$ alkyl. In certain embodiments, R$^{pb}$ is —NH$_2$. In certain embodiments, R$^{pb}$ is —NHR$^B$ and R$^B$ is optionally substituted $C_{1-6}$ alkyl. In certain embodiments, R$^{pb}$ is —N(R$^B$)$_2$ and each instance of R$^B$ is independently optionally substituted $C_{1-6}$ alkyl. In certain embodiments, R$^{pb}$ is optionally substituted $C_{3-6}$ carbocyclyl, optionally substituted aryl, optionally substituted heterocyclyl, or optionally substituted heteroaryl. In certain embodiments, R$^{pb}$ is optionally substituted five- or six-membered carbocyclyl, optionally substituted five- or six-membered aryl, optionally substituted five- or six-membered heterocyclyl, or optionally substituted five- or six-membered heteroaryl.

As used in any one of Formulae (I)-(IX), in certain embodiments, R$^{pc}$ is hydrogen. In certain embodiments, R$^{pd}$ is hydrogen. In certain embodiments, R$^{pc}$ and R$^{pd}$ are hydrogen. In certain embodiments, R$^{pc}$ and R$^{pd}$ are joined to form =O.

As used in any one of Formulae (I)-(IX), in certain embodiments, R$^{pe}$ is optionally substituted six-membered heterocyclyl. In certain embodiments, R$^{pe}$ is —OR$^A$, and and R$^A$ is optionally substituted $C_{1-6}$ alkyl. In certain embodiments, R$^{pe}$ is —N(R$^B$)$_2$ and each instance of R$^B$ is independently hydrogen or optionally substituted $C_{1-6}$ alkyl. In certain embodiments, R$^{pe}$ is —NH$_2$. In certain embodiments, R$^{pe}$ is —NHR$^B$ and R$^B$ is optionally substituted $C_{1-6}$ alkyl. In certain embodiments, R$^{pe}$ is —N(R$^B$)$_2$ and each instance of R$^B$ is independently optionally substituted $C_{1-6}$ alkyl.

In some embodiments, a provided compound is one of the compounds in Table 1.

TABLE 1

Exemplary compounds

| Structure | Example # |
|---|---|
| 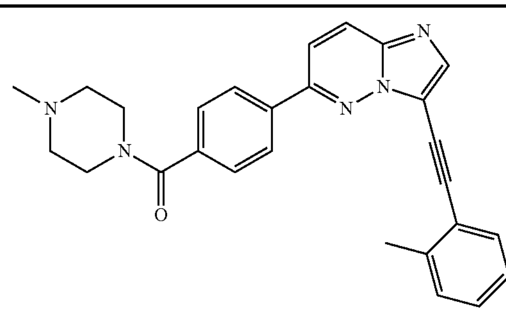 | 1 |

TABLE 1-continued

Exemplary compounds

| Structure | Example # |
|---|---|
| 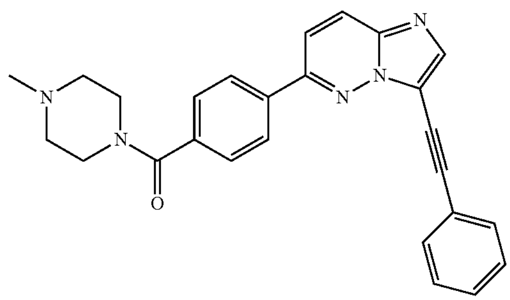 [SMILES: CN1CCN(C(=O)c2ccc(-c3ccc4ncc(C#Cc5ccccc5)n4n3)cc2)CC1] | 2 |
| 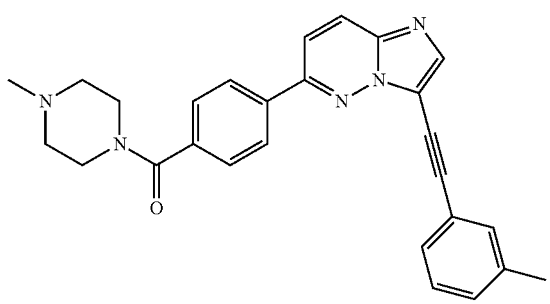 | 3 |
| 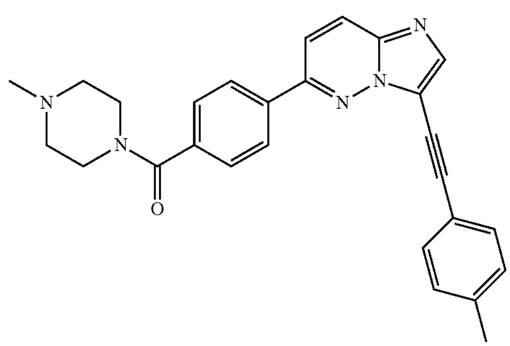 [SMILES: Cc1ccc(C#Cc2cnc3ccc(-c4ccc(C(=O)N5CCN(C)CC5)cc4)nn23)cc1] | 4 |
| 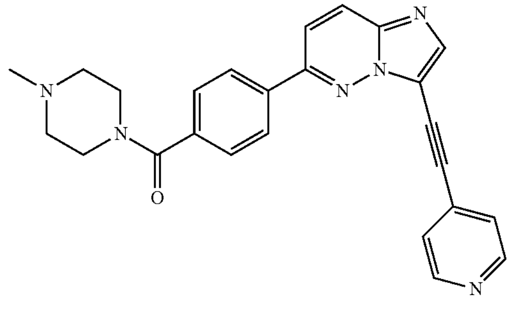 [SMILES: CN1CCN(C(=O)c2ccc(-c3ccc4ncc(C#Cc5ccncc5)n4n3)cc2)CC1] | 5 |

TABLE 1-continued

Exemplary compounds

| Structure | Example # |
|---|---|
| 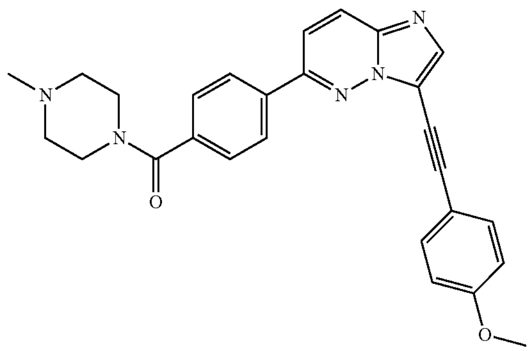 | 6 |
| 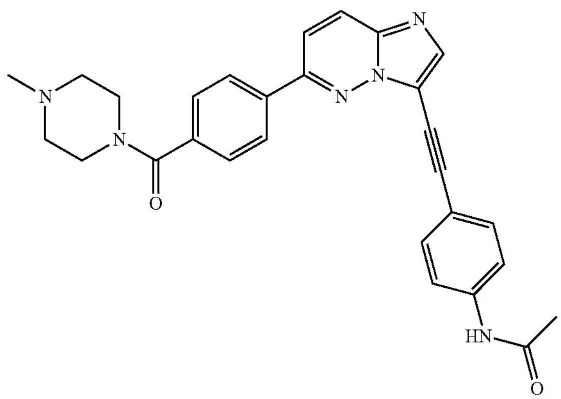 [SMILES: CC(=O)Nc1ccc(C#Cc2cnc3ccc(-c4ccc(C(=O)N5CCN(C)CC5)cc4)nn23)cc1] | 7 |
| 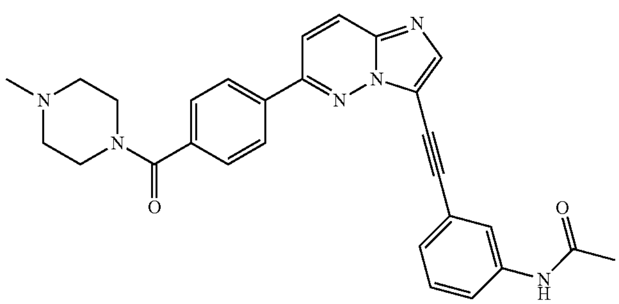 [SMILES: CC(=O)Nc1cccc(C#Cc2cnc3ccc(-c4ccc(C(=O)N5CCN(C)CC5)cc4)nn23)c1] | 8 |
| 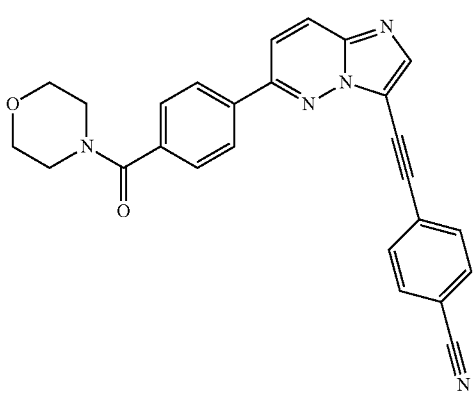 [SMILES: N#Cc1ccc(C#Cc2cnc3ccc(-c4ccc(C(=O)N5CCOCC5)cc4)nn23)cc1] | 9 |

TABLE 1-continued

Exemplary compounds

| Structure | Example # |
|---|---|
| 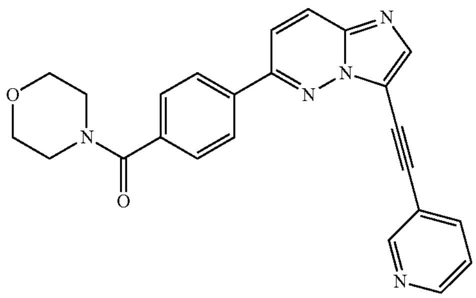 [SMILES: O=C(c1ccc(-c2ccc3ncc(C#Cc4cccnc4)n3n2)cc1)N1CCOCC1] | 10 |
| 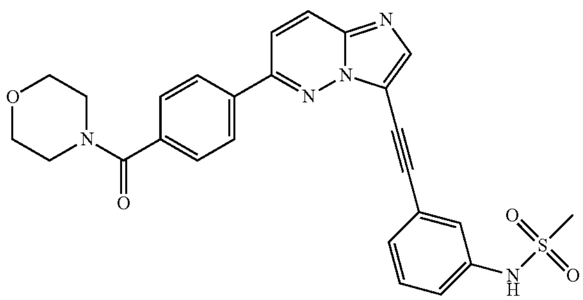 [SMILES: CS(=O)(=O)Nc1cccc(C#Cc2cnc3ccc(-c4ccc(C(=O)N5CCOCC5)cc4)nn23)c1] | 11 |
| 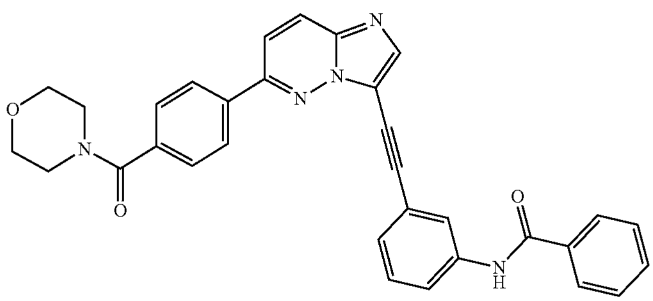 [SMILES: O=C(Nc1cccc(C#Cc2cnc3ccc(-c4ccc(C(=O)N5CCOCC5)cc4)nn23)c1)c1ccccc1] | 12 |
| 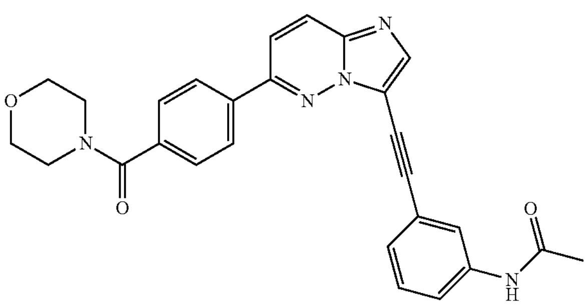 [SMILES: CC(=O)Nc1cccc(C#Cc2cnc3ccc(-c4ccc(C(=O)N5CCOCC5)cc4)nn23)c1] | 13 |
| 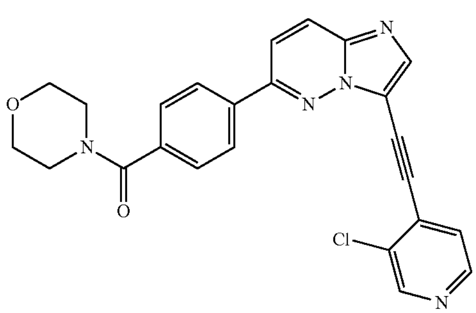 [SMILES: O=C(c1ccc(-c2ccc3ncc(C#Cc4ccncc4Cl)n3n2)cc1)N1CCOCC1] | 14 |

TABLE 1-continued
| Exemplary compounds | |
|---|---|
| Structure | Example # |
| 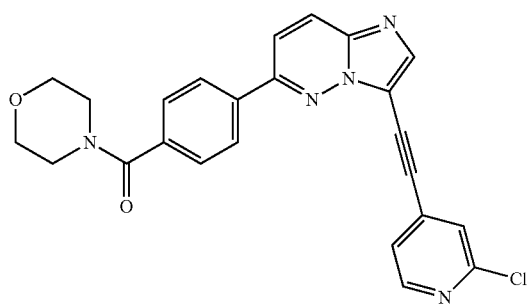 [SMILES: O=C(c1ccc(-c2ccc3ncc(C#Cc4ccnc(Cl)c4)n3n2)cc1)N1CCOCC1] | 15 |
| 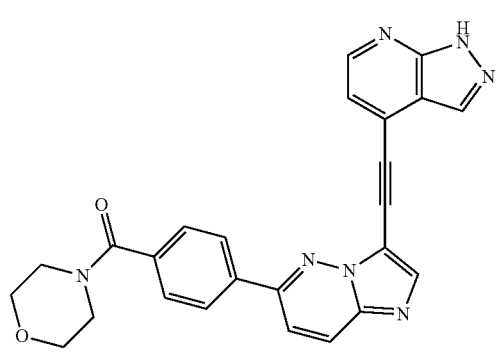 [SMILES: O=C(c1ccc(-c2ccc3ncc(C#Cc4ccnc5[nH]ncc45)n3n2)cc1)N1CCOCC1] | 16 |
| 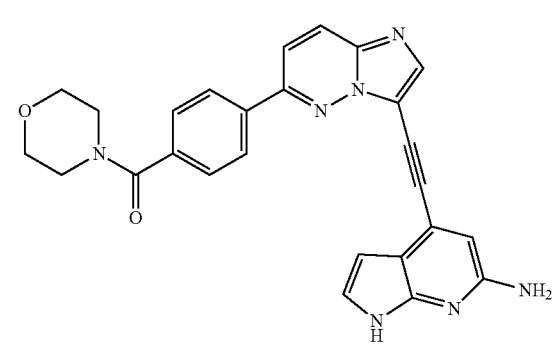 [SMILES: Nc1cc(C#Cc2cnc3ccc(-c4ccc(C(=O)N5CCOCC5)cc4)nn23)c2cc[nH]c2n1] | 17 |
| 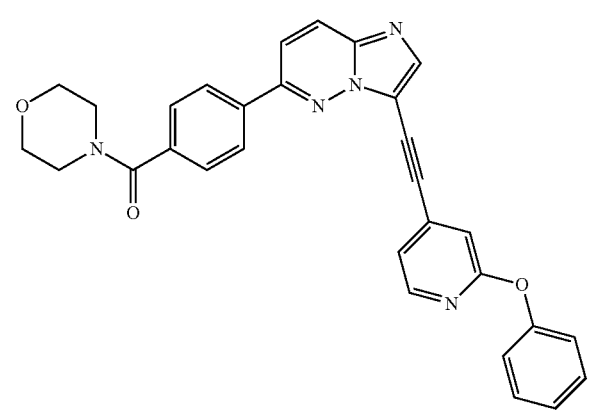 [SMILES: O=C(c1ccc(-c2ccc3ncc(C#Cc4ccnc(Oc5ccccc5)c4)n3n2)cc1)N1CCOCC1] | 18 |

TABLE 1-continued
Exemplary compounds
| Structure | Example # |
|---|---|
| 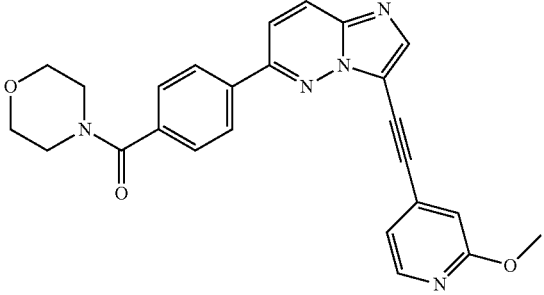 [SMILES: COc1cc(C#Cc2cnc3ccc(-c4ccc(C(=O)N5CCOCC5)cc4)nn23)ccn1] | 19 |
| 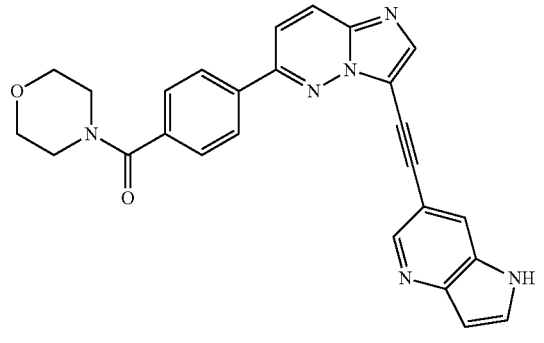 [SMILES: O=C(c1ccc(-c2ccc3ncc(C#Cc4cnc5cc[nH]c5c4)n3n2)cc1)N1CCOCC1] | 20 |
| 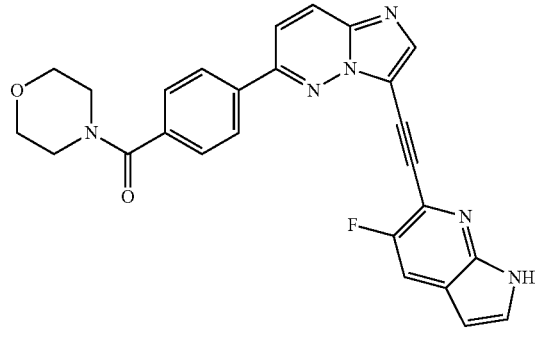 [SMILES: O=C(c1ccc(-c2ccc3ncc(C#Cc4nc5[nH]ccc5cc4F)n3n2)cc1)N1CCOCC1] | 21 |
| 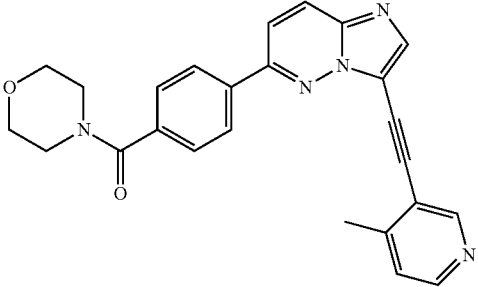 [SMILES: Cc1ccncc1C#Cc1cnc2ccc(-c3ccc(C(=O)N4CCOCC4)cc3)nn12] | 22 |

TABLE 1-continued
Exemplary compounds
| Structure | Example # |
|---|---|
| 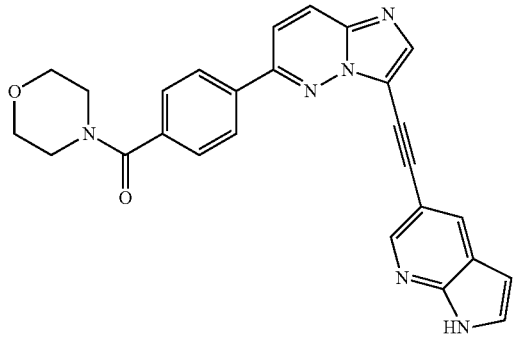 [SMILES: O=C(c1ccc(-c2ccc3ncc(C#Cc4cnc5[nH]ccc5c4)n3n2)cc1)N1CCOCC1] | 23 |
| 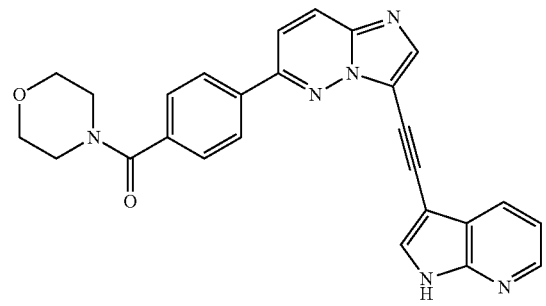 [SMILES: O=C(c1ccc(-c2ccc3ncc(C#Cc4c[nH]c5ncccc45)n3n2)cc1)N1CCOCC1] | 24 |
| 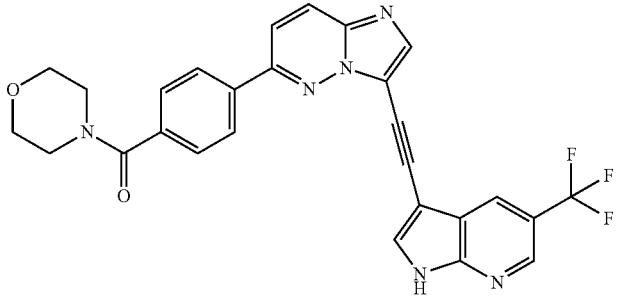 [SMILES: O=C(c1ccc(-c2ccc3ncc(C#Cc4c[nH]c5ncc(C(F)(F)F)cc45)n3n2)cc1)N1CCOCC1] | 25 |
| 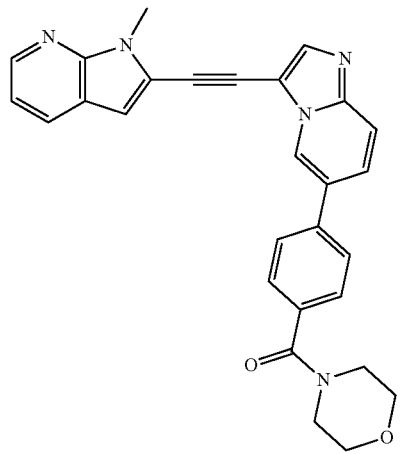 [SMILES: Cn1c(C#Cc2cnc3ccc(-c4ccc(C(=O)N5CCOCC5)cc4)cn23)cc2cccnc21] | 26 |

TABLE 1-continued
Exemplary compounds
| Structure | Example # |
|---|---|
| 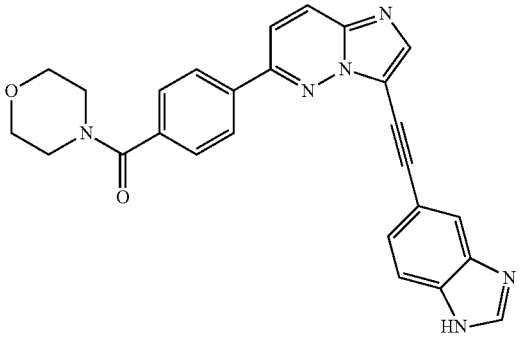 [SMILES: O=C(c1ccc(-c2ccc3ncc(C#Cc4ccc5[nH]cnc5c4)n3n2)cc1)N1CCOCC1] | 27 |
| 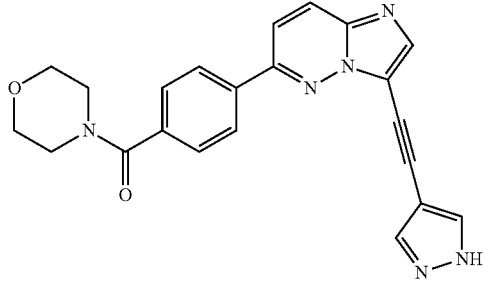 [SMILES: O=C(c1ccc(-c2ccc3ncc(C#Cc4cn[nH]c4)n3n2)cc1)N1CCOCC1] | 28 |
| 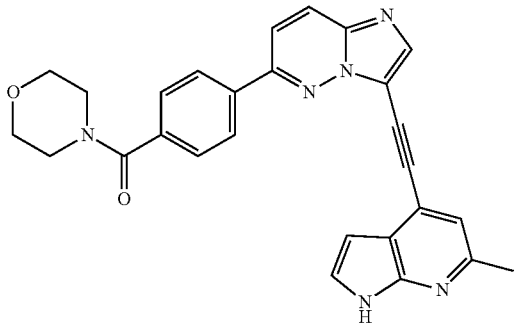 [SMILES: Cc1cc(C#Cc2cnc3ccc(-c4ccc(C(=O)N5CCOCC5)cc4)nn23)c2cc[nH]c2n1] | 29 |
| 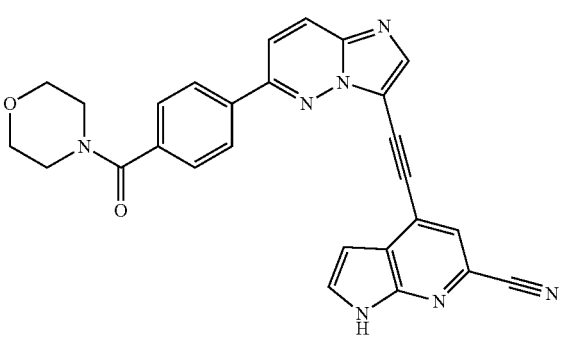 [SMILES: N#Cc1cc(C#Cc2cnc3ccc(-c4ccc(C(=O)N5CCOCC5)cc4)nn23)c2cc[nH]c2n1] | 30 |

TABLE 1-continued

Exemplary compounds

| Structure | Example # |
|---|---|
| 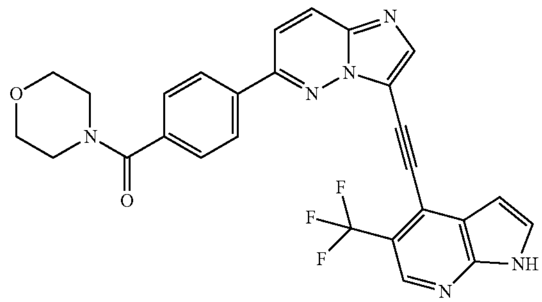 [SMILES: O=C(c1ccc(-c2ccc3ncc(C#Cc4c(C(F)(F)F)cnc5[nH]ccc45)n3n2)cc1)N1CCOCC1] | 31 |
| 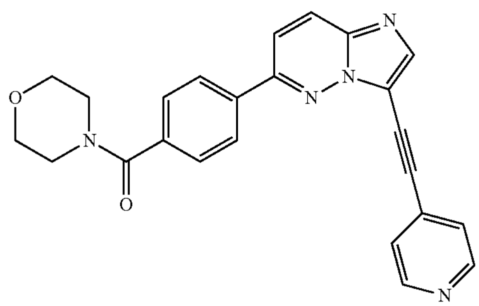 [SMILES: O=C(c1ccc(-c2ccc3ncc(C#Cc4ccncc4)n3n2)cc1)N1CCOCC1] | 32 |
| 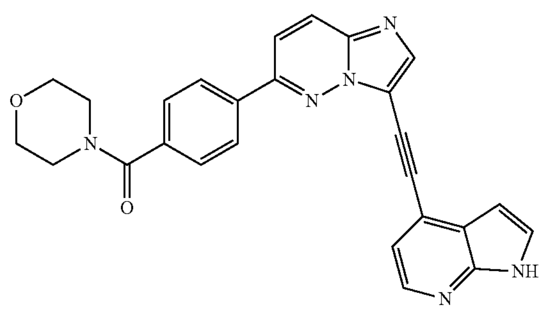 [SMILES: O=C(c1ccc(-c2ccc3ncc(C#Cc4ccnc5[nH]ccc45)n3n2)cc1)N1CCOCC1] | 33 |
| 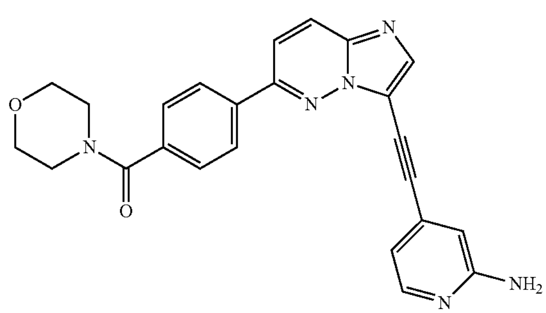 [SMILES: Nc1cc(C#Cc2cnc3ccc(-c4ccc(C(=O)N5CCOCC5)cc4)nn23)ccn1] | 34 |

TABLE 1-continued
Exemplary compounds
| Structure | Example # |
|---|---|
| 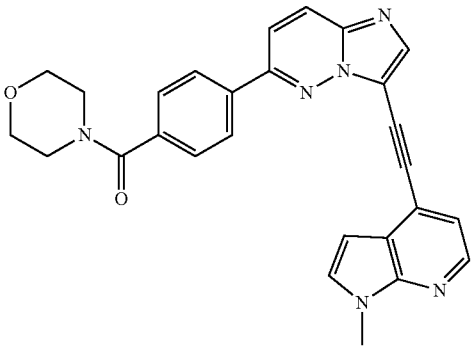 [SMILES: Cn1ccc2c(C#Cc3cnc4ccc(-c5ccc(C(=O)N6CCOCC6)cc5)nn34)ccnc21] | 35 |
| 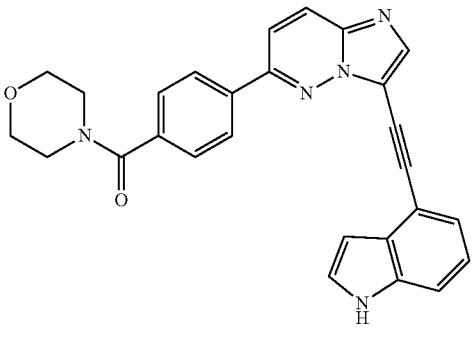 [SMILES: O=C(c1ccc(-c2ccc3ncc(C#Cc4cccc5[nH]ccc45)n3n2)cc1)N1CCOCC1] | 36 |
| 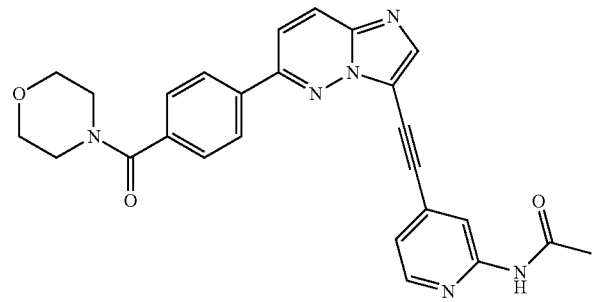 [SMILES: CC(=O)Nc1cc(C#Cc2cnc3ccc(-c4ccc(C(=O)N5CCOCC5)cc4)nn23)ccn1] | 37 |
| 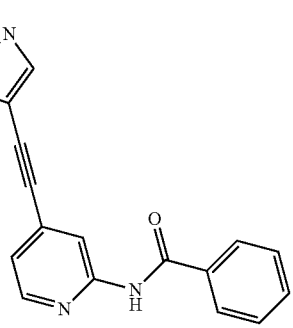 | 38 |

TABLE 1-continued
| Exemplary compounds | |
|---|---|
| Structure | Example # |
| 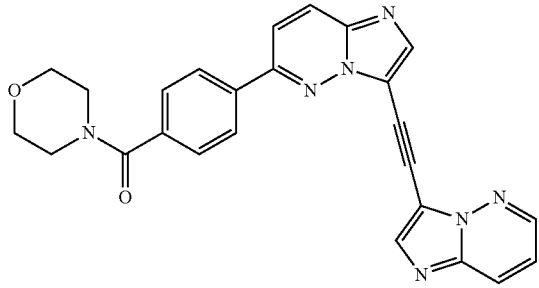 [SMILES: O=C(c1ccc(-c2ccc3ncc(C#Cc4cnc5cccnn45)n3n2)cc1)N1CCOCC1] | 39 |
| 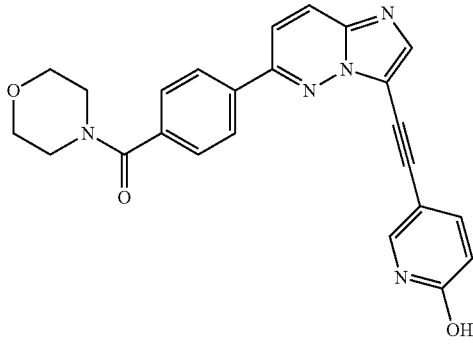 [SMILES: O=C(c1ccc(-c2ccc3ncc(C#Cc4ccc(O)nc4)n3n2)cc1)N1CCOCC1] | 40 |
| 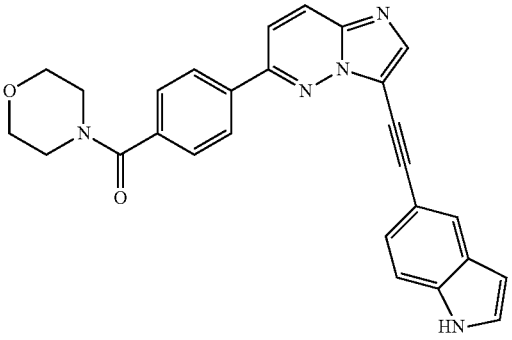 | 41 |
| 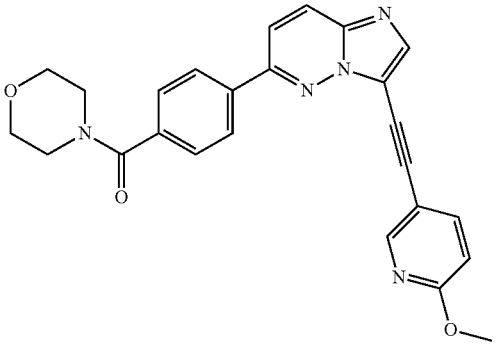 [SMILES: COc1ccc(C#Cc2cnc3ccc(-c4ccc(C(=O)N5CCOCC5)cc4)nn23)cn1] | 42 |

TABLE 1-continued

Exemplary compounds

| Structure | Example # |
|---|---|
| 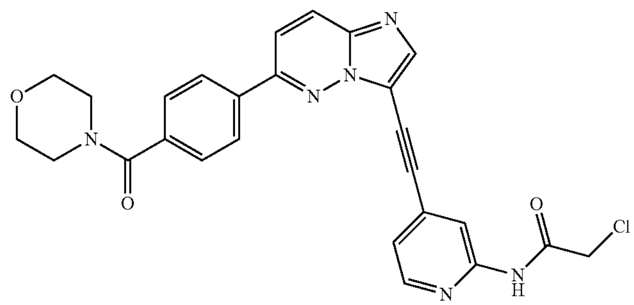 [SMILES: O=C(CCl)Nc1cc(C#Cc2cnc3ccc(-c4ccc(C(=O)N5CCOCC5)cc4)nn23)ccn1] | 43 |
| 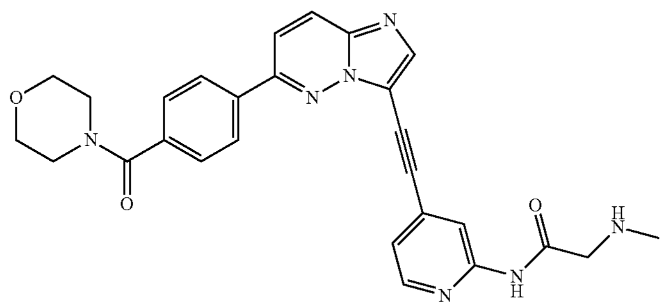 [SMILES: CNCC(=O)Nc1cc(C#Cc2cnc3ccc(-c4ccc(C(=O)N5CCOCC5)cc4)nn23)ccn1] | 44 |
| 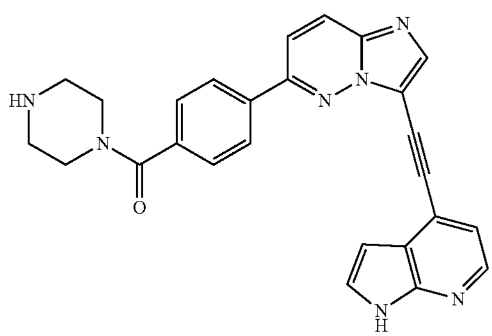 [SMILES: O=C(c1ccc(-c2ccc3ncc(C#Cc4ccnc5[nH]ccc45)n3n2)cc1)N1CCNCC1] | 45 |
| 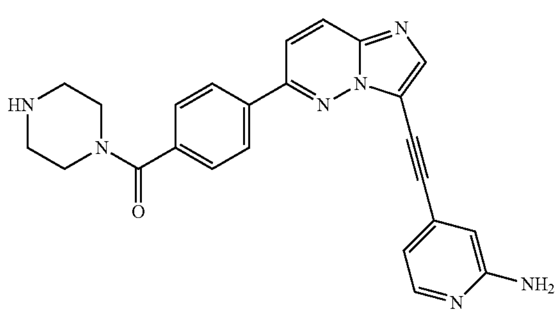 [SMILES: Nc1cc(C#Cc2cnc3ccc(-c4ccc(C(=O)N5CCNCC5)cc4)nn23)ccn1] | 46 |

TABLE 1-continued
Exemplary compounds
| Structure | Example # |
|---|---|
| 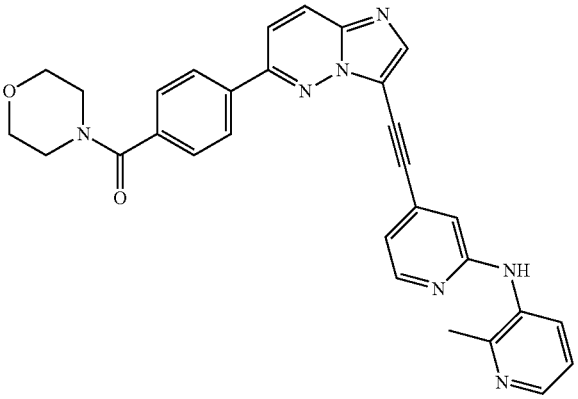 [SMILES: Cc1ncccc1Nc1cc(C#Cc2cnc3ccc(-c4ccc(C(=O)N5CCOCC5)cc4)nn23)ccn1] | 47 |
| 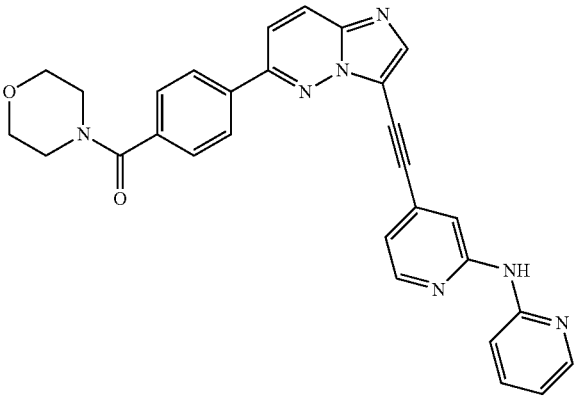 [SMILES: O=C(c1ccc(-c2ccc3ncc(C#Cc4ccnc(Nc5ccccn5)c4)n3n2)cc1)N1CCOCC1] | 48 |
| 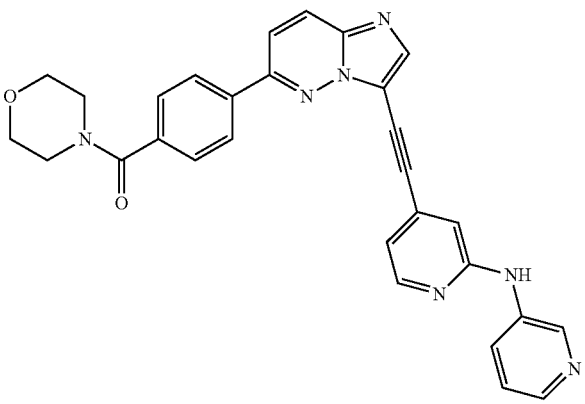 [SMILES: O=C(c1ccc(-c2ccc3ncc(C#Cc4ccnc(Nc5cccnc5)c4)n3n2)cc1)N1CCOCC1] | 49 |

TABLE 1-continued
Exemplary compounds
| Structure | Example # |
|---|---|
| 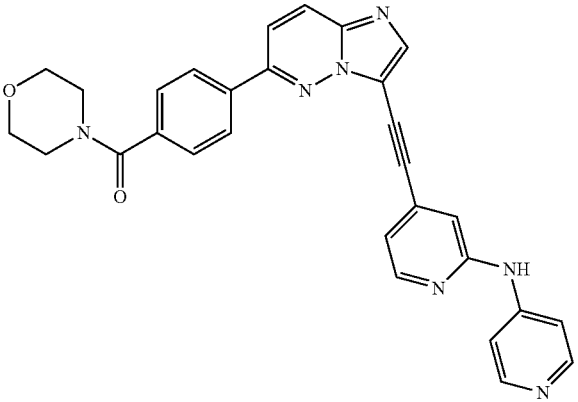 [SMILES: O=C(c1ccc(-c2ccc3ncc(C#Cc4ccnc(Nc5ccncc5)c4)n3n2)cc1)N1CCOCC1] | 50 |
| 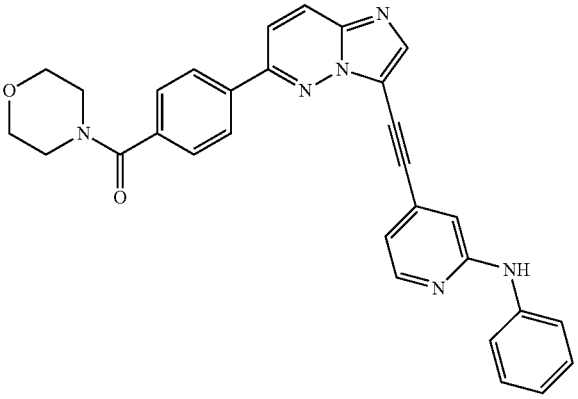 | 51 |
| 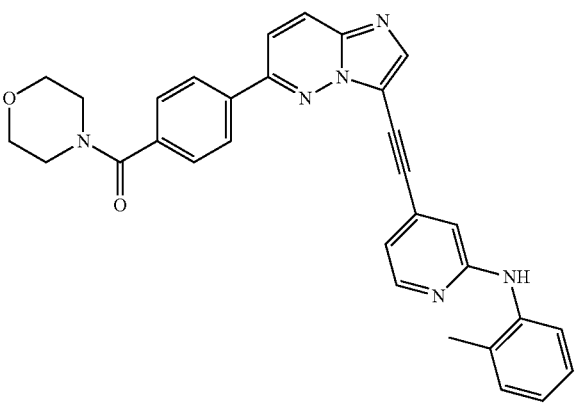 [SMILES: Cc1ccccc1Nc1cc(C#Cc2cnc3ccc(-c4ccc(C(=O)N5CCOCC5)cc4)nn23)ccn1] | 52 |

TABLE 1-continued
Exemplary compounds
| Structure | Example # |
|---|---|
| 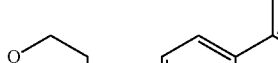 | 53 |
| 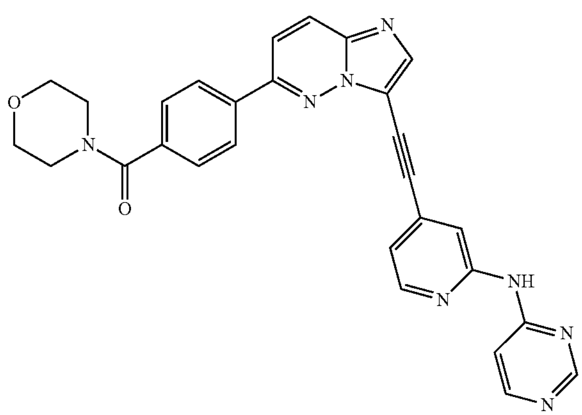 [SMILES: O=C(c1ccc(-c2ccc3ncc(C#Cc4ccnc(Nc5ccncn5)c4)n3n2)cc1)N1CCOCC1] | 54 |
| 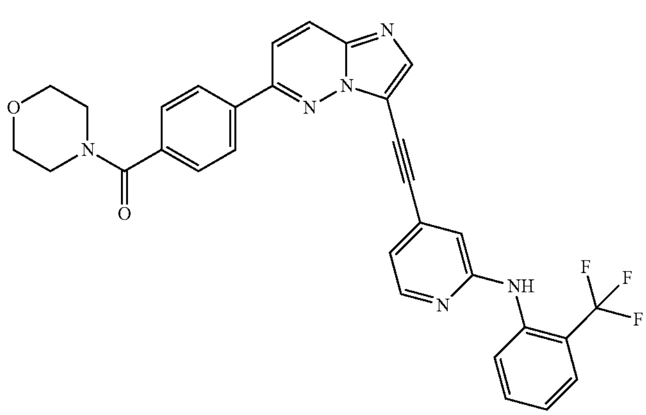 [SMILES: O=C(c1ccc(-c2ccc3ncc(C#Cc4ccnc(Nc5ccccc5C(F)(F)F)c4)n3n2)cc1)N1CCOCC1] | 55 |

TABLE 1-continued
Exemplary compounds
| Structure | Example # |
|---|---|
| 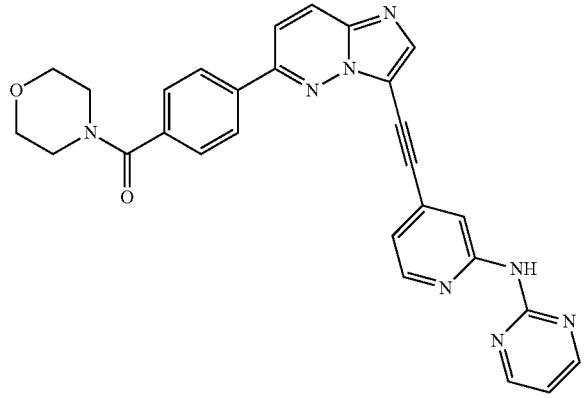 [SMILES: O=C(c1ccc(-c2ccc3ncc(C#Cc4ccnc(Nc5ncccn5)c4)n3n2)cc1)N1CCOCC1] | 56 |
| 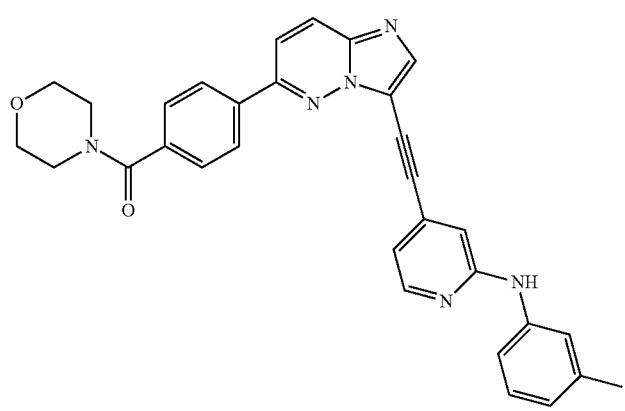 [SMILES: Cc1cccc(Nc2cc(C#Cc3cnc4ccc(-c5ccc(C(=O)N6CCOCC6)cc5)nn34)ccn2)c1] | 57 |
| 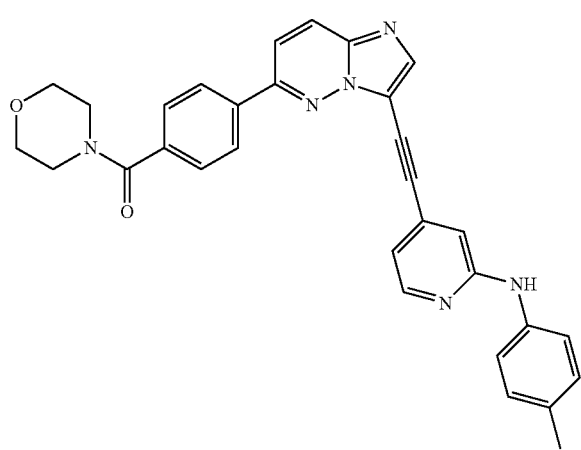 [SMILES: Cc1ccc(Nc2cc(C#Cc3cnc4ccc(-c5ccc(C(=O)N6CCOCC6)cc5)nn34)ccn2)cc1] | 58 |

TABLE 1-continued

Exemplary compounds

| Structure | Example # |
|---|---|
| 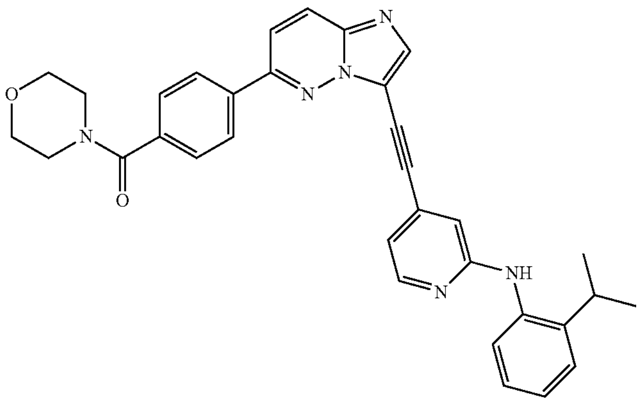 [SMILES: CC(C)c1ccccc1Nc1cc(C#Cc2cnc3ccc(-c4ccc(C(=O)N5CCOCC5)cc4)nn23)ccn1] | 59 |
| 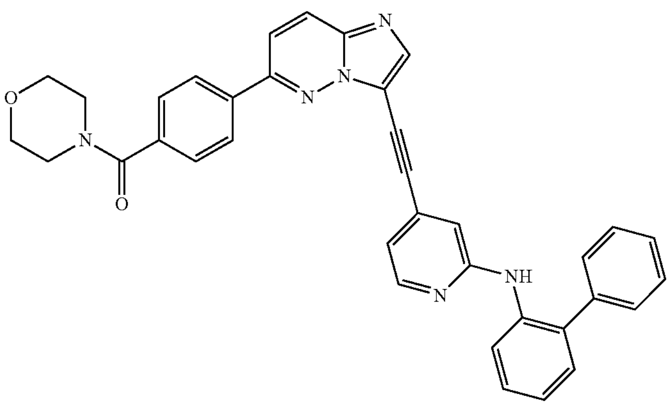 [SMILES: O=C(c1ccc(-c2ccc3ncc(C#Cc4ccnc(Nc5ccccc5-c5ccccc5)c4)n3n2)cc1)N1CCOCC1] | 60 |
| 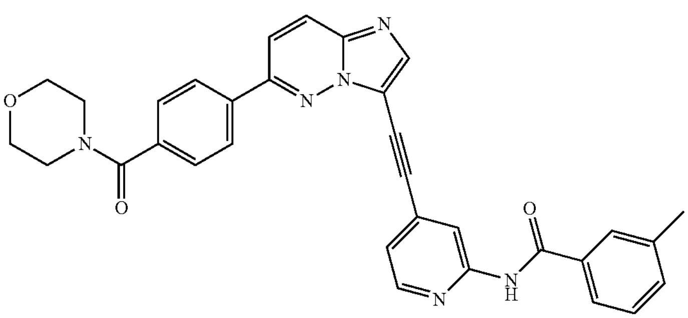 [SMILES: Cc1cccc(C(=O)Nc2cc(C#Cc3cnc4ccc(-c5ccc(C(=O)N6CCOCC6)cc5)nn34)ccn2)c1] | 61 |
| 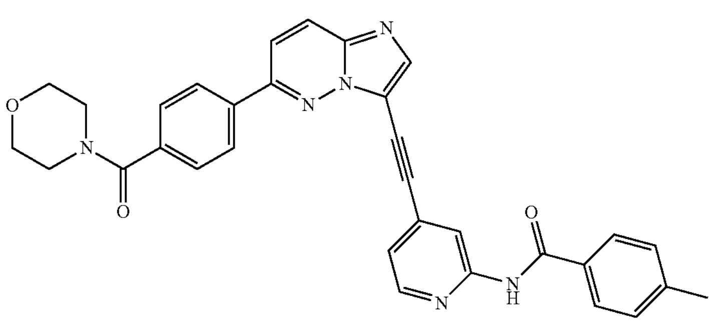 [SMILES: Cc1ccc(C(=O)Nc2cc(C#Cc3cnc4ccc(-c5ccc(C(=O)N6CCOCC6)cc5)nn34)ccn2)cc1] | 62 |

TABLE 1-continued

Exemplary compounds

| Structure | Example # |
|---|---|
| 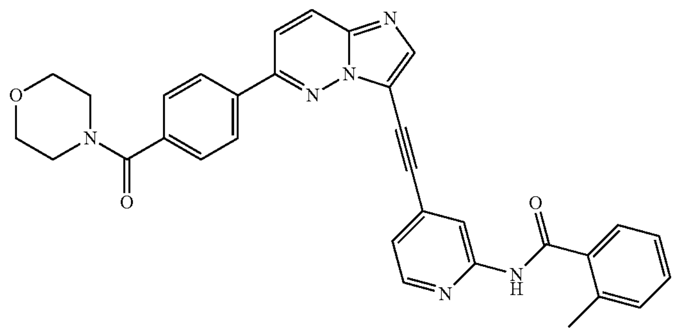 [SMILES: Cc1ccccc1C(=O)Nc1cc(C#Cc2cnc3ccc(-c4ccc(C(=O)N5CCOCC5)cc4)nn23)ccn1] | 63 |
| 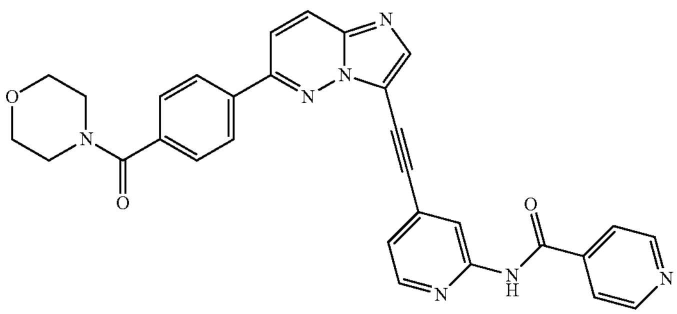 [SMILES: O=C(Nc1cc(C#Cc2cnc3ccc(-c4ccc(C(=O)N5CCOCC5)cc4)nn23)ccn1)c1ccncc1] | 64 |
| 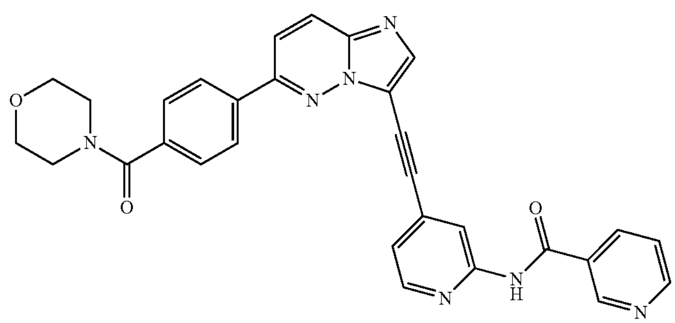 [SMILES: O=C(Nc1cc(C#Cc2cnc3ccc(-c4ccc(C(=O)N5CCOCC5)cc4)nn23)ccn1)c1cccnc1] | 65 |
| 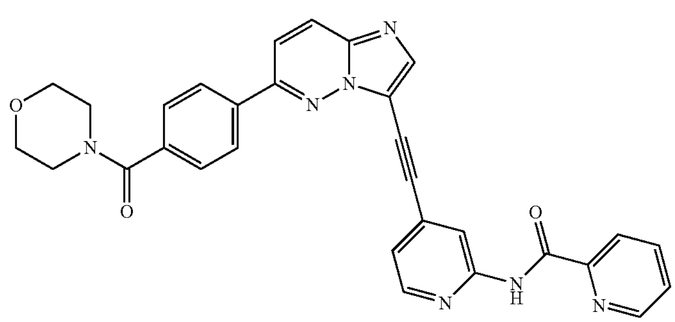 [SMILES: O=C(Nc1cc(C#Cc2cnc3ccc(-c4ccc(C(=O)N5CCOCC5)cc4)nn23)ccn1)c1ccccn1] | 66 |

TABLE 1-continued

Exemplary compounds

| Structure | Example # |
|---|---|
| 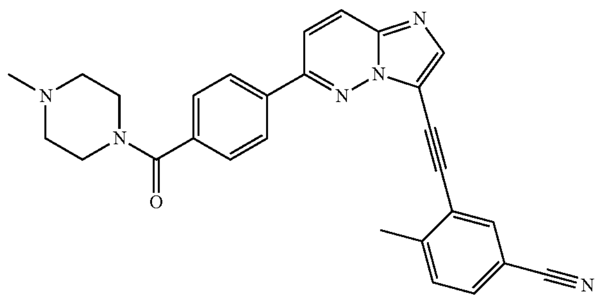 [SMILES: Cc1ccc(C#N)cc1C#Cc1cnc2ccc(-c3ccc(C(=O)N4CCN(C)CC4)cc3)nn12] | 67 |
| 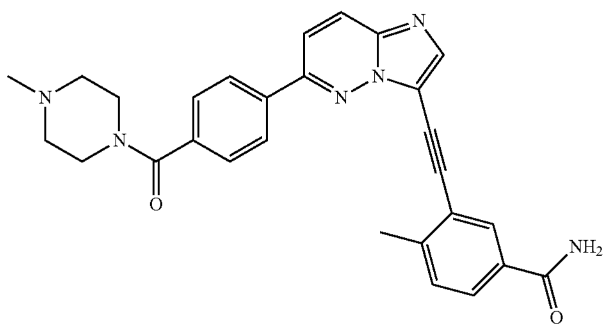 [SMILES: Cc1ccc(C(N)=O)cc1C#Cc1cnc2ccc(-c3ccc(C(=O)N4CCN(C)CC4)cc3)nn12] | 68 |
| 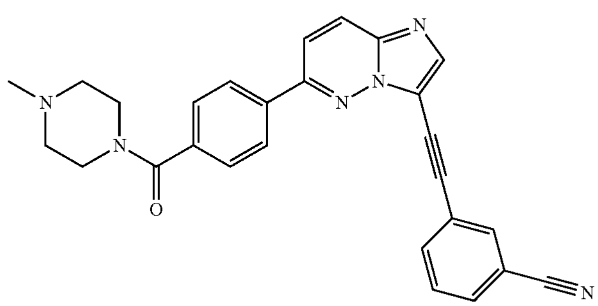 [SMILES: CN1CCN(C(=O)c2ccc(-c3ccc4ncc(C#Cc5cccc(C#N)c5)n4n3)cc2)CC1] | 69 |
| 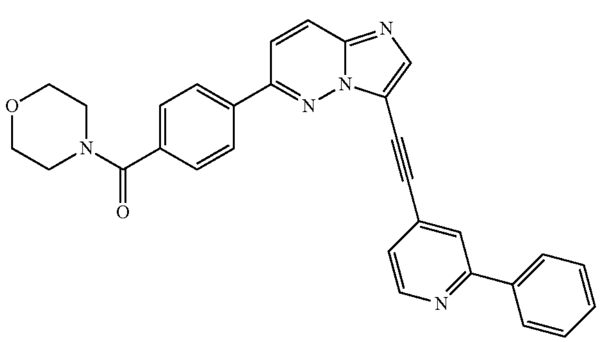 [SMILES: O=C(c1ccc(-c2ccc3ncc(C#Cc4ccnc(-c5ccccc5)c4)n3n2)cc1)N1CCOCC1] | 70 |

TABLE 1-continued
Exemplary compounds
| Structure | Example # |
|---|---|
| 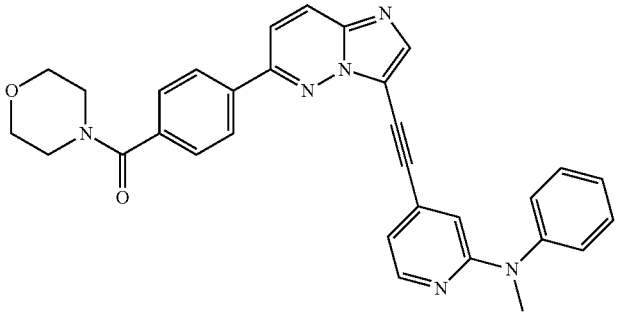 [SMILES: CN(c1ccccc1)c1cc(C#Cc2cnc3ccc(-c4ccc(C(=O)N5CCOCC5)cc4)nn23)ccn1] | 71 |
| 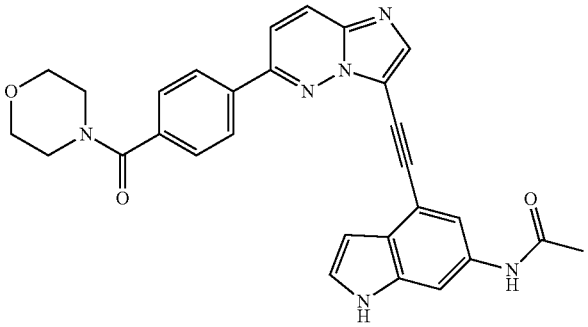 [SMILES: CC(=O)Nc1cc(C#Cc2cnc3ccc(-c4ccc(C(=O)N5CCOCC5)cc4)nn23)c2cc[nH]c2c1] | 72 |
| 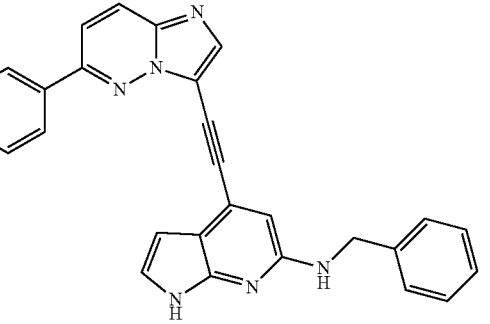 | 73 |
| 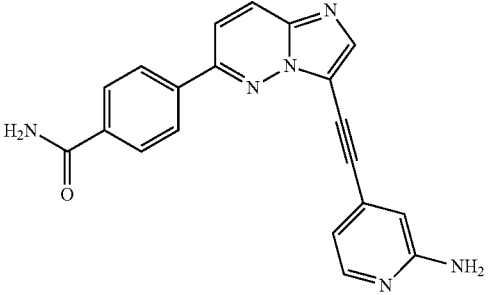 [SMILES: NC(=O)c1ccc(-c2ccc3ncc(C#Cc4ccnc(N)c4)n3n2)cc1] | 74 |

TABLE 1-continued
Exemplary compounds
| Structure | Example # |
|---|---|
| 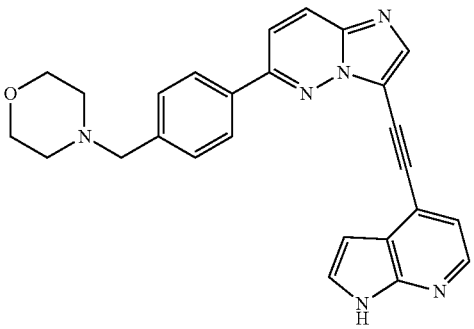 [SMILES: C(#Cc1cnc2ccc(-c3ccc(CN4CCOCC4)cc3)nn12)c1ccnc2[nH]ccc12] | 75 |
| 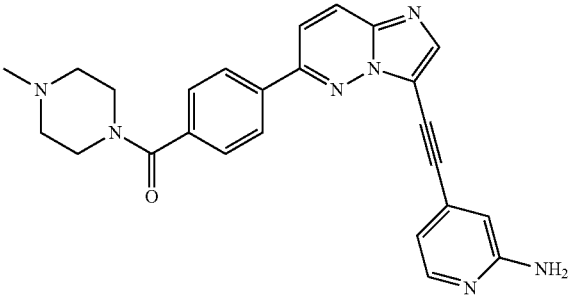 [SMILES: CN1CCN(C(=O)c2ccc(-c3ccc4ncc(C#Cc5ccnc(N)c5)n4n3)cc2)CC1] | 76 |
| 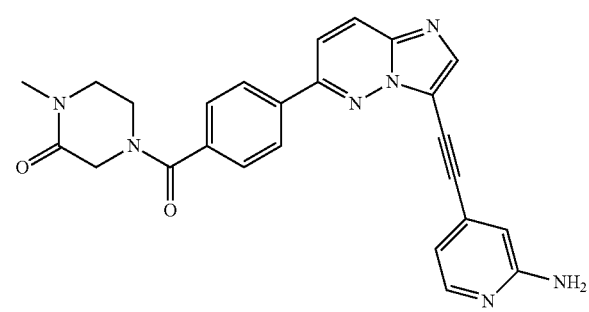 [SMILES: CN1CCN(C(=O)c2ccc(-c3ccc4ncc(C#Cc5ccnc(N)c5)n4n3)cc2)CC1=O] | 77 |
| 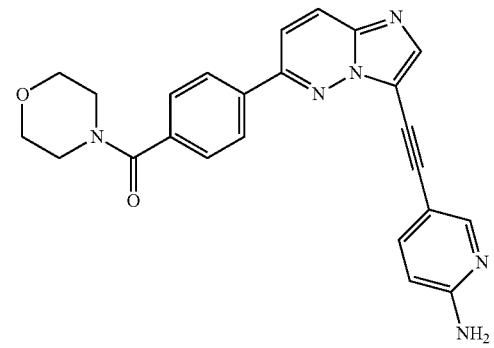 [SMILES: Nc1ccc(C#Cc2cnc3ccc(-c4ccc(C(=O)N5CCOCC5)cc4)nn23)cn1] | 78 |

TABLE 1-continued

Exemplary compounds

| Structure | Example # |
|---|---|
| 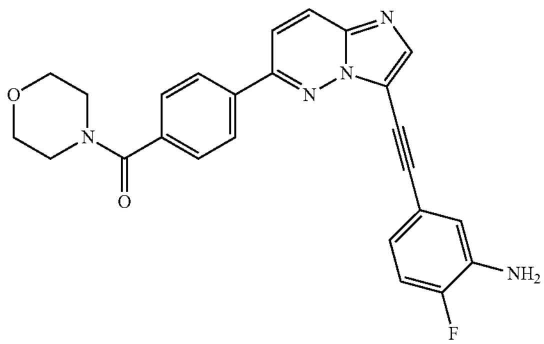 [SMILES: Nc1cc(C#Cc2cnc3ccc(-c4ccc(C(=O)N5CCOCC5)cc4)nn23)ccc1F] | 79 |
| 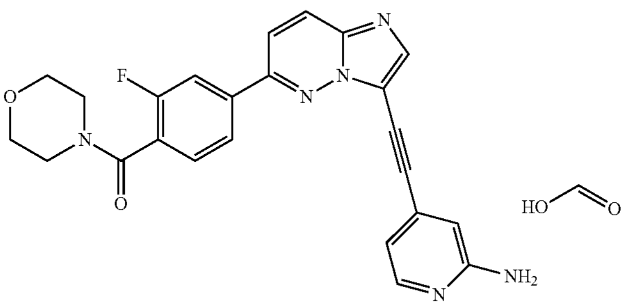 [SMILES: Nc1cc(C#Cc2cnc3ccc(-c4ccc(C(=O)N5CCOCC5)c(F)c4)nn23)ccn1 ; O=CO] | 80 |
| 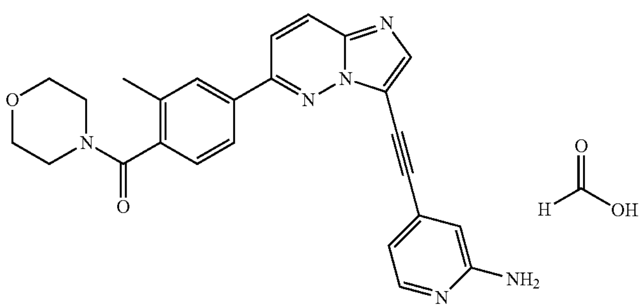 [SMILES: Cc1cc(-c2ccc3ncc(C#Cc4ccnc(N)c4)n3n2)ccc1C(=O)N1CCOCC1 ; O=CO] | 81 |
| 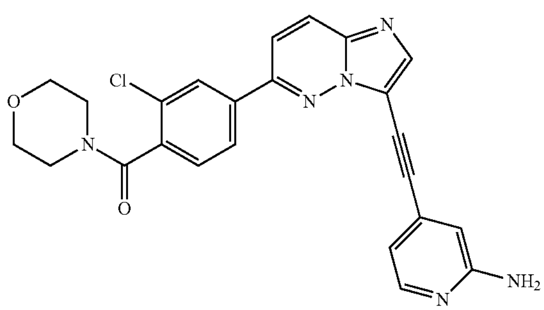 [SMILES: Nc1cc(C#Cc2cnc3ccc(-c4ccc(C(=O)N5CCOCC5)c(Cl)c4)nn23)ccn1] | 82 |
| 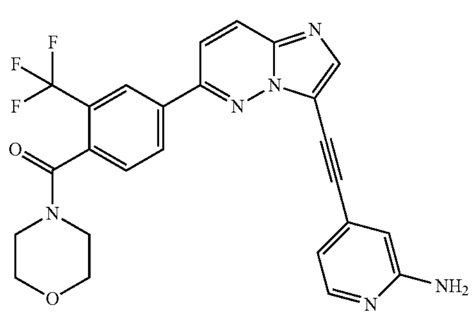 [SMILES: Nc1cc(C#Cc2cnc3ccc(-c4ccc(C(=O)N5CCOCC5)c(C(F)(F)F)c4)nn23)ccn1] | 83 |

TABLE 1-continued

Exemplary compounds

| Structure | Example # |
|---|---|
| 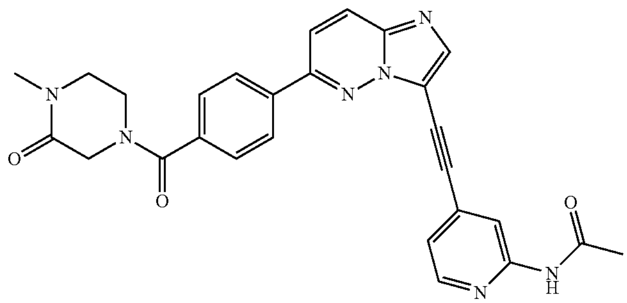 [SMILES: CC(=O)Nc1cc(C#Cc2cnc3ccc(-c4ccc(C(=O)N5CCN(C)C(=O)C5)cc4)nn23)ccn1] | 84 |
| 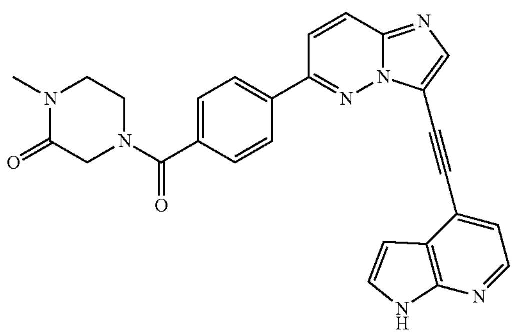 [SMILES: CN1CCN(C(=O)c2ccc(-c3ccc4ncc(C#Cc5ccnc6[nH]ccc56)n4n3)cc2)CC1=O] | 85 |
| 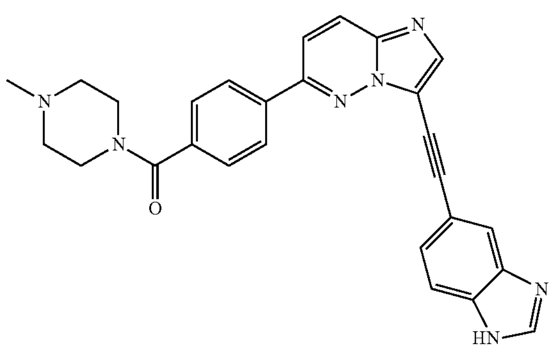 [SMILES: CN1CCN(C(=O)c2ccc(-c3ccc4ncc(C#Cc5ccc6[nH]cnc6c5)n4n3)cc2)CC1] | 86 |
| 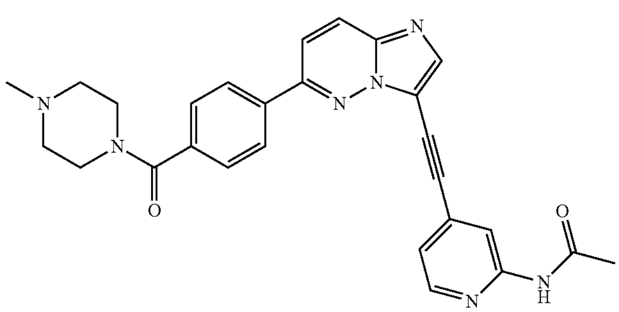 [SMILES: CC(=O)Nc1cc(C#Cc2cnc3ccc(-c4ccc(C(=O)N5CCN(C)CC5)cc4)nn23)ccn1] | 87 |

TABLE 1-continued

Exemplary compounds

| Structure | Example # |
|---|---|
| (structure) | 88 |
| (structure) | 89 |
| (structure) | 90 |
| (structure) | 91 |
| (structure) | 92 |

TABLE 1-continued

Exemplary compounds

| Structure | Example # |
|---|---|
| 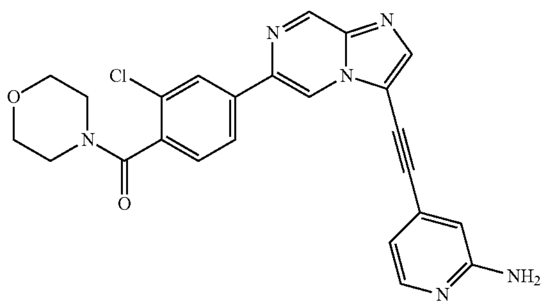 [SMILES: Nc1cc(C#Cc2cnc3cnc(-c4ccc(C(=O)N5CCOCC5)c(Cl)c4)cn23)ccn1] | 93 |
| 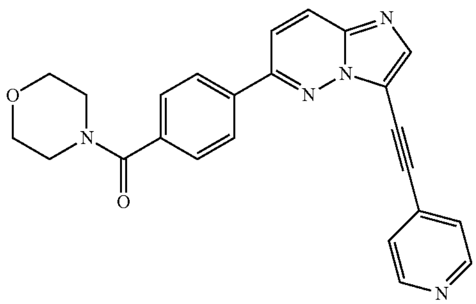 [SMILES: O=C(c1ccc(-c2ccc3ncc(C#Cc4ccncc4)n3n2)cc1)N1CCOCC1] | 94 |
| 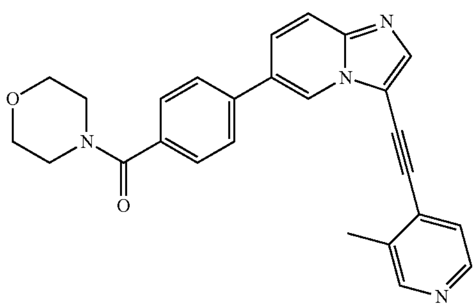 [SMILES: Cc1cnccc1C#Cc1cnc2ccc(-c3ccc(C(=O)N4CCOCC4)cc3)cn12] | 95 |
| 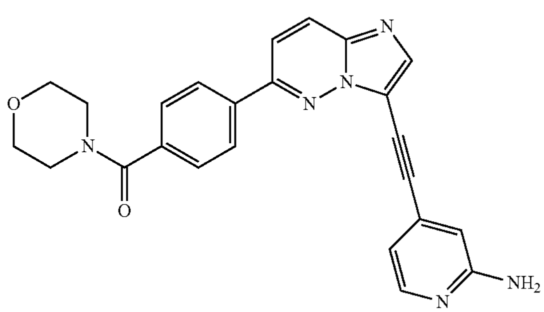 [SMILES: Nc1cc(C#Cc2cnc3ccc(-c4ccc(C(=O)N5CCOCC5)cc4)nn23)ccn1] | 96 |
| 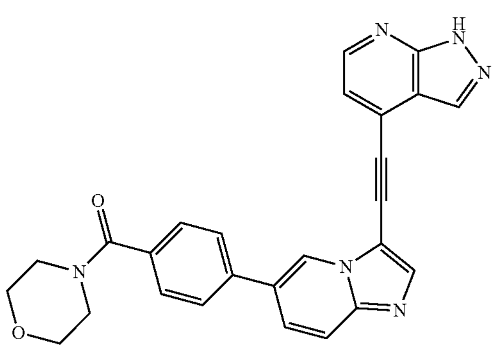 | 97 |

TABLE 1-continued

Exemplary compounds

| Structure | Example # |
|---|---|
| 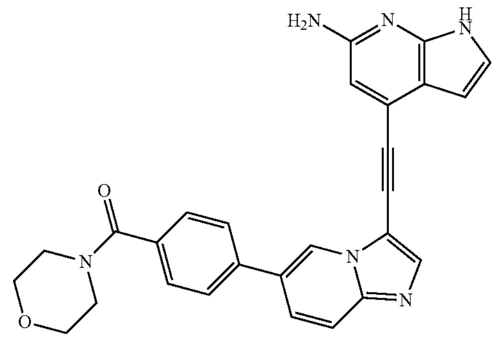 [SMILES: Nc1cc(C#Cc2cnc3ccc(-c4ccc(C(=O)N5CCOCC5)cc4)cn23)c2cc[nH]c2n1] | 98 |
| 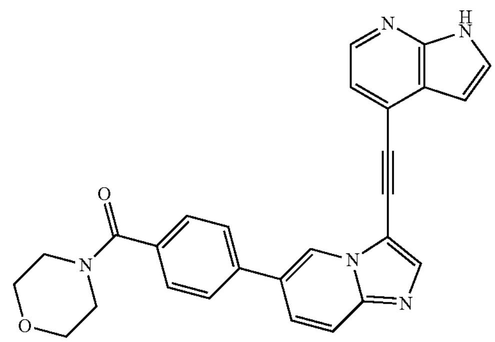 [SMILES: O=C(c1ccc(-c2ccc3ncc(C#Cc4ccnc5[nH]ccc45)n3c2)cc1)N1CCOCC1] | 99 |
| 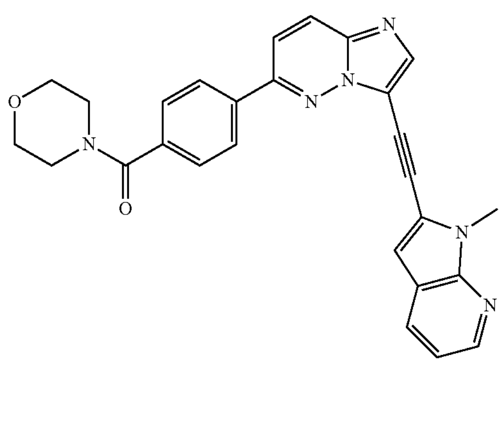 [SMILES: Cn1c(C#Cc2cnc3ccc(-c4ccc(C(=O)N5CCOCC5)cc4)nn23)cc2cccnc21] | 100 |
| 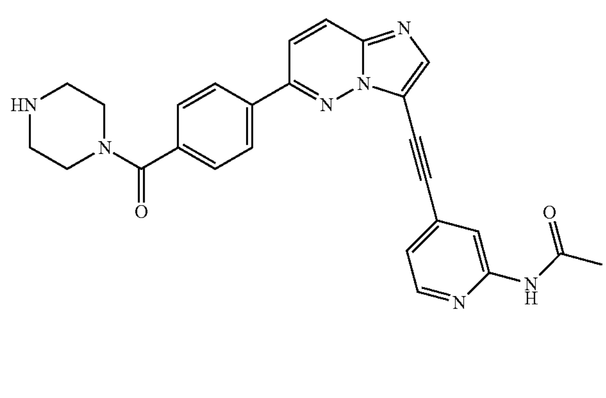 [SMILES: CC(=O)Nc1cc(C#Cc2cnc3ccc(-c4ccc(C(=O)N5CCNCC5)cc4)nn23)ccn1] | 101 |

TABLE 1-continued

Exemplary compounds

| Structure | Example # |
|---|---|
| 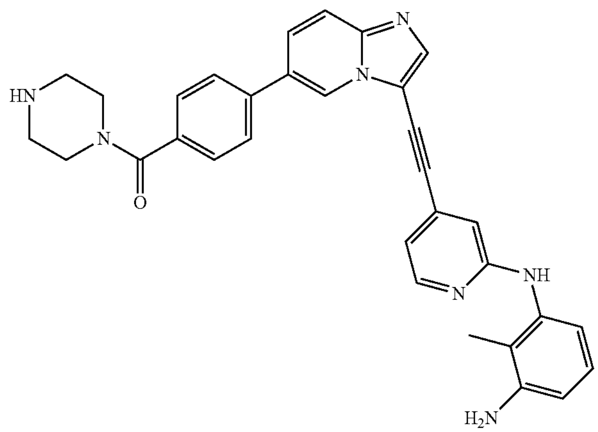 [SMILES: Cc1c(N)cccc1Nc1cc(C#Cc2cnc3ccc(-c4ccc(C(=O)N5CCNCC5)cc4)cn23)ccn1] | 102 |
| 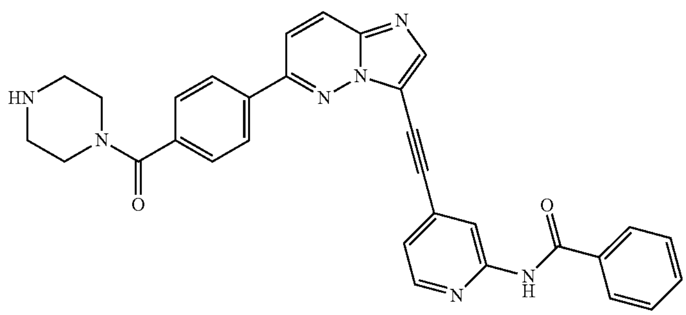 [SMILES: O=C(Nc1cc(C#Cc2cnc3ccc(-c4ccc(C(=O)N5CCNCC5)cc4)nn23)ccn1)c1ccccc1] | 103 |
| 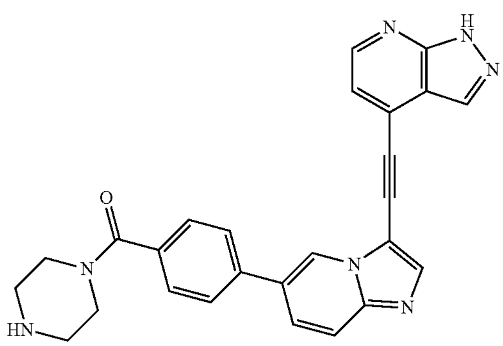 [SMILES: O=C(c1ccc(-c2ccc3ncc(C#Cc4ccnc5[nH]ncc45)n3c2)cc1)N1CCNCC1] | 104 |
| 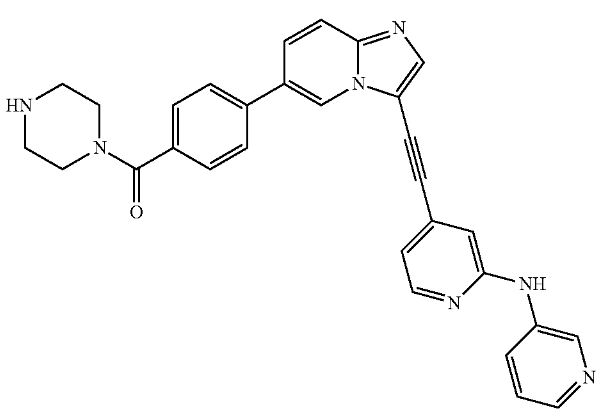 [SMILES: O=C(c1ccc(-c2ccc3ncc(C#Cc4ccnc(Nc5cccnc5)c4)n3c2)cc1)N1CCNCC1] | 105 |

TABLE 1-continued

Exemplary compounds

| Structure | Example # |
|---|---|
| 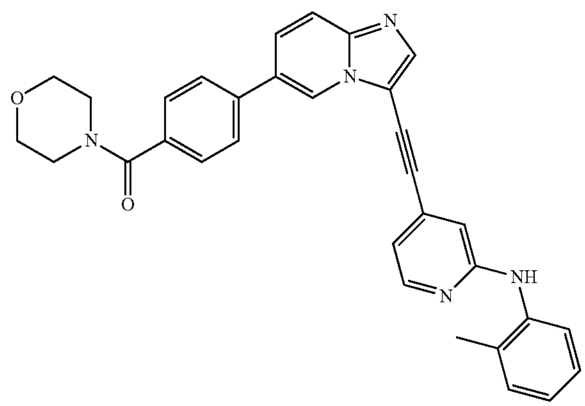 [SMILES: Cc1ccccc1Nc1cc(C#Cc2cnc3ccc(-c4ccc(C(=O)N5CCOCC5)cc4)cn23)ccn1] | 106 |
| 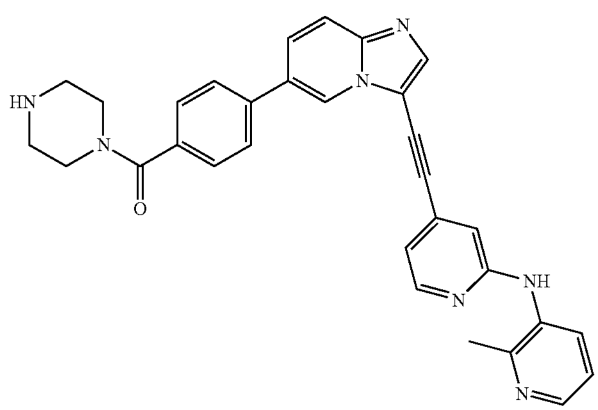 [SMILES: Cc1ncccc1Nc1cc(C#Cc2cnc3ccc(-c4ccc(C(=O)N5CCNCC5)cc4)cn23)ccn1] | 107 |
| 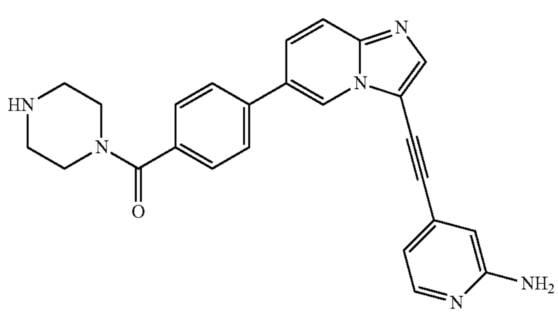 [SMILES: Nc1cc(C#Cc2cnc3ccc(-c4ccc(C(=O)N5CCNCC5)cc4)cn23)ccn1] | 108 |
| 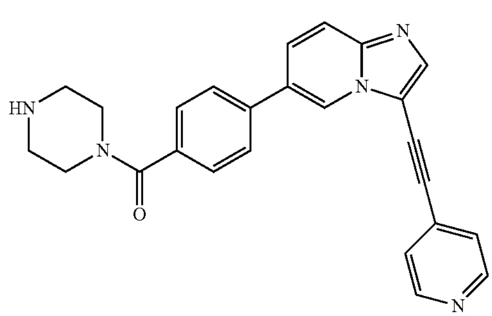 [SMILES: O=C(c1ccc(-c2ccc3ncc(C#Cc4ccncc4)n3c2)cc1)N1CCNCC1] | 109 |

TABLE 1-continued

Exemplary compounds

| Structure | Example # |
|---|---|
| 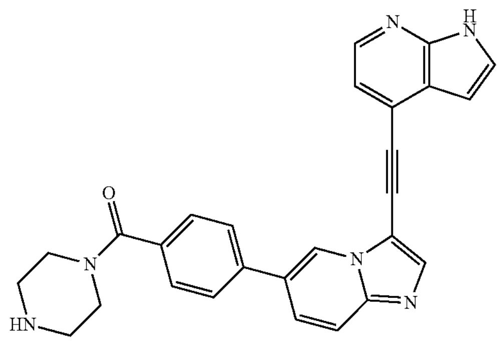 [SMILES: O=C(c1ccc(-c2ccc3ncc(C#Cc4ccnc5[nH]ccc45)n3c2)cc1)N1CCNCC1] | 110 |
| 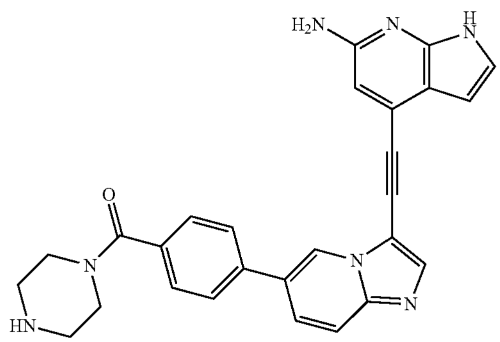 [SMILES: Nc1cc(C#Cc2cnc3ccc(-c4ccc(C(=O)N5CCNCC5)cc4)cn23)c2cc[nH]c2n1] | 111 |
| 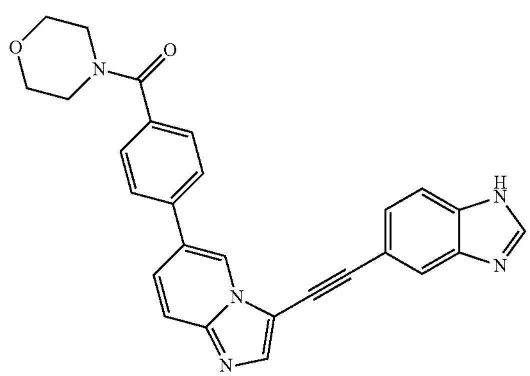 [SMILES: O=C(c1ccc(-c2ccc3ncc(C#Cc4ccc5[nH]cnc5c4)n3c2)cc1)N1CCOCC1] | 112 |
| 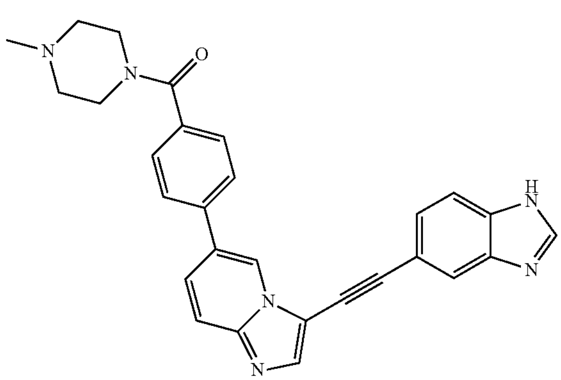 [SMILES: CN1CCN(C(=O)c2ccc(-c3ccc4ncc(C#Cc5ccc6[nH]cnc6c5)n4c3)cc2)CC1] | 113 |

TABLE 1-continued

| Exemplary compounds | |
|---|---|
| Structure | Example # |
| | 114 |
| | 115 |
| | 116 |
| | 117 |
| | 118 |

TABLE 1-continued
Exemplary compounds
| Structure | Example # |
|---|---|
| 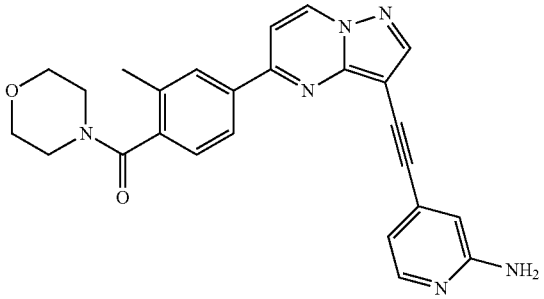 [SMILES: Cc1cc(-c2ccn3ncc(C#Cc4ccnc(N)c4)c3n2)ccc1C(=O)N1CCOCC1] | 119 |
| 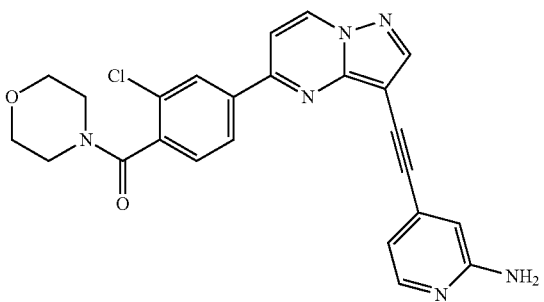 [SMILES: Nc1cc(C#Cc2cnn3ccc(-c4ccc(C(=O)N5CCOCC5)c(Cl)c4)nc23)ccn1] | 120 |
| 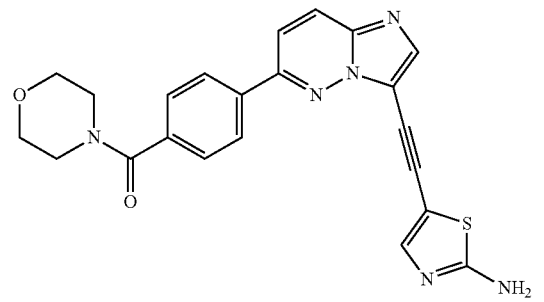 [SMILES: Nc1ncc(C#Cc2cnc3ccc(-c4ccc(C(=O)N5CCOCC5)cc4)nn23)s1] | 121 |
| 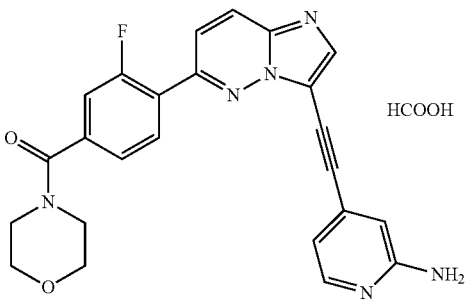 [SMILES: Nc1cc(C#Cc2cnc3ccc(-c4ccc(C(=O)N5CCOCC5)cc4F)nn23)ccn1 ; "HCOOH"] HCOOH | 122 |
| 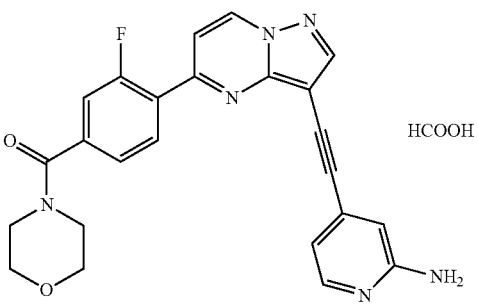 [SMILES: Nc1cc(C#Cc2cnn3ccc(-c4ccc(C(=O)N5CCOCC5)cc4F)nc23)ccn1 ; "HCOOH"] HCOOH | 123 |

Enzymatic assays have shown that compounds as described herein are inhibitors of MNK1 and MNK2 with $IC_{50}$ values in the range of less than approximately 500 nM. eIF4e phosphorylation inhibition in Hela cell line was found to have $IC_{50}s$ in average up to 10 times higher than the enzymatic $IC_{50}s$. These cell-based $IC_{50}s$ vary from as low as approximately 5 μM or lower.

Pharmaceutical Compositions

The present invention also provides pharmaceutical compositions comprising a therapeutically effective amount of a compound described herein, or a pharmaceutically acceptable form thereof (e.g., a pharmaceutically acceptable salt, solvate, hydrate, polymorph, co-crystal, tautomer, stereoisomer, isotopically labeled derivative, or prodrug thereof), and, optionally, a pharmaceutically acceptable excipient.

In another aspect, the present invention relates to pharmaceutical compositions comprising an inventive compound, and optionally a pharmaceutically acceptable excipient, and to their use for treating diseases associated with aberrant MNK1 or MNK2 activity or dysregulation of the MNK1 or MNK2 pathway, where MNK1 and MNK2 play a role (MNK overexpression, eIF4E overexpression, P38 MAPK kinase pathway). Exemplary MNK-related disorders include, but are not limited to; metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, neurodegenerative disorders such as Alzheimer's disease, and cancer such as breast, prostate, hematological malignancies (e.g., CML, AML), head and neck, colon, bladder, prostatic adenocarcinoma, lung, cervical, and lymphomas.

In another aspect, the present invention relates to pharmaceutical compositions comprising these compounds and to their use for the preparation of a medicament for the prophylaxis and treatment of a PI3-kinase (PI3K) related disorder. In certain embodiments, the PI3K-related disorder is PI3K α-related disorder. In certain embodiments, the PI3K-related disorder is PI3K β-related disorder. In certain embodiments, the PI3K-related disorder is PI3K γ-related disorder. In certain embodiments, the PI3K-related disorder is PI3K δ-related disorder. Exemplary PI3K-related disorders include, but are not limited to, cancers such as ovarian cancer, cervical cancer, breast cancer, colon cancer, rectal cancer, endometrial cancer, stomach cancer, liver cancer, lung cancer, thyroid cancer, acute myelogenous leukemia (AML), chronic myelogenous leukemia (CML), and glioblastomas.

In another aspect, the present invention relates to pharmaceutical compositions comprising these compounds and to their use for the preparation of a medicament for the prophylaxis and treatment of a Janus kinase (JAK) related disorder. In certain embodiments, the JAK-related disorder is JAK1-related disorder. In certain embodiments, the JAK-related disorder is JAK2-related disorder. In certain embodiments, the JAK-related disorder is JAK3-related disorder. Exemplary JAK-related disorders include, but are not limited to, psoriasis, rheumatoid arthritis, and cancers such as prostate, colon, ovarian and breast cancers, melanoma, leukemia and other haematopoietic malignancies.

In another aspect, the present invention relates to pharmaceutical compositions comprising these compounds and to their use for the prophylaxis and treatment of a Human Epidermal Growth Factor Receptor-related (HER-) disorder. In certain embodiments, the HER-related disorder is HER2-related disorder. In certain embodiments, the HER-related disorder is HER3-related disorder. Exemplary HER-related disorders include, but are not limited to, cancers such as breast, lung, kidney, brain, ovarian, colon, cervical, endometrial, prostate, liver, thyroid, GI tract, blood and lymphoma and other diseases such as multiple sclerosis.

In another aspect, the present invention relates to pharmaceutical compositions comprising these compounds and to their use for the preparation of a medicament for the prophylaxis and treatment of a mTOR-related disorder. Exemplary mTOR-related disorders include, but are not limited to, cancers such as breast, lung, kidney, brain, ovarian, colon, cervical, endometrial, prostate, liver, thyroid, GI tract, blood and lymphoma and other diseases such as hamartoma syndromes, rheumatoid arthritis, multiple sclerosis.

In certain embodiments, the kinase-related condition (e.g., MNK1- and/or MNK2-related condition) is selected from the group consisting of proliferative diseases, neurodegenerative diseases, autoimmune diseases, and inflammatory diseases.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., CREMOPHOR®), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer P188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose; ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as CREMOPHOR, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner.

Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquids to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered, by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Still further encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Optionally, a single container may comprise one or more compartments for containing an inventive pharmaceutical composition or compound, and/or a pharmaceutically acceptable excipient for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A kit may thus comprise such multi-compartment containers providing an inventive pharmaceutical composition or compound and one or more pharmaceutically acceptable excipients.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with an additional therapeutic agent.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In some embodiments, an additional therapeutically active agent is a kinase inhibitor. In some embodiments, an additional therapeutically active agent is an inhibitor of MAP kinase. In some embodiments, an additional therapeutically active agent is an inhibitor of JAK (e.g. JAK1, JAK2, or JAK3). In some embodiments, an additional therapeutically active agent is an inhibitor of PI3K (e.g. PI3Kα, PI3Kβ, PI3Kγ, or PI3Kδ). In some embodiments, an additional therapeutically active agent is an inhibitor of HER (e.g. HER2 or HER3 inhibitor). In some embodiments, an additional therapeutically active agent is an inhibitor of mTOR (e.g. mTORC1 or mTORC2). In some embodiments, an additional therapeutically active agent is a chemotherapeutic agent.

Also encompassed by the present disclosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kits further includes instructions for use.

Methods of Treatment and Uses

Compounds and compositions described herein are generally useful for the inhibition of one or more kinases. In certain embodiments, compounds and compositions described herein are generally useful for the inhibition of MNK1 and/or MNK2. In some embodiments, methods of treating kinase-related disorder in a subject are provided which comprise administering an effective amount of a compound described herein (e.g., a compound as described herein), or a pharmaceutically acceptable form thereof), to a subject in need of treatment. In some embodiments, methods of treating MNK1- and/or MNK2-related disorder in a subject are provided which comprise administering an effective amount of a compound described herein (e.g., a compound as described herein), or a pharmaceutically acceptable form thereof), to a subject in need of treatment. In certain embodiments, the effective amount is a therapeutically effective amount. In certain embodiments, the effective amount is a prophylactically effective amount. In certain embodiments, the subject is suffering from a MNK1-related disorder. In certain embodiments, the subject is susceptible to a MNK1-mediated disorder. In certain embodiments, the subject is suffering from a MNK2-related disorder. In certain embodiments, the subject is susceptible to a MNK2-mediated disorder.

As used herein, the term "kinase-related disorder" (e.g., "MNK1- and/or MNK2-related disorder") means any disease, disorder, or other pathological condition in which a kinase (e.g., MNK1 and/or MNK2) is known to play a role. In some embodiments, the present disclosure relates to treating or lessening the severity of one or more diseases in which MNK1 and/or MNK2 is known to play a role. Exemplary MNK-related disorders include, but are not limited to, metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, neurodegenerative disorders such as Alzheimer's disease, and cancer such as breast, prostate, hematological malignancies (e.g., CML, AML), head and neck, colon, bladder, prostatic adenocarcinoma, lung, cervical, and lymphomas.

In certain embodiments, a provided compound is useful for treating a proliferative disease, e.g., cancer. In certain embodiments, a provided compound is useful for treating solid tumor. In certain embodiments, a provided compound is useful for treating hematological cancer. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer [e.g., squamous cell carcinoma (SCC), keratoacanthoma (KA), melanoma, basal cell carcinoma (BCC)]; small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva). In certain embodiments, a provided compound is useful for treating breast cancer, prostate cancer, hematological malignancies (e.g., CML, AML), colon cancer, bladder cancer, prostatic adenocarcinoma, lung cancer, cervical cancer, and lymphomas.

In certain embodiments, a provided compound is useful for treating a neurodegenerative disease. Exemplary neurodegerierative diseases include, but are not limited to, autism, or autism spectrum disorders (e.g. Asperger syndrome or Mendelsohnn's Syndrome), Alzheimer's disease, Huntington's disease, progressive supranuclear palsy, corticobasal degeneration, frontotemporal lobar degeneration, Pick's disease, Parkinson's disease, Lewy body disease, and amyotropic lateral sclerosis (ALS).

In certain embodiments, a provided compound is useful for treating an autoimmune disease. Exemplary autoimmune diseases include, but are not limited to, rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic arthritis, juvenile arthritis, asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), Still's disease, myasthenia gravis, Hashimoto's thyroiditis, Ord's thyroiditis, Grave's disease, acute disseminated encephalomyelitis, Addison's disease, opsoclonus-myoclonus syndrome, antiphospholipid antibody syndrome, autoimmune hepatitis, celiac disease, Goodpasture's syndrome, optic neuritis, scleroderma, primary biliary cirrhosis, Reiter's syndrome, warm autoimmune hemolytic anemia, alopecia universalis, chronic fatigue, dysautonomia, neuromyotonia, vulvodynia and disorders ameliorated by a gastroprokinetic agent (e.g., ileus, postoperative ileus and ileus during sepsis; gastroesophageal reflux disease (GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, a provided compound is useful for treating an inflammatory disease. The term "inflammatory disease" refers to those conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory diseases include, but are not limited to inflammation associated with acne, asthma, arteritis (e.g., polyarteritis, temporal arteritis, periarteritis *nodosa*, Takayasu's arteritis), arthritis (e.g., crystalline arthritis, osteoarthritis, psoriatic arthritis, gouty arthritis, reactive arthritis, rheumatoid arthritis, and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, dry eye syndrome, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis), inflammatory bowel syndrome (IBS), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., autism, or autism spectrum disorders (e.g. Asperger syndrome or Mendelsohn's Syndrome), Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis, prostatistis, appendicitis, Blau syndrome, blepharitis, bronchiolitis, cerviciitis, cholangitis, cholecystitis, chronic recurrent multifocal osteomyelitis (CRMO), cryopyrin associated periodic syndrome (CAPS), dacryoadenitis, dermatomyositis, dry eye syndrome, encephalitis, endocarditis, endometritis, enterocolitis, epicondylitis, epididymitis, familial cold-induced autoinflammatory syndrome, familial Mediterranean fever (FMF), fasciitis, fibrositis, hepatitis, hidradenitis suppurativa, laryngitis, mastitis, meningitis, mevalonate kinase deficiency (MKD), Muckle-Well syndrome, myelitis myocarditis, myositis, nephritis, oophoritis, orchitis, osteitis, inflammatory osteolysis, otitis, pancreatitis, parotitis, pericarditis, peritonitis, pharyngitis, pleuritis, phlebitis, pneumonitis, pneumonia, proctitis, pulmonary fibrosis, pyelonephritis, pyoderma gangrenosum and acne syndrome (PAPA), pyogenic sterile arthritis, rhinitis, salpingitis, sinusitis, stomatitis, synovitis, TNF receptor associated periodic syndrome (TRAPS), tonsillitis, undifferentiated arthropathy, uveitis, vaginitis and vulvitis. In certain embodiments, the inflammatory condition is an acute inflammatory condition (e.g., inflammation resulting from infection). In certain embodiments, the inflammatory condition is a chronic inflammatory condition (e.g., conditions resulting from asthma, arthritis and inflammatory bowel disease). The compounds may also be useful in treating inflammation associated with trauma and non-inflammatory myalgia. The compounds may also be useful in treating inflammation associated with cancer.

In certain embodiments, a provided compound is useful for treating or lessening the severity of arthropathies and osteopathological diseases including, but not limited to, rheumatoid arthritis, osteoarthrtis, gout, polyarthritis, and psoriatic arthritis.

In certain embodiments, a provided compound is useful for treating or lessening the severity of acute and chronic inflammatory diseases including, but not limited to, ulcerative colitis, inflammatory bowel disease, Crohn's disease, dry eye syndrome, allergic rhinitis, allergic dermatitis, cystic fibrosis, chronic obstructive bronchitis, and asthma.

In certain embodiments, a provided compound is useful for treating or lessening the severity of hyperproliferative diseases including, but not limited to, psoriasis or smooth muscle cell proliferation including vascular proliferative disorders, atherosclerosis, and restenosis.

In certain embodiments, a provided compound is useful for treating or lessening the severity of endometriosis, uterine-fibroids, endometrial hyperplasia, and benign prostate hyperplasia.

In some embodiments, a provided compound is useful for treating or lessening the severity of one or more diseases and conditions, wherein the disease or condition is selected from immune-related conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, a provided compound is useful for treating tumorogenesis.

In some embodiments, a provided compound is useful for treating a metabolic disorder (e.g., obesity, diabetes).

In some embodiments, the present disclosure provides a method of inhibiting MNK1 comprising contacting MNK1 with an effective amount of a compound described herein (e.g., a compound as described herein), or a pharmaceutically acceptable form thereof. In some embodiments, the present disclosure provides a method of inhibiting MNK2 comprising contacting MNK2 with an effective amount of a compound described herein (e.g., a compound as described herein), or a pharmaceutically acceptable form thereof. The MNK1 or MNK2 may be purified or crude, and may be present in a cell, tissue, or subject. Thus, such methods encompass both inhibition of in vitro and in vivo MNK1 or MNK2 activity. In certain embodiments, the method is an in vitro method, e.g., such as an assay method. It will be understood by one of ordinary skill in the art that inhibition of MNK1 or MNK2 does not necessarily require that all of the MNK1 or MNK2 be occupied by an inhibitor at once. Exemplary levels of inhibition of MNK1 or MNK2 include at least 10% inhibition, about 10% to about 25% inhibition, about 25% to about 50% inhibition, about 50% to about 75% inhibition, at least 50% inhibition, at least 75% inhibition, about 80% inhibition, about 90% inhibition, and greater than 90% inhibition.

In some embodiments, provided is a method of inhibiting kinase activity in a subject in need thereof (e.g., a subject diagnosed as having a kinase-related disorder) comprising administering to the subject an effective amount of a compound described herein (e.g., a compound as described herein), or a pharmaceutically acceptable form thereof, or a pharmaceutical composition thereof. In some embodiments, provided is a method of inhibiting MNK1 and/or MNK2 activity in a subject in need thereof (e.g., a subject diagnosed as having a MNK1- and/or MNK2-related disorder) comprising administering to the subject an effective amount of a compound described herein, or a pharmaceutically acceptable form thereof, or a pharmaceutical composition thereof.

EXAMPLES

Compounds as described herein were synthesized and their ability to inhibit MNK1/2 kinase was evaluated both in enzymatic and in cell-based assays. In parallel, their ability to inhibit other kinases was also assessed (Table 2). Enzymatic assays have shown that compounds as described herein are inhibitors of MNK1 and MNK2 with $IC_{50}$ values lower than about 500 nM. eIF4e phosphorylation inhibition in Hela cell line was found to have $IC_{50}$s in average 10 time higher than the enzymatic $IC_{50}$s. These cell-based $IC_{50}$s are less than about 5 µM.

TABLE 2

Enzymatic and Cellular $IC_{50}$ Activities of Exemplified Compounds

| Example # | $IC_{50}$ (µM) | | |
|---|---|---|---|
| | MNK1 | MNK2 | Hela |
| 001 | <0.5 | <0.5 | <5 |
| 002 | <0.5 | <0.5 | <5 |
| 005 | <0.5 | <0.5 | <5 |
| 008 | <0.5 | <0.5 | <5 |
| 010 | <0.5 | <0.5 | <5 |
| 011 | <0.5 | <0.5 | <5 |
| 013 | <0.5 | <0.5 | <5 |
| 016 | <0.5 | <0.5 | <5 |
| 017 | <0.5 | <0.5 | <5 |
| 019 | <0.5 | <0.5 | <5 |
| 020 | <0.5 | <0.5 | <5 |
| 022 | <0.5 | <0.5 | <5 |
| 023 | <0.5 | <0.5 | <5 |
| 024 | <0.5 | <0.5 | <5 |
| 027 | <0.5 | <0.5 | <5 |
| 028 | <0.5 | <0.5 | <5 |
| 031 | <0.5 | <0.5 | <5 |
| 032 | <0.5 | <0.5 | <5 |
| 033 | <0.5 | <0.5 | <5 |
| 034 | <0.5 | <0.5 | <5 |
| 035 | <0.5 | <0.5 | <5 |
| 037 | <0.5 | <0.5 | <5 |
| 040 | <0.5 | <0.5 | <5 |
| 043 | <0.5 | <0.5 | <5 |
| 044 | <0.5 | <0.5 | <5 |
| 045 | <0.5 | <0.5 | <5 |
| 046 | <0.5 | <0.5 | <5 |
| 047 | <0.5 | <0.5 | <5 |
| 048 | <0.5 | <0.5 | <5 |
| 049 | <0.5 | <0.5 | <5 |
| 051 | <0.5 | <0.5 | <5 |
| 052 | <0.5 | <0.5 | <5 |
| 053 | <0.5 | <0.5 | <5 |
| 054 | <0.5 | <0.5 | <5 |
| 055 | <0.5 | <0.5 | <5 |
| 056 | <0.5 | <0.5 | <5 |
| 057 | <0.5 | <0.5 | <5 |
| 058 | <0.5 | <0.5 | <5 |
| 059 | <0.5 | <0.5 | <5 |
| 060 | <0.5 | <0.5 | <5 |
| 063 | <0.5 | <0.5 | <5 |
| 064 | <0.5 | <0.5 | <5 |
| 065 | <0.5 | <0.5 | <5 |
| 070 | <0.5 | <0.5 | <5 |
| 071 | <0.5 | <0.5 | <5 |
| 073 | <0.5 | <0.5 | <5 |
| 074 | <0.5 | <0.5 | <5 |
| 075 | <0.5 | <0.5 | <5 |
| 089 | <0.5 | <0.5 | <5 |
| 094 | <0.5 | <0.5 | <5 |
| 095 | <0.5 | <0.5 | <5 |
| 096 | <0.5 | <0.5 | <5 |
| 097 | <0.5 | <0.5 | <5 |
| 098 | <0.5 | <0.5 | <5 |
| 099 | <0.5 | <0.5 | <5 |
| 101 | <0.5 | <0.5 | <5 |
| 102 | <0.5 | <0.5 | <5 |
| 103 | <0.5 | <0.5 | <5 |
| 104 | <0.5 | <0.5 | <5 |
| 105 | <0.5 | <0.5 | <5 |
| 106 | <0.5 | <0.5 | <5 |
| 107 | <0.5 | <0.5 | <5 |
| 108 | <0.5 | <0.5 | <5 |
| 109 | <0.5 | <0.5 | <5 |
| 110 | <0.5 | <0.5 | <5 |
| 111 | <0.5 | <0.5 | <5 |
| 114 | <0.5 | <0.5 | <5 |
| 115 | <0.5 | <0.5 | <5 |
| 116 | <0.5 | <0.5 | <5 |
| 121 | <0.5 | <0.5 | <5 |
| 122 | <0.5 | <0.5 | <5 |
| 123 | <0.5 | <0.5 | <5 |

SYNTHETIC EXAMPLES

Abbreviations

CAN: acetonitrile
AcOEt: ethyl acetate
AcOH: acetic acid
AUC: area under the curve
Brine: saturated aqueous solution of NaCl
cat.: catalyst
d: day(s)
DCM: dichloromethane
DIPEA: diisopropyl-ethyl-amine
DMF: N,N-dimethylformamide
DMSO: dimethylsulfoxide
DMSO-$d_6$: per-deuterated dimethylsulfoxide
dppf: 1,1'-Bis(diphenylphosphino) ferrocene
EDCI: 1-ethyl-3-(3-dimethylaminopropyl) carbodiimide)
Ether: diethylether
EtOH: ethanol
h: hour(s)
HATU: 2-(1H-7-Azabenzotriazol-1-yl)-1,1,3,3-tetramethyl uronium hexafluorophosphate Methanaminium
HBTU: O-Benzotriazole-N,N,N',N'-tetramethyl-uronium-hexafluoro-phosphate
HOBt: N-Hydroxybenzotriazole
HPLC: high pressure liquid chromatography
L: litre(s)
LC-MS: Liquid chromatography-mass spectrometry Me: methyl
MeOH: methanol
min: minute(s)
m.p.: melting point
MS: mass spectrometry
NBS: N-Bromosuccinimide
Et$_3$N: triethylamine
NIS: N-iodosuccinimide
NMM: N-methylmorpholine
NMR: Nuclear Magnetic Resonance
Pd(dppf)Cl$_2$: [1,1'-Bis(diphenylphosphino)ferrocene]dichloropalladium(II)
THF: tetrahydrofuran
TFA: trifluoroacetic acid
TLC: thin layer chromatography
TMS: trimethylsilyl Synthesis of Intermediates Intermediate 1

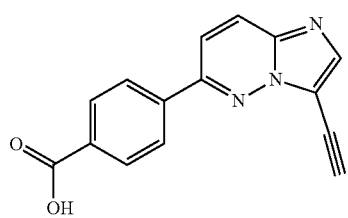

Intermediate 2

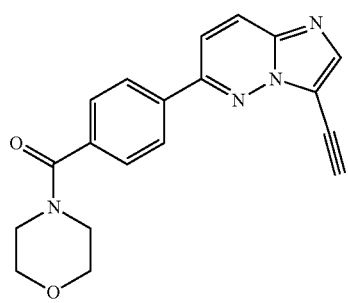

Intermediate 3

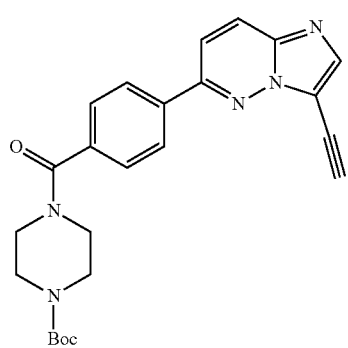

Intermediate 4

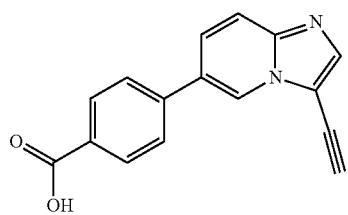

-continued

Intermediate 5

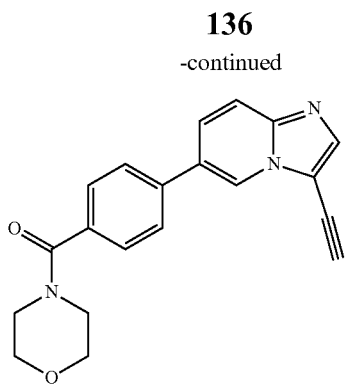

Intermediate 6

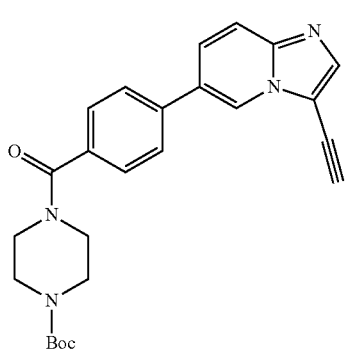

Intermediate 7

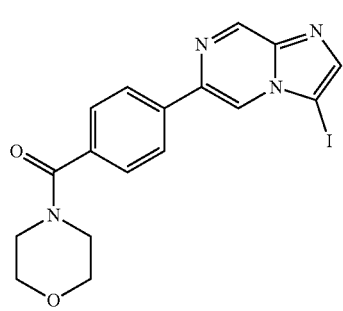

Intermediate 8

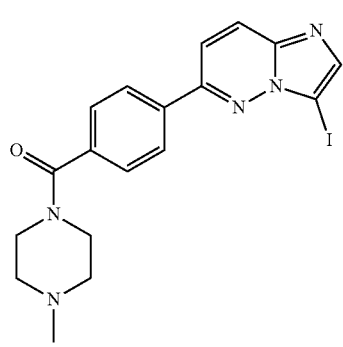

Intermediate 9

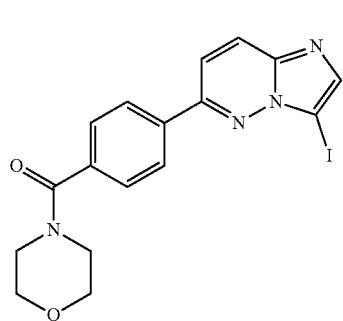

Intermediates 1: 4-(3-ethynylimidazo[1,2-b]pyridazin-6-yl)benzoic acid

Step 1: Preparation of ethyl 4-(imidazo[1,2-b]pyridazin-6-yl)benzoate

A mixture of 6-chloroimidazo[1,2-b]pyridazine (10 g, 65.34 mmol), 4-Ethoxycarbonyl phenylboronic acid (13.94 g, 71.88 mmol), $K_3PO_4$ (27.7 g, 130.68 mmol) in 1,4-dioxane (200 mL) and water (40 mL) was stirred under Argon for 1 h. $Pd(PPh_3)_4$ (3.76 g, 3.26 mmol) was added and the reaction mixture was heated at 90° C. for 4 h. The reaction mixture was diluted with EtOAc (2×200 mL) and washed with water (2×100 mL) and brine solution (2×100 mL). The organic layer was dried over anhydrous $Na_2SO_4$ and concentrated under reduced pressure to obtain crude product. The crude product was purified by column chromatography (silica gel, eluent petroleum ether/EtOAc 90:10 to 50:50) to afford ethyl 4-(imidazo[1,2-b]pyridazin-6-yl)benzoate (5 g, 45%) as an off-white solid. $^1$H NMR (400 MHz, DMSO-$d_6$) δ (ppm): 9.79 (s, 1H), 8.55 (s, 1H), 7.78-7.72 (m, 2H), 7.67-7.46 (m, 3H), 6.94 (d, J=12.0 Hz, 2H), 4.03 (q, J=7.2 Hz, 2H), 1.42 (t, J=7.2 Hz, 3H); MS (ESI) m/z 268.1 $[C_{16}H_{14}N_2O_2+H]^+$.

Step 2: Preparation of ethyl 4-(3-iodoimidazo[1,2-b]pyridazin-6-yl)benzoate To a solution of ethyl 4-(imidazo[1,2-b]pyridazin-6-yl)benzoate (5 g, 18.72 mmol) in DCM (50 mL) and ACN (100 mL) was added NIS (5.04 g, 22.46 mmol) at 0° C. and stirred at room temperature for 3 h. The reaction mixture was filtered and washed with water to afford ethyl 4-(3-iodoimidazo[1,2-b]pyridazin-6-yl)benzoate (7 g, 95%) as a yellow solid. $^1$H NMR (400 MHz, DMSO-$d_6$) δ (ppm): 9.79 (s, 1H), 8.55 (s, 1H), 7.78-7.72 (m, 2H), 7.67-7.46 (m, 2H), 6.94 (d, J=12.0 Hz, 2H), 4.03 (q, J=7.2 Hz, 2H), 1.42 (t, J=7.2 Hz, 3H); MS (ESI) m/z 393.1 $[C_{16}H_{13}IN_2O_2+H]^+$.

Step 3: Preparation of ethyl 4-(3-((trimethylsilyl)ethynyl)imidazo[1,2-b]pyridazin-6-yl)benzoate A mixture of ethyl 4-(3-iodoimidazo[1,2-b]pyridazin-6-yl)benzoate (7 g, 17.8 mmol), ethynyltrimethylsilane (2.99 mL, 21.36 mmol), $Pd(PPh_3)_4$ (1 g, 0.89 mmol), CuI (507 mg, 2.67 mmol), and DIPEA (4.65 mL, 26.7 mmol) in 100 mL of DMF was stirred at 80° C. under $N_2$ for 4 h. The organic layer was dried over anhydrous $Na_2SO_4$ and concentrated under reduced pressure. The crude residue was purified by flash column chromatography (silica gel, eluent $CH_2Cl_2$/$CH_3OH$ 95:5) to afford ethyl 4-(3-((trimethylsilyl)ethynyl)imidazo[1,2-b]pyridazin-6-yl)benzoate (5 g, 78%) as an off-white solid. $^1$H NMR (400 MHz, CDCl$_3$) δ (ppm): 8.20 (d, J=8.4 Hz, 2H), 8.12 (d, J=8.0 Hz, 2H), 8.11-8.03 (m, 2H), 7.60 (d, J=8.0 Hz, 1H), 4.43 (q, J=7.2 Hz, 2H), 1.44 (t, J=7.6 Hz, 3H); MS (ESI) m/z 364.49 $[C_{20}H_{21}N_3O_2Si+H]^+$.

Step 4: Preparation of 4-(3-ethynylimidazo[1,2-b]pyridazin-6-yl)benzoic acid To a solution of ethyl 4-(3-((trimethylsilyl)ethynyl)imidazo[1,2-b]pyridazin-6-yl)benzoate (5 g, 13.77 mmol) in THF (50 mL) was added LiOH (1.15 g, 27.54 mmol) in water (25 mL) and MeOH (20 mL) at room temperature and stirred for 5 h. The reaction mixture was concentrated under reduced pressure to afford 4-(3-ethynylimidazo[1,2-b]pyridazin-6-yl)benzoic acid (3.5 g, 96%, AUC HPLC 96.3%) as a light brown solid; m.p. 267-270° C.; $^1$H NMR (400 MHz, DMSO-$d_6$) δ (ppm): 13.2 (s, 1H), 8.35 (d, J=10 Hz, 1H), 8.23 (d, J=8.4 Hz, 2H), 8.18-8.11 (m, 3H), 8.01 (d, J=9.6 Hz, 1H), 5.03 (s, 1H); MS (ESI) m/z 264.25 $[C_{15}H_9N_3O+H]^+$.

Intermediate 2: (4-(3-ethynylimidazo[1,2-b]pyridazin-6 yl)phenyl)(morpholino)methanone To a solution of 4-(3-ethynylimidazo[1,2-b]pyridazin-6-yl)benzoic acid (1 g, 3.8 mmol) in DMF (10 mL) was added NMM (0.84 mL, 7.6 mmol) followed by HATU (2.16 g, 5.7 mmol) and the resulting mixture was stirred at room temperature for 20 min. Morpholine (0.4 g, 4.56 mmol) was added and the reaction mixture stirred at room temperature overnight, then diluted with EtOAc and washed in turn with water and brine solution. The organic layer was dried over anhydrous $Na_2SO_4$, filtered and concentrated under reduced pressure. The crude product was purified by column chromatography (silica gel, eluent $CHCl_3$/$CH_3OH$ 97:3) to afford (4-(3-ethynylimidazo[1,2-b]pyridazin-6-yl)phenyl)(morpholino)methanone (1.0 g, 79%, LC-MS 99%) as an off-white solid. $^1$H NMR (400 MHz, CDCl$_3$) δ (ppm): 8.10-8.03 (m, 4H), 7.59-7.57 (m, 3H), 3.79 (s, 1H), 3.66-3.49 (m, 8H).

Intermediate 3: (4-(3-ethynylimidazo[1,2-b]pyridazin-6-yl)phenyl)(4-methylpiperazin-1-yl)methanone To a solution of 4-(3-ethynylimidazo[1,2-b]pyridazin-6-yl)benzoic acid (816 mg, 3.10 mmol) in a mixture of DCM (6 mL) and DMF (6 mL) was added sequentially N-methyl piperazine (2.06 mL, 18.61 mmol), HBTU (2.93 g, 7.75 mmol), HOBt (795 mg, 5.89 mmol) and DIPEA (2.70 mL, 15.51 mmol), the resulting mixture was then stirred at room temperature for 12 h. The reaction mixture was concentrated under reduced pressure then was diluted water (5 mL) and extracted with DCM (3×10 mL). The combined extracts were dried over $Na_2SO_4$ filtered and concentrated to dryness under reduced pressure. The residue was purified by flash column chromatography (silica gel, eluent $CH_2Cl_2$/$CH_3OH$ 95:5) to afford (4-(3-ethynylimidazo[1,2-b]pyridazin-6-yl)phenyl)(4-methylpiperazin-1-yl)methanone (909 mg, 85%, AUC HPLC 95%) as light yellow foam. $^1$H NMR (DMSO-$d_6$, 600 MHz) δ (ppm): 8.31 (dd, J=9.5, 1.4 Hz, 1H), 8.21-8.09 (m, 3H), 7.96 (d, J=9.6 Hz, 1H), 7.58 (d, J=7.9 Hz, 2H), 5.04-4.97 (m, 1H), 3.64 (s, 2H), 2.47-2.22 (m, 4H), 2.20 (s, 3H); $^{13}$C NMR (DMSO-$d_6$, 150 MHz) δ (ppm): 168.3, 151.3, 139.0, 138.5, 137.6, 135.5, 127.6, 127.1, 126.4, 117.7, 111.8, 90.8, 70.9, 54.6, 54.1 and 45.6; MS (ESI) m/z 346 $[C_{20}H_{19}N_5O+H]^+$.

Intermediate 4: 4-(3-ethynylimidazo[1,2-a]pyridin-6-yl)benzoic acid

Step 1: Preparation of ethyl 4-(imidazo[1,2-a]pyridin-6-yl)benzoate 4-(ethoxycarbonyl)phenylboronic acid (7.09 g, 36.54 mmol), $K_3PO_4$ (19.37 g, 91.36 mmol) and $Pd(PPh_3)_4$ (1.75 g, 1.52 mmol) were added sequentially, under argon atmosphere, to a solution of 6-bromoimidazo[1,2-a]pyridine (6 g, 30.45 mmol) in a mixture of 1,4-dioxane (90 mL) and $H_2O$ (10 mL). The reaction mixture was refluxed overnight and the reaction mixture was diluted with EtOAc and washed in turn with water and brine. The organic layer was dried over anhydrous Na$_2$SO$_4$ and concentrated under reduced pressure. The crude product was purified by column chromatography (silica gel, eluent petroleum ether/EtOAc 1:1) to afford ethyl 4-(imidazo[1,2-a]pyridin-6-yl)benzoate (6.4 g, 79%, LC-MS 86.5%) as a solid. $^1$H NMR (400 MHz, CDCl$_3$) δ (ppm): 8.37 (s, 1H), 8.12 (d, J=7.9 Hz, 2H), 7.72-7.62 (m, 5H), 7.41 (d, J=9.3 Hz, 1H), 4.42 (q, J=7.0 Hz, 2H), 1.41 (t, J=7.1 Hz, 3H); MS (ESI) m/z 267.09 [C$_{16}$H$_{14}$N$_2$O$_2$+H]$^+$.

Step 2: Preparation of ethyl 4-(3-iodoimidazo[1,2-a]pyridin-6-yl)benzoate

To a solution of ethyl 4-(imidazo[1,2-a]pyridin-6-yl)benzoate (6.4 g, 24.06 mmol) in ACN (50 mL) was added NIS (6.49 g, 28.87 mmol) at 0° C. to room temperature and stirred at the same temperature for 3 h. TLC indicated absence of starting material and water (2×50 mL) was added to the reaction mixture. The reaction mixture was filtered and washed with water to afford ethyl 4-(3-iodoimidazo[1,2-a]pyridin-6-yl)benzoate (8.5 g, 90%, LC-MS 99.5%) as a yellow solid. $^1$H NMR (400 MHz, DMSO-d$_6$) δ (ppm): 8.50 (s, 1H), 8.01 (d, J=8.4 Hz, 2H), 7.95-7.92 (m, 2H), 7.74-7.72 (m, 3H), 4.31 (q, J=7.0 Hz, 2H), 1.32 (t, J=7.4 Hz, 3H); MS (ESI) m/z 392.5 [C$_{16}$H$_{13}$IN$_2$O$_2$+H]$^+$.

Step 3: Preparation of ethyl 4-(3-((trimethylsilyl)ethynyl)imidazo[1,2-a]pyridin-6-yl)benzoate To a solution of ethyl 4-(3-iodoimidazo[1,2-a]pyridin-6-yl)benzoate (6 g, 15.30 mmol) in DMF (50 mL) was added ethynyltrimethylsilane (2.57 mL, 18.36 mmol), CuI (860 mg, 4.81 mmol), and DIPEA (4.22 mL, 22.95 mmol) under argon. Pd(PPh$_3$)$_4$ (883 mg, 0.76 mmol) was added and the reaction mixture was heated at 80° C. for 4 h. The reaction mixture was diluted with water (2×100 mL) which triggered a precipitate formation which was filtered to give crude product. The crude product was purified by flash chromatography (silica gel, eluent petroleum ether/EtOAc 1:1) to afford ethyl 4-(3-((trimethylsilyl)ethynyl)imidazo[1,2-a]pyridin-6-yl)benzoate (54.5%, LC-MS 98%) as a solid. $^1$H NMR (400 MHz, DMSO-d$_6$) δ (ppm): 8.56 (s, 1H), 8.10-8.02 (m, 3H), 7.91 (d, J=8.3 Hz, 2H), 7.81 (q, J=9.2 Hz, 2H), 4.31 (q, J=7.5 Hz, 2H), 1.32 (t, J=7.1 Hz, 3H), 0.09 (s, 9H); MS (ESI) m/z 363.05 [C$_{21}$H$_{22}$N$_2$O$_2$Si+H].$^+$ Step 4: Preparation of 4-(3-ethynylimidazo[1,2-a]pyridin-6-yl)benzoic acid To a solution of ethyl 4-(3-((trimethylsilyl)ethynyl)imidazo[1,2-a]pyridin-6-yl)benzoate (3 g, 8.28 mmol) in THF (20 mL) was added LiOH (1.04 g, 24.86 mmol) in water (5 mL) at room temperature and stirred for 2 h. The reaction mixture was concentrated under reduced pressure to afford 4-(3-ethynylimidazo[1,2-a]pyridin-6-yl)benzoic acid as a solid. 1H NMR (400 MHz, DMSO-d$_6$) δ (ppm): 12.02 (s, 1H), 8.64 (s, 1H), 8.02 (t, J=7.9 Hz, 3H), 7.92 (d, J=8.4 Hz, 3H), 7.83 (s, 1H), 5.14 (s, 1H); MS (ESI) m/z 263 [C$_{16}$H$_{10}$N$_2$O$_2$+H]$^+$.

Intermediate 5: (4-(3-ethynylimidazo[1,2-a]pyridin-6-yl)phenyl)(morpholino)methanone To a solution of 4-(3-ethynylimidazo[1,2-a]pyridin-6-yl)benzoic acid (600 mg, 2.28 mmol) in DMF (10 mL) was added NMM (0.5 mL, 4.58 mmol) followed by HATU (1.3 g, 3.43 mmol) and the reaction mixture was stirred for 30 min. Morpholine (0.24 mL, 2.5 mmol) was added and stirred at room temperature for 16 h. The reaction mixture was diluted with EtOAc and washed with water and brine solution. The organic layer was dried over anhydrous Na$_2$SO$_4$ and concentrated under reduced pressure. The crude product was purified by column chromatography (silica gel, eluent CHCl$_3$/CH$_3$OH 95:5) to afford (4-(3-ethynylimidazo[1,2-a]pyridin-6-yl)phenyl)(morpholino)methanone (400 mg, 52.7%, LC-MS 96.7%) as a solid. $^1$H NMR (400 MHz, CDCl$_3$) δ (ppm): 8.47 (s, 1H), 7.92 (s, 1H), 7.72 (d, J=9.2 Hz, 2H), 7.61 (d, J=8.4 Hz, 2H), 7.54-7.52 (m, 2H), 5.12 (s, 1H), 3.86-3.84 (m, 8H); MS (ESI) m/z 332.09 [C$_{20}$H$_{17}$N$_3$O$_2$+H]$^+$.

Intermediate 6: tert-butyl 4-(4-(3-ethynylimidazo[1,2-a]pyridin-6-yl)benzoyl)piperazine-1-carboxylate To a solution of 4-(3-ethynylimidazo[1,2-a]pyridin-6-yl)benzoic acid (300 mg, 1.14 mmol) in DMF (10 mL) was added NMM (0.25 mL, 2.29 mmol) followed by HATU (652 mg, 1.71 mmol) at room temperature and stirred for 30 min. To the reaction mixture, morpholine (234 mg, 1.25 mmol) was added and stirred at room temperature for overnight. The reaction mixture was diluted with EtOAc and washed with water and brine solution. The organic layer was dried over Na$_2$SO$_4$, filtered and concentrated under reduced pressure. The residue was purified by column chromatography (silica gel, eluent CHCl$_3$/CH$_3$OH 95:5) to afford tert-butyl 4-(4-(3-ethynylimidazo[1,2-a]pyridin-6-yl)benzoyl)piperazine-1-carboxylate (200 mg, 40.6%, LC-MS 99%) as a solid. $^1$H NMR (400 MHz, CDCl$_3$) δ (ppm): 8.47 (s, 1H), 7.93 (s, 1H), 7.72 (d, J=9.2 Hz, 1H), 7.61 (d, J=8.3 Hz, 2H), 7.50 (d, J=7.9 Hz, 3H), 3.86-3.84 (m, 9H), 1.48 (s, 9H), 1.25 (s, 2H); MS (ESI) m/z 431.10 [C$_{25}$H$_{26}$N$_4$O$_3$+H]$^+$.

Intermediate 7: (4-(3-iodoimidazo[1,2-a]pyrazin-6-yl)phenyl) (morpholino) methanone

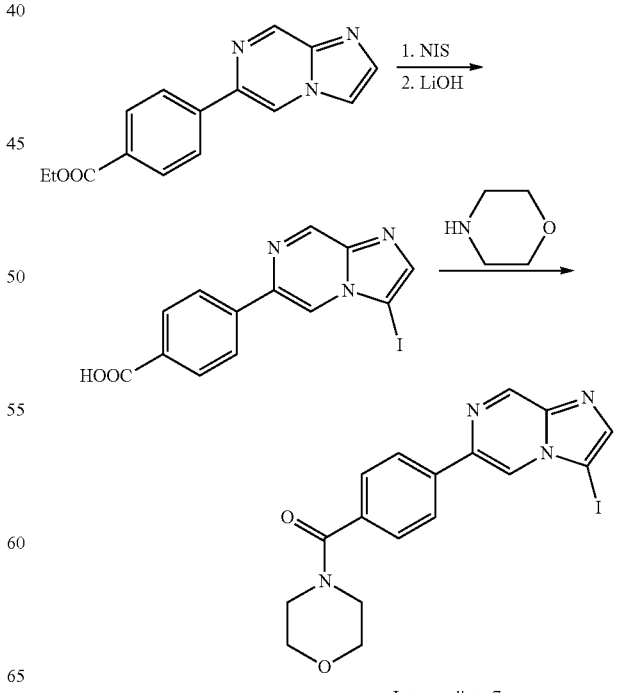

Intermediate 7

Step 1

To a solution of ethyl 4-(imidazo[1,2-a]pyrazin-6-yl)benzoate (8.00 g, 29.9 mmol) in DMF (200 mL), was added N-Iodosuccinimide (8.10 g, 36.0 mmol) and the mixture was heated at 60° C. for 2 h and poured onto ice water. The precipitate was isolated by filtration and dried to afford ethyl 4-(3-iodoimidazo[1,2-a]pyrazin-6-yl)benzoate (11 g, 94%) as yellow solid. $^1$H NMR (400 MHz, DMSO-$d_6$) δ 9.13 (s, 1H), 8.80 (s, 1H), 8.29 (d, J=8.4 Hz, 2H), 8.07 (d, J=8.4 Hz, 2H), 8.00 (s, 1H), 4.37-4.31 (m, 2H), 1.34 (t, J=7.2 Hz, 3H); MS (ESI) m/z 393 $[C_{15}H_{12}IN_3O_2]^+$.

Step 2

A solution of ethyl 4-(3-iodoimidazo[1,2-a]pyrazin-6-yl)benzoate (11 g, 30.5 mmol) and LiOH.H$_2$O (5.00 g, 121 mmol) in THF/CH$_3$OH/H$_2$O (200/50/50 mL) was stirred for 12 h. The reaction mixture was concentrated, diluted with water (20 mL) and acidified with an aqueous solution of HCl till pH 2, The precipitate was isolated by filtration and dried to afford 4-(3-iodoimidazo[1,2-a]pyrazin-6-yl)benzoic acid (8.00 g, 72%) as off white solid. $^1$H NMR (400 MHz, DMSO-$d_6$) δ: 9.12 (s, 1H), 8.78 (s, 1H), 8.26 (d, J=8.4 Hz, 2H), 8.06 (d, J=8.4 Hz, 2H), 8.05 (s, 1H); MS (ESI) m/z 366 $[C_{13}H_{81}IN_3O_2+H]^+$.

Step 3

N-methyl-morpholine (3.0 mL, 7.5 mmol), HATU (7.5 g, 27 mmol) and morpholine (1.26 g, 14.85 mmol) were added sequentially to a solution of 4-(3-iodoimidazo[1,2-a]pyrazin-6-yl)benzoic acid (5.0 g, 3.25 mmol) in DMF (10 mL) and the resulting mixture was stirred at room temperature for 3 h under nitrogen atmosphere. The reaction mixture was diluted with water (50 mL) and the precipitate that has formed was filtered off and dried to afford (4-(3-iodoimidazo[1,2-a]pyrazin-6-yl)phenyl)(morpholino)methanone (2.0 g, 65%) as off-white solid. $^1$H NMR (400 MHz, CDCl$_3$) δ 9.10 (s, 1H), 8.50 (s, 1H), 8.10 (d, 2H), 7.90 (s, 1H), 7.60 (d, 2H), 3.4-3.9 (m, 8H); MS (ESI) m/z 434 $[C_{17}H_{15}N_4O_2+H]^+$.

Intermediate 8: (4-(3-iodoimidazo[1,2-b]pyridazin-6-yl)phenyl)(4-methylpiperazin-1-yl)methanone

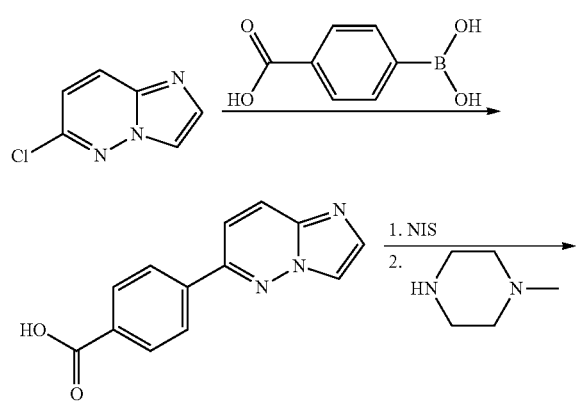

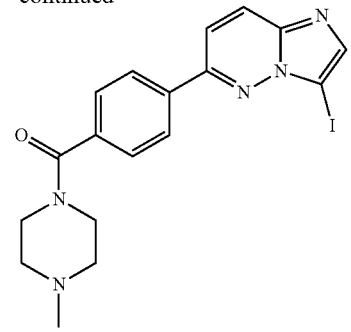

Intermediate 8

Step 1: Preparation of 4-(imidazo[1,2-b]pyridazin-6-yl)benzoic acid

To a solution of 6-chloroimidazo[1,2-b] pyridazine (2 g, 13.07 mmol) in 1,4-dioxane (20 mL) and water (10 mL) were successively added 4-boronobenzoic acid (2.58 g, 15.87 mmol), K$_2$CO$_3$ (3.6 g, 0.81 mmol), and Pd(PPh$_3$)$_4$ (0.75 g, 6.5 mmol). The reaction mixture was heated at 100° C. for 15 h under argon. The reaction mixture was diluted with water (50 mL) and extracted with ethyl acetate (3×20 mL). The combined organic phase was washed with brine (1×50 mL), dried over Na$_2$SO$_4$, filtered and concentrated under vacuum to afford 4-(imidazo[1,2-b]pyridazin-6-yl)benzoic acid (2 g, 64%) as a white solid (LC-MS 84%). $^1$H NMR (400 MHz, DMSO-$d_6$) δ 13.01 (bs, 1H), 8.04 (s, 1H), 8.3-8.01 (m, 5H), 7.85 (d, J=7.2 Hz, 2H); MS (ESI) m/z 240 $[M+H]^+$.

Step 2: Preparation of 4-(3-iodoimidazo [1,2-b] pyridazin-6-yl) benzoic acid A solution of 4-(imidazo[1,2-b] pyridazin-6-yl) benzoic acid (2 g, 84% purity, 7.02 mmol) and NIS (4.63 g, 20.77 mmol) in DMF (20 mL) was heated at 90° C. for 4 h. The reaction mixture was poured into ice-cold water, the precipitate was isolated by filtration and dried to afford 4-(3-iodoimidazo[1,2-b]pyridazin-6-yl)benzoic acid (1.5 g, 58%, HPLC 93%) as a yellow solid. $^1$H NMR (400 MHz, DMSO-$d_6$) δ 13.01 (bs, 1H), 8.3-8.01 (m, 5H), 7.85 (d, J=7.2 Hz, 2H); MS (ESI) m/z 366 $[M+H]^+$.

Step 3: Preparation of (4-(3-iodoimidazo[1,2-b] pyridazin-6-yl) phenyl) (4-methylpiperazin-1-yl) methanone A solution of 4-(3-iodoimidazo[1,2-b] pyridazin-6-yl) benzoic acid (1.5 g, 4.109 mmol), NMM (0.67 mL, 6.164 mmol) and HATU (3.12 g, 8.218 mmol) in DMF (20 mL) was stirred for 30 min. 1-methylpiperazine (0.546 mL, 4.90 mmol) was added and the mixture was stirred at room temperature for 6 h, then was diluted with EtOAc and washed with water and brine solution. The organic layer was dried over anhydrous Na$_2$SO$_4$, filtered and concentrated under reduced pressure. The crude product was purified by column chromatography (silica gel, eluent CHCl$_3$/CH$_3$OH 90:10) to give (4-(3-iodoimidazo[1,2-b]pyridazin-6-yl)phenyl)(4-methylpiperazin-1-yl)methanone (1.5 g, 82%, LC-MS 95%) as a yellow solid. MS (ESI) m/z: 448.06 [M+1].

Intermediate 9: (4-(3-iodoimidazo[1,2-b]pyridazin-6-yl)phenyl)(morpholino)methanone

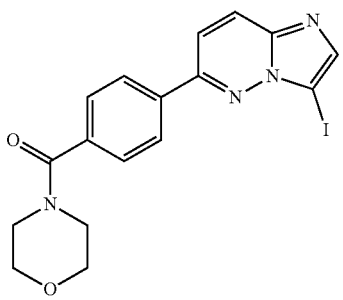

Intermediate 9

To a solution of 4-(3-iodoimidazo[1,2-b]pyridazin-6-yl)benzoic acid (4 g, 10.95 mmol) in DMF (50 mL) was added NMM (2.21 mL, 21.91 mmol), HATU (8.32 g, 21.91 mmol) and the mixture was stirred for 30 min prior to the addition of morpholine (1.14 mL, 13.14 mmol). The reaction mixture was stirred for 16 h and was diluted with EtOAc and washed with water and brine solution. The organic layer was dried over anhydrous $Na_2SO_4$ and concentrated under reduced pressure. The crude product was purified by column chromatography (silica gel, eluent $CH_2Cl_2$/MeOH 95:5) to afford (4-(3-iodoimidazo[1,2-b]pyridazin-6-yl)phenyl)(morpholino)methanone (4.2 g, 88%) as an off-white solid. MS (ESI) m/z 435 [M+1]+.

Example 1: (4-methylpiperazin-1-yl)(4-(3-(o-tolylethynyl)imidazo[1,2-b]pyridazin-6-yl)phenyl)methanone

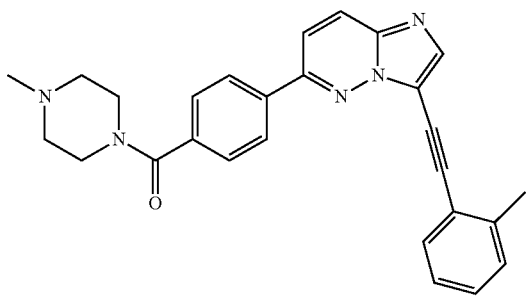

To a solution of (4-(3-ethynylimidazo[1,2-b]pyridazin-6-yl)phenyl)(4-methylpiperazin-1-yl)methanone (30 mg, 0.089 mmol), 1-iodo-2-methylbenzene (13.3 μL, 0.104 mmol) in a mixture of THF and DMF (2:1, 1.5 mL) was added $PdCl_2(PPh_3)_2$ (3.0 mg, 0.004 mmol), CuI (1.6 mg, 0.0086 mmol), $Et_3N$ (1 mL) and then the reaction mixture was stirred at room temperature for 12 h. The reaction mixture was concentrated in vacuo to dryness and then purified by flash column chromatography (silica gel, eluent $CH_2Cl_2$/$CH_3OH$ 95:5) to afford (4-methylpiperazin-1-yl)(4-(3-(o-tolylethynyl)imidazo[1,2-b]pyridazin-6-yl)phenyl)methanone (20 mg, 53%, AUC HPLC 98%) as a light yellow solid. 1H NMR (600 MHz, DMSO-d6) δ (ppm): 8.35 (d, J=9.4 Hz, 1H), 8.28-8.17 (m, 3H), 8.00 (d, J=9.3 Hz, 1H), 7.62 (d, J=8.4 Hz, 2H), 7.59 (d, J=7.8 Hz, 1H), 7.41-7.33 (m, 2H), 7.29 (td, J=7.2, 1.7 Hz, 1H), 3.84-3.56 (m, 3H), 2.72-2.51 (m, 6H), 2.37 (s, 3H); 13C NMR (150 MHz, DMSO-d6) δ (ppm): 168.4, 151.3, 139.5, 138.3, 137.3, 135.7, 131.1, 129.8, 129.1, 127.7, 127.1, 126.5, 126.1, 121.6, 117.6, 112.5, 97.5, 80.5, 54.0, 53.7, 44.7, and 20.3; MS (ESI) m/z 436 [$C_{27}H_{25}N_5O$+H]+.

Example 2: (4-methylpiperazin-1-yl) (4-(3-(phenylethynyl) imidazo[1,2-b]pyridazin-6-yl)phenyl)methanone

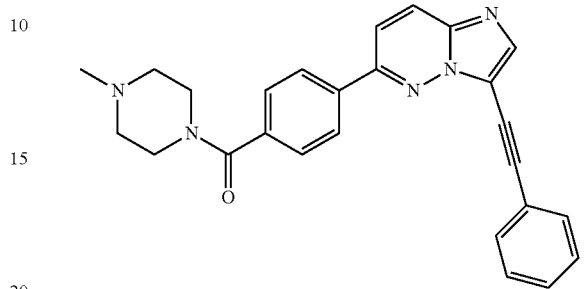

The title compound was synthesized from (4-(3-ethynylimidazo[1,2-b]pyridazin-6-yl)phenyl)(4-methylpiperazin-1-yl)methanone and iodobenzene in a similar method to that described for Example 1. The reaction crude product was purified by flash column chromatography (silica gel, eluent $CH_2Cl_2$/$CH_3OH$ 95:5) to afford (4-methylpiperazin-1-yl)(4-(3-(phenylethynyl)imidazo[1,2-b]pyridazin-6-yl)phenyl)methanone (18 mg, 50%, AUC HPLC 98%) as a light yellow solid; 1H NMR (600 MHz, DMSO-d6) δ (ppm): 8.34 (d, J=9.4 Hz, 1H), 8.29-8.15 (m, 3H), 7.98 (d, J=9.4 Hz, 1H), 7.68-7.62 (m, 2H), 7.62-7.56 (m, 2H), 7.48 (dd, J=5.1, 2.0 Hz, 3H), 3.68-3.65 (m, 2H), 2.48-2.32 (m, 4H), 2.26 (s, 3H); 13C NMR (150 MHz, DMSO-d6) δ (ppm): 168.3, 151.3, 138.8, 137.5, 135.6, 131.2, 129.3, 128.9, 127.7, 127.1, 126.4, 121.7, 117.6, 112.4, 98.4, 76.6, 54.4, 54.0, 45.2; MS (ESI) m/z 422 [$C_{26}H_{23}N_5O$+H]+.

Example 3: (4-methylpiperazin-1-yl)(4-(3-(m-tolylethynyl)imidazo[1,2-b]pyridazin-6-yl)phenyl)methanone

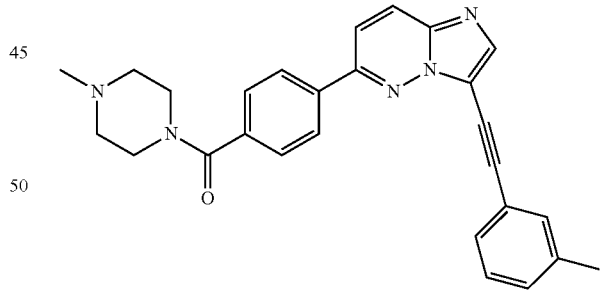

The title compound was synthesized from (4-(3-ethynylimidazo[1,2-b]pyridazin-6-yl)phenyl)(4-methylpiperazin-1-yl)methanone and 1-iodo-3-methylbenzene in a similar method to that described for Example 1. The reaction crude product was purified by flash column chromatography (silica gel, eluent $CH_2Cl_2$/$CH_3OH$ 95:5) to afford (4-methylpiperazin-1-yl)(4-(3-(m-tolylethynyl)imidazo[1,2-b]pyridazin-6-yl)phenyl)methanone (15 mg, 30%, AUC HPLC 98%) as a light yellow solid; 1H NMR (600 MHz, DMSO-d6) δ (ppm): 8.34 (d, J=9.5 Hz, 1H), 8.24-8.16 (m, 3H), 7.98 (d, J=9.5 Hz, 1H), 7.64-7.56 (m, 2H), 7.50-7.41 (m, 2H), 7.37 (t, J=7.6 Hz, 1H), 7.29 (ddt, J=7.9, 2.0, 0.9 Hz, 1H), 3.66-3.64 (m, 2H), 2.38-2.24 (m, 7H), 2.20 (s, 3H); $^{13}$C NMR (150 MHz, DMSO-d$_6$) δ (ppm): 168.3, 151.3, 138.9, 138.7, 138.3, 137.6, 135.5, 131.6, 130.0, 128.8, 128.4, 127.7, 127.2, 126.4, 121.5, 117.7, 112.3, 98.5, 76.2, 54.7, 54.2, 45.6, 20.7; MS (ESI) m/z 436 [C$_{27}$H$_{25}$N$_5$O+H]$^+$.

Example 4: (4-methylpiperazin-1-yl)(4-(3-(p-tolylethynyl)imidazo[1,2-b]pyridazin-6-yl)phenyl)methanone

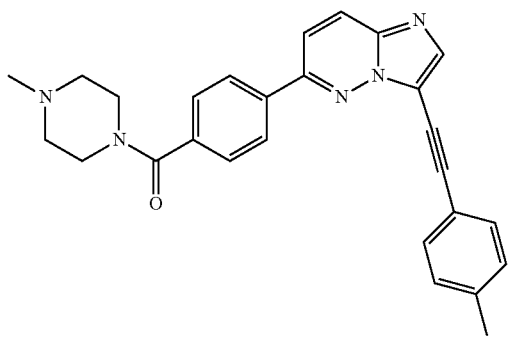 [SMILES: Cc1ccc(C#Cc2cnc3ccc(-c4ccc(C(=O)N5CCN(C)CC5)cc4)nn23)cc1]

The title compound was synthesized from (4-(3-ethynylimidazo[1,2-b]pyridazin-6-yl)phenyl)(4-methylpiperazin-1-yl)methanone and 1-iodo-4-methylbenzene in a similar method to that described for Example 1. The reaction crude product was purified by flash column chromatography (silica gel, eluent CH$_2$Cl$_2$/CH$_3$OH 95:5) to afford (4-methylpiperazin-1-yl) (4-(3-(p-tolylethynyl)imidazo[1,2-b]pyridazin-6-yl)phenyl)methanone (21 mg, 42%, AUC HPLC 98%) as a light yellow solid. $^1$H NMR (600 MHz, DMSO-d$_6$) δ (ppm): 8.33 (d, J=9.5 Hz, 1H), 8.28-8.12 (m, 3H), 7.97 (d, J=9.3 Hz, 1H), 7.59 (d, J=8.2 Hz, 2H), 7.57-7.50 (m, 2H), 7.29 (d, J=7.8 Hz, 2H), 3.67-3.59 (m, 2H), 2.41-2.22 (m, 7H), 2.20 (s, 3H); $^{13}$C NMR (150 MHz, DMSO-d$_6$) δ (ppm): 168.3, 151.3, 139.2, 138.6, 137.6, 135.6, 131.2, 129.5, 127.7, 127.1, 126.4, 118.7, 117.6, 112.5, 98.5, 76.0, 54.6, 54.2, 45.5, 21.1; MS (ESI) m/z 436 [C$_{27}$H$_{25}$N$_5$O+H]$^+$.

Example 5: (4-methylpiperazin-1-yl) (4-(3-(pyridin-4-ylethynyl)imidazo[1,2-b]pyridazin-6-yl)phenyl) methanone

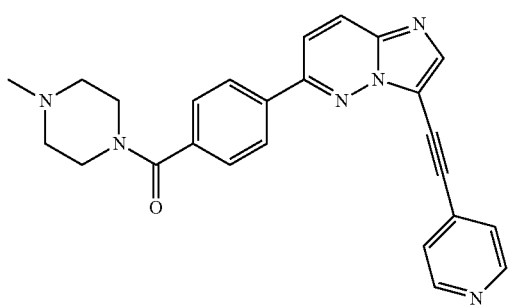 [SMILES: CN1CCN(C(=O)c2ccc(-c3ccc4ncc(C#Cc5ccncc5)n4n3)cc2)CC1]

The title compound was synthesized from (4-methylpiperazin-1-yl)(4-(3-(pyridin-4-ylethynyl)imidazo[1,2-b]pyridazin-6-yl)phenyl) methanone and 4-iodopyridine in a similar method to that described for Example 1. The reaction crude product was purified by flash column chromatography (silica gel, eluent CH$_2$Cl$_2$/CH$_3$OH 95:5) to afford (4-methylpiperazin-1-yl)(4-(3-(pyridin-4-ylethynyl)imidazo[1,2-b]pyridazin-6-yl)phenyl)methanone (16 mg, 46%, AUC HPLC 97%) as a light yellow solid. $^1$H NMR (600 MHz, DMSO-d$_6$) δ (ppm): 8.67 (d, J=4.9 Hz, 2H), 8.35 (d, J=9.5 Hz, 1H), 8.28 (s, 1H), 8.22 (d, J=8.0 Hz, 2H), 8.02 (d, J=9.5 Hz, 1H), 7.63 (d; J=8.0 Hz, 2H), 7.60 (d, J=5.3 Hz, 2H), 3.82-3.69 (m, 2H), 2.87-2.60 (m, 4H), 2.47 (s, 3H); $^{13}$C NMR (150 MHz, DMSO-d$_6$) δ (ppm): 168.6, 151.6, 150.2, 139.9, 139.5, 137.2, 135.7, 129.7, 128.0, 127.4, 126.7, 125.0, 118.4, 111.5, 96.2, 81.1, 53.5, 44.2; MS (ESI) m/z 423 [C$_{25}$H$_{22}$N$_6$O+H]$^+$.

Example 6. (4-(3-((4-methoxyphenyl)ethynyl)imidazo[1,2-b]pyridazin-6-yl)phenyl)(4-methylpiperazin-1-yl)methanone

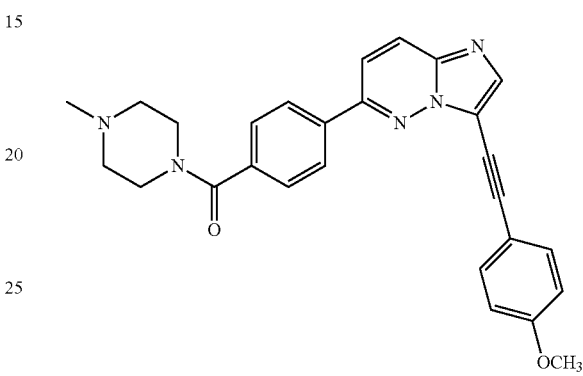

The title compound was synthesized from (4-(3-ethynylimidazo[1,2-b]pyridazin-6-yl)phenyl)(4-methylpiperazin-1-yl)methanone and 1-iodo-4-methoxybenzene in a similar method to that described for Example 1. The reaction crude product was purified by flash column chromatography (silica gel, eluent CH$_2$Cl$_2$/CH$_3$OH 95:5) to afford (4-(3-((4-methoxyphenyl)ethynyl)imidazo[1,2-b]pyridazin-6-yl)phenyl)(4-methylpiperazin-1-yl)methanone (16 mg, 41%, AUC HPLC 97%) as a light brown solid; $^1$H NMR (600 MHz, DMSO-d$_6$) δ (ppm): 8.45-8.12 (m, 4H), 7.96 (d, J=7.4 Hz, 1H), 7.65-7.53 (m, 4H), 7.03 (d, J=8.7 Hz, 2H), 3.81 (s, 3H), 3.74-3.56 (m, 2H), 3.39-3.28 (m, 2H), 2.43-2.31 (m, 4H), 2.21 (s, 3H); $^{13}$C NMR (150 MHz, DMSO-d$_6$) δ (ppm): 168.5, 160.0, 151.4, 137.6, 135.7, 133.1, 127.8, 127.3, 127.2, 117.6, 114.7, 113.6, 110.8, 98.6, 55.4, 54.6, 54.1 and 45.5; MS (ESI) m/z 452 [C$_{27}$H$_{25}$N$_5$O$_2$+H]$^+$.

Example 7: N-(4-((6-(4-(4-methylpiperazine-1-carbonyl)phenyl)imidazo[1,2-b]pyridazin-3-yl)ethynyl)phenyl)acetamide

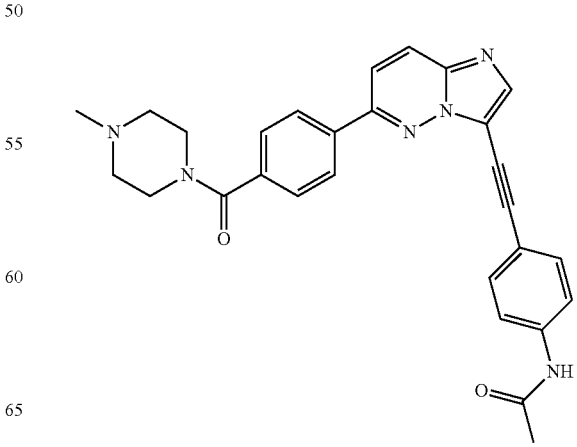

The title compound was synthesized from (4-(3-ethynylimidazo[1,2-b]pyridazin-6-yl)phenyl)(4-methylpiperazin-1-yl)methanone and N-(4-iodophenyl)acetamide in a similar method to that described for Example 1. The reaction crude product was purified by flash column chromatography (silica gel, eluent $CH_2Cl_2/CH_3OH$ 94:6) to afford N-(4-((6-(4-(4-methylpiperazine-1-carbonyl)phenyl)imidazo[1,2-b]pyridazin-3-yl)ethynyl)phenyl)acetamide (8 mg, 23%, AUC HPLC 99%) as a yellow solid; $^1$H NMR (600 MHz, DMSO-d$_6$) δ (ppm): 10.22 (s, 1H), 8.33 (d, J=9.5 Hz, 1H), 8.25-8.15 (m, 3H), 7.97 (d, J=9.5 Hz, 1H), 7.71 (d, J=8.4 Hz, 2H), 7.63-7.55 (m, 4H), 3.66-3.67 (m, 2H), 2.44-2.25 (m, 4H), 2.08 (s, 3H), 2.08 (s, 3H); $^{13}$C NMR (150 MHz, DMSO-d$_6$) δ (ppm): 168.7, 168.4, 151.3, 140.2, 138.7, 138.5, 135.6, 132.1, 127.8, 127.2, 126.4, 119.0, 117.5, 115.7, 112.5, 99.5, 98.6, 75.6, 54.2, 40.0, 24.1; MS (ESI) m/z 479 $[C_{28}H_{26}N_6O_2+H]^+$.

Example 8: Preparation of N-(3-((6-(4-(4-methylpiperazine-1-carbonyl)phenyl)imidazo[1,2-b]pyridazin-3-yl)ethynyl)phenyl)acetamide

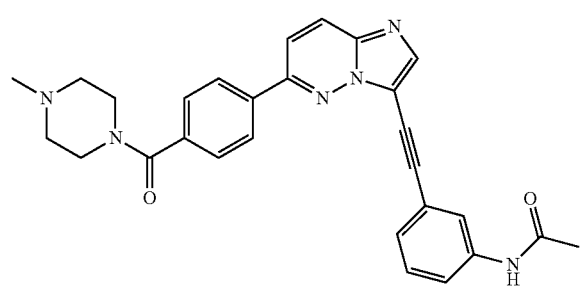 [SMILES: CC(=O)Nc1cccc(C#Cc2cnc3ccc(-c4ccc(C(=O)N5CCN(C)CC5)cc4)nn23)c1]

The title compound was synthesized from (4-(3-ethynylimidazo[1,2-b]pyridazin-6-yl)phenyl)(4-methylpiperazin-1-yl)methanone and N-(3-iodophenyl)acetamide in a similar method to that described for Example 1. The reaction crude product was purified by flash column chromatography (silica gel, eluent $CH_2Cl_2/CH_3OH$ 95:5) to afford N-(3-((6-(4-(4-methylpiperazine-1-carbonyl)phenyl)imidazo[1,2-b]pyridazin-3-yl)ethynyl)phenyl)acetamide (15 mg, 43%, AUC HPLC 98%) as a light yellow solid; $^1$H NMR (600 MHz, DMSO-d$_6$) δ (ppm): 10.24 (s, 1H), 8.33 (d, J=9.5 Hz, 1H), 8.24-8.20 (m, 3H), 8.05-7.91 (m, 2H), 7.67 (d, J=8.2 Hz, 2H), 7.57 (dd, J=7.9, 2.0 Hz, 1H), 7.40 (t, J=7.9 Hz, 1H), 7.30 (d, J=7.6 Hz, 1H), 3.74-3.59 (m, 4H), 3.20-3.14 (m, 4H), 2.72 (s, 3H), 2.08 (s, 3H); $^{13}$C NMR (150 MHz, DMSO-d$_6$) δ (ppm): 169.0, 168.7, 151.4, 139.8, 139.0, 138.8, 136.6, 136.1, 128.1, 127.3, 126.6, 125.9, 122.0, 121.3, 119.9, 117.9, 112.3, 98.6, 76.4, 52.4, 45.7, 24.2; MS (ESI) m/z 479 $[C_{28}H_{26}N_6O_2+H]^+$.

Example 9: 4-((6-(4-(morpholine-4-carbonyl)phenyl)imidazo[1,2-b]pyridazin-3-yl)ethynyl)benzonitrile

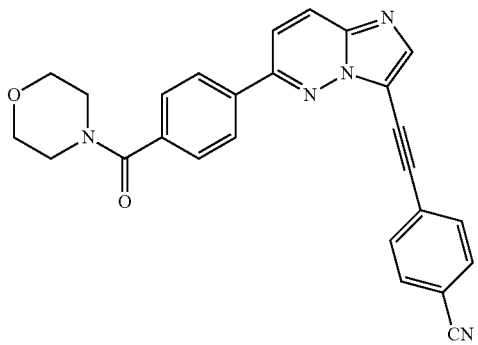 [SMILES: N#Cc1ccc(C#Cc2cnc3ccc(-c4ccc(C(=O)N5CCOCC5)cc4)nn23)cc1]

The title compound was synthesized from (4-(3-ethynylimidazo[1,2-b]pyridazin-6-yl)phenyl)(morpholino)methanone and 4-iodobenzonitrile (51 mg, 0.225 mmol) in a similar method to that described for Example 1. The reaction crude product was purified by flash column chromatography (silica gel, eluent $CH_2Cl_2/CH_3OH$ 96:4) to afford 4-((6-(4-(morpholine-4-carbonyl)phenyl)imidazo[1,2-b]pyridazin-3-yl)ethynyl)benzonitrile (50.5 mg, 77%, AUC HPLC 99%) as a light yellow solid. $^1$H NMR (600 MHz, DMSO-d$_6$) δ (ppm): 8.44-8.27 (m, 2H), 8.22 (d, J=8.2 Hz, 2H), 8.03 (d, J=9.1 Hz, 1H), 7.94 (d, J=8.3 Hz, 2H), 7.82 (d, J=8.3 Hz, 2H), 7.63 (d, J=8.2 Hz, 2H), 3.71-3.51 (m, 6H), 3.41-3.33 (m, 2H); $^{13}$C NMR (150 MHz, DMSO-d$_6$) δ (ppm): 168.5, 151.6, 139.8, 137.4, 135.6, 132.9, 131.9, 128.0, 127.3, 126.7, 126.6, 118.5, 118.4, 111.3, 97.4, 80.8, 66.2, 45.8; MS (ESI) m/z 434 $[C_{26}H_{19}N_5O_2+H]^+$.

Example 10: morpholino(4-(3-(pyridin-3-ylethynyl)imidazo[1,2-b]pyridazin-6-yl)phenyl)methanone

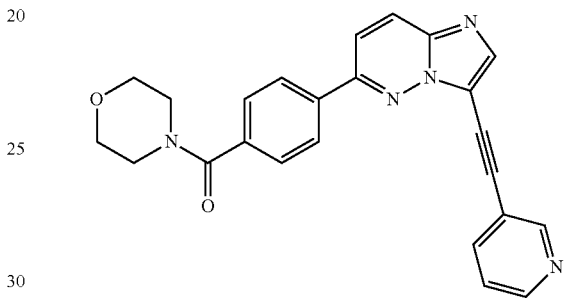

The title compound was synthesized from (4-(3-ethynylimidazo[1,2-b]pyridazin-6-yl)phenyl)(morpholino)methanone and 3-iodopyridine in a similar method to that described for Example 1. The reaction crude product was purified by flash column chromatography (silica gel, eluent $CH_2Cl_2/CH_3OH$ 95:5) to afford morpholino(4-(3-(pyridin-3-ylethynyl)imidazo[1,2-b]pyridazin-6-yl)phenyl)methanone (10.0 mg, 16%, AUC HPLC 96%) as a light yellow solid. $^1$H NMR (600 MHz, DMSO-d$_6$) δ (ppm): 8.85 (s, 1H), 8.68-8.58 (m, 1H), 8.35 (d, J=9.5 Hz, 1H), 8.26 (s, 1H), 8.22 (d, J=8.4 Hz, 2H), 8.08 (dt, J=7.9, 1.9 Hz, 1H), 8.01 (d, J=9.6 Hz, 1H), 7.63 (d, J=8.4 Hz, 2H), 7.54-7.51 (m, 1H), 3.68-3.51 (m, 8H); 13C NMR (150 MHz, DMSO-d$_6$) δ (ppm): 168.5, 151.5, 151.4, 149.5, 139.3, 139.2, 138.6, 137.4, 135.6, 128.0, 127.3, 126.6, 123.9, 119.0, 118.1, 111.9, 95.4, 79.7, 66.1, 47.7; MS (ESI) m/z 410 $[C_{24}H_{19}N_5O_2+H]^+$.

Example 11: N-(3-((6-(4-(morpholine-4-carbonyl)phenyl)imidazo[1,2-b]pyridazin-3-yl)ethynyl)phenyl)methane sulfonamide

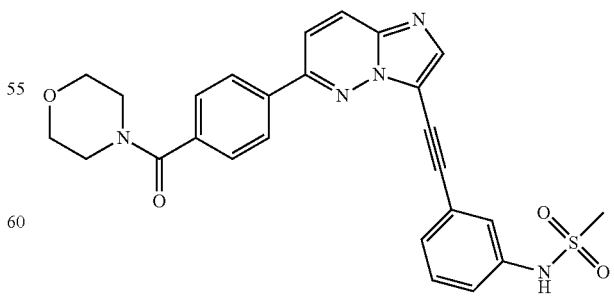

The title compound was synthesized from (4-(3-ethynylimidazo[1,2-b]pyridazin-6-yl)phenyl)(morpholino)methanone and N-(3-iodophenyl)methanesulfonamide in a similar method to that described for Example 1. The reaction crude product was purified by flash column chromatography (silica gel, eluent $CH_2Cl_2/CH_3OH$ 94:6) to afford N-(3-((6-(4-(morpholine-4-carbonyl)phenyl)imidazo[1,2-b]pyridazin-3-yl)ethynyl)phenyl)methane sulfonamide (20.0 mg, 28%, AUC HPLC 97%) as a light yellow solid; $^1$H NMR (600 MHz, DMSO-$d_6$) δ (ppm): 8.34 (d, J=9.5 Hz, 1H), 8.26-8.18 (m, 3H), 7.99 (d, J=9.5 Hz, 1H), 7.63 (d, J=8.1 Hz, 2H), 7.46-7.39 (m, 2H), 7.32 (d, J=7.6 Hz, 1H), 7.25 (dd, J=8.1, 2.1 Hz, 1H), 3.71-3.55 (m, 8H), 3.01 (s, 3H); $^{13}$C NMR (150 MHz, DMSO-$d_6$) δ (ppm): 168.5, 151.4, 140.2, 139.0, 138.8, 137.3, 135.7, 130.1, 128.0, 127.2, 126.5, 125.7, 122.5, 121.5, 120.5, 117.8, 112.2, 98.4, 76.7, 66.1, 48.7, 47.7; MS (ESI) m/z 502 [$C_{26}H_{23}N_5O_4S$+H]$^+$.

Example 12: N-(3-((6-(4-(morpholine-4-carbonyl)phenyl)imidazo[1,2-b]pyridazin-3-yl)ethynyl)phenyl)benzamide

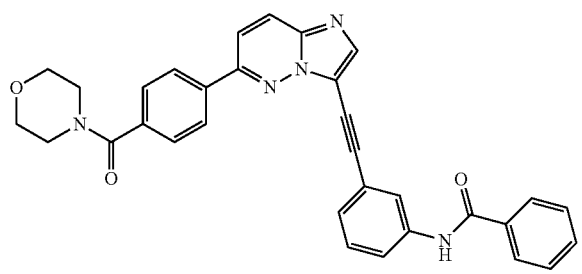 [SMILES: O=C(Nc1cccc(C#Cc2cnc3ccc(-c4ccc(C(=O)N5CCOCC5)cc4)nn23)c1)c1ccccc1]

The title compound was synthesized from (4-(3-ethynylimidazo[1,2-b]pyridazin-6-yl)phenyl)(morpholino)methanone and N-(3-iodophenyl)benzamide in a similar method to that described for Example 1. The reaction crude product was purified by flash column chromatography (silica gel, eluent $CH_2Cl_2/CH_3OH$ 95:5) to afford N-(3-((6-(4-(morpholine-4-carbonyl)phenyl)imidazo[1,2-b]pyridazin-3-yl)ethynyl)phenyl)benzamide (20.0 mg, 25%, AUC HPLC 97%) as a yellow solid; $^1$H NMR (600 MHz, DMSO-$d_6$) δ (ppm): 10.43 (s, 1H), 8.34 (d, J=9.4 Hz, 1H), 8.30-8.13 (m, 4H), 8.03-7.92 (m, 3H), 7.81 (dt, J=8.5, 1.3 Hz, 1H), 7.67-7.58 (m, 3H), 7.58-7.51 (m, 2H), 7.47 (t, J=7.9 Hz, 1H), 7.38 (dt, J=7.8, 1.3 Hz, 1H), 3.69-3.52 (m, 4H), 3.37-3.22 (m, 4H); $^{13}$C NMR (150 MHz, DMSO-$d_6$) δ (ppm): 168.6, 166.0, 151.4, 139.6, 138.8, 137.3, 135.7, 134.7, 131.9, 129.5, 128.6, 128.0, 127.8, 127.2, 126.6, 126.4, 122.7, 122.0, 121.2, 117.8, 98.6, 76.6, 66.1, 47.8; MS (ESI) m/z 528 [$C_{32}H_{25}N_5O_3$+H]$^+$.

Example 13: N-(3-((6-(4-(morpholine-4-carbonyl)phenyl)imidazo[1,2-b]pyridazin-3-yl)ethynyl)phenyl)acetamide

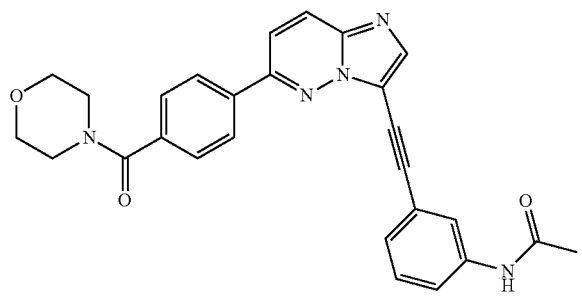 [SMILES: CC(=O)Nc1cccc(C#Cc2cnc3ccc(-c4ccc(C(=O)N5CCOCC5)cc4)nn23)c1]

The title compound was synthesized from (4-(3-ethynylimidazo[1,2-b]pyridazin-6-yl)phenyl)(morpholino)methanone and N-(3-iodophenyl)acetamide in a similar method to that described for Example 1. The reaction crude product was purified by flash column chromatography (silica gel, eluent $CH_2Cl_2/CH_3OH$ 95:5) to afford N-(3-((6-(4-(morpholine-4-carbonyl)phenyl)imidazo[1,2-b]pyridazin-3-yl)ethynyl)phenyl)acetamide (15.0 mg, 21%, AUC HPLC 99%) as a yellow solid; $^1$H NMR (600 MHz, DMSO-$d_6$) δ (ppm): 10.15 (s, 1H), 8.33 (d, J=9.5 Hz, 1H), 8.27-8.16 (m, 3H), 8.01-7.97 (m, 2H), 7.64 (d, J=8.3 Hz, 2H), 7.55 (ddd, J=8.1, 2.2 Hz, 1H), 7.40 (t, J=7.9 Hz, 1H), 7.31 (dt, J=7.6, 1.3 Hz, 1H), 3.68-3.54 (m, 8H), 2.08 (s, 3H). $^{13}$C NMR (150 MHz, DMSO-$d_6$) δ (ppm): 168.9, 168.6, 151.4, 139.7, 139.0, 138.8, 137.3, 135.7, 129.6, 128.0, 127.2, 126.5, 125.8, 122.0, 121.3, 119.9, 117.8, 112.3, 98.6, 76.4, 66.2, 24.1; MS (ESI) m/z 466 [$C_{27}H_{23}N_5O_3$+H]$^+$.

Example 14: (4-(3-((3-chloropyridin-4-yl)ethynyl)imidazo[1,2-b]pyridazin-6-yl)phenyl) (morpholino) methanone

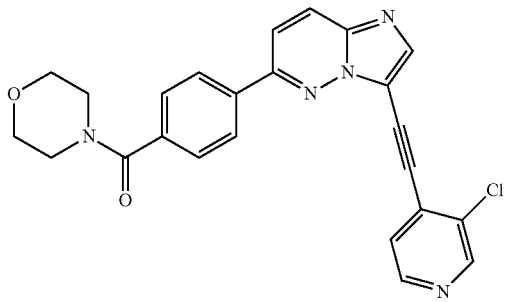 [SMILES: O=C(c1ccc(-c2ccc3ncc(C#Cc4ccncc4Cl)n3n2)cc1)N1CCOCC1]

The title compound was synthesized from (4-(3-ethynylimidazo[1,2-b]pyridazin-6-yl)phenyl)(morpholino)methanone and 3-chloro-4-iodopyridine in a similar method to that described for Example 1. The reaction crude product was purified by flash column chromatography (silica gel, eluent EtOAc/$CH_3OH$ 95:5) to afford (4-(3-((3-chloropyridin-4-yl)ethynyl)imidazo[1,2-b]pyridazin-6-yl)phenyl) (morpholino)methanone (22.8 mg, 34.5%, AUC HPLC 96%) as a yellow solid; $^1$H NMR (600 MHz, DMSO-$d_6$) δ (ppm): 8.26 (d, J=7.0 Hz, 4H), 8.13 (s, 2H), 7.84 (s, 2H), 7.63 (d, J=7.7 Hz, 5H), 3.67 (s), 3.58 (s), 2.57 (s, 2H), 1.40-1.10 (m, 4H); $^{13}$C NMR (150 MHz, DMSO-$d_6$) δ (ppm): 179.9, 168.8, 152.1, 149.6, 148.5, 137.9, 135.9, 129.5, 128.3, 127.6, 118.9, 93.9, 66.5, 48.0, 42.5, 40.3, 40.2, 40.1, 39.9, 39.8, 39.6, 39.5, 29.9; MS (ESI) m/z 444 [$C_{24}H_{18}ClN_5O_2$+H]$^+$.

Example 15: (4-(3-((2-chloropyridin-4-yl)ethynyl)imidazo[1,2-b]pyridazin-6-yl)phenyl) (morpholino) methanone

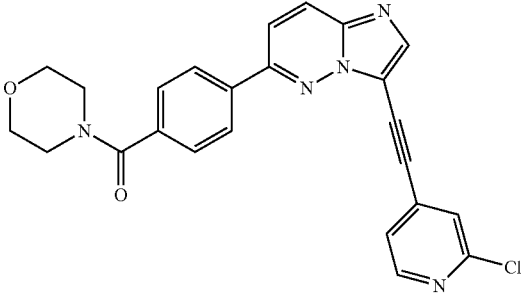 [SMILES: O=C(c1ccc(-c2ccc3ncc(C#Cc4ccnc(Cl)c4)n3n2)cc1)N1CCOCC1]

The title compound was synthesized from (4-(3-ethynylimidazo[1,2-b]pyridazin-6-yl)phenyl)(morpholino)methanone and 2-chloro-4-iodopyridine in a similar method to that described for Example 1. The reaction crude product was purified by flash column chromatography (silica gel, eluent EtOAc/CH$_3$OH 93:7) to afford (4-(3-((2-chloropyridin-4-yl)ethynyl)imidazo[1,2-b]pyridazin-6-yl)phenyl)(morpholino)methanone (85 mg, 64%, AUC HPLC 96.0%) as a light brown solid; $^1$H NMR (600 MHz, DMSO-d$_6$) δ (ppm): 8.48 (d, J=4.8 Hz, 1H), 8.37-8.33 (m, 1H), 8.20 (d, J=7.8 Hz, 2H), 8.04-8.00 (m, 1H), 7.73 (s, 1H), 7.64-7.57 (m, 4H), 3.39-3.31 (m, 4H); $^{13}$C-NMR (150 MHz, DMSO-d$_6$) δ (ppm): 168.9, 152.1, 151.1, 150.7, 137.6, 135.7, 133.2, 128.2, 127.6, 127.0, 125.2, 124.6, 122.3, 119.0, 95.4, 83.1, 66.3 and 46.5; MS (ESI) m/z 444 [C$_{24}$H$_{18}$ClN$_5$O$_2$+H]$^+$.

Example 16: (4-(3-((1H-pyrazolo[3,4-b]pyridin-4-yl)ethynyl)imidazo[1,2-b]pyridazin-6-yl)phenyl)(morpholino)methanone

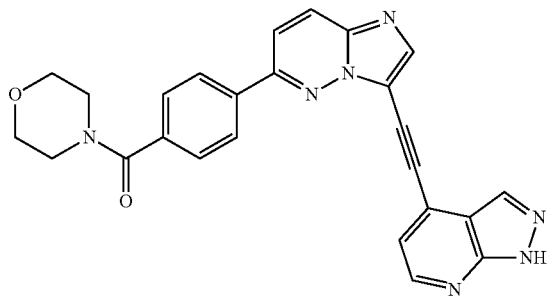 [SMILES: O=C(c1ccc(-c2ccc3ncc(C#Cc4ccnc5[nH]ncc45)n3n2)cc1)N1CCOCC1]

The title compound was synthesized from (4-(3-ethynylimidazo[1,2-b]pyridazin-6-yl)phenyl)(morpholino)methanone and 4-iodo-1H-pyrazolo[3,4-b]pyridine in a similar method to that described for Example 1. The reaction crude product was purified by flash column chromatography (silica gel, eluent EtOAc/CH$_3$OH 95:5) to afford (4-(3-((1H-pyrazolo[3,4-b]pyridin-4-yl)ethynyl)imidazo[1,2-b]pyridazin-6-yl)phenyl)(morpholino)methanone (22.0 mg, 20.3%, AUC HPLC 97%) as a yellow solid; $^1$H NMR (600 MHz, DMSO-d$_6$) δ (ppm): 8.59 (d, J=4.7 Hz, 1H), 8.38-8.35 (m, 2H), 8.32 (s, 1H), 8.23 (d, J=7.8 Hz, 2H), 8.03 (d, J=9.5 Hz, 1H), 7.64 (d, J=7.9 Hz, 2H), 7.41 (d, J=4.7 Hz, 1H), 3.68-3.38 (m, 8H); $^{13}$C NMR (150 MHz, DMSO-d$_6$) δ (ppm): 168.7, 152.0, 149.3, 140.2, 139.8, 137.5, 135.8, 132.2, 128.0, 127.4, 126.8, 122.9, 118.8, 118.2, 114.1, 111.6, 99.7, 94.9, 84.5, 66.2 and 47.8; MS (ESI) m/z 450 [C$_{25}$H$_{19}$N$_7$O$_2$+H]$^+$.

Example 17: (4-(3-((6-amino-1H-pyrrolo[2,3-b]pyridin-4-yl)ethynyl)imidazo[1,2-b]pyridazin-6-yl)phenyl)(morpholino)methanone

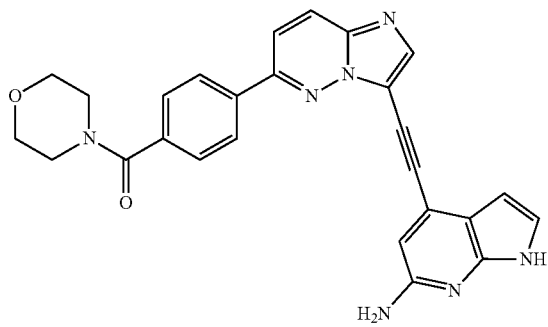 [SMILES: Nc1cc(C#Cc2cnc3ccc(-c4ccc(C(=O)N5CCOCC5)cc4)nn23)c2cc[nH]c2n1]

The title compound was synthesized from (4-(3-ethynylimidazo[1,2-b]pyridazin-6-yl)phenyl)(morpholino)methanone and 4-iodo-1H-pyrrolo[2,3-b]pyridin-6-amine in a similar method to that described for Example 1. The reaction crude product was purified by flash column chromatography (silica gel, eluent CH$_2$Cl$_2$/CH$_3$OH 94:6) to afford (4-(3-((6-amino-1H-pyrrolo[2,3-b]pyridin-4-yl)ethynyl)imidazo[1,2-b]pyridazin-6-yl)phenyl)(morpholino)methanone (8 mg, AUC HPLC 95%) as a light yellow solid. $^1$H NMR (600 MHz, DMSO-d$_6$) δ (ppm): 11.03 (s, 1H), 8.32 (d, J=6.0 Hz, 1H), 8.26 (s, 1H), 8.22 (d, J=6.0 Hz, 2H), 7.99 (d, J=6.0 Hz, 1H), 7.64 (d, J=6.0 Hz, 2H), 7.10 (d, J=6.0 Hz, 1H), 6.52 (s, 1H), 6.47 (d, J=6.0 Hz, 1H), 5.75 (s, 2H); $^{13}$C NMR (150 MHz, DMSO-d$_6$) δ (ppm): 169.1, 156.1, 152.1, 147.9, 139.6, 137.6, 136.1, 128.3, 127.6, 126.8, 122.7, 121.9, 118.7, 112.6, 111.9, 104.2, 99.6, 96.9, 80.7, 66.4, 63.3; MS (ESI) m/z 464 [C$_{26}$H$_{21}$N$_7$O$_2$+H]$^+$.

Example 18: morpholino(4-(3-((2-phenoxypyridin-4-yl)ethynyl)imidazo[1,2-b]pyridazin-6-yl)phenyl)methanone

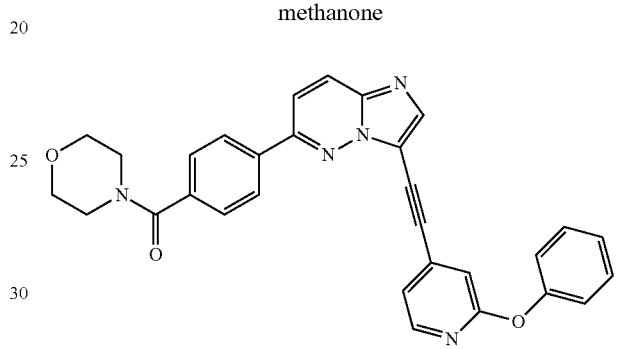

The title compound was synthesized from (4-(3-ethynylimidazo[1,2-b]pyridazin-6-yl)phenyl)(morpholino)methanone and 4-iodo-2-phenoxypyridine in a similar method to that described for Example 1. The reaction crude product was purified by flash column chromatography (silica gel, eluent EtOAc/CH$_3$OH 94:6) to afford morpholino(4-(3-((2-phenoxypyridin-4-yl)ethynyl)imidazo[1,2-b]pyridazin-6-yl)phenyl)methanone (12.0 mg, 20%, AUC HPLC 98%) as a light yellow solid. $^1$H NMR (600 MHz, DMSO-d$_6$) δ (ppm): 8.39 (d, J=9.5 Hz, 1H), 8.32 (s, 1H), 8.27-8.23 (m, 3H), 8.05 (d, J=9.5 Hz, 1H), 7.64 (d, J=8.3 Hz, 2H), 7.45 (t, J=7.9 Hz, 2H), 7.34 (d, J=5.0 Hz, 1H), 7.16 (m, 4H), 3.68-3.59 (m, 8H). $^{13}$C NMR (150 MHz, DMSO-d$_6$) δ (ppm): 168.4, 163.4, 153.5, 151.5, 148.2, 140.0, 139.5, 137.4, 135.4, 133.1, 129.8, 127.9, 127.2, 126.6, 124.8, 121.3, 120.2, 118.4, 112.3, 111.3, 95.8, 81.3, 72.5, 66.1 and 63.1; MS (ESI) m/z 502 [C$_{30}$H$_{23}$N$_5$O$_3$+H]$^+$.

Example 19: (4-(3-((2-methoxypyridin-4-yl)ethynyl)imidazo[1,2-b]pyridazin-6-yl)phenyl)(morpholino)methanone

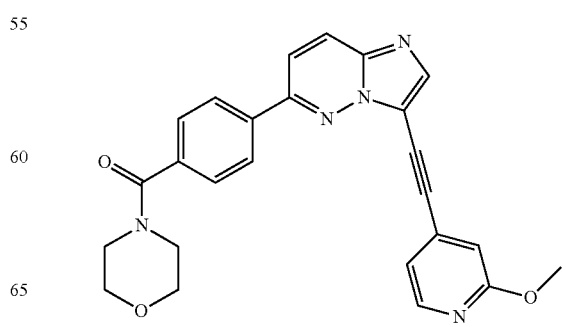

The title compound was synthesized from (4-(3-ethynylimidazo[1,2-b]pyridazin-6-yl)phenyl)(morpholino)methanone and 4-iodo-2-methoxypyridine in a similar method to that described for Example 1. The reaction crude product was purified by flash column chromatography (silica gel, eluent CH$_2$Cl$_2$/MeOH 95:5 to 90:10) to afford (4-(3-((2-methoxypyridin-4-yl)ethynyl)imidazo[1,2-b]pyridazin-6-yl)phenyl)(morpholino)methanone (99 mg, 75%, AUC HPLC 97%) as yellow solid. $^1$H NMR (400 MHz, DMSO-d$_6$) δ (ppm): 8.39 (d, J=9.5 Hz, 1H), 8.31 (s, 1H), 8.27 (d, J=5.3 Hz, 1H), 8.24 (d, J=8.3 Hz, 2H), 8.04 (d, J=9.5 Hz, 1H), 7.64 (d, J=8.3 Hz, 2H), 7.19 (dd, J=5.3, 1.2 Hz, 1H), 7.04 (s, 1H), 3.90 (s, 3H), 3.64 (bs, 6H), 3.40 (bs, 2H); 13C NMR (100 MHz, DMSO-d$_6$) δ (ppm): 168.34, 163.76, 151.46, 147.58, 139.76, 137.32, 135.42, 132.12, 127.79, 127.13, 126.52, 118.25, 118.18, 111.55, 95.93, 80.46, 65.99, 53.34; MS (ESI) m/z 440 [C$_{25}$H$_{21}$N$_5$O$_3$+H]$^+$.

Example 20: (4-(3-((1H-pyrrolo[3,2-b]pyridin-6-yl)ethynyl)imidazo[1,2-b]pyridazin-6-yl)phenyl) (morpholino)methanone

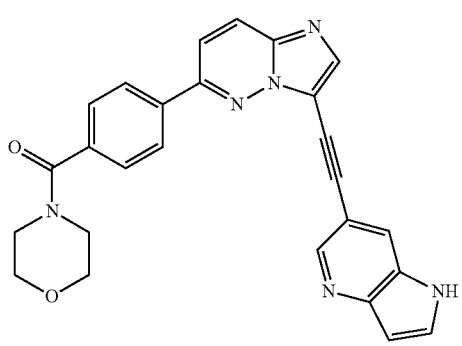 [SMILES: O=C(c1ccc(-c2ccc3ncc(C#Cc4cnc5cc[nH]c5c4)n3n2)cc1)N1CCOCC1]

The title compound was synthesized from (4-(3-ethynylimidazo[1,2-b]pyridazin-6-yl)phenyl)(morpholino)methanone and 6-iodo-1H-pyrrolo[3,2-b]pyridine in a similar method to that described for Example 1. The residue was purified by column chromatography (silica gel, eluent CH$_2$Cl$_2$/MeOH 95:5 to 90:10) to afford (4-(3-((1H-pyrrolo[3,2-b]pyridin-6-yl)ethynyl)imidazo[1,2-b]pyridazin-6-yl)phenyl)(morpholino)methanone (2.4 mg, AUC HPLC 99%) as yellow solid. 1H NMR (400 MHz, CD$_3$OD) δ (ppm): 8.47 (s, 1H), 8.27-8.25 (m, 3H), 8.16 (d, J=9.5 Hz, 1H), 8.07 (s, 1H), 7.92 (d, J=9.5 Hz, 1H), 7.64 (d, J=8.5 Hz, 2H), 7.47 (d, J=3.5 Hz, 1H), 6.56 (d, J=3.5 Hz, 1H), 3.77-3.66 (m, 6H), 3.50-3.48 (bs, 2H); MS (ESI) m/z 449 [C$_{26}$H$_{20}$N$_6$O$_2$+H]$^+$.

Example 21: (4-(3-((5-fluoro-1H-pyrrolo[2,3-b]pyridin-6-yl)ethynyl)imidazo[1,2-b]pyridazin-6-yl)phenyl)(morpholino)methanone

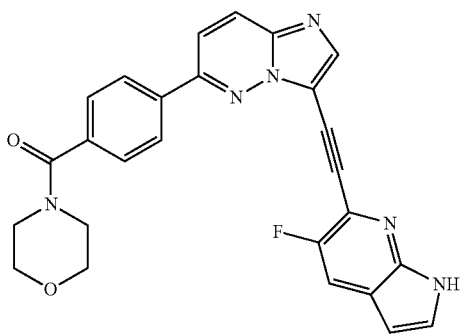 [SMILES: O=C(c1ccc(-c2ccc3ncc(C#Cc4nc5[nH]ccc5cc4F)n3n2)cc1)N1CCOCC1]

The title compound was synthesized from (4-(3-ethynylimidazo[1,2-b]pyridazin-6-yl)phenyl)(morpholino)methanone and 5-fluoro-6-iodo-1H-pyrrolo[2,3-b]pyridine in a similar method to that described for Example 1. The residue was purified by column chromatography (silica gel, eluent CH$_2$Cl$_2$/MeOH 95:5 to 90:10) to afford (4-(3-((5-fluoro-1H-pyrrolo[2,3-b]pyridin-6-yl)ethynyl)imidazo[1,2-b]pyridazin-6-yl)phenyl)(morpholino)methanone (13 mg, AUC HPLC 98%) as yellow solid. $^1$H NMR (400 MHz, CDCl$_3$) δ (ppm): 10.06 (bs, 1H), 8.17 (s, 1H), 8.14 (d, J=8.3 Hz, 2H), 8.11 (d, J=9.5 Hz, 1H), 7.71 (d, J=9.1 Hz, 1H), 7.62 (d, J=9.5 Hz, 1H), 7.55 (d, J=8.3 Hz, 2H), 7.52-7.51 (m, 1H), 6.45-6.44 (m, 1H), 3.90-3.48 (bs, 8H); 13C NMR (100 MHz, CDCl$_3$) δ (ppm): 169.66, 156.28, 151.65, 144.91, 139.75, 139.25, 137.01, 136.60, 129.12, 127.91, 127.50, 127.50, 126.18, 124.45, 121.29, 116.94, 114.56, 113.26, 101.51, 93.81, 80.59, 66.88, 46.20; MS (ESI) m/z 467 [C$_{26}$H$_{19}$FN$_6$O$_2$+H]$^+$.

Example 22: ((4-(3-((4-methylpyridin-3-yl)ethynyl)imidazo[1,2-b]pyridazin-6-yl)phenyl)(morpholino)methanone

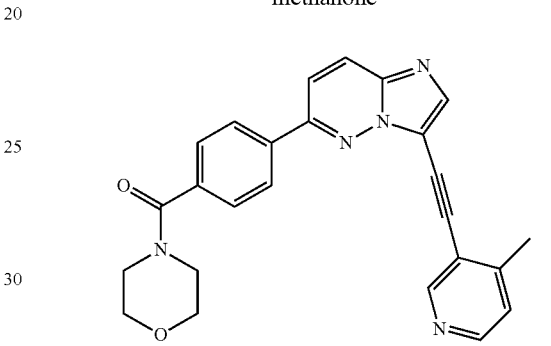

The title compound was synthesized from (4-(3-ethynylimidazo[1,2-b]pyridazin-6-yl)phenyl)(morpholino)methanone and 3-iodo-4-methylpyridine in a similar method to that described for Example 1. The reaction crude product was purified by column chromatography (silica gel, eluent CH$_2$Cl$_2$/MeOH 95:5 to 90:10) to afford ((4-(3-((4-methylpyridin-3-yl)ethynyl)imidazo[1,2-b]pyridazin-6-yl)phenyl)(morpholino)methanone (6.2 mg, AUC HPLC 99.9%) as yellow solid. $^1$H NMR (400 MHz, CD$_3$OD) δ (ppm): 8.63 (s, 1H), 8.38 (d, J=5.1 Hz, 1H), 8.20 (d, J=8.4 Hz, 2H), 8.14 (d, J=9.6 Hz, 1H), 8.07 (s, 1H), 7.90 (d, J=9.6 Hz, 1H), 7.62 (d, J=8.4 Hz, 2H), 7.38 (d, J=5.1 Hz, 1H), 3.78-3.68 (m, 6H), 3.50 (bs, 2H), 2.64 (s, 3H); $^{13}$C NMR (100 MHz, CD$_3$OD) δ (ppm): 171.69, 153.54, 151.92, 151.27, 149.33, 140.73, 138.96, 138.44, 137.89, 129.02, 128.61, 126.86, 126.14, 121.78, 119.47, 114.50, 95.20, 84.19, 67.79, 20.54; MS (ESI) m/z 424 [C$_{25}$H$_{21}$N$_5$O$_2$+H]$^+$.

Example 23: (4-(3-((1H-pyrrolo[2,3-b]pyridin-5-yl)ethynyl)imidazo[1,2-b]pyridazin-6-yl)phenyl) (morpholino)methanone

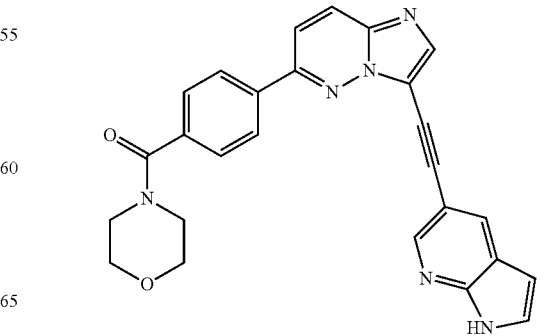

The title compound was synthesized from (4-(3-ethynylimidazo[1,2-b]pyridazin-6-yl)phenyl)(morpholino)methanone and 5-iodo-1H-pyrrolo[2,3-b]pyridine in a similar method to that described for Example 1. The residue was purified by column chromatography (silica gel, eluent CH$_2$Cl$_2$/MeOH 95:5 to 90:10) to afford (4-(3-((1H-pyrrolo[2,3-b]pyridin-5-yl)ethynyl)imidazo[1,2-b]pyridazin-6-yl)phenyl)(morpholino)methanone (6.2 mg, AUC HPLC 98%) as yellow solid. $^1$H NMR (400 MHz, CD$_3$OD) δ (ppm): 8.53 (d, J=1.7 Hz, 1H), 8.24 (d, J=8.4 Hz, 2H), 8.13 (d, J=9.5 Hz, 1H), 8.05-8.03 (m, 2H), 7.88 (d, J=9.5 Hz, 1H), 7.71 (d, J=3.3 Hz, 1H), 7.61 (d, J=8.4 Hz, 2H), 6.67-6.66 (m, 1H), 3.77-3.65 (m, 6H), 3.49 (bs, 2H); $^{13}$C NMR (100 MHz, CD$_3$OD) δ (ppm): 171.7, 153.4, 146.8, 145.8, 140.3, 138.7, 138.3, 138.1, 132.7, 129.7, 129.0, 128.6, 126.7, 122.8, 119.1, 115.0, 112.8, 103.0, 98.32, 77.66, 67.7; MS (ESI) m/z 449 [C$_{26}$H$_{20}$N$_6$O$_2$+H]$^+$.

Example 24: (4-(3-((1H-pyrrolo[2,3-b]pyridin-3-yl)ethynyl)imidazo[1,2-b]pyridazin-6-yl)phenyl) (morpholino)methanone

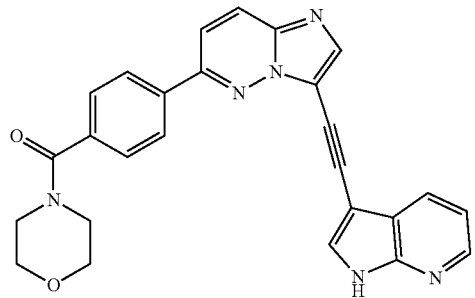 [SMILES: O=C(c1ccc(-c2ccc3ncc(C#Cc4c[nH]c5ncccc45)n3n2)cc1)N1CCOCC1]

The title compound was synthesized from (4-(3-ethynylimidazo[1,2-b]pyridazin-6-yl)phenyl)(morpholino)methanone and 3-iodo-1H-pyrrolo[2,3-b]pyridine in a similar method to that described for Example 1. The residue was purified by column chromatography (silica gel, eluent CH$_2$Cl$_2$/MeOH 95:5 to 90:10) and preparative HPLC (C18, eluents ACN/H$_2$O/HCOOH 0.01%) to afford (4-(3-((1H-pyrrolo[2,3-b]pyridin-3-yl)ethynyl)imidazo[1,2-b]pyridazin-6-yl)phenyl)(morpholino)methanone (27 mg, 20%, AUC HPLC 96%) as brown solid. $^1$H NMR (400 MHz, CDCl$_3$) δ (ppm): 9.46 (bs, 1H), 8.44 (dd, J=4.7, 1.4 Hz, 1H), 8.24 (dd, J=7.9, 1.4 Hz, 1H), 8.16 (d, J=8.4 Hz, 2H), 8.14-8.08 (m, 2H), 7.74 (d, J=1.9 Hz, 1H), 7.62-7.57 (m, 3H), 7.25 (dd, J=7.9, 4.7 Hz, 1H), 3.98-3.35 (m, 8H); $^{13}$C NMR (100 MHz, CDCl$_3$) δ (ppm): 169.66, 151.43, 147.77, 144.66, 138.75, 138.51, 136.96, 128.73, 128.65, 127.88, 127.47, 126.08, 120.92, 117.21, 116.33, 114.27, 97.22, 91.78, 77.20, 66.88; MS (ESI) m/z 449 [C$_{26}$H$_{20}$N$_6$O$_2$+H]$^+$.

Example 25: morpholino(4-(3-((5-(trifluoromethyl)-1H-pyrrolo[2,3-b]pyridin-3-yl)ethynyl)imidazo[1,2-b]pyridazin-6-yl)phenyl)methanone

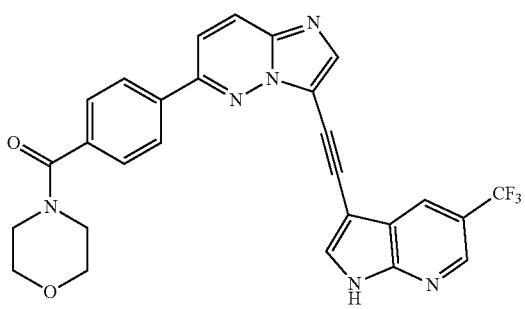 [SMILES: O=C(c1ccc(-c2ccc3ncc(C#Cc4c[nH]c5ncc(C(F)(F)F)cc45)n3n2)cc1)N1CCOCC1]

The title compound was synthesized from (4-(3-ethynylimidazo[1,2-b]pyridazin-6-yl)phenyl)(morpholino)methanone and 3-iodo-5-(trifluoromethyl)-H-pyrrolo[2,3-b]pyridine in a similar method to that described for Example 1. The residue was purified by column chromatography (silica gel, eluent CH$_2$Cl$_2$/MeOH 95:5-90:10) to afford morpholino(4-(3-((5-(trifluoromethyl)-1H-pyrrolo[2,3-b]pyridin-3-yl)ethynyl)imidazo[1,2-b]pyridazin-6-yl)phenyl)methanone (5.3 mg, AUC HPLC 96%) as a yellow solid. $^1$H NMR (400 MHz, DMSO-d$_6$) δ (ppm): 8.70-8.68 (m, 1H), 8.40-8.39 (m, 1H), 8.35 (d, J=9.5 Hz, 1H), 8.29 (s, 1H), 8.23 (d, J=8.4 Hz, 2H), 8.22 (s, 1H), 7.98 (d, J=9.5 Hz, 1H), 7.59 (d, J=8.4 Hz, 2H), 3.78-3.42 (m, 8H); MS (ESI) m/z 517 [C$_{27}$H$_{19}$F$_3$N$_6$O$_2$+H]$^+$.

Example 26: (4-(3-((1-methyl-1H-pyrrolo[2,3-b]pyridin-2-yl)ethynyl)imidazo[1,2-b]pyridazin-6-yl)phenyl) (morpholino)methanone

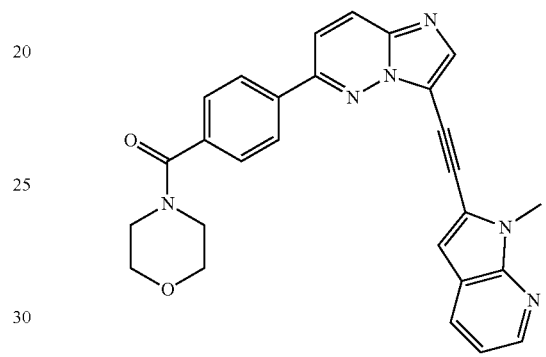

The title compound was synthesized from (4-(3-ethynylimidazo[1,2-b]pyridazin-6-yl)phenyl)(morpholino)methanone and 2-iodo-1-methyl-1H-pyrrolo[2,3-b]pyridine in a similar method to that described for Example 1. The residue was purified by column chromatography (silica gel, eluent CH$_2$Cl$_2$/MeOH 95:5 to 90:10) to afford (4-(3-((1-methyl-1H-pyrrolo[2,3-b]pyridin-2-yl)ethynyl)imidazo[1,2-b]pyridazin-6-yl)phenyl)(morpholino)methanone (62 mg, 45%, AUC HPLC 96%) as a yellow solid. $^1$H NMR (400 MHz, CDCl$_3$) δ (ppm): 8.41 (dd, J=4.8, 1.5 Hz, 1H), 8.12-8.10 (m, 4H), 7.93 (dd, J=8.0, 1.5 Hz, 1H), 7.62 (d, J=9.5 Hz, 1H), 7.59 (d, J=8.4 Hz, 2H), 7.11 (dd, J=7.8, 4.7 Hz, 1H), 6.90 (s, 1H), 4.08 (s, 1H), 3.75-3.48 (m, 8H); $^{13}$C NMR (100 MHz, CDCl$_3$) δ (ppm): 169.56, 151.75, 148.09, 144.80, 139.25, 139.13, 137.21, 136.68, 129.02, 127.99, 127.41, 126.27, 122.02, 119.87, 116.99, 116.57, 113.25, 105.94, 90.35, 83.01, 66.91, 29.50; MS (ESI) m/z 463 [C$_{27}$H$_{22}$N$_6$O$_2$+H]$^+$.

Example 27: (4-(3-((1H-benzo[d]imidazol-5-yl)ethynyl)imidazo[1,2-b]pyridazin-6-yl)phenyl)(morpholino)methanone

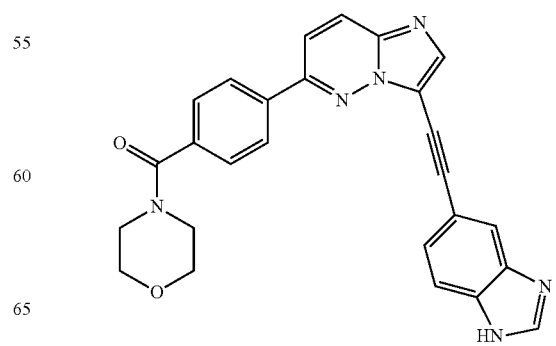

The title compound was synthesized from (4-(3-ethynylimidazo[1,2-b]pyridazin-6-yl)phenyl)(morpholino)methanone and 5-iodo-1H-benzo[d]imidazole in a similar method to that described for Example 1. The residue was purified by column chromatography (silica gel, eluent CH$_2$Cl$_2$/MeOH 95:5-90:10) to afford (4-(3-((1H-benzo[d]imidazol-5-yl)ethynyl)imidazo[1,2-b]pyridazin-6-yl)phenyl)(morpholino)methanone (90 mg, 67%, AUC HPLC 99%) as a yellow solid. $^1$H NMR (400 MHz, DMSO-d$_6$) δ (ppm): 8.35 (s, 1H), 8.32 (d, J=9.5 Hz, 1H), 8.21 (d, J=8.4 Hz, 2H), 8.20 (s, 1H), 7.96 (d, J=9.5 Hz, 1H), 7.91 (s, 1H), 7.70 (d, J=8.2 Hz, 1H), 7.63 (d, J=8.4 Hz, 2H), 7.49 (dd, J=8.2, 1.2 Hz, 1H), 3.79-3.32 (m, 8H); $^{13}$C NMR (100 MHz, DMSO-d$_6$) δ (ppm): 168.52, 151.31, 143.81, 138.66, 138.31, 137.19, 135.74, 127.84, 127.13, 126.34, 125.42, 117.50, 114.82, 112.69, 99.59, 74.78, 66.04, 47.66; MS (ESI) m/z 449 [C$_{26}$H$_{20}$N$_6$O$_2$+H]$^+$.

Example 28: (4-(3-((1H-pyrazol-4-yl)ethynyl)imidazo[1,2-b]pyridazin-6-yl)phenyl)(morpholino)methanone

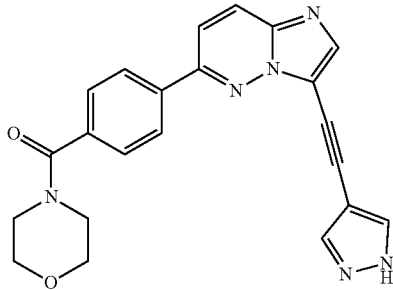 [SMILES: O=C(c1ccc(-c2ccc3ncc(C#Cc4cn[nH]c4)n3n2)cc1)N1CCOCC1]

The title compound was synthesized from (4-(3-ethynylimidazo[1,2-b]pyridazin-6-yl)phenyl)(morpholino)methanone and 4-iodo-1H-pyrazole in a similar method as described for Example 1. The residue was purified by column chromatography (silica gel, eluent CH$_2$Cl$_2$/MeOH 95:5 to 90:10) to afford (4-(3-((1H-pyrazol-4-yl)ethynyl)imidazo[1,2-b]pyridazin-6-yl)phenyl)(morpholino)methanone (13.7 mg, 11%, AUC HPLC 99%) as a yellow solid. $^1$H NMR (400 MHz, CDCl$_3$) δ (ppm): 8.28 (d, J=8.3 Hz, 2H), 8.07 (d, J=9.5 Hz, 1H), 8.02 (s, 1H), 7.88 (s, 2H), 7.59-7.54 (m, 3H), 3.79-3.49 (m, 8H); $^{13}$C NMR (100 MHz, DMSO-d$_6$) δ (ppm): 169.77, 151.55, 138.72, 138.63, 136.91, 136.89, 127.90, 127.54, 126.09, 116.57, 113.99, 102.58, 90.29, 66.88, 48.32, 42.81; MS (ESI) m/z 399 [C$_{22}$H$_{18}$N$_6$O$_2$+H]$^+$.

Example 29: (4-(3-((6-methyl-1H-pyrrolo[2,3-b]pyridin-4-yl)ethynyl)imidazo[1,2-b]pyridazin-6-yl)phenyl) (morpholino)methanone

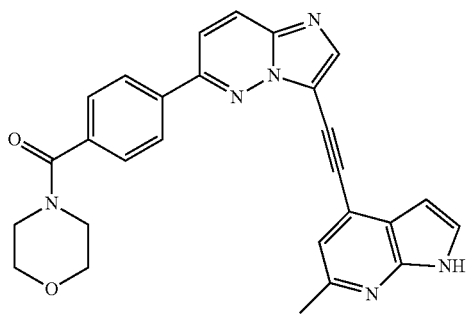 [SMILES: Cc1cc(C#Cc2cnc3ccc(-c4ccc(C(=O)N5CCOCC5)cc4)nn23)c2cc[nH]c2n1]

The title compound was synthesized from (4-(3-ethynylimidazo[1,2-b]pyridazin-6-yl)phenyl)(morpholino)methanone and 4-iodo-6-methyl-1H-pyrrolo[2,3-b]pyridine in a similar method to that described for Example 1. The residue was purified by column chromatography (silica gel, eluent CH$_2$Cl$_2$/MeOH 95:5 to 90:10) to afford (4-(3-((6-methyl-1H-pyrrolo[2,3-b]pyridin-4-yl)ethynyl)imidazo[1,2-b]pyridazin-6-yl)phenyl)(morpholino)methanone (24 mg, 35%, AUC HPLC 99%) as brown solid. $^1$H NMR (400 MHz, DMSO-d$_6$) δ (ppm): 11.75 (s, 1H), 8.39 (d, J=9.5 Hz, 1H), 8.33 (s, 1H), 8.27 (d, J=8.2 Hz, 2H), 8.04 (d, J=9.5 Hz, 1H), 7.66 (d, J=8.2 Hz, 2H), 7.56-7.55 (m, 1H), 7.18 (s, 1H), 6.68-6.64 (m, 1H), 3.65-3.41 (m, 8H), 2.57 (s, 3H); $^{13}$C NMR (100 MHz, DMSO-d$_6$) δ (ppm): 168.33, 151.47, 150.94, 148.22, 139.20, 139.15, 137.35, 135.62, 127.74, 127.10, 126.47, 126.32, 120.69, 117.96, 117.53, 116.24, 111.99, 98.71, 96.08, 81.56, 65.97, 23.76; MS (ESI) m/z 463 [C$_{27}$H$_{22}$N$_6$O$_2$+H]$^+$.

Example 30: 4-((6-(4-(morpholine-4-carbonyl)phenyl)imidazo[1,2-b]pyridazin-3-yl)ethynyl)-1H-pyrrolo[2,3-b]pyridine-6-carbonitrile

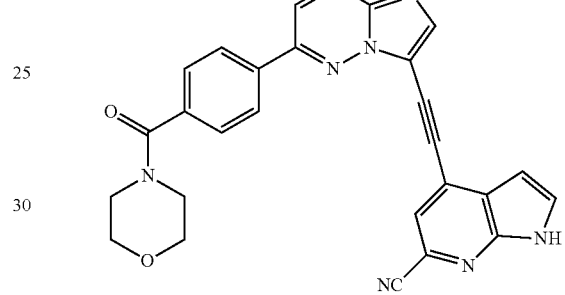

The title compound was synthesized from (4-(3-ethynylimidazo[1,2-b]pyridazin-6-yl)phenyl)(morpholino)methanone and 4-iodo-1H-pyrrolo[2,3-b]pyridine-6-carbonitrile in a similar method to that described for Example 1. The residue was purified by column chromatography (silica gel, eluent CH$_2$Cl$_2$/MeOH 95:5-90:10) to afford 4-((6-(4-(morpholine-4-carbonyl)phenyl)imidazo[1,2-b]pyridazin-3-yl)ethynyl)-1H-pyrrolo[2,3-b]pyridine-6-carbonitrile (15 mg, 21%, AUC HPLC 98%) as brown solid. $^1$H NMR (400 MHz, DMSO-d$_6$) δ (ppm): 12.59 (s, 1H), 8.42 (d, J=9.5 Hz, 1H), 8.39 (s, 1H), 8.28 (d, J=8.4 Hz, 2H), 8.07 (d, J=9.5 Hz, 1H), 8.04 (d, J=3.4 Hz, 1H), 7.90 (s, 1H), 7.67 (d, J=8.4 Hz, 2H), 6.90 (d, J=3.4 Hz, 1H), 3.65-3.41 (m, 8H); $^{13}$C NMR (100 MHz, DMSO-d$_6$) δ (ppm): 168.33, 151.66, 147.83, 139.87, 139.58, 137.41, 135.51, 132.58, 127.76, 127.15, 126.57, 124.03, 122.98, 121.55, 120.63, 118.39, 118.32, 111.47, 99.98, 94.43, 84.33, 65.98; MS (ESI) m/z 474 [C$_{27}$H$_{19}$N$_7$O$_2$+H]$^+$.

Example 31: morpholino(4-(3-((5-(trifluoromethyl)-1H-pyrrolo[2,3-b]pyridin-4-yl)ethynyl)imidazo[1,2-b]pyridazin-6-yl)phenyl)methanone

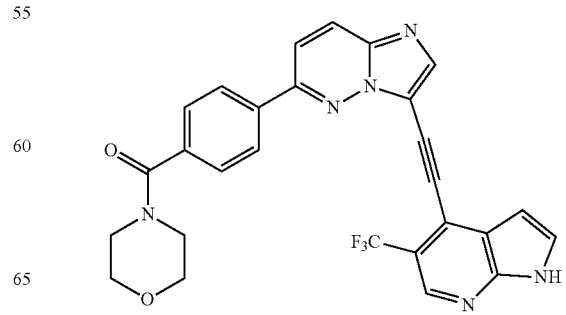

Step 1 tert-butyl 4-((6-(4-(morpholine-4-carbonyl)phenyl)imidazo[1,2-b]pyridazin-3-yl)ethynyl)-5-(trifluoromethyl)-1H-pyrrolo[2,3-b]pyridine-1-carboxylate was synthesized from (4-(3-ethynylimidazo[1,2-b]pyridazin-6-yl)phenyl)(morpholino)methanone and tert-butyl 4-iodo-5-(trifluoromethyl)-1H-pyrrolo[2,3-b]pyridine-1-carboxylate in a similar method to that described for Example 1. The residue was purified by column chromatography (silica gel, eluent $CH_2Cl_2$/MeOH 95:5 to 90:10) to afford tert-butyl 4-((6-(4-(morpholine-4-carbonyl)phenyl)imidazo[1,2-b]pyridazin-3-yl)ethynyl)-5-(trifluoromethyl)-1H-pyrrolo[2,3-b]pyridine-1-carboxylate (50 mg, 30%) as a yellow solid. $^1$H NMR (400 MHz, $CDCl_3$) δ (ppm): 8.81 (s, 1H), 8.20 (s, 1H), 8.17 (d, J=8.4 Hz, 2H), 8.12 (d, J=9.5 Hz, 1H), 7.82 (d, J=4.0 Hz, 1H), 7.67 (d, J=9.5 Hz, 1H), 7.62 (d, J=8.4 Hz, 2H), 6.98 (d, J=4.0 Hz, 1H), 3.79-3.52 (m, 8H), 1.71 (s, 9H); MS (ESI) m/z 617 $[C_{32}H_{27}F_3N_6O_4+H]^+$.

Step 2

To a solution of tert-butyl 4-((6-(4-(morpholine-4-carbonyl)phenyl)imidazo[1,2-b]pyridazin-3-yl)ethynyl)-5-(trifluoromethyl)-1H-pyrrolo[2,3-b]pyridine-1-carboxylate (50 mg, 0.081 mmol) in DCM (1 mL) was added TFA (1 mL) and the was stirred at room temperature for 3 h. The reaction mixture was concentrated and the reaction mixture was basified with $NaHCO_3$, diluted with EtOAc and washed with water and brine solution. The organic layer was dried over anhydrous $Na_2SO_4$ and concentrated under reduced pressure to obtain the reaction crude product which was purified by column chromatography (silica gel, eluent $CH_2Cl_2$/MeOH 95:5-90:10) to afford morpholino(4-(3-((5-(trifluoromethyl)-1H-pyrrolo[2,3-b]pyridin-4-yl)ethynyl)imidazo[1,2-b]pyridazin-6-yl)phenyl)methanone (36 mg, 86%, AUC HPLC 98%) as a yellow solid. $^1$H NMR (400 MHz, DMSO-$d_6$) δ (ppm): 12.46 (s, 1H), 8.65 (s, 1H), 8.44-8.42 (m, 2H), 8.31 (d, J=8.4 Hz, 2H), 8.11 (d, J=9.6 Hz, 1H), 7.89 (d, J=3.4 Hz, 1H), 7.67 (d, J=8.4 Hz, 2H), 6.96 (d, J=3.4 Hz, 1H), 3.66-3.42 (m, 8H); $^{13}$C NMR (100 MHz, DMSO-$d_6$) δ (ppm): 168.3, 151.6, 149.6, 140.1, 139.7, 139.5, 137.4, 135.4, 130.27, 127.6, 127.0, 126.6, 120.3, 119.0, 118.4, 116.0, 111.4, 100.1, 92.3, 87.9, 65.9; MS (ESI) m/z 517 $[C_{27}H_{19}F_3N_6O_2+H]^+$.

Example 32: morpholino(4-(3-(pyridin-4-ylethynyl)imidazo[L 2-b]pyridazin-6-yl)phenyl)methanone

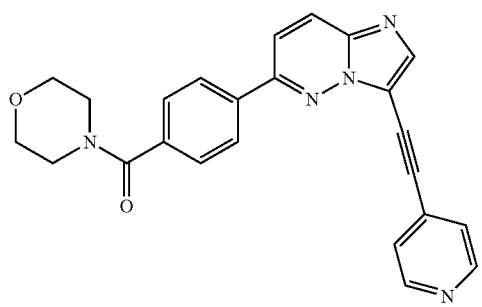 [SMILES: O=C(c1ccc(-c2ccc3ncc(C#Cc4ccncc4)n3n2)cc1)N1CCOCC1]

The title compound was synthesized from (4-(3-ethynylimidazo[1,2-b]pyridazin-6-yl)phenyl)(morpholino)methanone (100 mg, 0.301 mmol), 4-bromopyridine hydrochloride (87.6 mg, 0.451 mmol), $PdCl_2(PPh_3)_2$ (13.7 mg, 0.0195 mmol), CuI (5.7 mg, 0.030 mmol) and $PPh_3$ (27.6 mg, 0.105 mmol), in DMF (1.0 mL) was added DIPEA (1.0 mL) and purged with $N_2$ for 10 min. The reaction mixture was heated at 70° C. in a sealed tube for 12 h and was concentrated in vacuo to dryness. The residue was purified by flash column chromatography (silica gel, eluent $CH_2Cl_2$/$CH_3OH$ 94:6) to afford morpholino(4-(3-(pyridin-4-ylethynyl)imidazo[1,2-b]pyridazin-6-yl)phenyl)methanone (72.0 mg, 58.5%, AUC HPLC 97%) as a light yellow solid; $^1$H NMR (600 MHz, DMSO-$d_6$) δ (ppm): 8.69 (d, J=6.0 Hz, 2H), 8.38 (d, J=9.5 Hz, 1H), 8.31 (s, 1H), 8.24 (d, J=8.4 Hz, 2H), 8.04 (d, J=9.6 Hz, 1H), 7.66-7.60 (m, 4H), 3.69-3.58 (m, 8H); $^{13}$C NMR (150 MHz, DMSO-$d_6$) δ (ppm): 168.5, 152.6, 150.1, 149.8, 139.4, 137.8, 135.5, 139.6, 127.9, 127.3, 126.6, 124.9, 118.4, 111.5, 96.1, 81.1, 66.1, 47.6.; MS (ESI) m/z 410 $[C_{24}H_{19}N_5O_2+H]^+$.

Example 33: (4-(3-((1H-pyrrolo[2,3-b]pyridin-4-yl)ethynyl)imidazo[1,2-b]pyridazin-6-yl)phenyl) (morpholino)methanone

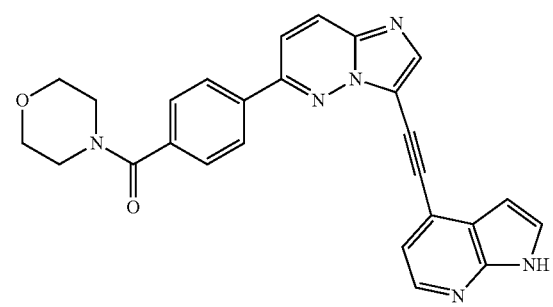 [SMILES: O=C(c1ccc(-c2ccc3ncc(C#Cc4ccnc5[nH]ccc45)n3n2)cc1)N1CCOCC1]

The title compound was synthesized from (4-(3-ethynylimidazo[1,2-b]pyridazin-6-yl)phenyl)(morpholino)methanone and 4-bromo-1H-pyrrolo[2,3-b]pyridine in a similar method to that described for Example 32. The reaction crude product was purified by flash column chromatography (silica gel, eluent $CH_2Cl_2$/$CH_3OH$ 96:4) to afford (4-(3-((1H-pyrrolo[2,3-h]pyridin-4-yl)ethynyl)imidazo[1,2-b]pyridazin-6-yl)phenyl)(morpholino)methanone (18.0 mg, 25%, AUC HPLC 97%) as a yellow solid; $^1$H NMR (600 MHz, DMSO-$d_6$) δ (ppm): 11.98 (s, 1H), 8.37 (d, J=9.5 Hz, 1H), 8.33 (s, 1H), 8.30-8.24 (m, 3H), 8.04 (d, J=9.5 Hz, 1H), 7.69-7.64 (m, 3H), 7.29 (d, J=4.9 Hz, 1H), 6.74 (s, 1H), 3.69-3.56 (m, 8H); $^{13}$C NMR (150 MHz, DMSO-$d_6$) δ (ppm): 168.6, 151.7, 148.4, 142.6, 139.4, 139.3, 137.5, 135.8, 128.0, 127.7, 127.3, 126.6, 120.6, 120.0, 118.3, 116.7, 112.1, 99.1, 96.1, 82.3, 66.1, and 48.7; MS (ESI) m/z 449 $[C_{26}H_{20}N_6O_2+H]^+$.

Example 34: (4-(3-((2-aminopyridin-4-yl)ethynyl)imidazo[1,2-b]pyridazin-6-yl)phenyl) (morpholino)methanone

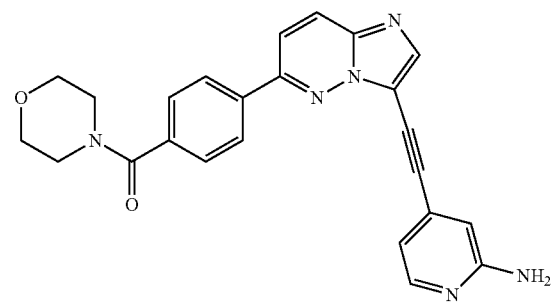 [SMILES: Nc1cc(C#Cc2cnc3ccc(-c4ccc(C(=O)N5CCOCC5)cc4)nn23)ccn1]

The title compound was synthesized from (4-(3-ethynylimidazo[1,2-b]pyridazin-6-yl)phenyl)(morpholino)methanone and 4-bromopyridin-2-amine in a similar method to that described for Example 32. The reaction crude product was purified by flash column chromatography (silica gel, eluent CH$_2$Cl$_2$/CH$_3$OH 94:6) to afford (4-(3-((2-aminopyridin-4-yl)ethynyl)imidazo[1,2-b]pyridazin-6-yl)phenyl)(morpholino)methanone (14.0 mg, 18%, AUC HPLC 97%) as a light yellow solid; $^1$H NMR (600 MHz, DMSO-d$_6$) δ (ppm): 8.34 (d, J=9.5 Hz, 1H), 8.25 (s, 1H), 8.19 (d, J=8.1 Hz, 2H), 7.99 (d, J=9.6 Hz, 2H), 7.66-7.37 (m, 4H), 6.69-6.63 (m, 1H), 6.18 (s, 1H), 3.68-3.64 (m, 4H); $^{13}$C NMR (150 MHz, DMSO-d$_6$) δ (ppm): 168.6, 159.9, 151.6, 148.6, 139.4, 137.4, 135.7, 130.2, 128.0, 127.3, 126.6, 118.2, 113.0, 111.9, 109.2, 97.1, 78.8, 66.2, 48.0 and 42.2; MS (ESI) m/z 425 [C$_{24}$H$_{20}$N$_6$O$_2$+H]$^+$.

Example 35: (4-(3-((1-methyl-1H-pyrrolo[2,3-b]pyridin-4-yl)ethynyl)imidazo[1,2-b]pyridazin-6-yl)phenyl)(morpholino) methanone

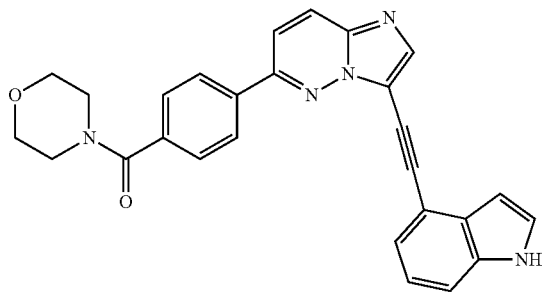 [SMILES: O=C(c1ccc(-c2ccc3ncc(C#Cc4cccc5[nH]ccc45)n3n2)cc1)N1CCOCC1]

The title compound was synthesized from (4-(3-ethynylimidazo[1,2-b]pyridazin-6-yl)phenyl)(morpholino)methanone and 4-bromo-1-methyl-1H-pyrrolo[2,3-b]pyridine in a similar method to that described for Example 32. The reaction crude product was purified by flash column chromatography (silica gel, eluent EtOAc/CH$_3$OH 90:10) to afford (4-(3-((1-methyl-1H-pyrrolo[2,3-b]pyridin-4-yl)ethynyl)imidazo[1,2-b]pyridazin-6-yl)phenyl)(morpholino)methanone (24.0 mg, 29%, AUC HPLC 98%) as a yellow solid; $^1$H NMR (600 MHz, DMSO-d$_6$) δ (ppm): 8.41 (s, 1H), 8.34 (d, J=4.6 Hz, 1H), 8.27 (d, J=7.8 Hz, 2H), 8.06 (d, J=7.7 Hz, 1H), 7.72 (d, J=2.7 Hz, 1H), 7.66 (d, J=7.9 Hz, 2H), 7.64-7.52 (m, 1H), 7.32 (d, J=4.6 Hz, 1H), 6.75 (d, J=2.7 Hz, 1H), 3.88 (s, 3H), 3.63 (m, 8H); $^{13}$C NMR (150 MHz, DMSO-d$_6$) δ (ppm): 168.9, 152.1, 147.7, 142.8, 137.9, 136.1, 131.9, 129.2, 128.3, 127.6, 121.3, 120.6, 118.6, 117.1, 98.4, 96.3, 66.5, 31.5; MS (ESI) m/z 463 [C$_{27}$H$_{22}$N$_6$O$_2$+H]$^+$.

Example 36: (4-(3-((1H-indol-4-yl)ethynyl)imidazo[1,2-b]pyridazin-6-yl)phenyl) (morpholino)methanone

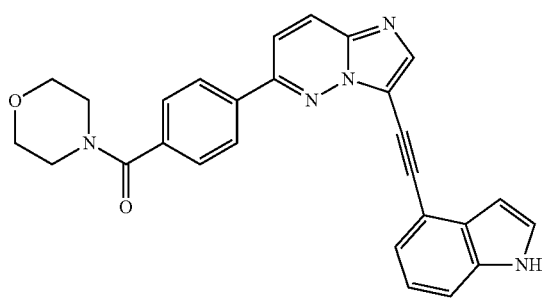 [SMILES: O=C(c1ccc(-c2ccc3ncc(C#Cc4cccc5[nH]ccc45)n3n2)cc1)N1CCOCC1]

The title compound was synthesized from (4-(3-ethynylimidazo[1,2-b]pyridazin-6-yl)phenyl)(morpholino)methanone and 4-bromo-1H-indole in a similar method to that described for Example 32. The reaction crude product was purified by flash column chromatography (silica gel, eluent EtOAc/CH$_3$OH 90:10) to afford (4-(3-((1H-indol-4-yl)ethynyl)imidazo[1,2-b]pyridazin-6-yl)phenyl)(morpholino)methanone (25.9 mg, 29.0%, AUC HPLC 97%) as a yellow solid; $^1$H NMR (600 MHz, DMSO-d$_6$) δ (ppm): 11.45 (s, 1H), 8.37 (s, 1H), 8.27 (d, J=8.1 Hz, 2H), 8.05-7.99 (m, 1H), 7.93 (t, J=7.4 Hz, 1H), 7.77 (td, J=7.9, 3.7 Hz, 2H), 7.72 (dd, J=12.9, 7.5 Hz, 2H), 7.65 (d, J=8.2 Hz, 1H), 7.55-7.52 (m, 2H), 7.32 (d, J=7.2 Hz, 1H), 7.18 (t, J=7.7 Hz, 1H), 6.77 (s, 1H), 3.61 (m, 9H); $^{13}$C NMR (150 MHz, DMSO-d$_6$) δ (ppm): 168.4, 151.5, 137.3, 135.8, 135.5, 135.1, 134.4, 134.3, 130.4, 130.4, 128.8, 127.8, 127.2, 126.8, 122.3, 121.1, 117.8, 117.4, 113.1, 112.4, 100.4, 98.4, 66.0; MS (ESI) m/z 448 [C$_{27}$H$_{21}$N$_5$O$_2$+H]$^+$.

Example 37: N-(4-((6-(4-(morpholine-4-carbonyl)phenyl)imidazo[1,2-b]pyridazin-3-yl)ethynyl)pyridin-2-yl)acetamide

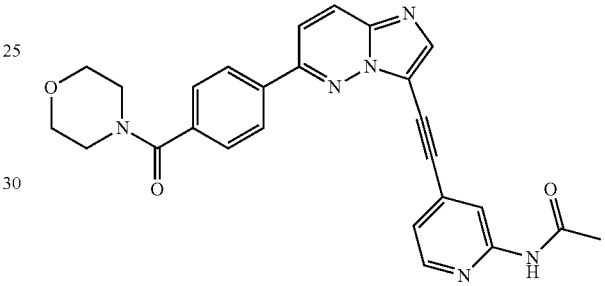

The title compound was synthesized from (4-(3-ethynylimidazo[1,2-b]pyridazin-6-yl)phenyl)(morpholino)methanone and N-(4-bromopyridin-2-yl)acetamide in a similar method to that described for Example 32. The reaction crude product was purified by flash column chromatography (silica gel, eluent CH$_2$Cl$_2$/CH$_3$OH 90:10) to afford N-(4-((6-(4-(morpholine-4-carbonyl)phenyl)imidazo[1,2-b]pyridazin-3-yl)ethynyl)pyridin-2-yl)acetamide (24.7 mg, 29.0%, AUC HPLC 100%) as a yellow solid; $^1$H NMR (600 MHz, DMSO-d$_6$) δ (ppm): 10.69 (s, 1H), 8.39 (t, J=7.8 Hz, 2H), 8.32 (d, J=8.6 Hz, 2H), 8.25 (d, J=8.2 Hz, 2H), 8.05 (d, J=9.5 Hz, 1H), 7.65 (d, J=8.2 Hz, 2H), 7.29 (d, J=4.7 Hz, 1H), 3.76-3.49 (m, 8H), 2.14 (s, 3H); $^{13}$C NMR (150 MHz, DMSO-d$_6$) δ (ppm): 169.7, 168.4, 152.4, 151.4, 148.7, 139.7, 137.3, 135.5, 131.2, 127.9, 127.2, 126.6, 120.0, 118.2, 114.1, 111.5, 96.7, 80.7, 79.2, 66.1, 47.7, 24.0; MS (ESI) m/z 467 [C$_{26}$H$_{22}$N$_6$O$_3$+H]$^+$.

Example 38: N-(4-((6-(4-(morpholine-4-carbonyl)phenyl)imidazo[1,2-b]pyridazin-3-yl)ethynyl)pyridin-2-yl)benzamide

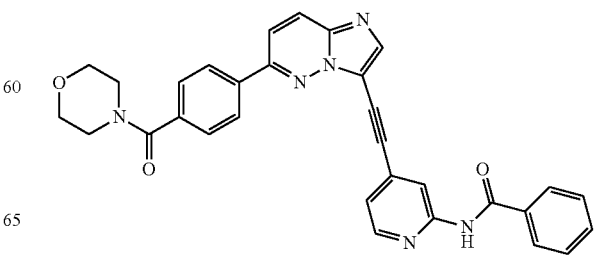

The title compound was synthesized from (4-(3-ethynylimidazo[1,2-b]pyridazin-6-yl)phenyl)(morpholino)methanone and N-(4-bromopyridin-2-yl)benzamide in a similar method to that described for Example 32. The reaction crude product was purified by flash column chromatography (silica gel, eluent EtOAc/CH$_3$OH 90:10) to afford N-(4-((6-(4-(morpholine-4-carbonyl)phenyl)imidazo[1,2-b]pyridazin-3-yl)ethynyl)pyridin-2-yl)benzamide (40.8 mg, 43.0%, AUC HPLC 99%) as a yellow solid; $^1$H NMR (600 MHz, DMSO-d$_6$) δ (ppm): 11.02 (s, 1H), 8.50 (d, J=4.9 Hz, 1H), 8.48 (s, 1H), 8.40 (d, J=9.5 Hz, 1H), 8.34 (s, 1H), 8.28 (d, J=7.8 Hz, 2H), 8.06 (d, J=7.5 Hz, 3H), 7.66 (d, J=7.8 Hz, 2H), 7.63 (t, J=7.3 Hz, 1H), 7.54 (t, J=7.5 Hz, 2H), 7.38 (d, J=4.9 Hz, 1H), 3.59 (m, 8H); $^{13}$C NMR (150 MHz, DMSO-d$_6$) δ (ppm): 168.5, 166.4, 152.6, 151.5, 148.8, 139.7, 139.5, 137.4, 135.5, 133.9, 132.2, 131.3, 128.4, 128.1, 127.9, 127.2, 126.6, 120.5, 118.32, 115.61, 111.5, 96.8, 80.9, 66.0; MS (ESI) m/z 529 [C$_{31}$H$_{24}$N$_6$O$_3$+H]$^+$.

Example 39: (4-(3-(imidazo[1,2-b]pyridazin-3-ylethynyl)imidazo[1,2-b]pyridazin-6-yl)phenyl)(morpholino)methanone

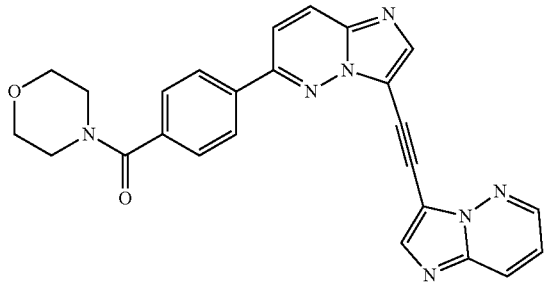 [SMILES: O=C(c1ccc(-c2ccc3ncc(C#Cc4cnc5cccnn45)n3n2)cc1)N1CCOCC1]

The title compound was synthesized from (4-(3-ethynylimidazo[1,2-b]pyridazin-6-yl)phenyl)(morpholino)methanone and 3-bromoimidazo[1,2-b]pyridazine in a similar method to that described for Example 32. The reaction crude product was purified by flash column chromatography (silica gel, eluent EtOAc/CH$_3$OH 93:7) to afford (4-(3-(imidazo[1,2-b]pyridazin-3-ylethynyl)imidazo[1,2-b]pyridazin-6-yl)phenyl)(morpholino)methanone (31.5 mg, 50.8%, AUC HPLC 99%) as a yellow solid; $^1$H NMR (600 MHz, DMSO-d$_6$) δ (ppm): 8.74 (dd, J=4.4; 1.3 Hz, 1H), 8.41-8.26 (m, 4H), 8.23 (d, J=8.3 Hz, 2H), 8.04 (d, J=9.5 Hz, 1H), 7.63 (d, J=8.4 Hz, 2H), 7.42 (dd, J=9.1, 4.4 Hz, 1H), 3.66-3.54 (m, 8H); $^{13}$C NMR (150 MHz, DMSO-d$_6$) δ (ppm): 168.4, 151.4, 145:1, 139.3, 138.8, 137.3, 135.5, 127.8, 127.2, 126.5, 126.2, 119.4, 118.0, 112.0, 85.6, 85.3, 66.0, 42.0; MS (ESI) m/z 450 [C$_{25}$H$_{19}$N$_7$O$_2$+H]$^+$.

Example 40: (4-(3-((6-hydroxypyridin-3-yl)ethynyl)imidazo[1,2-b]pyridazin-6-yl)phenyl) (morpholino)methanone

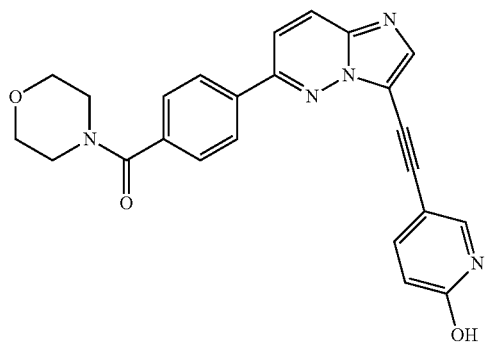 [SMILES: O=C(c1ccc(-c2ccc3ncc(C#Cc4ccc(O)nc4)n3n2)cc1)N1CCOCC1]

The title compound was synthesized from (4-(3-ethynylimidazo[1,2-b]pyridazin-6-yl)phenyl)(morpholino)methanone and 5-bromopyridin-2-ol a procedure similar to that described for Example 32. The reaction crude product was purified by flash column chromatography (silica gel, eluent CH$_2$Cl$_2$/CH$_3$OH 95:5) to afford (4-(3-((6-hydroxypyridin-3-yl)ethynyl)imidazo[1,2-b]pyridazin-6-yl)phenyl)(morpholino)methanone (23.0 mg, 65%, AUC HPLC 98%) as a light yellow solid; 1H NMR (600 MHz, DMSO-d$_6$) δ (ppm): 8.34 (d, J=9.5 Hz, 1H), 8.19 (d, J=8:1 Hz, 2H), 8.15 (s, 1H), 7.97 (d, J=9.5 Hz, 1H), 7.61 (d, J=8.3 Hz, 3H), 6.43 (d, J=9.4 Hz, 1H), 3.61 (m, 6H); $^{13}$C NMR (150 MHz, DMSO-d$_6$) δ (ppm): 168.9, 161.7, 151.7, 142.9, 141.0, 139.1, 139.0, 137.7, 136.1, 128.3, 127.6, 126.9, 120.7, 118.0, 112.9, 95.4, 76.4, 66.5, 40.5, 40.3, 40.2, 40.1, 39.9, 39.8, 39.6, 39.5; MS (ESI) m/z 426 [C$_{24}$H$_{19}$N$_5$O$_3$+H]$^+$.

Example 41: (4-(3-((1H-indol-5-yl)ethynyl)imidazo[1,2-b]pyridazin-6-yl)phenyl) (morpholino)methanone

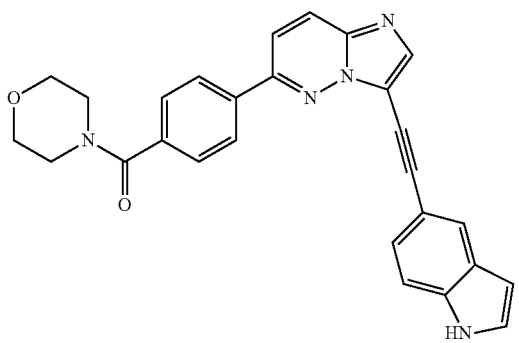 [SMILES: O=C(c1ccc(-c2ccc3ncc(C#Cc4ccc5[nH]ccc5c4)n3n2)cc1)N1CCOCC1]

The title compound was synthesized from (4-(3-ethynylimidazo[1,2-b]pyridazin-6-yl)phenyl)(morpholino)methanone and 5-bromo-1H-indole in a similar method to that described for Example 32. The reaction crude product was purified by preparative HPLC (C18, eluents ACN/H$_2$O/HCOOH 0.1%) to afford (4-(3-((1H-indol-5-yl)ethynyl)imidazo[1,2-b]pyridazin-6-yl)phenyl)(morpholino)methanone (1.7 mg, AUC HPLC 96%) as a yellow solid. $^1$H NMR (400 MHz, CDCl$_3$) δ (ppm): 8.33 (s, 1H), 8.14 (d, J=8.4 Hz, 2H), 8.07-8.04 (m, 2H), 7.98 (s, 1H), 7.59 (d, J=8.4 Hz, 2H), 7.55 (d, J=9.5 Hz, 1H), 7.48 (dd, J=8.4, 1.4 Hz, 1H), 7.42 (d, J=8.4 Hz, 1H), 7.29-7.27 (m, 1H), 6.61-6.60 (m, 1H), 3.77-3.48 (m, 8H); $^{13}$C NMR (400 MHz, CDCl$_3$) δ (ppm): 169.7, 151.3, 138.6, 138.4, 137.0, 136.8, 135.8, 127.9, 127.4, 126.0, 125.7, 125.3, 124.9, 116.1, 114.4, 113.7, 111.2, 103.1, 100.6, 77.2, 73.5, 66.9; MS (ESI) m/z 448 [C$_{27}$H$_{21}$N$_5$O$_2$+H]$^+$.

Example 42: (4-(3-((6-methoxypyridin-3-yl)ethynyl)imidazo[1,2-b]pyridazin-6-yl)phenyl) (morpholino)methanone

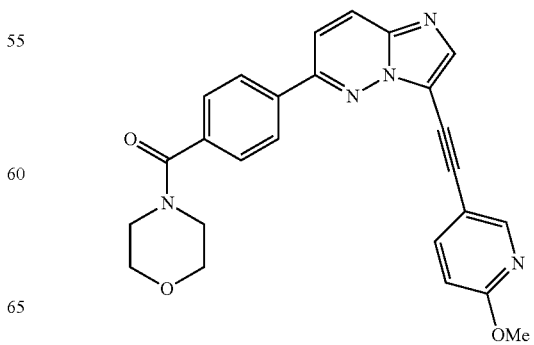

The title compound was synthesized from (4-(3-ethynylimidazo[1,2-b]pyridazin-6-yl)phenyl)(morpholino)methanone and 5-bromo-2-methoxypyridine in a similar method to that described for Example 32. The reaction crude product was purified by column chromatography (silica gel, eluent CHCl₃/CH₃OH 98:2) to afford (4-(3-((6-methoxypyridin-3-yl)ethynyl)imidazo[1,2-b]pyridazin-6-yl)phenyl)(morpholino)methanone (50 mg, LC-MS 99%) as a light yellow solid. $^1$H NMR (400 MHz, CDCl₃) δ (ppm): 8.47 (s, 1H), 8.10 (d, J=7.9 Hz, 4H), 7.78 (dd, J=6.6 Hz, 1H), 7.59-7.57 (m, 3H), 6.79 (d, J=8.8 Hz, 1H), 3.99 (s, 3H), 3.80-3.50 (m, 8H); MS (ESI) m/z 440.4 [$C_{25}H_{21}N_5O_3$+H]⁺.

Example 43: 2-chloro-N-(4-((6-(4-(morpholine-4-carbonyl)phenyl)imidazo[1,2-b]pyridazin-3-yl)ethynyl)pyridin-2-yl)acetamide and Example 44: 2-(methylamino)-N-(4-((6-(4-(morpholine-4-carbonyl)phenyl)imidazo[1,2-b]pyridazin-3-yl)ethynyl) pyridin-2-yl)acetamide

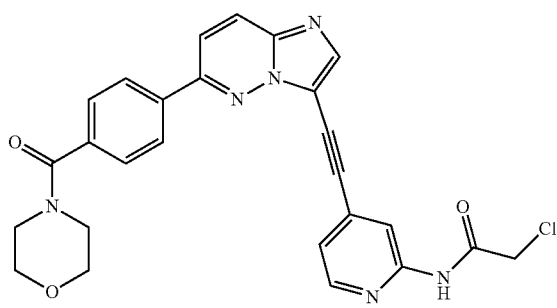 [SMILES: O=C(CCl)Nc1cc(C#Cc2cnc3ccc(-c4ccc(C(=O)N5CCOCC5)cc4)nn23)ccn1]

Step 1: Preparation of 2-chloro-N-(4-((6-(4-(morpholine-4-carbonyl)phenyl)imidazo[1,2-b]pyridazin-3-yl)ethynyl)pyridin-2-yl)acetamide The title compound was synthesized from (4-(3-ethynylimidazo[1,2-b]pyridazin-6-yl)phenyl)(morpholino)methanone and N-(4-bromopyridin-2-yl)-2-chloroacetamide in a similar method to that described for Example 32. The compound was purified by preparative TLC (eluent acetone/CH₂Cl₂ 1:1) to afford 2-chloro-N-(4-((6-(4-(morpholine-4-carbonyl)phenyl)imidazo[1,2-b]pyridazin-3-yl)ethynyl)pyridin-2-yl)acetamide as a brown solid (2.1 mg, AUC HPLC 97.4%). $^1$H NMR (600 MHz, DMSO-d₆) δ (ppm): 11.05 (s, 1H), 8.44 (d, J=5.0 Hz, 1H), 8.39 (d, J=9.5 Hz, 1H), 8.33 (d, J=3.3 Hz, 2H), 8.28 (d, J=8.3 Hz, 2H), 8.07 (d, J=9.5 Hz, 1H), 7.68 (d, J=8.2 Hz, 2H), 7.36 (dd, J=5.1, 1.1 Hz, 1H), 4.41 (s, 2H), 3.79-3.48 (m, 8H); $^{13}$C NMR (150 MHz, DMSO-d₆) δ (ppm): 168.5, 165.9, 151.8, 151.4, 149.0, 139.5, 137.4, 135.4, 131.6, 128.0, 127.2, 126.6, 120.5, 118.3, 114.4, 111.4, 96.7, 81.1, 66.1, 43.5, 40.0; MS (ESI) m/z 501 [$C_{26}H_{21}ClN_6O_3$+H]⁺.

Step 2: Preparation of 2-(methylamino)-N-(4-((6-(4-(morpholine-4-carbonyl)phenyl)imidazo[1,2-b]pyridazin-3-yl)ethynyl) pyridin-2-yl)acetamide

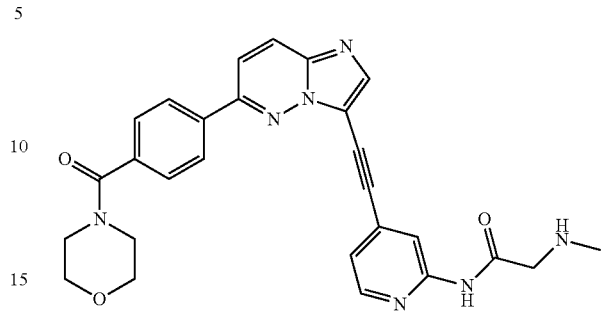

To a solution of 2-chloro-N-(4-((6-(4-(morpholine-4-carbonyl)phenyl)imidazo[1,2-b]pyridazin-3-yl)ethynyl)pyridin-2-yl)acetamide (12 mg, 0.024 mmol) and ethanol:DMF (1:0.5, 1.5 mL) was added a solution of methylamine in ethanol (33% wt) and the reaction stirred for 12 h at room temperature. The reaction mixture was concentrated in-vacuo to dryness. The crude product was purified by preparative TLC (eluent CH₂Cl₂/CH₃OH 92:8%) to afford 2-(methylamino)-N-(4-((6-(4-(morpholine-4-carbonyl)phenyl)imidazo[1,2-b]pyridazin-3-yl)ethynyl) pyridin-2-yl)acetamide (1.8 mg, 15%, AUC HPLC 95%) as a light yellow solid. $^1$H NMR (600 MHz, DMSO-d₆) δ (ppm): 8.42 (d, J=5.1 Hz, 1H), 8.39 (d, J=9.5 Hz, 1H), 8.35 (s, 1H), 8.34 (s, 1H), 8.26 (d, J=8.2 Hz, 2H), 8.06 (d, J=9.6 Hz, 1H), 7.66 (d, J=8.2 Hz, 2H), 7.33 (d, J=5.0 Hz, 1H), 3.63 (m, 8H), 2.54 (d, J=4.6 Hz, 2H), 2.35 (s, 3H); MS (ESI) m/z 496 [$C_{27}H_{25}N_7O_3$+H]⁺.

Example 45: (4-(3-((1H-pyrrolo[2,3-b]pyridin-4-yl)ethynyl)imidazo[1,2-b]pyridazin-6-yl)phenyl)(piperazin-1-yl) methanone

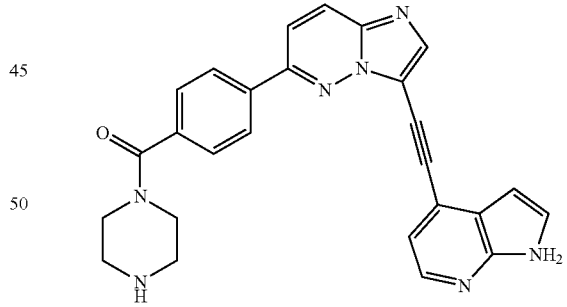

Step 1 tert-butyl 4-(4-(3-((1H-pyrrolo[2,3-b]pyridin-4-yl)ethynyl)imidazo[1,2-b]pyridazin-6-yl)benzoyl)piperazine-1-carboxylate was synthesized from tert-butyl 4-(4-(3-ethynylimidazo[1,2-b]pyridazin-6-yl)benzoyl)piperazine-1-carboxylate and 4-bromo-7-azaindole in a similar method to that described for Example 32. The compound was purified by flash column chromatography (silica gel, eluent CH₂Cl₂/CH₃OH 90:10) to afford tert-butyl 4-(4-(3-((1H-pyrrolo[2,3-b]pyridin-4-yl)ethynyl)imidazo[1,2-b]pyridazin-6-yl)benzoyl)piperazine-1-carboxylate (34.8 mg, 27%). $^1$H NMR (600 MHz, DMSO-$d_6$) δ (ppm): 11.99 (s, 1H), 8.39 (d, J=9.5 Hz, 1H), 8.34 (s, 1H), 8.29 (d, J=4.9 Hz, 1H), 8.27 (d, J=8.4 Hz, 2H), 8.05 (d, J=9.5 Hz, 1H), 7.69-7.66 (m, 2H), 7.65 (s, 1H), 7.29 (d, J=4.9 Hz, 1H), 6.74 (dd, J=3.3, 1.9 Hz, 1H), 3.42 (m, 4H), 3.35 (m, 4H), 1.41 (s, 9H); $^{13}$C NMR (150 MHz, DMSO-$d_6$) δ (ppm): 168.6, 153.8, 151.6, 148.4, 142.5, 139.3, 137.6, 135.7, 127.8, 127.6, 127.2, 126.6, 120.6, 119.9, 118.1, 116.6, 112.0, 99.5, 99.0, 96.0, 82.2, 79.3, 40.0, 28.0; MS (ESI) m/z 548 $[C_{31}H_{29}N_7O_3+H]^+$.

Step 2

To a solution of tert-butyl 4-(4-(3-((1H-pyrrolo[2,3-b]pyridin-4-yl)ethynyl)imidazo[1,2-b]pyridazin-6-yl)benzoyl)piperazine-1-carboxylate (12:4 mg, 0.0226 mmol) and DCM (2.5 mL) was added TFA (0.5 mL) and the mixture was stirred at room temperature for 12 h. The reaction mixture was purified by preparative TLC (eluent $CH_2Cl_2$/$CH_3OH$ 80:20) to afford (4-(3-((1H-pyrrolo[2,3-b]pyridin-4-yl)ethynyl)imidazo[1,2-b]pyridazin-6-yl)phenyl)(piperazin-1-yl) methanone (4.5 mg, 44%, AUC HPLC 97%) as a yellow oil. 1H NMR (600 MHz, DMSO-$d_6$) δ (ppm): 12.00 (s, 1H), 8.39 (d, J=9.5 Hz, 1H), 8.33 (s, 1H), 8.29 (d, J=4.9 Hz, 1H), 8.26 (d, J=8.3 Hz, 2H), 8.04 (d, J=9.6 Hz, 1H), 7.69-7.66 (m, 1H), 7.64 (d, J=8.3 Hz, 2H), 7.29 (d, J=4.9 Hz, 1H), 6.74 (dd, J=3.2, 1.7 Hz, 1H), 3.65 (m, 4H), 2.83 (m, 4H); $^{13}$C NMR (150 MHz, DMSO-$d_6$) δ (ppm): 168.4, 158.0, 157.8, 151.6, 148.4, 142.5, 139.3, 137.7, 135.6, 127.8, 127.6, 127.2, 126.6, 120.6, 119.9, 118.3, 118.2, 116.6, 116.3, 112.07, 99.08, 96.0, 82.2, 40.0; MS (ESI) m/z 448 $[C_{26}H_{21}N_7O+H]^+$.

Example 46: (4-(3-((2-aminopyridin-4-yl)ethynyl)imidazo[1,2-b]pyridazin-6-yl)phenyl)(piperazin-1-yl)methanone

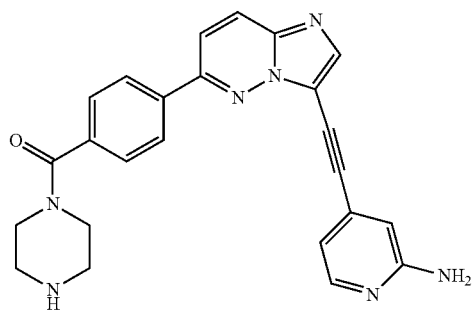 [SMILES: Nc1cc(C#Cc2cnc3ccc(-c4ccc(C(=O)N5CCNCC5)cc4)nn23)ccn1]

Step-1: tert-butyl 4-(4-(3-((1H-pyrrolo[2,3-b]pyridin-4-yl)ethynyl)imidazo[1,2-b]pyridazin-6-yl)benzoyl)piperazine-1-carboxylate was synthesized from tert-butyl 4-(4-(3-ethynylimidazo[1,2-b]pyridazin-6-yl)benzoyl)piperazine-1-carboxylate and 4-bromo-2-aminopyridine in a similar method to that described for Example 32. The compound was purified by flash column chromatography (eluent $CH_2Cl_2$/$CH_3OH$ 90:10) to afford tert-butyl 4-(4-(3-((1H-pyrrolo[2,3-b]pyridin-4-yl)ethynyl)imidazo[1,2-b]pyridazin-6-yl)benzoyl)piperazine-1-carboxylate (52.5 mg, 43%); $^1$H NMR (600 MHz, CDCl$_3$) δ (ppm): 8.12-8.08 (m, 3H), 8.08-8.04 (m, 2H), 7.58 (dd, J=8.8, 1.6 Hz, 3H), 6.83 (dd, J=5.3, 1.4 Hz, 1H), 6.70 (s, 1H), 4.58 (s, 2H), 3.65-3.30 (m, 8H), 1.47 (s, 9H); $^{13}$C NMR (150 MHz, CDCl$_3$) δ (ppm): 169.8, 158.5, 154.6, 151.7, 148.4, 139.7, 137.3, 136.7, 132.2, 132.1, 132.1, 128.6, 128.5, 128.0, 127.6, 126.3, 117.1, 115.8, 110.1, 97.1, 80.6, 79.3, 47.6, 42.2, 28.4; MS (ESI) m/z 524 $[C_{29}H_{29}N_7O_3+H]^+$ Step 2

(4-(3-((2-aminopyridin-4-yl)ethynyl)imidazo[1,2-b]pyridazin-6-yl)phenyl)(piperazin-1-yl)methanone was synthesized from tert-butyl 4-(4-(3-((1H-pyrrolo[2,3-b]pyridin-4-yl)ethynyl)imidazo[1,2-b]pyridazin-6-yl)benzoyl)piperazine-1-carboxylate in a similar method to that described in step 2 of Example 45 synthesis. The reaction mixture was purified by preparative TLC (eluent $CH_2Cl_2$/$CH_3OH$ 80:20) to afford (4-(3-((2-aminopyridin-4-yl)ethynyl)imidazo[1,2-b]pyridazin-6-yl)phenyl)(piperazin-1-yl) methanone (9.5 mg, 22%, AUC HPLC 95.9%) as a yellow solid; $^1$H NMR (600 MHz, DMSO-$d_6$) δ (ppm): 8.36 (d, J=9.4 Hz, 1H), 8.25 (s, 1H), 8.20 (d, J=7.8 Hz, 2H), 8.01 (d, J=9.5 Hz, 1H), 7.98 (d, J=4.8 Hz, 1H), 7.62 (d, J=7.8 Hz, 2H), 6.66 (d, J=4.9 Hz, 1H), 6.64 (s, 1H), 6.18 (s, 2H), 3.64 (m, 4H), 2.82 (m, 4H); $^{13}$C NMR (150 MHz, DMSO-$d_6$) δ (ppm): 168.4, 159.9, 158.0, 148.6, 139.2, 137.7, 135.5, 130.1, 127.8, 127.2, 126.6, 118.1, 116.3, 112.8, 111.7, 109.0, 97.0, 78.7, 47.5, 45.0; MS (ESI) m/z 424 $[C_{24}H_{21}N_7O+H]^+$.

Example 47: (4-(3-((2-((2-methylpyridin-3-yl)amino)pyridin-4-yl)ethynyl)imidazo[1,2-b]pyridazin-6-yl)phenyl) (morpholino)methanone

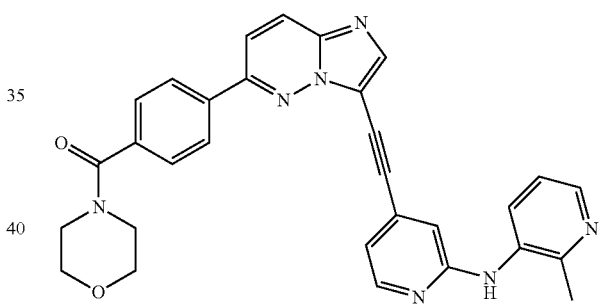

To a solution of (4-(3-((2-chloropyridin-4-yl)ethynyl)imidazo[1,2-b]pyridazin-6-yl)phenyl)(morpholino)methanone (20 mg, 0.045 mmol), 2-methylpyridin-3-amine (9.7 mg, 0.090 mmol)) in a mixture of 1,4 dioxane and DMF (9:1, 1 mL) was added BINAP (5.6 mg, 0.0090 mmol)), t-BuONa (13 mg, 0.135 mmol)) and then Pd$_2$(dba)$_3$ (4.2 mg, 0.0045 mmol)). The resulting mixture was microwave at 90° C. for 24 hand was filtered. The filtrate was purified by column chromatography (silica gel, eluent EtOAc/$CH_3OH$ 90:10) to afford (4-(3-((2-((2-methylpyridin-3-yl)amino)pyridin-4-yl)ethynyl)imidazo[1,2-b]pyridazin-6-yl)phenyl) (morpholino) methanone (5.3 mg, 23%, AUC HPLC 98.7%) as a light yellow solid. $^1$H NMR (600 MHz, DMSO-$d_6$) δ (ppm): 8.53 (s, 1H), 8.38 (d, J=9.5 Hz, 1H), 8.30 (s, 1H), 8.21 (d, J=8.4 Hz, 2H), 8.16 (t, J=4.9 Hz, 2H), 8.07 (dd, J=8.1, 1.4 Hz, 1H), 8.03 (d, J=9.5 Hz, 1H), 7.64 (d, J=8.4 Hz, 2H), 7.21 (dd, J=8.0, 4.7 Hz, 1H), 7.05 (s, 1H), 6.93 (dd, J=5.2, 1.3 Hz, 1H), 3.63 (m, 8H), 2.46 (s, 3H); $^{13}$C NMR (150 MHz, DMSO-$d_6$) δ (ppm): 168.4, 156.5, 151.6, 150.9, 148.1, 143.3, 139.7, 137.3, 135.6, 134.8, 130.5, 129.7, 127.9, 127.2, 126.6, 124.3, 121.3, 118.2, 115.3, 111.1, 96.6, 91.8, 79.6, 66.1, 63.0, 21.3; MS (ESI) m/z 516 $[C_{30}H_{25}N_7O_2+H]^+$.

Example 48: morpholino(4-(3-((2-(pyridin-2-ylamino)pyridin-4-yl)ethynyl)imidazo[1,2-b]pyridazin-6-yl)phenyl)methanone

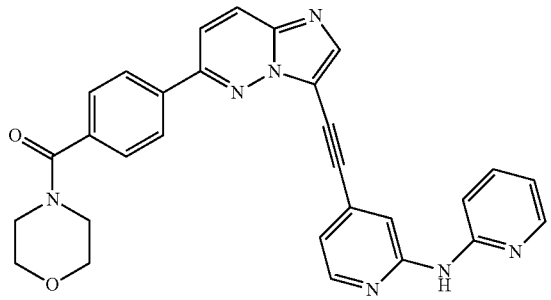 [SMILES: O=C(c1ccc(-c2ccc3ncc(C#Cc4ccnc(Nc5ccccn5)c4)n3n2)cc1)N1CCOCC1]

The title compound was synthesized from (4-(3-((2-chloropyridin-4-yl)ethynyl)imidazo[1,2-b]pyridazin-6-yl)phenyl)(morpholino)methanone and pyridin-2-amine in a similar method to that described for Example 47. The reaction crude product was purified by flash column chromatography (silica gel, eluent CH$_2$Cl$_2$/CH$_3$OH 95:5) to afford morpholino(4-(3-((2-(pyridin-2-ylamino)pyridin-4-yl)ethynyl) imidazo[1,2-b]pyridazin-6-yl)phenyl)methanone (9 mg, 32.4%, AUC HPLC 99%) as a light yellow solid. $^1$H NMR (600 MHz, DMSO-d$_6$) δ (ppm): 9.80 (s, 1H), 8.35-8.28 (m, 3H), 8.25-8.20 (m, 3H), 8.05 (s, 1H), 8.00 (d, J=12.0 Hz, 1H), 7.62-7.61 (m, 1H), 7.62-7.61 (m, 3H), 7.08 (d, J=6.0 Hz, 1H), 6.92 (t, J=6.0 Hz, 1H); $^{13}$C NMR (150 MHz, DMSO-d$_6$) δ (ppm): 169.1, 154.9, 154.4, 152.1, 148.7, 147.8, 139.8, 139.7, 138.2, 137.6, 136.0, 131.1, 128.3, 127.6, 126.9, 118.8, 117.3, 116.8, 112.9, 112.5, 112.0, 97.3, 80.1, 66.4; MS (ESI) m/z 502 [C$_{29}$H$_{23}$N$_7$O$_2$+H]$^+$.

Example 49: morpholino(4-(3-((2-(pyridin-3-ylamino)pyridin-4-yl)ethynyl)imidazo[1,2-b]pyridazin-6 yl)phenyl)methanone

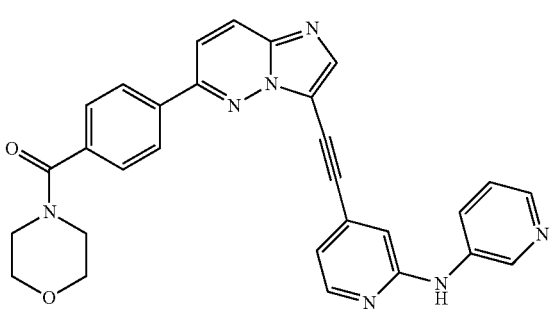 [SMILES: O=C(c1ccc(-c2ccc3ncc(C#Cc4ccnc(Nc5cccnc5)c4)n3n2)cc1)N1CCOCC1]

The title compound was synthesized from (4-(3-((2-chloropyridin-4-yl)ethynyl)imidazo[1,2-b]pyridazin-6-yl)phenyl) (morpholino)methanone and pyridin-3-amine in a similar method to that described for Example 47. The reaction crude product was purified by flash column chromatography (silica gel, eluent CH$_2$Cl$_2$/CH$_3$OH 95:5) to afford morpholino(4-(3-((2-(pyridin-3-ylamino)pyridin-4-yl)ethynyl) imidazo[1,2-b]pyridazin-6 yl)phenyl)methanone (12 mg, 42.8%, AUC HPLC 97%) as a light yellow solid. $^1$H NMR (600 MHz, DMSO-d$_6$) δ (ppm): 9.49 (s, 1H), 8.78 (d, J=2.6 Hz, 1H), 8.30 (d, J=9.5 Hz, 1H), 8.25-8.22 (m, 2H), 8.18 (dd, J=9.2, 2.7 Hz, 3H), 8.10 (dd, J=4.8, 1.5 Hz, 1H), 7.97 (d, J=9.5 Hz, 1H), 7.61 (d, J=8.0 Hz, 1H), 7.31 (dd, J=8.3, 4.7 Hz, 1H), 7.02 (s, 1H), 6.96 (dd, J=5.1, 1.4 Hz, 1H), 3.55-3.32 (m, 4H); $^{13}$C NMR (150 MHz, DMSO-d$_6$) δ (ppm): 169.1, 156.0, 152.1, 148.5, 142.1, 140.4, 139.9, 139.7, 138.3, 137.6, 136.0, 131.0, 128.3, 127.6, 126.9, 125.4, 124.1, 118.8, 116.2, 112.4, 112.0, 96.9, 80.2, 66.5, 48.1; MS (ESI) m/z 502 [C$_{29}$H$_{23}$N$_7$O$_2$+H]$^+$.

Example 50: morpholino(4-(3-((2-(pyridin-4-ylamino)pyridin-4-yl)ethynyl)imidazo[1,2-b]pyridazin-6-yl)phenyl)methanone

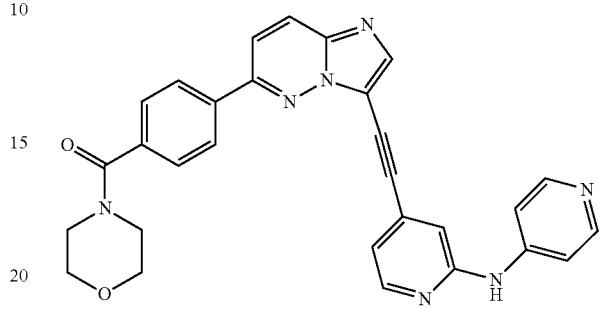

The title compound was synthesized from (4-(3-((2-chloropyridin-4-yl)ethynyl)imidazo[1,2-b]pyridazin-6-yl)phenyl)(morpholino)methanone and pyridin-4-amine in a similar method to that described for Example 47. The reaction crude product was purified by flash column chromatography (Silica gel, eluent CH$_2$Cl$_2$/CH$_3$OH 94:6) to afford morpholino(4-(3-((2-(pyridin-4-ylamino)pyridin-4-yl)ethynyl) imidazo[1,2-b]pyridazin-6-yl)phenyl)methanone (12 mg, 26%, AUC HPLC 99%) as a off white solid; $^1$H NMR (600 MHz, DMSO-d$_6$) δ (ppm): 9.81 (s, 1H), 8.34-8.28 (m, 4H), 8.25 (s, 1H), 8.19 (d, J=6.0 Hz, 2H), 7.98 (d, J=6.0 Hz, 1H), 7.68 (d, J=6.0 Hz, 2H), 7.62 (d, J=12.0 Hz, 2H), 7.10 (s, 1H), 7.07 (s, 1H), 3.69-3.61 (m, 4H); $^{13}$C NMR (150 MHz, DMSO-d$_6$) δ (ppm): 169.1, 155.5, 152.1, 150.1, 148.5, 148.1, 140.0, 139.7, 137.6, 136.0, 131.3, 128.3, 127.6, 126.9, 118.9, 117.4, 113.3, 112.5, 111.9, 96.7, 80.6, 66.4 and 48.4; MS (ESI) m/z 502 [C$_{29}$H$_{23}$N$_7$O$_2$+H]$^+$.

Example 51: morpholino(4-(3-((2-(phenylamino)pyridin-4-yl)ethynyl)imidazo[1,2-b]pyridazin-6-yl)phenyl)methanone

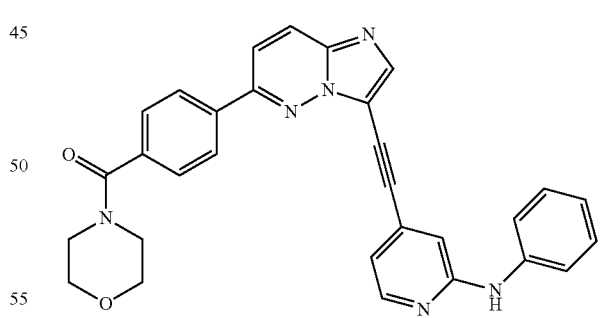

The title compound was synthesized from (4-(3-((2-chloropyridin-4-yl)ethynyl)imidazo[1,2-b]pyridazin-6-yl)phenyl)(morpholino)methanone and aniline in a similar method to that described for Example 47. The reaction crude product was purified by preparative TLC (eluent CH$_2$Cl$_2$/CH$_3$OH 95:5) to afford morpholino(4-(3-((2-(phenylamino)pyridin-4-yl)ethynyl)imidazo[1,2-b]pyridazin-6-yl)phenyl)methanone (8.9 mg, 18%, AUC HPLC 99.7%) as a yellow solid. $^1$H NMR (600 MHz, DMSO-d$_6$) δ (ppm): 9.22 (s, 1H), 8.38 (d, J=9.5 Hz, 1H), 8.30 (s, 1H), 8.23 (d, J=5.7 Hz, 2H), 8.21 (s, 1H), 8.03 (d, J=9.5 Hz, 1H), 7.70-7.66 (m, 2H), 7.64 (d, J=8.3 Hz, 2H), 7.29 (dd, J=8.4, 7.5 Hz, 2H), 7.02 (s, 1H), 6.95-6.91 (m, 2H), 3.62 (m, 8H); $^{13}$C NMR (150 MHz, DMSO-$d_6$) δ (ppm): 168.4, 156.1, 151.6, 148.1, 141.1, 139.6, 139.3, 137.4, 135.6, 130.3, 128.7, 127.9, 127.2, 126.6, 121.0, 118.5, 118.2, 115.0, 111.6, 96.6, 79.5, 66.1, 40.0; MS (ESI) m/z 501 $[C_{30}H_{24}N_6O_2+H]^+$.

Example 52: morpholino(4-(3-((2-(o-tolylamino) pyridin-4-yl)ethynyl)imidazo[1,2-b]pyridazin-6-yl) phenyl)methanone

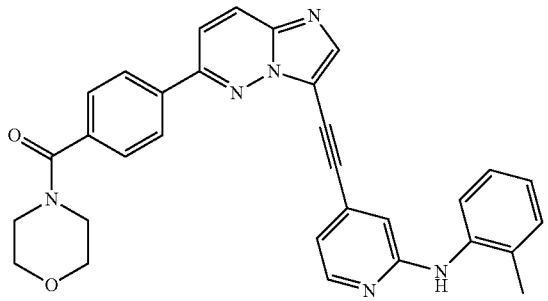 [SMILES: Cc1ccccc1Nc1cc(C#Cc2cnc3ccc(-c4ccc(C(=O)N5CCOCC5)cc4)nn23)ccn1]

The title compound was synthesized from (4-(3-((2-chloropyridin-4-yl)ethynyl)imidazo[1,2-b]pyridazin-6-yl)phenyl)(morpholino)methanone and o-toluidine in a similar method to that described for Example 47. The reaction crude product was purified by flash column chromatography (silica gel, eluent EtOAc/CH$_3$OH 90:10) to afford morpholino(4-(3-((2-(o-tolylamino)pyridin-4-yl)ethynyl)imidazo[1,2-b]pyridazin-6-yl)phenyl)methanone (6.3 mg, 14%, AUC HPLC 99.9%) as a yellow solid; $^1$H NMR (600 MHz, DMSO-$d_6$) δ (ppm): 8.42-8.34 (m, 2H), 8.27 (s, 1H), 8.19 (d, J=8.2 Hz, 2H), 8.13 (d, J=5.0 Hz, 1H), 8.02 (d, J=9.5 Hz, 1H), 7.62 (d, J=8.1 Hz, 2H), 7.56 (d, J=7.9 Hz, 1H), 7.24 (d, J=7.4 Hz, 1H), 7.18 (t, J=7.6 Hz, 1H), 7.04 (t, J=7.4 Hz, 1H), 6.86 (d, J=7.3 Hz, 2H), 3.62 (m, 8H), 2.23 (s, 3H); $^{13}$C NMR (150 MHz, DMSO-$d_6$) δ (ppm): 168.4, 157.2, 151.5, 148.4, 139.6, 139.3, 138.5, 137.3, 135.6, 131.4, 130.6, 130.4, 127.9, 127.2, 126.6, 126.2, 123.9, 118.2, 114.5, 111.6, 109.9, 96.8, 79.3, 66.1, 40.0, 18.1; MS (ESI) m/z 515 $[C_{31}H_{26}N_6O_2+H]^+$.

Example 53: morpholino(4-(3-((2-(thiazol-2-ylamino)pyridin-4-yl)ethynyl)imidazo[1,2-b] pyridazin-6-yl)phenyl)methanone

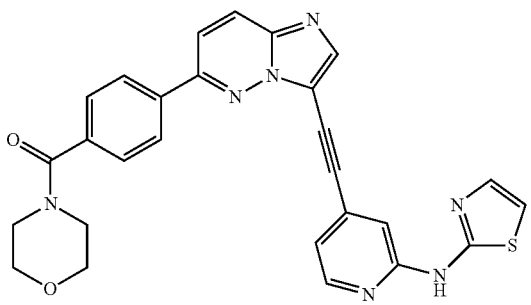 [SMILES: O=C(c1ccc(-c2ccc3ncc(C#Cc4ccnc(Nc5nccs5)c4)n3n2)cc1)N1CCOCC1]

The title compound was synthesized from (4-(3-((2-chloropyridin-4-yl)ethynyl)imidazo[1,2-b]pyridazin-6-yl)phenyl)(morpholino)methanone and thiazol-2-amine in a similar method to that described for Example 47. The reaction crude product was purified by flash column chromatography (silica gel, eluent CH$_2$Cl$_2$/CH$_3$OH 96:4) to afford morpholino(4-(3-((2-(thiazol-2-ylamino)pyridin-4-yl)ethynyl) imidazo[1,2-b]pyridazin-6-yl)phenyl)methanone (8.9 mg, 20%, AUC HPLC 98%) as a off white solid. $^1$H NMR (600 MHz, DMSO-$d_6$) δ (ppm): 8.35 (d, J=5.2 Hz, 1H), 8.31 (d, J=9.5 Hz, 1H), 8.27 (s, 1H), 8.19 (d, J=8.0 Hz, 2H), 7.99 (d, J=9.5 Hz, 1H), 7.62 (d, J=7.9 Hz, 2H), 7.38 (d, J=3.6 Hz, 1H), 7.26 (s, 1H), 7.08 (d, J=5.2 Hz, 1H), 7.03 (d, J=3.6 Hz, 1H), 3.58-3.51 (m, 4H); $^{13}$C NMR (150 MHz, DMSO-$d_6$) δ (ppm): 169.1, 160.0, 152.5, 152.1, 147.8, 140.0, 139.8, 137.9, 137.6, 136.0, 131.3, 128.3, 127.7, 126.9, 118.9, 117.2, 112.0, 111.9, 96.8, 80.7, 72.7, 63.3 and 42.4; MS (ESI) m/z 508 $[C_{27}H_{21}N_7O_2S+H]^+$.

Example 54: morpholino(4-(3-((2-(pyrimidin-4-ylamino)pyridin-4-yl)ethynyl)imidazo[1,2-b] pyridazin-6-yl)phenyl)methanone

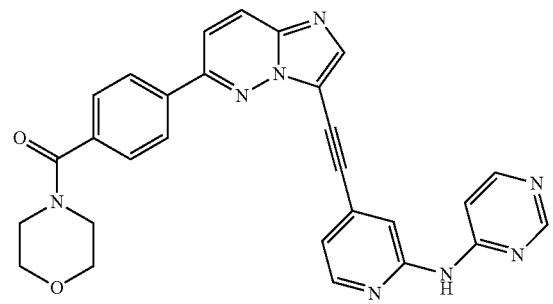 [SMILES: O=C(c1ccc(-c2ccc3ncc(C#Cc4ccnc(Nc5ccncn5)c4)n3n2)cc1)N1CCOCC1]

The title compound was synthesized from (4-(3-((2-chloropyridin-4-yl)ethynyl)imidazo[1,2-b]pyridazin-6-yl)phenyl)(morpholino)methanone and pyrimidin-4-amine in a similar method to that described for Example 47. The reaction crude product was purified by flash column chromatography (silica gel, eluent CH$_2$Cl$_2$/CH$_3$OH 94:6) to afford morpholino(4-(3-((2-(pyrimidin-4-ylamino)pyridin-4-yl)ethynyl)imidazo[1,2-b]pyridazin-6-yl)phenyl)methanone (18 mg, 26%, AUC HPLC 98%) as a off white solid; $^1$H NMR (600 MHz, DMSO-$d_6$) δ (ppm): 10.35 (s, 1H), 8.71 (s, 1H), 8.43 (d, J=6.0 Hz, 1H), 8.38 (d, J=6.0 Hz, 1H), 8.31 (d, J=12.0 Hz, 2H), 8.27 (s, 1H), 8.21-8.18 (m, 2H), 8.01-7.99 (m, 1H), 7.98 (s, 1H), 7.65 (d, J=6.0 Hz, 1H), 7.61 (d, J=6.0 Hz, 2H), 7.20 (d, J=12.0 Hz, 1H), 3.58-3.53 (m, 4H); $^{13}$C NMR (150 MHz, DMSO-$d_6$) δ (ppm): 169.1, 159.2, 158.1, 156.7, 153.7, 152.1, 148.9, 140.0, 139.8, 137.6, 136.0, 131.5, 128.3, 127.6, 126.9, 119.1, 118.9, 114.4, 111.9, 108.9, 97.0, 80.8, 66.4, and 42.5; MS (ESI) m/z 503 $[C_{28}H_{22}N_8O_2+H]^+$.

Example 55: morpholino(4-(3-((2-((2-(trifluoromethyl)phenyl)amino)pyridin-4-yl)ethynyl)imidazo[1, 2-b]pyridazin-6-yl)phenyl)methanone

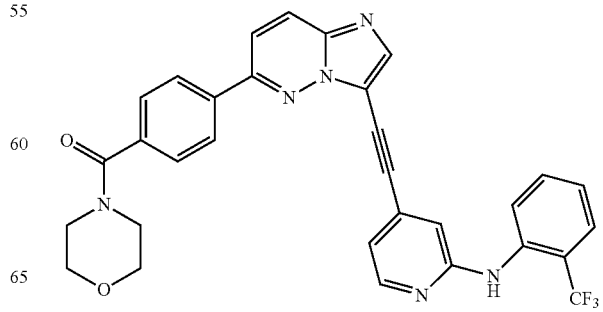

The title compound was synthesized from (4-(3-((2-chloropyridin-4-yl)ethynyl)imidazo[1,2-b]pyridazin-6-yl)phenyl)(morpholino)methanone and 2-(trifluoromethyl)aniline in a similar method to that described for Example 47. The reaction crude product was purified by preparative TLC (eluent EtOAc/CH$_3$OH 95:5) to afford morpholino(4-(3-((2-((2-(trifluoromethyl)phenyl)amino)pyridin-4-yl)ethynyl)imidazo[1,2-b]pyridazin-6-yl)phenyl)methanone (3.3 mg, 13%, AUC HPLC 96.9%) as a off yellow solid; $^1$H NMR (600 MHz, DMSO-d$_6$) δ (ppm): 8.48 (s, 1H), 8.37 (d, J=9.5 Hz, 1H), 8.28 (s, 1H), 8.20 (d, J=8.3 Hz, 2H), 8.11 (d, J=5.1 Hz, 1H), 8.02 (d, J=9.5 Hz, 1H), 7.73 (d, J=7.9 Hz, 1H), 7.71 (d, J=8.0 Hz, 1H), 7.66 (d, J=8.1 Hz, 1H), 7.63 (d, J=8.3 Hz, 2H), 7.35 (t, J=7.6 Hz, 1H), 7.02 (s, 1H), 6.93 (dd, J=5.1, 1.3 Hz, 1H), 3.62 (m, 8H); $^{13}$C NMR (150 MHz, DMSO-d$_6$) δ (ppm): 168.5, 157.2, 151.6, 148.3, 139.7, 139.3, 138.3, 137.4, 135.6, 133.0, 130.7, 128.4, 127.9, 127.2, 126.6, 126.5, 126.5, 124.9, 124.8, 118.3, 115.6, 111.6, 110.8, 96.6, 79.7, 66.1, 47.7; MS (ESI) m/z 569 [C$_{31}$H$_{23}$F$_3$N$_6$O$_2$+H]$^+$ Example 56: morpholino(4-(3-((2-(pyrimidin-2-ylamino)pyridin-4-yl)ethynyl)imidazo[1,2-b]pyridazin-6 yl)phenyl)methanone

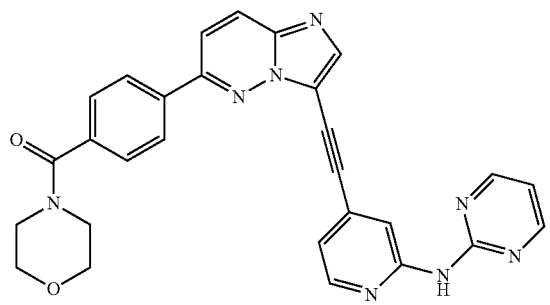 [SMILES: O=C(c1ccc(-c2ccc3ncc(C#Cc4ccnc(Nc5ncccn5)c4)n3n2)cc1)N1CCOCC1]

The title compound was synthesized from (4-(3-((2-chloropyridin-4-yl)ethynyl)imidazo[1,2-b]pyridazin-6-yl)phenyl)(morpholino)methanone and pyrimidin-2-amine in a similar method to that described for Example 47. The reaction crude product was purified by flash column chromatography (silica gel, eluent CH$_2$Cl$_2$/CH$_3$OH 94:6) to afford morpholino(4-(3-((2-(pyrimidin-2-ylamino)pyridin-4-yl)ethynyl)imidazo[1,2-b]pyridazin-6 yl)phenyl)methanone (21 mg, 32.3%, AUC HPLC 95%) as a light brown solid; $^1$H NMR (600 MHz, DMSO-d$_6$) δ (ppm): 9.99 (s, 1H), 8.59-8.47 (m, 3H), 8.37-8.31 (m, 3H), 8.20 (d, J=7.8 Hz, 2H), 8.01 (d, J=9.6 Hz, 1H), 7.61 (d, J=7.8 Hz, 2H), 7.20 (s, 1H), 7.01 (s, 1H), 3.42-3.37 (m, 4H); $^{13}$C NMR (150 MHz, DMSO-d$_6$) δ (ppm): 169.0, 159.3, 158.6, 158.5, 153.6, 152.1, 149.1, 139.9, 137.7, 136.0, 132.1, 131.3, 128.5, 128.3, 127.7, 127.0, 118.8, 114.5, 113.7, 112.0, 97.4, 80.5, 66.5, 48.1; MS (ESI) m/z 503 [C$_{28}$H$_{22}$N$_8$O$_2$+H]$^+$.

Example 57: morpholino(4-(3-((2-(m-tolylamino)pyridin-4-yl)ethynyl)imidazo[1,2-b]pyridazin-6-yl)phenyl)methanone

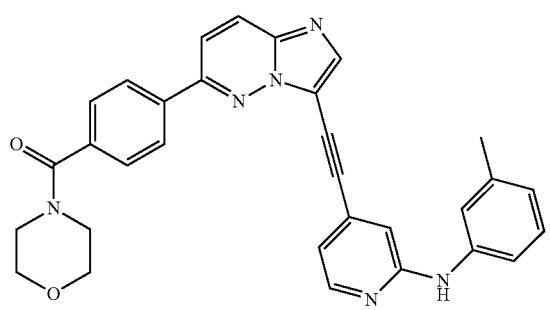 [SMILES: Cc1cccc(Nc2cc(C#Cc3cnc4ccc(-c5ccc(C(=O)N6CCOCC6)cc5)nn34)ccn2)c1]

The title compound was synthesized from (4-(3-((2-chloropyridin-4-yl)ethynyl)imidazo[1,2-b]pyridazin-6-yl)phenyl)(morpholino)methanone and m-toluidine amine in a similar method to that described for Example 47. The residue was purified by preparative HPLC (C18, eluents CH$_3$CN/H$_2$O/HCOOH 0.01%) to afford morpholino(4-(3-((2-(m-tolylamino)pyridin-4-yl)ethynyl)imidazo[1,2-b]pyridazin-6-yl)phenyl)methanone (1.8 mg, AUC HPLC 99%) as a yellow solid. $^1$H NMR (400 MHz, CH$_3$OD) δ (ppm): 8.25 (d, J=8.3 Hz, 2H), 8.18 (d; J=9.5 Hz, 1H), 8.14-8.10 (m, 2H), 7.96 (d, J=9.6 Hz, 1H), 7.63 (d, J=8.4 Hz, 2H), 7.34-7.28 (m, 2H), 7.18 (t, J=7.7 Hz, 1H), 6.99 (s, 1H), 6.89-6.87 (m, 1H), 6.84 (d, J=7.4 Hz, 1H), 3.90-3.51 (m, 8H), 2.33 (s, 3H); MS (ESI) m/z 515 [C$_{31}$H$_{26}$N$_6$O$_2$+H]$^+$.

Example 58: morpholino(4-(3-((2-(p-tolylamino)pyridin-4-yl)ethynyl)imidazo[1,2-b]pyridazin-6-yl)phenyl)methanone

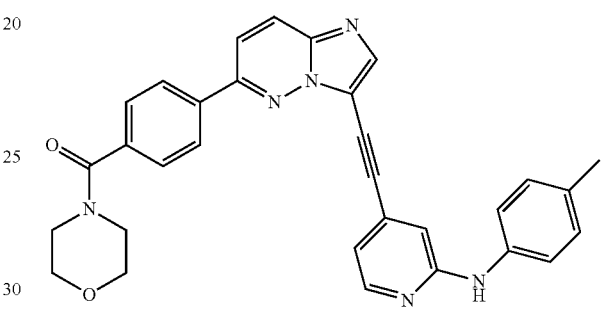

The title compound was synthesized from (4-(3-((2-chloropyridin-4-yl)ethynyl)imidazo[1,2-b]pyridazin-6-yl)phenyl)(morpholino)methanone and p-toluidine in a similar method to that described for Example 47. The reaction crude product was purified by preparative HPLC (C18, eluent CH$_3$CN/H$_2$O/HCOOH 0.1%) to afford morpholino(4-(3-((2-(p-tolylamino)pyridin-4-yl)ethynyl)imidazo[1,2-b]pyridazin-6-yl)phenyl)methanone (2.2 mg, AUC HPLC 98%) as a brown solid. $^1$H NMR (400 MHz, CH$_3$OD) δ (ppm): 8.24 (d, J=8.3 Hz, 2H), 8.17 (d, J=9.5 Hz, 1H), 8.14-8.10 (m, 2H), 7.94 (d, J=9.5 Hz, 1H), 7.62 (d, J=8.3 Hz, 2H), 7.37 (d, J=8.3 Hz, 2H), 7.13 (d, J=8.3 Hz, 2H), 6.96 (s, 1H), 6.85 (d, J=8.3 Hz, 1H), 3.85-3.46 (m, 8H), 2.31 (s, 3H); $^{13}$C NMR (100 MHz, CH$_3$OD) δ (ppm): 171.79, 158.34, 153.62, 148.99, 140.89, 139.64, 139.48, 138.47, 137.94, 133.30, 133.11, 130.57, 129.05, 128.70, 126.94, 121.66, 119.64, 116.27, 114.38, 112.22, 98.06, 79.84, 67.85, 20.94; MS (ESI) m/z 515 [C$_{31}$H$_{26}$N$_6$O$_2$+H]$^+$.

Example 59: (4-(3-((2-(2-isopropylphenylamino)pyridin-4-yl)ethynyl)imidazo[1,2-b]pyridazin-6-yl)phenyl)(morpholino)methanone

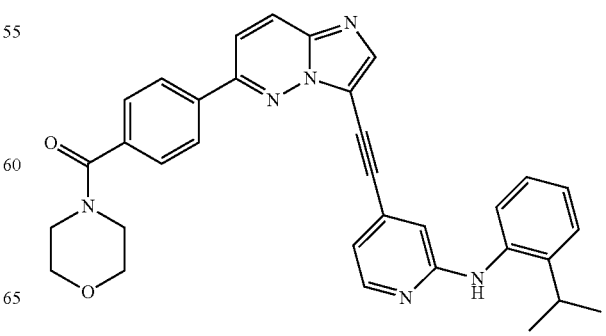

The title compound was synthesized from (4-(3-((2-chloropyridin-4-yl)ethynyl)imidazo[1,2-b]pyridazin-6-yl)phenyl)(morpholino)methanone and 2-isopropylaniline in a similar method to that described for Example 47. The reaction crude product was purified by preparative HPLC (C18, eluent CH$_3$CN/H$_2$O/HCOOH 0.1%) to afford (4-(3-((2-(2-isopropylphenylamino)pyridin-4-yl)ethynyl)imidazo[1,2-b]pyridazin-6-yl)phenyl)(morpholino)methanone (5.63 mg, 15%, AUC HPLC 96%) as a brown solid. $^1$H NMR (400 MHz, CDCl$_3$) δ (ppm): 8.18 (d, J=5.2 Hz, 1H), 8.09-8.04 (m, 4H), 7.60-7.55 (m, 3H), 7.41-7.36 (m, 2H), 7.26-7.23 (m, 2H), 6.90-6.87 (m, 1H), 6.73 (s, 1H), 6.61 (s, 1H), 4.78-3.30 (m, 8H), 3.24 (m, J=6.8 Hz, 1H), 1.25 (d, J=6.8 Hz, 6H); $^{13}$C NMR (100 MHz, CDCl$_3$) δ (ppm): 169.61, 157.88, 151.65, 148.30, 143.88, 139.69, 139.24, 137.14, 136.58, 136.37, 132.27, 127.96, 127.43, 126.74, 126.61, 126.28, 126.21, 125.72, 117.01, 115.96, 113.02, 108.38, 97.21, 66.92, 28.03, 23.30; MS (ESI) m/z 543 [C$_{33}$H$_{30}$N$_6$O$_2$+H]$^+$.

Example 60: (4-(3-((2-(biphenyl-2-ylamino)pyridin-4-yl)ethynyl)imidazo[1,2-b]pyridazin-6-yl)phenyl)(morpholino)methanone

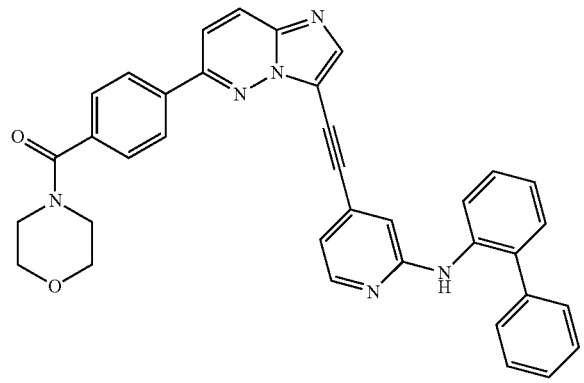 [SMILES: O=C(c1ccc(-c2ccc3ncc(C#Cc4ccnc(Nc5ccccc5-c5ccccc5)c4)n3n2)cc1)N1CCOCC1]

The title compound was synthesized from (4-(3-((2-chloropyridin-4-yl)ethynyl)imidazo[1,2-b]pyridazin-6-yl)phenyl)(morpholino)methanone and biphenyl-2-amine in a similar method to that described for Example 47. The reaction crude product was purified by preparative HPLC (C18, eluent CH$_3$CN/H$_2$O/HCOOH 0.1%) to afford (4-(3-((2-(biphenyl-2-ylamino)pyridin-4-yl)ethynyl)imidazo[1,2-b]pyridazin-6-yl)phenyl)(morpholino)methanone (6.4 mg, 17%, AUC HPLC 99%) as a brown solid. $^1$H NMR (400 MHz, CH$_3$OD) δ (ppm): 8.18 (d, J=5.2 Hz, 1H), 8.11-8.07 (m, 4H), 7.82 (d, J=7.5 Hz, 1H), 7.59 (t, J=8.7 Hz, 3H), 7.45-7.26 (m, 7H), 7.21-7.16 (m, 1H), 6.99 (s, 1H), 6.91-6.89 (m, 1H), 6.60 (s, 1H), 4.16-3.08 (m, 8H); $^{13}$C NMR (100 MHz, CH$_3$OD) δ (ppm): 169.58, 156.12, 151.69, 148.37, 139.68, 139.26, 138.65, 137.13, 136.90, 134.07, 132.10, 130.92, 129.26, 128.90, 128.35, 127.97, 127.70, 127.43, 126.22, 123.70, 121.51, 117.08, 116.52, 117.08, 116.52, 113.00, 109.92, 97.07, 79.65, 66.89; MS (ESI) m/z 577 [C$_{36}$H$_{28}$N$_6$O$_2$+H]$^+$.

Example 61: 3-methyl-N-(4-((6-(4-(morpholine-4 carbonyl)phenyl)imidazo[1,2-b]pyridazin-3-yl)ethynyl)pyridin-2-yl)benzamide

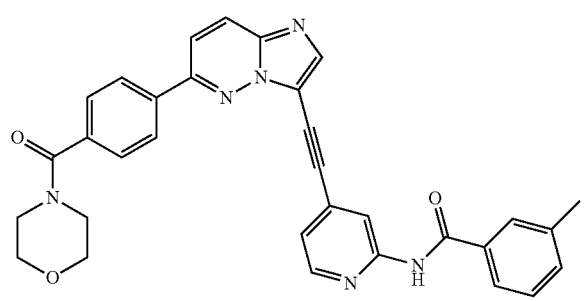 [SMILES: Cc1cccc(C(=O)Nc2cc(C#Cc3cnc4ccc(-c5ccc(C(=O)N6CCOCC6)cc5)nn34)ccn2)c1]

To a solution of (4-(3-((2-aminopyridin-4-yl)ethynyl)imidazo[1,2-b]pyridazin-6-yl)phenyl)(morpholino)methanone (30 mg, 0.07 mmol) in DCM (5 mL) was added 3-methylbenzoyl chloride (60 mg, 0.35 mmol), DMAP (43 mg, 0.35 mmol) and TEA (22 mg, 0.21 mmol). The resulting mixture was stirred at room temperature 6 h. The reaction mixture was then filtered and the filtrate was purified by preparative HPLC (C18, eluent CH$_3$CN/H$_2$O/HCOOH 0.1%) to afford the mono and bis benzamide derivatives 3-methyl-N-(4-((6-(4-(morpholine-4-carbonyl)phenyl)imidazo[1,2-b]pyridazin-3-yl)ethynyl)pyridin-2-yl)benzamide and 3-methyl-N-(3-methylbenzoyl)-N-(4-((6-(4-(morpholine-4-carbonyl)phenyl)imidazo[1,2-b]pyridazin-3-yl)ethynyl)pyridin-2-yl)benzamide. 3-methyl-N-(4-((6-(4-(morpholine-4-carbonyl)phenyl)imidazo[1,2-b]pyridazin-3-yl)ethynyl)pyridin-2-yl)benzamide (13.4 mg, 35%, AUC HPLC 99%) as yellow solid. $^1$H NMR (400 MHz, CDCl$_3$) δ (ppm): 8.82 (s, 1H), 8.29 (d, J=5.2 Hz, 1H), 8.18-8.11 (m, 4H), 7.88 (s, 2H), 7.67-7.64 (m, 3H), 7.44-7.42 (m, 2H), 7.31 (d, J=5.6 Hz, 1H), 4.11-3.34 (m, 8H), 2.48 (s, 3H); $^{13}$C NMR (100 MHz, CDCl$_3$) δ (ppm): 169.68, 165.95, 164.34, 151.81, 147.91, 139.86, 138.88, 137.11, 136.52, 134.08, 133.21, 133.16, 128.82, 128.07, 127.92, 127.51, 126.21, 124.316, 121.35, 117.19, 115.72, 112.94, 97.00, 80.98, 66.89, 53.42, 48.23, 42.60, 21.41; MS (ESI) m/z 543 [C$_{32}$H$_{26}$N$_6$O$_3$+H]$^+$.

3-methyl-N-(3-methylbenzoyl)-N-(4-((6-(4-(morpholine-4-carbonyl)phenyl)imidazo[1,2-b]pyridazin-3-yl)ethynyl)pyridin-2-yl)benzamide (6.2 mg, 14%, AUC HPLC 99%) as brown solid. $^1$H NMR (400 MHz, CDCl$_3$) δ (ppm): 8.40 (d, J=8.4 Hz, 1H), 8.10 (d, J=8.4 Hz, 4H), 7.70-7.52 (m, 8H), 7.34-7.21 (m, 5H), 4.04-3.31 (m, 8H), 2.33 (s, 6H); $^{13}$C NMR (100 MHz, CDCl$_3$) δ (ppm): 173.15, 169.55, 154.17, 151.40, 149.28, 140.10, 138.61, 137.23, 136.47, 134.61, 133.04, 130.02, 128.44, 128.02, 127.50, 126.34, 126.31, 123.58, 123.21, 117.41, 96.04, 81.83, 66.88, 21.29; MS (ESI) m/z 661 [C$_{40}$H$_{32}$N$_6$O$_4$+H]$^+$.

Example 62: 4-methyl-N-(4-((6-(4-(morpholine-4-carbonyl)phenyl)imidazo[1,2-b]pyridazin-3-yl)ethynyl)pyridin-2-yl)benzamide

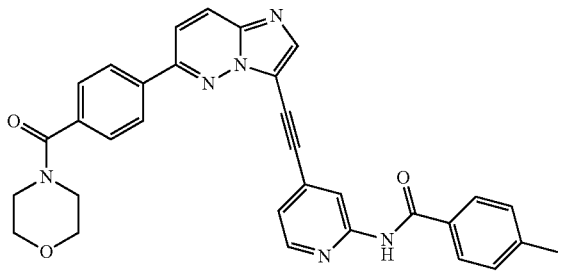 [SMILES: Cc1ccc(C(=O)Nc2cc(C#Cc3cnc4ccc(-c5ccc(C(=O)N6CCOCC6)cc5)nn34)ccn2)cc1]

The title compound was synthesized from (4-(3-((2-aminopyridin-4-yl)ethynyl)imidazo[1,2-b]pyridazin-6-yl)phenyl)(morpholino)methanone and 4-methylbenzoyl chloride in a similar method to that described for Example 61. The reaction crude product was purified by preparative HPLC (C18, eluent CH$_3$CN/H$_2$O/HCOOH 0.1%) to afford 4-methyl-N-(4-((6-(4-(morpholine-4-carbonyl)phenyl)imidazo[1,2-b]pyridazin-3-yl)ethynyl)pyridin-2-yl)benzamide (4.48 mg, 12%, AUC HPLC 95%) as yellow solid. $^1$H NMR (400 MHz, CDCl$_3$) δ (ppm): 9.07 (s, 1H), 8.71 (s, 1H), 8.321-8.29 (m, 1H), 8.18-8.10 (m, 4H), 7.89 (d, J=7.9 Hz, 2H), 7.64 (d, J=8.0 Hz, 3H), 7.34 (d, J=7.9 Hz, 2H), 7.28-7.25 (m, 1H), 4.11-3.34 (m, 8H), 2.45 (s, 3H); $^{13}$C NMR (100 MHz, CDCl$_3$) δ (ppm): 169.68, 165.66, 151.78, 151.68, 147.17, 143.31, 140.05, 137.14, 136.51, 133.63, 131.05, 129.65, 129.53, 129.39, 128.08, 127.53, 127.35, 126.23, 121.22, 117.26, 115.88, 97.00, 66.90, 21.58; MS (ESI) m/z 543 [C$_{32}$H$_{26}$N$_6$O$_3$+H]$^+$.

Example 63: 2-methyl-N-(4-((6-(4-(morpholine-4-carbonyl)phenyl)imidazo[1,2-b]pyridazin-3-yl)ethynyl)pyridin-2-yl)benzamide

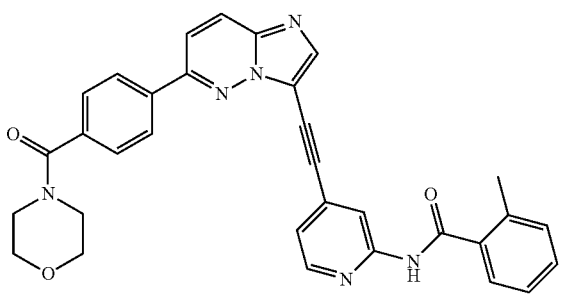 [SMILES: Cc1ccccc1C(=O)Nc1cc(C#Cc2cnc3ccc(-c4ccc(C(=O)N5CCOCC5)cc4)nn23)ccn1]

The title compound was synthesized from (4-(3-((2-aminopyridin-4-yl)ethynyl)imidazo[1,2-b]pyridazin-6-yl)phenyl)(morpholino)methanone and 2-methylbenzoyl chloride in a similar method to that described for Example 61. The reaction crude product was purified by preparative HPLC (C18, eluent CH$_3$CN/H$_2$O/HCOOH 0.1%) to afford 2-methyl-N-(4-((6-(4-(morpholine-4-carbonyl)phenyl)imidazo[1,2-b]pyridazin-3-yl)ethynyl)pyridin-2-yl)benzamide (1 mg, AUC HPLC 99%) as yellow solid. $^1$H NMR (400 MHz, CDCl$_3$) δ (ppm): 8.73 (s, 1H), 8.29 (d, J=5.1 Hz, 1H), 8.18-8.10 (m, 4H), 7.71-7.61 (m, 4H), 7.43 (t, J=7.4 Hz, 1H), 7.33-7.30 (m, 3H), 4.96-3.36 (m, 8H), 2.57 (s, 3H); $^{13}$C NMR (100 MHz, CDCl$_3$) δ (ppm): 169.68, 165.89, 151.78, 151.72, 147.69, 139.95, 138.92, 137.15, 136.54, 134.03, 133.36, 133.27, 128.86, 128.09, 127.92, 127.52, 126.23, 124.31, 121.36, 117.21, 115.73, 97.00, 81.19, 66.91, 21.41; MS (ESI) m/z 543 [C$_{32}$H$_{26}$N$_6$O$_3$+H]$^+$.

Example 064: N-(4-((6-(4-(morpholine-4-carbonyl)phenyl)imidazo[1,2-b]pyridazin-3-yl)ethynyl)pyridin-2-yl)isonicotinamide

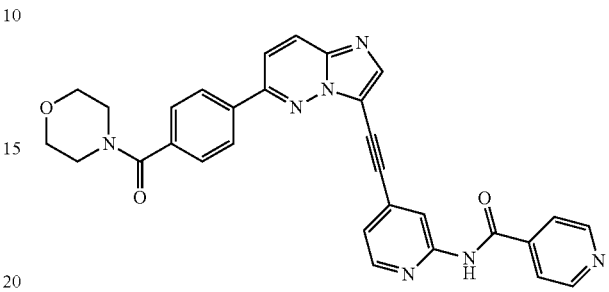

To a solution of isonicotinic acid (29 mg, 0.24 mmol) in DMF (5 mL) were added HATU (68 mg, 0.18 mmol), N-methyl morpholine (24 mg, 0.24 mmol) and (4-(3-((2-aminopyridin-4-yl) ethynyl)imidazo[1,2-b]pyridazin-6-yl)phenyl)(morpholino)methanone (50 mg, 0.12 mmol). The reaction mixture was stirred at room temperature under inert atmosphere for 18 h, and was diluted with H$_2$O (10 mL) and extracted with DCM (3×10 mL). The combined organic layer was dried over Na$_2$SO$_4$, filtered and concentrated under reduced pressure. The crude residue was purified by flash column chromatography (C18, eluents ACN/H$_2$O/HCOOH 0.01%) to afford N-(4-((6-(4-(morpholine-4-carbonyl)phenyl)imidazo[1,2-b]pyridazin-3-yl)ethynyl)pyridin-2-yl)isonicotinamide (9.4 mg, 15%, AUC HPLC 96%) as a yellow solid. $^1$H NMR (400 MHz, DMSO-d$_6$) δ (ppm): 11.40 (s, 1H), 8.85 (s, 2H), 8.53 (d, J=4.9 Hz, 1H), 8.46 (s, 1H), 8.41 (d, J=9.4 Hz, 1H), 8.36 (s, 1H), 8.28 (d, J=7.9 Hz, 2H), 8.08 (d, J=9.6 Hz, 1H), 8.02 (d, J=4.8 Hz, 2H), 7.66 (d, J=8.1 Hz, 2H), 7.44 (d, J=4.6 Hz, 1H), 3.62-3.22 (m, 8H); $^{13}$C NMR (100 MHz, DMSO-d$_6$) δ (ppm): 168.36, 164.80, 152.03, 151.44, 149.46, 148.76, 139.65, 137.33, 135.42, 131.44, 127.83, 127.11, 126.51, 122.11, 120.94, 115.61, 96.52, 81.03, 69.22, 65.98; MS (ESI) m/z 530 [C$_{30}$H$_{23}$N$_7$O$_3$+H]$^+$.

Example 65: N-(4-((6-(4-(morpholine-4-carbonyl)phenyl)imidazo[1,2-b]pyridazin-3-yl)ethynyl)pyridin-2-yl)nicotinamide

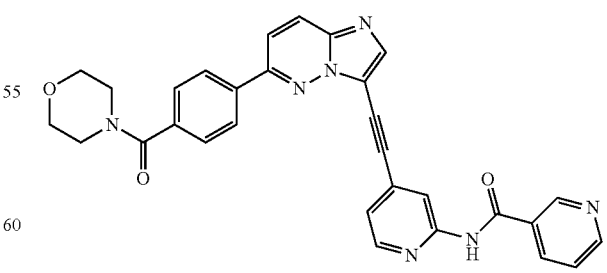

The title compound was synthesized from (4-(3-((2-aminopyridin-4-yl)ethynyl)imidazo[1,2-b]pyridazin-6-yl)phenyl)(morpholino)methanone and nicotinic acid in a similar method to that described for Example 64. The crude residue was purified by column chromatography (C18, eluents ACN/H₂O/HCOOH 0.01%) to afford N-(4-((6-(4-(morpholine-4-carbonyl)phenyl)imidazo[1,2-b]pyridazin-3-yl)ethynyl)pyridin-2-yl)nicotinamide (19 mg, 27%, AUC HPLC 98%) as a yellow solid. ¹H NMR (400 MHz, DMSO-d₆) δ (ppm): 11.30 (s, 1H), 9.18 (s, 1H), 8.80 (d, J=4.2 Hz, 1H), 8.52 (d, J=5.0 Hz, 1H), 8.47 (s, 1H), 8.42-8.35 (m, 3H), 8.28 (d, J=8.3 Hz, 2H), 8.07 (d, J=9.6 Hz, 1H), 7.67 (d, J=8.2 Hz, 2H), 7.60 (dd, J=7.7, 5.0 Hz, 1H), 7.42-7.41 (m, 1H), 3.83-3.52 (m, 8H); ¹³C NMR (100 MHz, DMSO-d₆) δ (ppm): 168.50, 165.11, 152.31, 151.50, 148.88, 148.82, 139.67, 139.49, 137.36, 135.98, 135.48, 131.44, 129.82, 127.91, 127.18, 126.57, 123.51, 120.76, 115.58, 111.44, 96.69, 80.99, 69.27, 66.04, 65.44, 62.60; MS (ESI) m/z 530 [C₃₀H₂₃N₇O₃+H]⁺.

Example 66: N-(4-((6-(4-(morpholine-4-carbonyl)phenyl)imidazo[1,2-b]pyridazin-3-yl) ethynyl)pyridin-2-yl)picolinamide

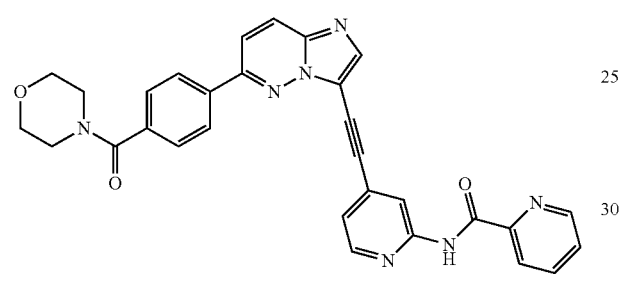

The title compound was synthesized from (4-(3-((2-aminopyridin-4-yl)ethynyl)imidazo[1,2-b]pyridazin-6-yl)phenyl)(morpholino)methanone and picolinic acid in a similar method to that described for Example 64. The reaction crude product was purified by column chromatography (C18, eluents ACN/H₂O/HCOOH 0.01%) to afford N-(4-((6-(4-(morpholine-4-carbonyl)phenyl)imidazo[1,2-b]pyridazin-3-yl) ethynyl)pyridin-2-yl)picolinamide (39 mg, 61%, AUC HPLC 99%) as a yellow solid. ¹H NMR (400 MHz, DMSO-d₆) δ (ppm): 11.40 (s, 1H), 8.85 (s, 2H), 8.53 (d, J=4.9 Hz, 1H), 8.46 (s, 1H), 8.41 (d, J=9.4 Hz, 1H), 8.36 (s, 1H), 8.28 (d, J=7.9 Hz, 2H), 8.08 (d, J=9.6 Hz, 1H), 8.02 (d, J=4.8 Hz, 2H), 7.66 (d, J=8.1 Hz, 2H), 7.44 (d, J=4.6 Hz, 1H), 3.62-3.22 (m, 8H); ¹³C NMR (100 MHz, DMSO-d₆) δ (ppm): 169.71, 162.71, 151.72, 151.41, 149.18, 148.36, 148.34, 139.83, 139.37, 137.66, 137.09, 136.56, 132.88, 128.04, 127.53, 126.91, 126.19, 122.53, 121.38, 117.16, 115.45, 113.00, 97.03, 80.70, 66.91, 48.35, 42.74; MS (ESI) m/z 530 [C₃₀H₂₃N₇O₃+H]⁺.

Example 67: 4-methyl-3-((6-(4-(4-methylpiperazine-1-carbonyl)phenyl)imidazo[1,2-b]pyridazin-3-yl)ethynyl)benzonitrile

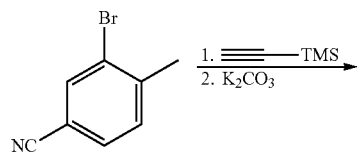

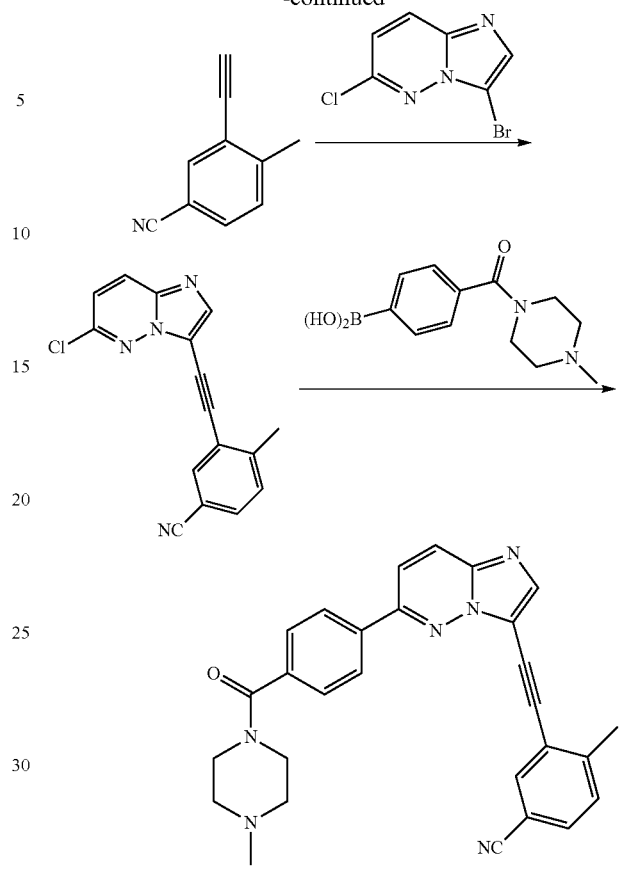

Step 1: Preparation of 4-methyl-3-((trimethylsilyl)ethynyl)benzonitrile

To a mixture of 3-bromo-4-methylbenzonitrile (0.5 g, 2.57 mmol), PdCl₂(PPh₃)₂ (117 mg, 0.167 mmol), PPh₃ (236 mg, 0.902 mmol) and CuI (50 mg, 0.257 mmol) was added THF (15 mL) followed by TMS-acetylene (0.878 mL, 6.18 mmol) and Et₃N (15 mL). The resulting mixture was stirred at 90° C. for 12 h and was concentrated in vacuo. The residue was purified by flash column chromatography (silica gel, eluent hexanes/EtOAc 4:1) to afford 4-methyl-3-((trimethylsilyl)ethynyl)benzonitrile (0.398 g, 72%). ¹H NMR (600 MHz, CDCl₃) δ (ppm): 7.67 (d, J=1.7 Hz, 1H), 7.44 (dd, J=7.9, 1.8 Hz, 1H), 7.27 (dt, J=8.0, 0.8 Hz, 1H), 2.46 (s, 3H), 0.25 (s, 9H); ¹³C NMR (150 MHz, CDCl₃) δ (ppm): 146.1, 135.6, 131.5, 130.3, 124.7, 118.4, 109.9, 101.4, 101.4, 21.2, −0.0; MS (ESI) m/z 214 [C₁₃H₁₅NSi+H]⁺.

Step 2: Preparation of 3-ethynyl-4-methylbenzonitrile

To a solution of 4-methyl-3-((trimethylsilyl)ethynyl)benzonitrile (350 mg, 1.62 mmol) and THF:MeOH (1:1, 8 mL), K₂CO₃ (247 mg, 1.79 mmol) was added and the mixture stirred at room temperature for 30 min. The reaction mixture was concentrated in vacuo to dryness and then suspended between ethyl acetate (10 mL) and saturated aqueous ammonium chloride (5 mL). The layers were separated and the aqueous layer extracted with ethyl acetate (2×10 mL). The organic layers were combined, dried over Na$_2$SO$_4$ and concentrated under reduced pressure. The residue was purified by flash column chromatography (silica gel, eluent hexanes/EtOAc 1:1) to afford 3-ethynyl-4-methylbenzonitrile (0.118 g, 82%). 1H NMR (600 MHz, CDCl$_3$) δ (ppm): 7.70 (d, J=1.7 Hz, 1H), 7.48 (dd, J=8.0, 1.8 Hz, 1H), 7.29 (dd, J=8.0, 0.9 Hz, 1H), 3.36 (s, 1H), 2.49 (s, 3H). $^{13}$C NMR (150 MHz, CDCl$_3$) δ (ppm): 146.3, 135.9, 131.9, 130.5, 123.7, 118.2, 110.1, 83.5, 80.2, 21.1; MS (ESI) m/z 142 [C$_{10}$H$_7$N+H]$^+$.

Step 3: Preparation of 3-((6-chloroimidazo[1,2-b]pyridazin-3-yl)ethynyl)-4-methylbenzonitrile To a solution of 3-bromo-6-chloroimidazo[1,2-b]pyridazine (90.5 mg, 0.390 mmol), PdCl$_2$(PPh$_3$)$_2$ (12.4 mg, 0.017 mmol), PPh$_3$ (27.8 mg, 0.106 mmol), CuI (6.73 mg, 0.035 mmol) in a mixture of THF and DMF (1:1, 2 mL) was added 3-ethynyl-4-methylbenzonitrile (50 mg, 0.354 mmol) and Et$_3$N (1 mL). The resulting mixture was stirred at 90° C. for 4 h and was concentrated in vacuo. The residue was purified by flash column chromatography (silica gel, eluent hexanes/EtOAc 2:3) to afford 3-((6-chloroimidazo[1,2-b]pyridazin-3-yl)ethynyl)-4-methylbenzonitrile (71.6 mg, 69%). $^1$H NMR (600 MHz, CDCl$_3$) δ (ppm): 8.07 (s, 1H), 7.98 (d, J=9.4 Hz, 1H), 7.88 (d, J=1.7 Hz, 1H), 7.57 (dd, J=7.9, 1.8 Hz, 1H), 7.41 (dt, J=8.1, 0.6 Hz, 1H), 7.18 (d, J=9.4 Hz, 1H), 2.68 (s, 3H). $^{13}$C NMR (150 MHz, CDCl$_3$) δ (ppm): 148.3, 145.9, 138.9, 135.1, 132.0, 130.7, 127.3, 123.9, 120.2, 118.3, 113.5, 110.2, 105.2, 96.3, 81.4, 21.3. MS (ESI) m/z 293 [C$_{16}$H$_9$ClN$_4$+H]$^+$.

Step 4: Preparation of 4-methyl-3-((6-(4-(4-methylpiperazine-1-carbonyl)phenyl)imidazo[1,2-b]pyridazin-3-yl)ethynyl)benzonitrile To a solution of 3-((6-chloroimidazo[1,2-b]pyridazin-3-yl)ethynyl)-4-methylbenzonitrile (35 mg, 0.119 mmol), (4-(4-methylpiperazine-1-carbonyl)phenyl)boronic acid (50 mg, 0.175 mmol) in a mixture of 1,4 dioxane and H$_2$O (1:1, 3 mL) was added sodium carbonate (63 mg, 0.595 mmol) and tetrakis-(triphenylphosphine) palladium (13.7 mg, 0.011 mmol). The resulting mixture was heated in a microwave reactor at 110° C. for 4 h. Upon cooling to room temperature, the reaction mixture was extracted with EtOAc (3×10 mL). The organic layers were combined, dried over Na$_2$SO$_4$ and concentrated under reduced pressure. The residue was purified by flash column chromatography (silica gel, eluent CH$_2$Cl$_2$/CH$_3$OH 95:5) to afford 4-methyl-3-((6-(4-(4-methylpiperazine-1-carbonyl)phenyl)imidazo[1,2-b]pyridazin-3-yl)ethynyl)benzonitrile (41 mg, 75%, AUC HPLC 95%) as a yellow solid. $^1$H NMR (DMSO-d$_6$) δ (ppm): 8.38 (d, J=9.5 Hz, 1H), 8.26 (s, 1H), 8.21 (d, J=8.4 Hz, 2H), 8.07 (d, J=1.7 Hz, 1H), 8.03 (d, J=9.6 Hz, 1H), 7.81 (dd, J=7.9, 1.8 Hz, 1H), 7.64-7.56 (m, 3H), 3.66-3.63 (m, 2H), 2.69 (s, 3H), 2.46-2.23 (m, 4H), 2.21 (s, 3H); $^{13}$C NMR (150 MHz, DMSO-d$_6$) δ (ppm): 168.3, 151.6, 145.4, 139.2, 139.0, 137.9, 135.5, 134.2, 132.3, 131.0, 127.7, 127.2, 126.6, 123.1, 118.6, 118.1, 111.9, 109.4, 95.5, 82.5, 45.6, and 20.8; MS (ESI) m/z 461 [C$_{28}$H$_{24}$N$_6$O+H]$^+$.

Example 68: 4-methyl-3-((6-(4-(4-methylpiperazine-1-carbonyl)phenyl)imidazo[1,2-b]pyridazin-3-yl)ethynyl)benzamide

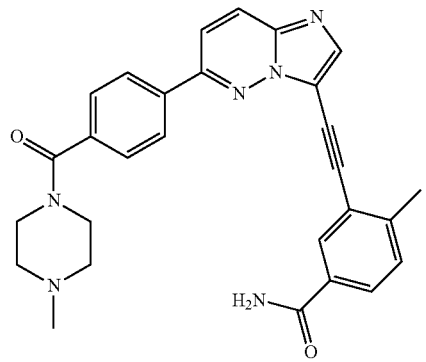 [SMILES: Cc1ccc(C(N)=O)cc1C#Cc1cnc2ccc(-c3ccc(C(=O)N4CCN(C)CC4)cc3)nn12]

To a solution of 4-methyl-3-((6-(4-(4-methylpiperazine-1-carbonyl)phenyl)imidazo[1,2-b]pyridazin-3-yl)ethynyl)benzonitrile (30 mg, 0.065 mmol) in a mixture of DMSO, EtOH and H$_2$O (1:4:3, 4 mL) were added H$_2$O$_2$ (20 mL), followed by NaOH (6.0N, 20 mL). The resulting mixture was stirred at 40° C. for 3 h and was extracted with EtOAc (3×10 mL). The organic layers were combined, dried over Na$_2$SO$_4$ and concentrated under reduced pressure. The resulting residue was purified by flash column chromatography (silica gel, eluent CH$_2$Cl$_2$/CH$_3$OH 95:5) to afford 4-methyl-3-((6-(4-(4-methylpiperazine-1-carbonyl)phenyl)imidazo[1,2-b]pyridazin-3-yl)ethynyl)benzamide (22 mg, 71%, AUC HPLC 96%) as a light yellow solid. $^1$H NMR (600 MHz, DMSO-d$_6$) δ (ppm): 8.36 (d, J=9.5 Hz, 1H), 8.26-8.19 (m, 3H), 8.11 (d, J=1.9 Hz, 1H), 8.05 (bs, 1H), 8.01 (d, J=9.6 Hz, 1H), 7.86 (dd, J=7.9, 1.9 Hz, 1H), 7.62-7.56 (m, 2H), 7.47 (d, J=8.0 Hz, 1H), 7.39 (bs, 1H), 3.66-3.63 (m, 2H), 2.65 (s, 3H), 2.47-2.23 (m, 4H), 2.21 (s, 3H); $^{13}$C NMR (150 MHz, DMSO-d$_6$) δ (ppm): 168.2, 166.8, 151.5, 142.7, 139.0, 138.4, 137.7, 135.5, 132.2, 130.0, 129.8, 128.1, 127.6, 127.0, 126.4, 121.6, 117.7, 112.2, 97.0, 80.8, 54.6, 54.1, 45.5, 20.2; MS (ESI) m/z 479 [C$_{28}$H$_{26}$N$_6$O$_2$+H]$^+$.

Example 69: 3-((6-(4-(4-methylpiperazine-1-carbonyl)phenyl)imidazo[1,2-b]pyridazin-3-yl)ethynyl)benzonitrile

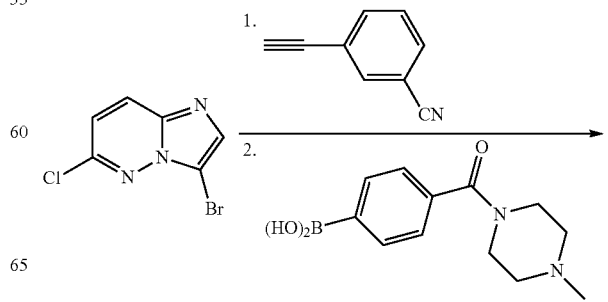

-continued

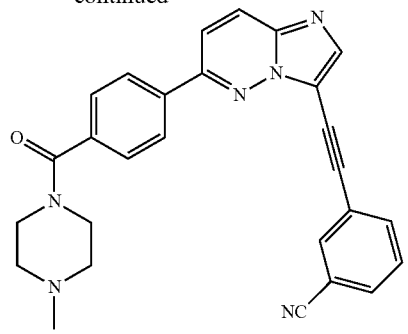

Step 1: Preparation of 3-((6-chloroimidazo[1,2-b]pyridazin-3-yl)ethynyl)benzonitrile The title compound was synthesized from 3-bromo-6-chloroimidazo[1,2-b]pyridazine and 3-ethenylbenzonitrile in a similar method to that described in step 3 of Example 67 synthesis. The reaction crude product was purified by flash column chromatography (silica gel, eluent Hexanes/EtOAc 70:30) to afford 3-((6-chloroimidazo[1,2-b]pyridazin-3-yl)ethynyl)benzonitrile (234 mg, 71%); $^1$H NMR (600 MHz, DMSO-$d_6$) δ (ppm): 8.36 (d, J=9.5 Hz, 1H), 8.28 (s, 1H), 8.15 (t, J=1.6 Hz, 1H), 7.96 (ddt, J=8.0, 3.2, 1.4 Hz, 2H), 7.69 (t, J=7.9 Hz, 1H), 7.55 (d, J=9.5 Hz, 1H); $^{13}$C NMR (150 MHz, DMSO-$d_6$) δ (ppm): 147.8, 139.5, 135.9, 134.6, 133.0, 130.3, 128.3, 122.7, 121.1, 112.4, 117.9, 111.7, 99.5, 96.6, 77.8; MS (ESI) m/z 279 $[C_{15}H_7ClN_4+H]^+$.

Step 2: Preparation of 3-((6-(4-(4-methylpiperazine-1-carbonyl)phenyl)imidazo[1,2-b]pyridazin-3-yl)ethynyl)benzonitrile The title compound was synthesized from 3-((6-chloroimidazo[1,2-b]pyridazin-3-yl)ethynyl)benzonitrile and (4-(4-methylpiperazine-1-carbonyl)phenyl)boronic acid in a similar method to that described in step 4 of Example 67 synthesis. The reaction crude product was purified by flash column chromatography (silica gel, eluent $CH_2Cl_2/CH_3OH$ 95:5) to afford 3-((6-(4-(4-methylpiperazine-1-carbonyl)phenyl)imidazo[1,2-b]pyridazin-3-yl)ethynyl)benzonitrile (16 mg, 40%, AUC HPLC 96%) as a light yellow solid. $^1$H NMR (600 MHz, DMSO-$d_6$) δ (ppm): 8.37 (d, J=9.5 Hz, 1H), 8.27 (s, 1H), 8.25-8.20 (m, 2H), 8.16 (td, J=1.7, 0.7 Hz, 1H), 8.02 (d, J=9.5 Hz, 1H), 8.00-7.96 (m, 1H), 7.94 (dt, J=7.9, 1.4 Hz, 1H), 7.70 (td, J=7.8, 0.6 Hz, 1H), 7.62-7.57 (m, 2H), 3.66-3.64 (m, 2H), 2.41-2.27 (m, 4H), 2.20 (s, 3H); $^{13}$C NMR (150 MHz, DMSO-$d_6$) δ (ppm): 168.3, 151.5, 139.4, 139.1, 137.7, 135.8, 135.4, 134.4, 132.7, 130.3, 127.7, 127.2, 126.5, 123.1, 118.1, 117.9, 112.3, 111.7, 96.3, 78.6, 54.5, 45.6, 40.0; MS (ESI) m/z 447 $[C_{27}H_{22}N_6O+H]^+$.

Example 70: morpholino(4-(3-((2-phenylpyridin-4-yl)ethynyl)imidazo[1,2-b]pyridazin-6-yl)phenyl)methanone

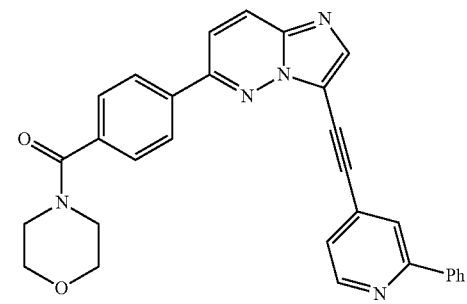 [SMILES: O=C(c1ccc(-c2ccc3ncc(C#Cc4ccnc(-c5ccccc5)c4)n3n2)cc1)N1CCOCC1]

To a solution of (4-(3-((2-chloropyridin-4-yl)ethynyl)imidazo[1,2-b]pyridazin-6-yl)phenyl)(morpholino)methanone (50 mg, 0.112 mmol), phenyl boronic acid (16.3 mg, 0.135 mmol) and 1,4 Dioxane:$H_2O$ (1:1, 2 mL) was added Pd(PPh$_3$)$_4$ (13.0 mg, 0.011 mmol) and Na$_2$CO$_3$ (35.8 mg, 0.336 mmol). The reaction mixture was stirred at 80° C. for 12 h. Solvents were evaporated and the crude material was purified by flash column chromatography (silica gel, eluent EtOAc/CH$_3$OH 95:5) to afford morpholino(4-(3-((2-phenylpyridin-4-yl)ethynyl)imidazo[1,2-b]pyridazin-6-yl)phenyl)methanone (17 mg, 32%, AUC HPLC 97%) as a light yellow solid; $^1$H NMR (600 MHz, DMSO-$d_6$) δ (ppm): 8.74 (d, J=6.0 Hz, 1H), 8.29-8.27 (m, 2H), 8.23-8.20 (m, 3H), 8.11-8.08 (m, 3H), 7.99 (dd, J=9.5, 2.8 Hz, 1H), 7.63-7.61 (m, 2H), 7.56 (d, J=6.0 Hz, 1H), 7.55-7.51 (m, 2H), 7.49-7.47 (m, 1H), 3.41-3.37 (m, 2H); $^{13}$C NMR (600 MHz, DMSO-$d_6$) δ (ppm): 169.2, 157.0, 152.2, 150.5, 138.1, 137.6, 135.9, 133.3, 131.2, 129.4, 128.3, 127.7, 127.1, 126.9, 125.3, 124.7, 124.0, 121.7, 118.9, 96.9, 81.4, 66.4, 63.1, 42.5; MS (ESI) m/z 486 $[C_{30}H_{23}N_5O_2+H]^+$.

Example 71: (4-(3-((2-(methyl(phenyl)amino)pyridin-4-yl)ethynyl)imidazo[1,2-b]pyridazin-6-yl)phenyl) (morpholino) methanone

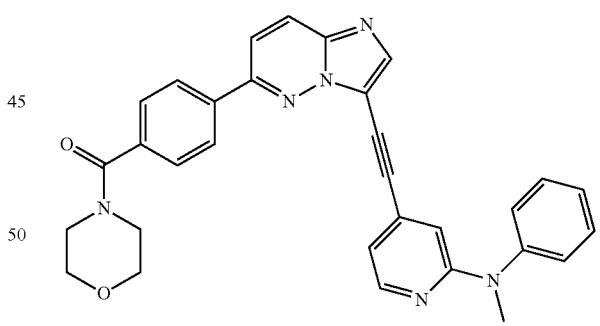

To a solution of morpholino(4-(3-((2-(phenylamino)pyridin-4-yl)ethynyl)imidazo[1,2-b]pyridazin-6-yl)phenyl) methanone (8 mg, 0.0165 mmol) and dry DMF (1 mL) was added Potassium tert-butoxide (3.6 mg, 0.0320 mmol)) and the reaction mixture stirred at room temperature for 10 min, followed by addition of methyl iodide (1.8 μL, 0.288 mmol) and stirring at room temperature for 12 h. DMF was removed under vacuum and the residue was purified by preparative TLC (eluent $CH_2Cl_2/CH_3OH$ 95:5) to afford (4-(3-((2-(methyl(phenyl)amino)pyridin-4-yl)ethynyl)imidazo[1,2-b]pyridazin-6-yl)phenyl) (morpholino) methanone as a light yellow solid (3.7 mg, 45%, AUC.HPLC 98.0%); $^1$H NMR (600 MHz, DMSO-$d_6$) δ (ppm): 8.33 (d, J=9.5 Hz, 1H), 8.24 (d, J=5.1 Hz, 1H), 8.22 (s, 1H), 8.14 (d, J=8.3 Hz, 2H), 7.99 (d, J=9.5 Hz, 1H), 7.60 (d, J=8.3 Hz, 2H), 7.49 (t, J=7.9 Hz, 2H), 7.39-7.34 (m, 2H), 7.30 (t, J=7.4 Hz, 1H), 6.85 (dd, J=5.1, 1.2 Hz, 1H), 6.57 (s, 1H), 3.64 (m, 8H), 3.42 (s, 3H); $^{13}$C NMR (150 MHz, DMSO-$d_6$) δ (ppm): 168.5, 158.3, 151.4, 148.5, 145.8, 139.5, 139.3, 137.3, 135.5, 130.1, 130.0, 127.9, 127.1, 126.5, 126.5, 126.0, 118.2, 113.9, 111.5, 109.0, 96.9, 79.4, 66.1, 47.7, 38.2; MS (ESI) m/z 515 [$C_{31}H_{26}N_6O_2$+H]$^+$.

Example 72: N-(4-((6-(4-(morpholine-4-carbonyl)phenyl)imidazo[1,2-b]pyridazin-3-yl)ethynyl)-1H-pyrrolo[2,3-b]pyridin-6-yl)acetamide

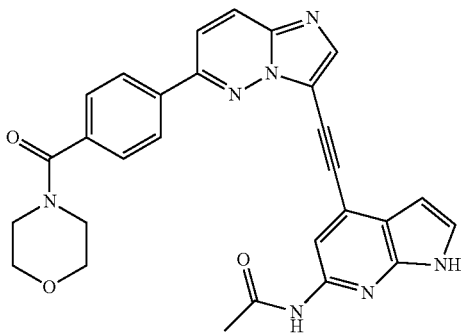 [SMILES: CC(=O)Nc1cc(C#Cc2cnc3ccc(-c4ccc(C(=O)N5CCOCC5)cc4)nn23)c2cc[nH]c2n1]

To a solution of (4-(3-((6-amino-1H-pyrrolo[2,3-b]pyridin-4-yl)ethynyl)imidazo[1,2-b]pyridazin-6-yl)phenyl)(morpholino)methanone (20 mg, 0.0432 mmol) and DCM (2 mL) was added triethylamine (12.0 μL, 0.0863 mmol) followed by acetyl chloride (6.1 μL, 0.0863 mmol). The mixture was stirred at room temperature for 12 h, and then concentrated in vacuo. The reaction crude product was purified by preparative TLC (eluent $CH_2Cl_2/CH_3OH$ 95:5) to afford N-(4-((6-(4-(morpholine-4-carbonyl)phenyl)imidazo[1,2-b]pyridazin-3-yl)ethynyl)-1H-pyrrolo[2,3-b]pyridin-6-yl)acetamide (6.4 mg, 29%, AUC HPLC 97%) as a yellow solid. $^1$H NMR (600 MHz, DMSO-$d_6$) δ (ppm): 11.73 (s, 1H), 10.44 (s, 1H), 8.39 (d, J=9.5 Hz, 1H), 8.36 (s, 1H), 8.28 (d, J=8.4 Hz, 2H), 8.13 (s, 1H), 8.05 (d, J=9.5 Hz, 1H), 7.71-7.65 (m, 2H), 7.53 (dd, J=3.3; 2.5 Hz, 1H), 6.66 (dd, J=3.4, 1.9 Hz, 1H), 3.63 (m, 8H), 2.13 (s, 3H); $^{13}$C NMR (150 MHz, DMSO-$d_6$) δ (ppm): 169.0, 168.4, 159.7, 151.5, 146.8, 146.4, 139.4, 137.4, 135.7, 127.9, 127.1, 126.6, 126.1, 122.0, 118.1, 116.7, 111.9, 107.6, 99.1, 96.4, 81.8, 66.0, 48.6, 24.0; MS (ESI) m/z 506 [$C_{28}H_{23}N_7O_3$+H]$^+$.

Example 73: (4-(3-((6-(benzylamino)-1H-pyrrolo[2,3-b]pyridin-4-yl)ethynyl)imidazo[1,2-b]pyridazin-6-yl)phenyl)(morpholino)methanone

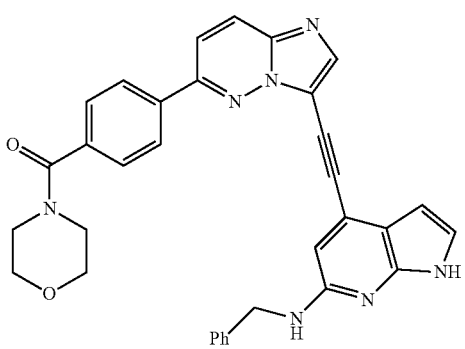 [SMILES: O=C(c1ccc(-c2ccc3ncc(C#Cc4cc(NCc5ccccc5)nc5[nH]ccc45)n3n2)cc1)N1CCOCC1]

To a solution of (4-(3-((6-amino-1H-pyrrolo[2,3-b]pyridin-4-yl)ethynyl)imidazo[1,2-b]pyridazin-6-yl)phenyl)(morpholino)methanone (20 mg, 0.0432 mmol) and DMF (1.5 mL) was added NaH (2 mg, 0.0475 mmol) and stirred for 15 minutes at room temperature. Benzyl bromide (6 μL, 0.0475) in DMF (0.5 mL) was then added. The mixture was stirred at room temperature for 12 h, and then concentrated in vacuo. The reaction crude product was purified by preparative TLC (eluent $CH_2Cl_2/CH_3OH$ 95:5) to afford (4-(3-((6-(benzylamino)-1H-pyrrolo[2,3-b]pyridin-4-yl)ethynyl)imidazo[1,2-b]pyridazin-6-yl)phenyl)(morpholino)methanone (1.8 mg, AUC HPLC 99%) as a light yellow solid. $^1$H NMR (600 MHz, DMSO-$d_6$) δ (ppm): 8.38 (d, J=9.5 Hz, 1H), 8.31 (s, 1H), 8.27-8.22 (m, 2H), 8.02 (d, J=9.6 Hz, 1H), 7.67-7.62 (m, 2H), 7.33-7.29 (m, 2H), 7.25 (d, J=7.4 Hz, 1H), 7.22 (d, J=3.4 Hz, 1H), 7.21-7.17 (m, 2H), 6.54 (s, 1H), 6.52 (d, J=3.4 Hz, 1H), 5.98 (s, 2H), 5.33 (s, 2H), 3.61 (m, 8H); $^{13}$C NMR (150 MHz, DMSO-$d_6$) δ (ppm): 168.8, 156.5, 152.0, 147.1, 139.7, 139.1, 137.8, 136.2, 132.8, 128.9, 128.3, 127.6, 127.4, 127.0, 124.9, 123.1, 118.5, 112.5, 111.8, 104.5, 100.0, 99.4, 96.6, 81.0, 66.5, 47.3, 42.5; MS (ESI) m/z 554 [$C_{33}H_{27}N_7O_2$+H]$^+$.

Example 74: 4-(3-((2-aminopyridin-4-yl)ethynyl)imidazo[1,2-b]pyridazin-6-yl)benzamide

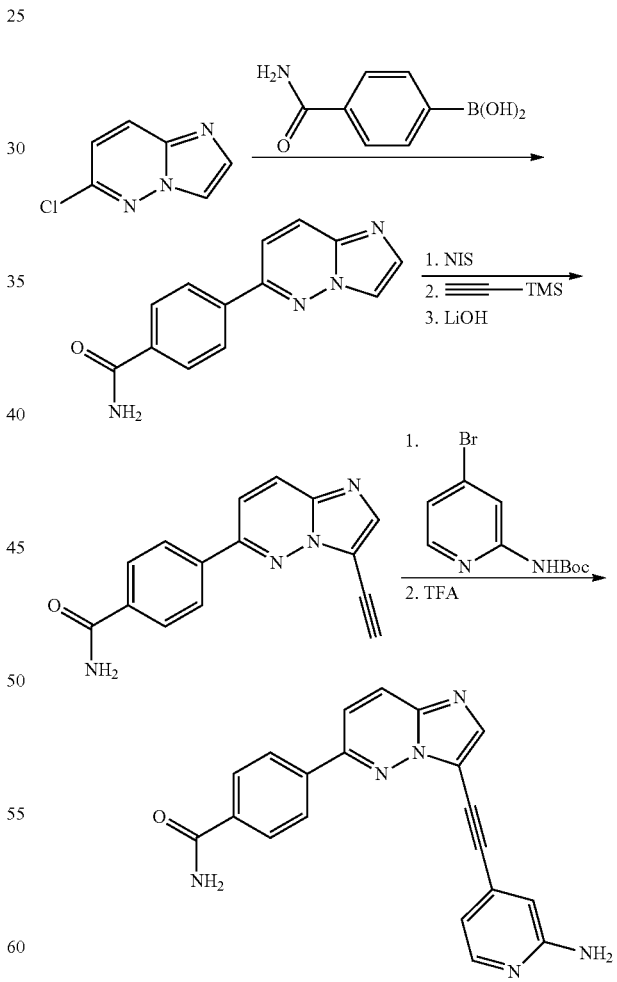

Step 1: Preparation of 4-(imidazo[1,2-b]pyridazin-6-yl)benzamide

A mixture of 6-chloroimidazo[1,2-b]pyridazine (1.5 g, 9.76 mmol), 4-carbamoylphenylboronic acid (1.93 g, 11.72 mmol), Na$_2$CO$_3$ (2.07 g, 19.52 mmol) in 1,4-dioxane (30 mL) and water (8 mL) was stirred under Argon for 20 min. Pd(PPh$_3$)$_4$ (563 mg, 0.49 mmol) was added and the reaction mixture was heated at 100° C. for 16 h. The reaction mixture was diluted with EtOAc and filtered through a short pad of celite. The filtrate was washed with EtOAc and dried over Na$_2$SO$_4$ and concentrated under reduced pressure. The crude product was purified by column chromatography (silica gel, eluent CHCl$_3$/MeOH 97:3) to afford 4-(imidazo[1,2-b]pyridazin-6-yl)benzamide (1.6 g, 68.9%, LC-MS 90%) as a brown solid.

Step 2: Preparation of 4-(3-iodoimidazo[1,2-b]pyridazin-6-yl)benzamide

To a solution of 4-(imidazo[1,2-b]pyridazin-6-yl)benzamide (1.6 g, 6.72 mmol) in DMF (20 mL) was added NIS (1.82 g, 8.06 mmol) at room temperature and stirred at 90° C. for 4 h. The reaction mixture was subjected to an aqueous work-up and dried to afford 4-(3-iodoimidazo[1,2-b]pyridazin-6-yl)benzamide (1.6 g, 65.5% as a green solid.

Step 3: Preparation of 4-(3-((trimethylsilyl)ethynyl)imidazo[1,2-b]pyridazin-6-yl)benzamide A mixture of 4-(3-iodoimidazo[1,2-b]pyridazin-6-yl)benzamide (1.6 g, 4.39 mmol), ethynyltrimethylsilane (0.74 mL, 5.27 mmol), CuI (125.6 mg, 0.66 mmol), and diisopropylethylamine (1.13 mL, 6.58 mmol) in DMF (20 mL) was stirred under argon for 20 min. Pd(PPh$_3$)$_4$ (253 mg, 0.22 mmol) was added and the reaction mixture was heated at 90° C. for 3 h. Water (2×100 mL) was added to the reaction mixture and the precipitate was isolated by filtration and purified by column chromatography (silica gel, eluent CHCl$_3$/MeOH 97:3) to afford 4-(3-((trimethylsilyl)ethynyl)imidazo[1,2-b]pyridazin-6-yl)benzamide (800 mg, 54.8%, LC-MS 94.7%) as a light green solid. $^1$H NMR (400 MHz, DMSO-d$_6$) δ (ppm): 8.33 (d, J=9.7 Hz, 1H), 8.22-8.01 (m, 7H), 7.50 (bs, 1H), 0.32 (s, 9H); MS (ESI) m/z 335 [C$_{18}$H$_{18}$N$_4$OSi+H]$^+$.

Step 4: Preparation of 4-(3-ethynylimidazo[1,2-b]pyridazin-6-yl)benzamide

To a solution of 4-(3-((trimethylsilyl)ethynyl)imidazo[1,2-b]pyridazin-6-yl)benzamide (500 mg, 1.5 mmol) in a mixture of THF, EtOH and H$_2$O (1:1:1, 15 mL) was added LiOH.H$_2$O (126 mg, 3 mmol) and the reaction mixture was stirred at room temperature for 2 h. The solvents were evaporated under reduced pressure and the residue was diluted with EtOAc and washed in turn with water and brine solution. The organic layer was dried over anhydrous Na$_2$SO$_4$ and concentrated under reduced pressure. The crude product was washed with diethyl ether and n-pentane to afford 4-(3-ethynylimidazo[1,2-b]pyridazin-6-yl)benzamide (305 mg, 77.8%, LC-MS 96.6%) as a green solid. $^1$H NMR (400 MHz, DMSO d$_6$) δ (ppm): 8.33 (d, J=9.7 Hz, 1H), 8.20-7.90 (m, 7H), 7.52 (bs, 1H), 5.02 (s, 1H); MS (ESI) m/z 261 [C$_{15}$H$_{10}$N$_4$O+H]$^+$.

Step 5: Preparation of tert-butyl 4-((6-(4-carbamoylphenyl)imidazo[1,2-b]pyridazin-3-yl)ethynyl)pyridin-2-ylcarbamate A mixture of 4-(3-ethynylimidazo[1,2-b]pyridazin-6-yl)benzamide (300 mg, 1.14 mmol), tert-butyl 4-bromopyridin-2-ylcarbamate (374 mg, 1.37 mmol), CuI (32.37 mg, 0.17 mmol), and DIPEA (0.3 mL, 1.72 mmol) in DMF (10 mL) was stirred under argon for 20 min. Pd(PPh$_3$)$_4$ (69.3 mg, 0.06 mmol) was added and the reaction mixture was heated at 90° C. for 3 h. Water (2×100 mL) was added and the solid that has precipitated was isolated by filtration to give the reaction crude product which was purified by column chromatography (silica gel, eluent CHCl$_3$/MeOH 97:3) to afford tert-butyl 4-((6-(4-carbamoylphenyl)imidazo[1,2-b]pyridazin-3-yl)ethynyl)pyridin-2-ylcarbamate mixed with its diboc analog (260 mg, mixture of mono and diboc compounds) as a light green solid.

Step 6: Preparation of 4-(3-((2-aminopyridin-4-yl)ethynyl)imidazo[1,2-b]pyridazin-6-yl)benzamide To a solution of tert-butyl 4-((6-(4-carbamoylphenyl)imidazo[1,2-b]pyridazin-3-yl)ethynyl)pyridin-2-ylcarbamate (260 mg, 0.57 mmol) in DCM (10 mL) was added TFA (2 mL) at 0° C. and stirred at room temperature for 3 h. The reaction mixture was diluted with water and basified with NaHCO$_3$, extracted with CHCl$_3$, and washed with brine solution. The organic layer was dried over anhydrous Na$_2$SO$_4$ and concentrated under reduced. The crude product was purified by flash column chromatography (silica gel, eluent CHCl$_3$/MeOH 96:4) to afford 4-(3-((2-aminopyridin-4-yl)ethynyl)imidazo[1,2-b]pyridazin-6-yl)benzamide (120 mg, 59.4%, LC-MS 95.3%) as a pale yellow solid. $^1$H NMR (400 MHz, DMSO d$_6$) δ (ppm): 8.37 (d, J=9.6 Hz, 1H), 8.26-8.22 (m, 3H), 8.12-8.04 (m, 4H), 7.99 (d, J=5.2 Hz, 1H), 7.51 (bs, 1H), 6.66-6.63 (m, 2H), 6.17 (s, 2H); MS (ESI) m/z 355.12 [C$_2$OH$_{14}$N$_6$O+H]$^+$.

Example 75: 4-(4-(3-((1H-pyrrolo[2,3-b]pyridin-4-yl)ethynyl)imidazo[1,2-b]pyridazin-6-yl)benzyl)morpholine

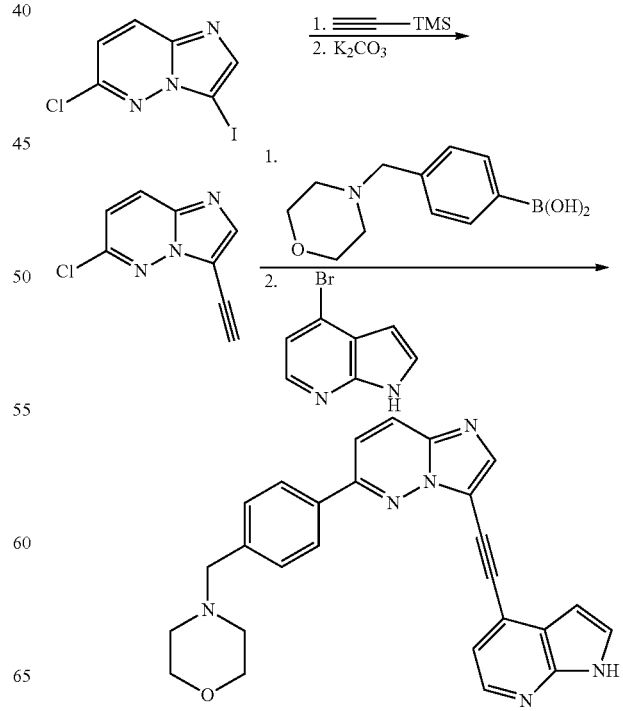

Step 1: Preparation of 6-chloro-3-((trimethylsilyl)ethynyl)imidazo[1,2-b]pyridazine to a solution of 6-chloro-3-iodoimidazo[1,2-b]pyridazine (200 mg, 0.716 mmol), and THF (2 mL) was added PdCl$_2$(PPh$_3$)$_2$ (25 mg, 0.035 mmol), CuI (13.6 mg, 0.071 mmol), Et$_3$N (1 mL) and TMS acetylene (102 µL, 0.716 mmol) and then the reaction mixture was stirred at room temperature for 12 h. The reaction mixture was concentrated in vacuo to dryness and then purified by flash column chromatography (silica gel, eluent Hexanes/EtOAac 85:15) to afford 6-chloro-3-((trimethylsilyl)ethynyl)imidazo[1,2-b]pyridazine (153 mg, 86%).

Step 2: Preparation of 6-chloro-3-ethynylimidazo[1,2-b]pyridazine to a solution of 6-chloro-3-((trimethylsilyl)ethynyl)imidazo[1,2-b]pyridazine (170 mg, 0.682 mmol) in a mixture of THF and MeOH (1:1, 3 mL) was added K$_2$CO$_3$ (113 mg, 0.819 mmol) and the mixture stirred at room temperature for 30 min. The reaction mixture was concentrated in vacuo to dryness and the residue was suspended in a mixture ethyl acetate (6 mL) and saturated aqueous ammonium chloride (3 mL). The aqueous layer extracted with ethyl acetate (2×8 mL) and the combined extracts were dried over Na$_2$SO$_4$ and concentrated under reduced pressure. The residue was purified by flash column chromatography (silica gel, eluent hexanes/EtOAc 85:15) to afford 6-chloro-3-ethynylimidazo[1,2-b]pyridazine (68 mg, 56.3%).

Step 3: Preparation of 4-(4-(3-ethynylimidazo[1,2-b]pyridazin-6-yl)benzyl)morpholine to a solution of 6-chloro-3-ethynylimidazo[1,2-b]pyridazine (130 mg, 0.734 mmol) in a mixture of 1,4 dioxane and H$_2$O (2:1, 6 mL) was added (4-(morpholinomethyl)phenyl)boronic acid (238 mg, 0.881 mmol), sodium carbonate (389 mg, 3.67 mmol) and tetrakis-(triphenylphosphine)palladium (84.8 mg, 0.073 mmol). The resulting mixture was heated at 80° C. in a microwave apparatus for 5 h. The reaction mixture was extracted with EtOAc (3×10 mL). The organic layers were combined, dried over Na$_2$SO$_4$ and concentrated under reduced pressure. The resulting residue was purified by flash column chromatography (silica gel, eluent hexanes/EtOAc 20:80) to afford 4-(4-(3-ethynylimidazo[1,2-b]pyridazin-6-yl)benzyl)morpholine (87 mg, 37.3%); MS (ESI) m/z 319 [C$_{19}$H$_{18}$N$_4$O+H]$^+$.

Step 4: Preparation of 4-(4-(3-((1H-pyrrolo[2,3-b]pyridin-4-yl)ethynyl)imidazo[1,2-b]pyridazin-6-yl)benzyl)morpholine to a solution of 4-(4-(3-ethynylimidazo[1,2-b]pyridazin-6-yl)benzyl)morpholine (20 mg, 0.062 mmol) and DMF (1 mL) was added 4-bromo-1H-pyrrolo[2,3-b]pyridine (18.5 mg, 0.094 mmol), PdCl$_2$(PPh$_3$)$_2$ (2.8 mg, 0.004 mmol), CuI (1.2 mg, 0.006 mmol), PPh$_3$ (5.76 mg, 0.022 mmol) and DIPEA (1 mL). The resulting mixture was stirred at 90° C. for 12 h. Upon cooling to room temperature, DMF was then removed in vacuo and the resulting residue was purified by flash column chromatography (eluent CH$_2$Cl$_2$/CH$_3$OH 95:5) to afford 4-(4-(3-((1H-pyrrolo[2,3-b]pyridin-4-yl)ethynyl)imidazo[1,2-b]pyridazin-6-yl)benzyl)morpholine (3.0 mg, 11.1%, AUC HPLC 94%) as a light yellow solid; $^1$H NMR (600 MHz, DMSO-d$_6$) δ (ppm): 8.34 (s, 1H), 8.21 (d, J=9.6 Hz, 1H), 8.03 (d, J=7.9 Hz, 3H), 7.83-7.76 (m, 3H), 7.50 (d, J=7.9 Hz, 3H), 3.59 (t, J=4.8 Hz, 4H), 3.55 (s, 2H), 2.41-2.36 (m, 4H); MS (ESI) m/z 435 [C$_{26}$H$_{22}$N$_6$O+H]$^+$.

Example 76: (4-(3-((2-aminopyridin-4-yl)ethynyl)imidazo[1,2-b]pyridazin-6-yl)phenyl)(4-methylpiperazin-1-yl)methanone

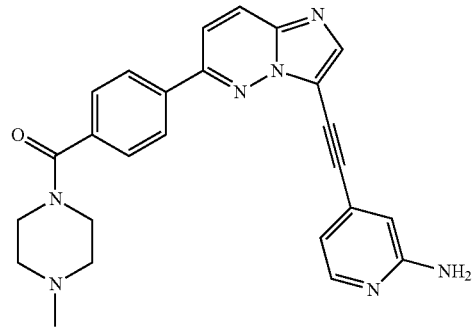 [SMILES: CN1CCN(C(=O)c2ccc(-c3ccc4ncc(C#Cc5ccnc(N)c5)n4n3)cc2)CC1]

To a solution of (4-(3-ethynylimidazo[1,2-b]pyridazin-6-yl)phenyl)(4-methylpiperazin-1-yl)methanone (160 mg, 0.46 mmol) in acetonitrile (6 mL) under inert atmosphere was added 4-iodopyridin-2-amine (132 mg, 0.60 mmol), Pd(PPh$_3$)$_4$ (26.6 mg, 0.02 mmol), CuI (8.8 mg, 0.05 mmol) and 3 mL of DIPEA. The reaction mixture was heated at 70° C. for 2.5 h, was diluted with water (10 mL) and extracted with dichloromethane (25 mL×3). The combined organic layers were dried over sodium sulfate, filtered and concentrated under reduced pressure. The residue was purified by flash column chromatography (silica gel, eluent DCM/Methanol 94:6) and washed with saturated NaHCO$_3$ solution (5 mL×2). The organic phase was dried over Na$_2$SO$_4$, filtered and concentrated under reduced pressure and high vacuum to afford (4-(3-((2-aminopyridin-4-yl)ethynyl)imidazo[1,2-b]pyridazin-6-yl)phenyl)(4-methylpiperazin-1-yl)methanone (91.2 mg, 45%, AUC HPLC 99.08%) as yellow solid mp: 120-122° C. $^1$H NMR (400 MHz, CDCl$_3$) δ (ppm): 8.20-8.00 (m, 5H), 7.70-7.50 (m, 3H), 6.85 (d, J=4.8 Hz, 1H), 6.71 (s, 1H), 4.52 (bs, 2H), 3.84 (bs, 2H), 3.49 (bs, 2H), 2.60-2.30 (m, 4H), 2.21 (s, 3H); $^{13}$C NMR (400 MHz, CDCl$_3$) δ (ppm): 169.49, 158.41, 151.76, 148.31, 139.52, 139.20, 137.61, 136.40, 132.03, 127.88, 127.38, 126.12, 117.08, 115.73, 113.03, 110.05, 97.00, 79.26, 46.02; MS (ESI) m/z 438.20 [C$_{25}$H$_{23}$N$_7$O+H]$^+$.

Example 77: 4-(4-(3-((2-aminopyridin-4-yl)ethynyl)imidazo[1,2-b]pyridazin-6-yl)benzoyl)-1-methylpiperazin-2-one

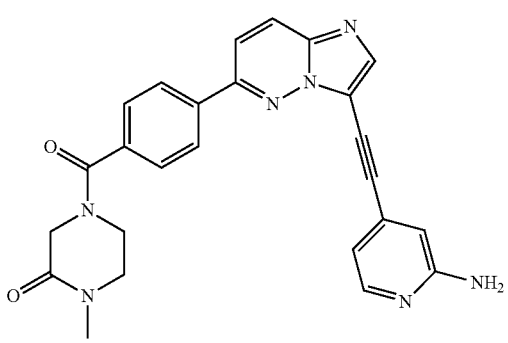 [SMILES: CN1CCN(C(=O)c2ccc(-c3ccc4ncc(C#Cc5ccnc(N)c5)n4n3)cc2)CC1=O]

The title compound was synthesized in a similar fashion as described for Example 76 starting from 4-(4-(3-iodoimidazo[1,2-b]pyridazin-6-yl)benzoyl)-1-methylpiperazin-2-one (130 mg, 0.28 mmol) and 4-ethynylpyridin-2-amine hydrochloride (56.29 mg, 0.36 mmol). The reaction crude product was purified by flash column chromatography (silica gel, eluent DCM/Methanol 94:6) and washed with NaHCO$_3$ (5 mL×3). The organic phase was dried over Na$_2$SO$_4$, filtered and concentrated under reduced pressure to afford 4-(4-(3-((2-aminopyridin-4-yl)ethynyl)imidazo[1,2-b]pyridazin-6-yl)benzoyl)-1-methylpiperazin-2-one (96 mg, 0.21 mmol, 76%, AUC HPLC 96.48%) as yellow solid mp: 193.6-194.6° C. $^1$H NMR (400 MHz, DMSO) δ (ppm): 8.38 (d, J=9.5 Hz, 1H), 8.27 (s, 1H); 8.23 (d, J=8.0 Hz, 2H), 8.03 (d, J=9.5 Hz, 1H), 7.99 (d, J=5.1 Hz, 1H), 7.68 (d, J=8.0 Hz, 2H), 6.75-6.55 (m, 2H), 6.17 (s, 2H), 4.30-3.50 (m, 4H), 3.45-3.30 (m, 2H), 2.88 (s, 3H); $^{13}$C NMR (400 MHz, DMSO) δ (ppm): 168.74, 164.74, 159.96, 151.49, 148.61, 142.99, 139.46, 139.24, 130.14, 128.03, 127.29, 126.58, 118.17, 112.91, 111.81, 109.05, 97.11, 78.74, 33.71; MS (ESI) m/z 452.10[C$_{25}$H$_{21}$N$_7$O$_2$+H]$^+$.

Example 78: (4-(3-((6-aminopyridin-3-yl)ethynyl) imidazo[1,2-b]pyridazin-6-yl)phenyl)(morpholino) methanone

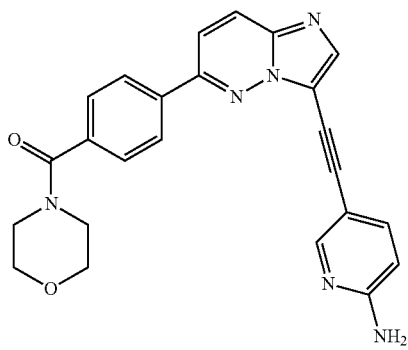 [SMILES: Nc1ccc(C#Cc2cnc3ccc(-c4ccc(C(=O)N5CCOCC5)cc4)nn23)cn1]

Step 1: Preparation of tert-butyl 5-((6-(4-(morpholine-4-carbonyl)phenyl)imidazo[1,2-b]pyridazin-3-yl)ethynyl)pyridin-2-ylcarbamate To a solution of (4-(3-iodoimidazo[1,2-b]pyridazin-6-yl)phenyl)(morpholino)methanone (500 mg, 1.15 mmol) and diisopropylethylamine (0.4 mL, 2.30 mmol) in acetonitrile (10 mL) were successively added Pd(PPh$_3$)$_4$ (66 mg, 0.057 mmol), PPh$_3$ (15 mg, 0.057 mmol), CuI (32.8 mg, 0.172 mmol) and tert-butyl 5-ethynylpyridine-2-ylcarbamate (274 mg, 1.26 mmol). The reaction mixture was heated at 80° C. for 10 h under argon and was concentrated under reduced pressure. The residue was purified by column chromatography (silica gel, eluent methanol/dichloromethane 3:97) to afford tert-butyl 5-((6-(4-(morpholine-4-carbonyl)phenyl) imidazo[1,2-b]pyridazin-3-yl)ethynyl)pyridin-2-ylcarbamate (300 mg, 40%, LC-MS 86%) as a yellow solid. $^1$H NMR (400 MHz, (DMSO-d$_6$) δ (ppm): 10.15 (s, 1H), 8.54 (d, J=1.2 Hz, 1H), 8.35 (d, J=9.2 Hz, 1H), 8:21-8.14 (m, 2H), 8.01-7.99 (m, 2H), 7.92 (d, J=8.8 Hz, 1H), 7.81-7.75 (m, 1H), 7.64 (d, J=8.4 Hz, 2H), 3.65-3.41 (m, 8H), 1.49 (s, 9H); MS (ESI) m/z: 525.25 [C$_{29}$H$_{28}$N$_6$O$_4$+H]$^+$.

Step 2: Preparation of (4-(3-((6-aminopyridin-3-yl) ethynyl)imidazo[1,2-b]pyridazin-6-yl)phenyl)(morpholino)methanone A solution of tert-butyl 5-((6-(4-(morpholine-4-carbonyl) phenyl)imidazo[1,2-b]pyridazin-3-yl)ethynyl)pyridin-2-ylcarbamate (300 mg, 0.49 mmol) and trifluoroacetic acid (3 mL) in dichloromethane (10 mL) was stirred at room temperature for 3 h and was concentrated under reduced pressure. The residue was basified with an aqueous solution of saturated NaHCO$_3$ solution, extracted with 5% methanol in dichloromethane. The organic layer was washed with water and brine, dried over Na$_2$SO$_4$, filtered and concentrated under reduced pressure. The residue was purified by preparative HPLC to afford (4-(3-((6-aminopyridin-3-yl) ethynyl)imidazo[1,2-b]pyridazin-6-yl)phenyl)(morpholino) methanone (120 mg, 71%, AUC HPLC 98%) as a yellow solid. $^1$H NMR (400 MHz, (DMSO-d$_6$) δ (ppm): 8.33 (d, J=9.6 Hz, 1H), 8.21-8.18 (m, 3H), 8.13 (s, 1H), 7.97 (d, J=9.2 Hz, 1H), 7.63-7.58 (m, 3H), 6.53-6.49 (m, 3H), 3.66-3.62 (m, 8H); MS (ESI) m/z: 425.24 [C$_{24}$H$_{20}$N$_6$O$_2$+H]$^+$.

Example 79: (4-(3-((3-amino-4-fluorophenyl)ethynyl)imidazo[1,2-b]pyridazin-6-yl)phenyl) (morpholino)methanone

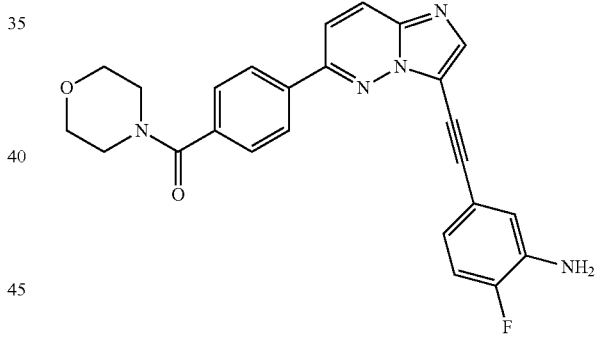

To a solution of 2-fluoro-5-iodoaniline (342 mg, 1.44 mmol) and diisopropylethylamine (0.43 mL, 2.4 mmol) in acetonitrile (10 mL) under argon were successively added Pd(PPh$_3$)$_4$ (69 mg, 0.0602 mmol), PPh$_3$ (15.7 mg, 0.0602 mmol), CuI (34.3 mg, 0.18 mmol) and (4-(3-ethynylimidazo [1,2-b]pyridazin-6-yl)phenyl)(morpholino)methanone (400 mg, 1.20 mmol), the reaction mixture was heated at 80° C. for 4 h. The reaction mixture was concentrated under reduced pressure. The residue was purified by column chromatography (silica gel, eluent dichloromethane/methanol 3:97) and by preparative HPLC to afford (4-(3-((3-amino-4-fluorophenyl)ethynyl)imidazo[1,2-b]pyridazin-6-yl)phenyl)(morpholino)methanone (150 mg, 28.2%, AUC HPLC 99%) as a pale yellow solid. $^1$H NMR (400 MHz, (DMSO-d$_6$) δ (ppm): 8.33 (d, J=9.2 Hz, 1H), 8.21 (d, J=8.4 Hz, 2H), 8.13 (s, 1H), 7.96 (d, J=9.6 Hz, 1H), 7.63 (d, J=7.6 Hz, 2H), 7.26 (dd, J=12.0, 2.0 Hz, 1H), 7.17 (dd, J=8.4, 2.0 Hz, 1H), 6.82-6.78 (m, 1H), 5.76 (bs, 2H), 3.66-3.37 (m, 8H); MS (ESI) m/z: 442.26 [C$_{25}$H$_{20}$FN$_5$O$_2$+H]$^+$.

Example 80: (4-(3-((2-aminopyridin-4-yl)ethynyl)imidazo[1,2-b]pyridazin-6-yl)-2-fluorophenyl)(morpholino)methanone formate salt

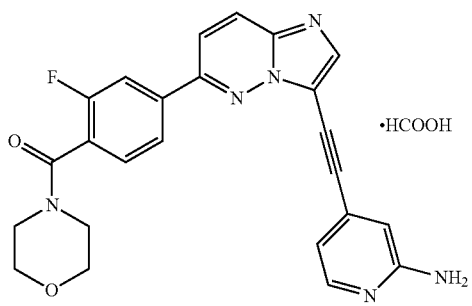 [SMILES: Nc1cc(C#Cc2cnc3ccc(-c4ccc(C(=O)N5CCOCC5)c(F)c4)nn23)ccn1 ; "·HCOOH"]

The title compound was synthesized in a similar fashion as described for Example 76 starting from (2-fluoro-4-(3-iodoimidazo[1,2-b]pyridazin-6-yl)phenyl)(morpholino)methanone (100 mg, 0.221 mmol) and 4-ethynylpyridin-2-amine hydrochloride (41 mg, 0.265 mmol). The solvents were then removed in vacuo and the resulting residue was purified by flash column chromatography (silica gel, eluent $CH_2Cl_2/CH_3OH$ 90:10) and by preparatory HPLC to afford (4-(3-((2-aminopyridin-4-yl)ethynyl)imidazo[1,2-b]pyridazin-6-yl)-2-fluorophenyl)(morpholino)methanone formate salt (38.8 mg, 36%, AUC HPLC 99.8%) as a light green solid; $^1$H NMR (600 MHz, DMSO-$d_6$) δ 8.40 (d, J=9.5 Hz, 1H), 8.30 (s, 1H), 8.13 (s, 1H), 8.10-8.04 (m, 3H), 8.00 (d, J=5.3 Hz, 1H), 7.66 (t, J=7.5 Hz, 1H), 6.72-6.65 (m, 2H), 6.35 (s, 2H), 3.68 (m, 4H), 3.56 (t, J=4.7 Hz, 2H); $^{13}$C NMR (150 MHz, DMSO-$d_6$) δ 163.4, 163.0, 159.4, 158.7, 157.1, 150.4, 139.8, 137.8, 130.5, 129.8, 126.6, 125.3, 123.5, 118.1, 114.4, 112.8, 111.7, 109.4, 96.9, 79.1, 66.0, 47.0, 41.9; MS (ESI) m/z 443 $[C_{24}H_{19}FN_6O_2+H]^+$

Example 81: (4-(3-((2-aminopyridin-4-yl)ethynyl)imidazo[1,2-b]pyridazin-6-yl)-2-methylphenyl)(morpholino)methanone formate salt

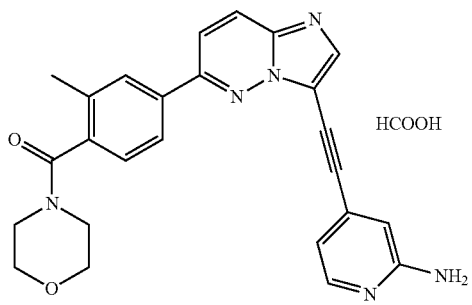 [SMILES: Cc1cc(-c2ccc3ncc(C#Cc4ccnc(N)c4)n3n2)ccc1C(=O)N1CCOCC1 ; "HCOOH"]

The title compound was synthesized in a similar fashion as described for Example 76 starting from (4-(3-iodoimidazo[1,2-b]pyridazin-6-yl)-2-methylphenyl)(morpholino)methanone (100 mg, 0.223 mmol) and 4-ethynylpyridin-2-amine hydrochloride. The reaction crude product was purified by flash column chromatography (eluent EtOAc/$CH_3OH$ 85:15) and by preparative HPLC to afford (4-(3-((2-aminopyridin-4-yl) ethynyl)imidazo[1,2-b]pyridazin-6-yl)-2-methylphenyl)(morpholino)methanone formate salt (62.9 mg, 58%, AUC HPLC 96.2%) as a light yellow solid; $^1$H NMR (600 MHz, DMSO-$d_6$) δ 8.37 (d, J=9.6 Hz, 1H), 8.28 (s, 1H), 8.13 (s, 1H), 8.05 (d, J=1.7 Hz, 1H), 8.03-7.98 (m, 3H), 7.42 (d, J=7.9 Hz, 1H), 6.74-6.69 (m, 2H), 6.53 (s, 1H), 3.68 (m, 4H), 3.52 (m, 2H), 3.19 (m, 2H), 2.36 (s, 3H); $^{13}$C NMR (150 MHz, DMSO-$d_6$) δ 168.0, 163.0, 158:7, 151.7, 146.3, 139.6, 137.9, 13419, 131.2, 128.9, 126.7, 126.5, 124.6, 118.3, 112.8, 111.5, 109.8, 96.7, 66.2, 46.7, 41.4, 18.8; MS (ESI) m/z 439 $[C_{25}H_{22}N_6O_2+H]^+$

Example 82: (4-(3-((2-aminopyridin-4-yl)ethynyl)imidazo[1,2-b]pyridazin-6-yl)-2-chlorophenyl)(morpholino)methanone

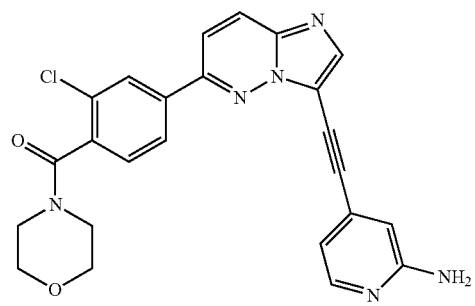 [SMILES: Nc1cc(C#Cc2cnc3ccc(-c4ccc(C(=O)N5CCOCC5)c(Cl)c4)nn23)ccn1]

The title compound was synthesized in a similar fashion as described for Example 76 starting from (2-chloro-4-(3-iodoimidazo[1,2-b]pyridazin-6-yl)phenyl)(morpholino)methanone and 4-ethynylpyridin-2-amine (98.97 mg, 0.64 mmol). The reaction crude product was purified by flash column chromatography (silica gel, DCM/Methanol 94:6) to afford (4-(3-((2-aminopyridin-4-yl)ethynyl)imidazo[1,2-b]pyridazin-6-yl)-2-chlorophenyl)(morpholino)methanone (53.69 mg, 0.12 mmol, 27.4%, AUC HPLC 99.36%) as yellow solid, mp: 193.7-194.8° C. $^1$H NMR (400 MHz, CDCl$_3$) δ (ppm): 8.25-8.05 (m, 4H), 8.00 (d, J=8.0 Hz, 1H), 7.57 (d, J=8.8 Hz, 1H), 7.50 (d, J=7.6 Hz, 1H), 6.87 (s, 1H), 6.76 (s, 1H), 4.70 (bs, 2H), 4.00-3.88 (m, 1H), 3.87-3.78 (m, 3H), 3.77-3.58 (m, 2H), 3.45-3.20 (m, 2H); $^{13}$C NMR (400 MHz, CDCl$_3$) 166.26, 158.08, 150.50, 147.50, 139.94, 138.94, 137.52, 137.00, 132.38, 131.42, 128.67, 128.41, 126.45, 126.03, 116.73, 115.65, 113.09, 110.32, 97.17, 80.00, 66.80, 66.72, 47.19, 42.17; MS (ESI) m/z 459.10 $[C_{24}H_{19}ClN_6O_2+H]^+$.

Example 83: (4-(3-((2-aminopyridin-4-yl)ethynyl)imidazo[1,2-b]pyridazin-6-yl)-2-(trifluoromethyl)phenyl) (morpholino)methanone

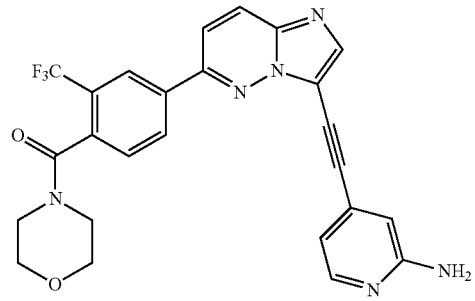 [SMILES: Nc1cc(C#Cc2cnc3ccc(-c4ccc(C(=O)N5CCOCC5)c(C(F)(F)F)c4)nn23)ccn1]

The title compound was synthesized in a similar fashion as described for Example 76 starting from (4-(3-iodoimidazo[1,2-b]pyridazin-6-yl)-2-(trifluoromethyl)phenyl)(morpholino)methanone (130 mg, 0.26 mmol) and 4-ethynylpyridin-2-amine (60 mg, 0.39 mmol), Pd(PPh$_3$)$_4$ (14.96 mg, 0.013 mmol). The reaction crude product was purified by flash column chromatography (silica gel, eluent DCM/methanol 96:4) to afford (4-(3-((2-aminopyridin-4-yl)ethynyl)imidazo[1,2-b]pyridazin-6-yl)-2-(trifluoromethyl)(morpholino)methanone (41.99 mg, 0.085 mmol, 32.9%, AUC HPLC 97.91%) as yellow solid mp: 258.5-258.9° C. $^1$H NMR (400 MHz, CDCl$_3$) δ (ppm): 8.47 (s, 1H), 8.28 (d, J=7.2 Hz, 1H), 8.20-8.15 (m, 3H), 7.63 (d, J=9.2 Hz, 1H), 7.54 (d, J=8.0 Hz, 1H), 6.85 (d, J=4.8 Hz, 1H), 6.72 (s, 1H), 4.71 (s, 2H), 4.00-3.87 (m, 1H), 3.86-3.74 (m, 3H), 3.67-3.56 (m, 2H); 3.30-3.20 (m, 2H); $^{13}$C NMR (400 MHz, CDCl$_3$) δ (ppm): 166.69, 154.42, 144.96, 144.05, 137.87, 136.53, 136.35, 132.67, 130.94, 128.42, 127.93, 126.32, 125.66, 125.61, 119.16, 109.62, 109.55, 105.63, 66.61, 66.27, 47.53, 42.22; MS (ESI) m/z 493.10 [C$_{25}$H$_{19}$F$_3$N$_6$O$_2$+H]$^+$.

Example 84: N-(4-((6-(4-(4-methyl-3-oxopiperazine-1-carbonyl)phenyl)imidazo[1,2-b]pyridazin-3-yl)ethynyl)pyridin-2-yl)acetamide

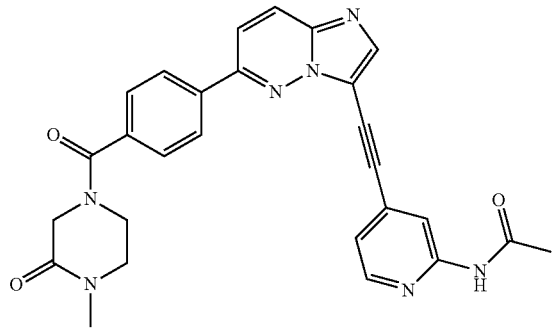 [SMILES: CC(=O)Nc1cc(C#Cc2cnc3ccc(-c4ccc(C(=O)N5CCN(C)C(=O)C5)cc4)nn23)ccn1]

The title compound was synthesized in a similar fashion as described for Example 76 starting from 4-(4-(3-iodoimidazo[1,2-b]pyridazin-6-yl)benzoyl)-1-methylpiperazin-2-one (110 mg, 0.24 mmol) and N-(4-ethynylpyridin-2-yl)acetamide (49.50 mg, 0.31 mmol). The reaction crude product was purified by flash column chromatography (silica gel, eluent DCM/Methanol 95:5) to give N-(4-((6-(4-(4-methyl-3-oxopiperazine-1-carbonyl)phenyl)imidazo[1,2-b]pyridazin-3-yl)ethynyl)pyridin-2-yl)acetamide (56.64 mg, 0.11 mmol, 48%, AUC HPLC 98.85%) as yellow solid mp: 258.2-259.5° C. $^1$H NMR (400 MHz, DMSO) δ (ppm): 10.69 (s, 1H), 8.42-8.37 (m, 2H), 8.40-8.30 (m, 2H), 8.27 (d, J=8.3 Hz, 2H), 8.07 (d, J=9.5 Hz, 1H), 7.70 (d, J=8.3 Hz, 2H), 7.30 (dd, J=5.0, 1.3 Hz, 1H), 4.30-3.50 (m, 4H), 3.40 (bs, 2H), 2.88 (s, 3H), 2.14 (s, 3H); $^{13}$C NMR (400 MHz, DMSO) 3 (ppm): 170.25, 168.69, 152.88, 151.89, 149.16, 140.19, 137.26, 136.32, 131.73, 128.49, 127.66, 127.03, 120.50, 118.73, 114.63, 111.97, 97.20, 81.11, 55.33, 34.11, 24.45; MS (ESI) m/z 494.20 [C$_{27}$H$_{23}$N$_7$O$_3$+H]$^+$.

Example 85: 4-(4-(3-((1H-pyrrolo[2,3-b]pyridin-4-yl)ethynyl)imidazo[1,2-b]pyridazin-6-yl)benzoyl)-1-methylpiperazin-2-one

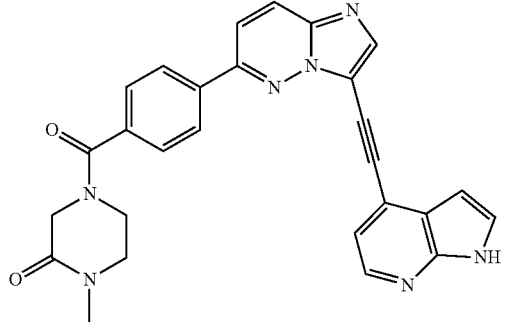 [SMILES: CN1CCN(C(=O)c2ccc(-c3ccc4ncc(C#Cc5ccnc6[nH]ccc56)n4n3)cc2)CC1=O]

The title compound was synthesized in a similar fashion as described for Example 76 starting from 4-(4-(3-iodoimidazo[1,2-b]pyridazin-6-yl)benzoyl)-1-methylpiperazin-2-one (101 mg, 0.22 mmol) and 4-ethynyl-1H-pyrrolo[2,3-b]pyridine (40.5 mg, 0.29 mmol). The reaction crude product was purified by flash column chromatography (silica gel, eluent DCM/Methanol 92:8) to give 4-(4-(3-((1H-pyrrolo[2,3-b]pyridin-4-yl)ethynyl)imidazo[1,2-b]pyridazin-6-yl)benzoyl)-1-methylpiperazin-2-one (72.6 mg, 0.15 mmol, 69%, AUC HPLC 99.85%) as yellow solid mp: 207.2-208.2° C. $^1$H NMR (400 MHz, CDCl$_3$) δ (ppm): 9.03 (s, 1H), 8.34 (d, J=5.0 Hz, 1H), 8.20-8.15 (m, 3H), 8.12 (d, J=9.4 Hz, 1H), 7.68-7.60 (m, 3H), 7.45-7.40 (m, 1H), 7.31 (d, J=5.0 Hz, 1H), 6.86 (s, 1H), 4.45-3.60 (m, 4H), 3.46 (bs, 2H), 3.04 (s, 3H); $^{13}$C NMR (400 MHz, DMSO) δ (ppm): 168.74, 164.74, 152.02, 148.84, 142.99, 139.80, 139.74, 137.32, 136.52, 128.39, 128.07, 127.70, 127.02, 121.04, 120.41, 118.62, 117.10, 112.52, 99.51, 96.48, 82.66, 34.11; MS (ESI) m/z 476.10 [C$_{27}$H$_{21}$N$_7$O$_2$+H]$^+$.

Example 86: 4-(4-(3-((1H-pyrrolo[2,3-b]pyridin-4-yl)ethynyl)imidazo[1,2-b]pyridazin-6-yl)benzoyl)-1-methylpiperazin-2-one

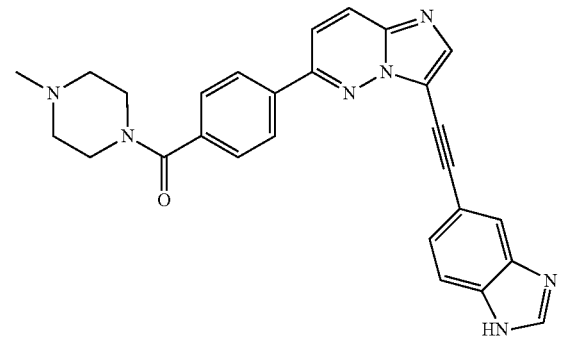 [SMILES: CN1CCN(C(=O)c2ccc(-c3ccc4ncc(C#Cc5ccc6[nH]cnc6c5)n4n3)cc2)CC1]

A mixture of (4-(3-iodoimidazo[1,2-b]pyridazin-6-yl)phenyl)(4-methylpiperazin-1-yl)methanone (500 mg 1.118 mmol in DMF (10 mL), 5-ethynyl-1H-benzo[d]imidazole (190 mg, 1.342 mmol), CuI (32 mg, 0.167 mmol), DIPEA (0.422 mL, 2.36 mmol) and Pd(PPh$_3$)$_4$ (64 mg, 0.0520 mmol) in DMF was heated at 80° C. for 4 h under argon. The reaction mixture was diluted with water (25 mL), extracted with ethyl acetate (50 mL), and washed with brine solution. The organic layer was dried over anhydrous Na$_2$SO$_4$ and concentrated under reduced pressure. The crude product was purified by column chromatography (silica gel, eluent CHCl$_3$/CH$_3$OH 90:10) to give (4-(3-((1H-benzo[d]imidazol-5-yl)ethynyl)imidazo[1,2-b]pyridazin-6-yl)phenyl)(4- methylpiperazin-1-yl)methanone (160 mg, 29%, HPLC 95%) as a yellow solid. $^1$H NMR (400 MHz, DMSO d$_6$) ppm δ 12.70 (s, 1H), 8.38 (s, 2H), 8.23-8.21 (m, 3H), 7.96 (s, 1H), 7.89 (s, 1H), 7.66 (s, 1H), 7.60 (s, 1H), 7.47 (s, 1H), 3.64 (s, 2H) 3.39-3.32 (m, 3H), 2.36-2.29 (m, 4H), 2.19 (m, 3H); MS (ESI) m/z 462.5 [C$_{27}$H$_{23}$N$_7$O+H]$^+$.

Example 87: N-(4-((6-(4-(4-methylpiperazine-1-carbonyl)phenyl)imidazo[1,2-b]pyridazin-3-yl)ethynyl)pyridin-2-yl)acetamide

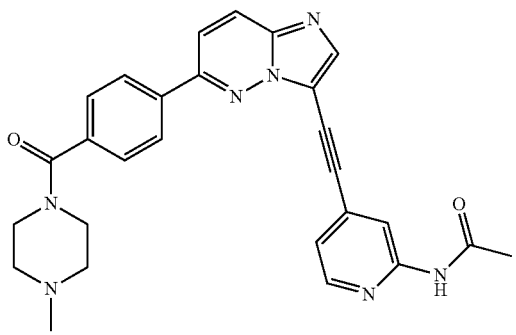 [SMILES: CC(=O)Nc1cc(C#Cc2cnc3ccc(-c4ccc(C(=O)N5CCN(C)CC5)cc4)nn23)ccn1]

To a solution of (4-(3-iodoimidazo[1,2-b]pyridazin-6-yl)phenyl)(4-methylpiperazin-1-yl)methanone (200 mg, 0.45 mmol) in acetonitrile (6 mL) under inert atmosphere was added N-(4-ethynylpyridin-2-yl)acetamide (94.5 mg, 0.59 mmol), Pd(PPh$_3$)$_4$ (26.6 mg, 0.02 mmol), CuI (8.6 mg, 0.05 mmol) and 3 mL of DIPEA. The reaction mixture was heated at 70° C. for 2.5 h, was diluted with water (10 mL) and extracted with dichloromethane (20 mL×3). The combined organic layers were dried over sodium sulfate filtered and concentrated under reduced pressure. The residue was purified by flash column chromatography (silica gel, eluent, DCM/Methanol 94:6) to give N-(4-((6-(4-(4-methylpiperazine-1-carbonyl)phenyl)imidazo[1,2-b]pyridazin-3-yl)ethynyl)pyridin-2-yl)acetamide (122 mg, 0.25 mmol, 57%, AUC HPLC 99.49%) as yellow solid mp: 216.8-217.9° C. 1H NMR (400 MHz, CDCl$_3$) δ (ppm): 8.44 (s, 1H), 8.28 (d, J=5.0 Hz, 1H), 8.15-8.05 (m, 4H), 7.96 (s, 1H), 7.64-7.60 (m, 3H), 7.22 (dd, J=5.1, 1.3 Hz, 1H), 3.85 (bs, 2H), 3.52 (bs, 2H), 2.60-2.30 (m, 7H), 2.25 (s, 3H); $^{13}$C NMR (400 MHz, CDCl$_3$) δ (ppm): 169.56, 168.79, 151.81, 151.61, 147.78, 139.80, 139.36, 137.58, 136.29, 133.02, 127.96, 127.39, 126.15, 121.26, 117.22, 115.44, 112.88, 96.87, 80.84, 46.01, 24.76; MS (ESI) m/z 480.2 [C$_{27}$H$_{25}$N$_7$O$_2$+H]$^+$.

Example 88: (4-(3-((2-aminopyridin-4-yl)ethynyl)imidazo[1,2-a]pyrazin-6-yl)phenyl)(morpholino)methanone

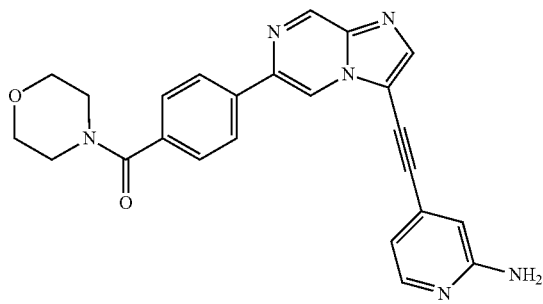 [SMILES: Nc1cc(C#Cc2cnc3cnc(-c4ccc(C(=O)N5CCOCC5)cc4)cn23)ccn1]

To a solution of (4-(3-iodoimidazo[1,2-a]pyrazin-6-yl)phenyl)(morpholino)methanone (180 mg, 0.41 mmol) in acetonitrile (3 mL) was added 4-ethynylpyridin-2-amine (95.9 mg, 0.62 mmol), Pd(PPh$_3$)$_4$ (24.3 mg, 0.021 mmol), CuI (7.8 mg, 0.041 mmol) and DIPEA (1.5 mL). The reaction mixture was heated at 85° C. for 1.5 h under nitrogen. The resulting mixture was diluted with dichloromethane (50 mL), filtered through celite and concentrated under reduced pressure. The residue was purified by flash column chromatography (silica gel, 100% DCM to DCM/Methanol 96:4). The fractions containing the products were concentrated under reduced pressure. The residue was diluted with DCM (50 mL) and washed with saturated sodium bicarbonate solution (2×5 mL). The combined organic layer was dried over sodium sulfate, filtered and concentrated under reduced pressure to afford (4-(3-((2-aminopyridin-4-yl)ethynyl)imidazo[1,2-a]pyrazin-6-yl)phenyl)(morpholino)methanone (93 mg, 0.22 mmol, 53.4%, AUC HPLC 99.46%) as light yellow solid mp: 143.5-144.2° C. $^1$H NMR (400 MHz, CDCl$_3$) δ (ppm): 9.22 (d, J=1.2 Hz, 1H), 8.58 (d, J=1.2 Hz, 1H), 8.14 (d, J=4.8 Hz, 1H), 8.10-8.05 (m, 3H), 7.57 (d, J=8.4 Hz, 2H), 6.83 (dd, J=5.2; 1.2 Hz, 1H), 6.69 (s, 1H), 4.61 (s, 2H), 4.00-3.40 (m, 8H); MS (ESI) m/z 425.10 [C$_{24}$H$_{20}$N$_6$O$_2$+H]$^+$.

Example 89: (4-methylpiperazin-1-yl) (4-(3-(phenylethynyl)imidazo[1,2-a]pyrazin-6-yl)phenyl)methanone

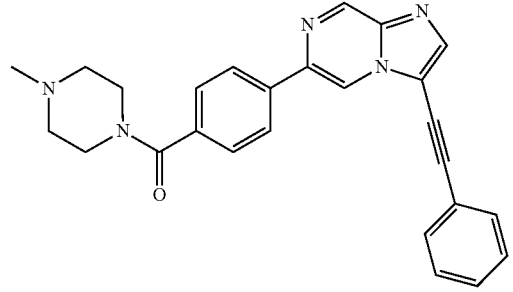 [SMILES: CN1CCN(C(=O)c2ccc(-c3cn4c(C#Cc5ccccc5)cnc4cn3)cc2)CC1]

To a solution of (4-(3-iodoimidazo[1,2-a]pyrazin-6-yl)phenyl)(4-methylpiperazin-1-yl)methanone (100 mg, 0.223 mmol), PdCl$_2$ (PPh$_3$)$_2$, (8 mg, 0.011 mmol), and CuI (4.2 mg, 0.022 mmol) in THF (1 mL) was added phenyl acetylene (25 μL, 0.223 mmol) and triethylamine (1 mL). The reaction mixture was stirred at room temperature for 12 h and was concentrated under reduced pressure. The residue was purified by flash chromatography to afford (4-methylpiperazin-1-yl)(4-(3-(phenylethynyl)imidazo[1,2-a]pyrazin-6-yl)phenyl)methanone as a light yellow solid (51 mg, 56%, AUC HPLC 98.19%). $^1$H NMR (DMSO-d$_6$) δ (ppm): 9.29 (s, 1H), 9.09 (s, 1H), 8.28-8.21 (m, 3H), 7.81-7.76 (m, 2H), 7.56-7.48 (m, 5H), 3.71-3.32 (m, 4H), 2.41-2.22 (m, 4H), 2.20 (s, 3H). $^{13}$C NMR (DMSO-d$_6$) δ (ppm): 168.5, 142.5, 140.1, 139.8, 138.7, 136.8, 136.1, 131.4, 129.4, 128.7, 127.4, 126.3, 121.4, 115.5, 110.0, 100.2, 75.3, 54.2, and 45.5. MS (ESI): m/z 422 [C$_{26}$H$_{23}$N$_5$O+H]$^+$.

Example 90: (4-(3-((1H-pyrazolo[3,4-b]pyridin-4-yl)ethynyl)imidazo[1,2-a]pyrazin-6-yl)phenyl) (morpholino)methanone

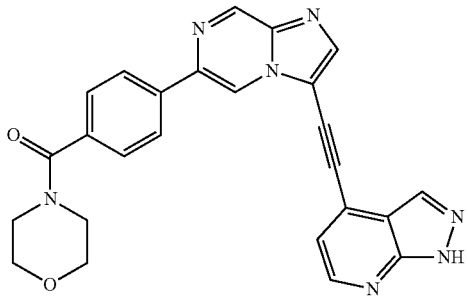 [SMILES: O=C(c1ccc(-c2cn3c(C#Cc4ccnc5[nH]ncc45)cnc3cn2)cc1)N1CCOCC1]

To a solution of (4-(3-iodoimidazo[1,2-a]pyrazin-6-yl)phenyl)(morpholino)methanone (180 mg, 0.41 mmol) in acetonitrile (3 mL) was added 4-ethynyl-1H-pyrazolo[3,4-b]pyridine (88.04 mg, 0.62 mmol), Pd(PPh$_3$)$_4$ (24.3 mg, 0.021 mmol), CuI (7.8 mg, 0.041 mmol) and DIPEA (1.5 mL). The reaction mixture was heated at 80° C. overnight under nitrogen, was then diluted with dichloromethane (50 mL), filtered through celite and concentrated under reduced pressure. The residue was purified by flash column chromatography (silica gel, eluent DCM/Methanol 96:4) to yield (4-(3-((1H-pyrazolo[3,4-b]pyridin-4-yl)ethynyl)imidazo[1,2-a]pyrazin-6-yl)phenyl)(morpholino)methanone (77 mg, 0.17 mmol, 41.8%, AUC HPLC 98.87%) as yellow solid mp: 192.8-193.8° C. $^1$H NMR (400 MHz, CDCl$_3$) δ (ppm): 9.31 (d, J=1.3 Hz, 1H), 8.70 (d, J=1.3 Hz, 1H), 8.67 (d, J=4.7 Hz, 1H), 8.33 (s, 1H), 8.24 (s, 1H), 8.10 (d, J=8.4 Hz, 2H), 7.62 (d, J=8.4 Hz, 2H), 7.41 (d, J=4.7 Hz, 1H) 4.00-3.40 (m, 8H); MS (ESI) m/z 450.10 [C$_{25}$H$_{19}$N$_7$O$_2$+H]$^+$.

Example 91: (4-(3-((2-aminopyridin-4-yl)ethynyl)imidazo[1,2-a]pyrazin-6-yl)-2-fluorophenyl) (morpholino)methanone

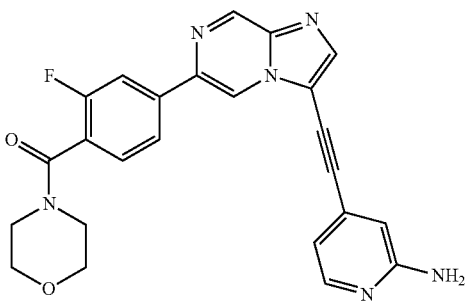 [SMILES: Nc1cc(C#Cc2cnc3cnc(-c4ccc(C(=O)N5CCOCC5)c(F)c4)cn23)ccn1]

A round bottom flask was loaded with (2-fluoro-4-(3-iodoimidazo[1,2-a]pyrazin-6-yl)phenyl)(morpholino)methanone (100 mg, 0.221 mmol), 4-ethynylpyridin-2-amine (39 mg, 0.332 mmol), PdCl$_2$(PPh$_3$)$_2$ (20 mg, 0.0287 mmol) and CuI (4.2 mg, 0.0221 mmol) followed by the addition of DMF (1.0 mL) and DIPEA (1.0 mL). The mixture was heated at 90° C. for 2 h under argon. The solvents were removed in vacuo and the crude residue was purified by column chromatography (silica gel, eluent EtOAc/CH$_3$OH 95:5) followed by preparative HPLC to afford (4-(3-((2-aminopyridin-4-yl)ethynyl)imidazo[1,2-a]pyrazin-6-yl)-2-fluorophenyl)(morpholino)methanone (42.9 mg, 44%, AUC HPLC: 99.0%) as a light brown solid. $^1$H NMR (600 MHz, DMSO-d$_6$) δ (ppm): 9.33 (d, J=1.5 Hz, 1H), 9.22 (d, J=1.5 Hz, 1H), 8.34 (s, 1H), 8.14 (s, 1H), 8.13-8.10 (m, 1H), 8.01 (d, J=5.6 Hz, 1H), 7.58 (t, J=7.7 Hz, 1H), 6.90 (dd, J=5.5, 1.4 Hz, 1H), 6.86 (s, 1H), 6.69 (bs, 2H), 3.68 (s, 4H), 3.56 (t, J=4.7 Hz, 2H) 3.35-3.25 (m, 2H); MS (ESI) m/z 443 [C$_{24}$H$_{19}$FN$_6$O$_2$+H]$^+$

Example 92: (4-(3(4-(3-((2-aminopyridin-4-yl)ethynyl)imidazo[1,2-a]pyrazin-6-yl)-2-fluorophenyl) (morpholino)methanone

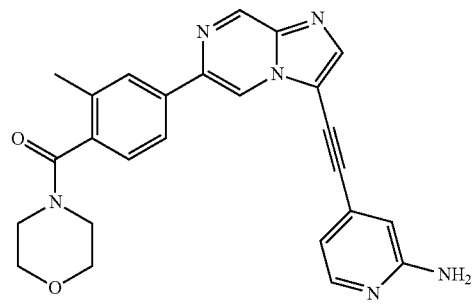 [SMILES: Cc1cc(-c2cn3c(C#Cc4ccnc(N)c4)cnc3cn2)ccc1C(=O)N1CCOCC1]

The title compound was synthesized in a similar fashion as described for Example 91 starting from (4-(3-iodoimidazo[1,2-a]pyrazin-6-yl)-2-methylphenyl)(morpholino) methanone and 4-ethynylpyridin-2-amine (40 mg, 0.335 mmol). The reaction crude product was purified by column chromatography (silica gel, eluent EtOAc/CH$_3$OH 95:5) to afford (4-(3-((2-aminopyridin-4-yl)ethynyl)imidazo[1,2-a]pyrazin-6-yl)-2-fluorophenyl)(morpholino)methanone (70.2 mg, 72%, AUC HPLC: 96.6%) as a brown solid. $^1$H NMR (600 MHz, DMSO-d$_6$) δ (ppm): 9.33 (d, J=1.5 Hz, 1H), 9.14 (d, J=1.5 Hz, 1H), 8.35 (s, 1H), 8.09 (d, J=1.7 Hz, 1H), 8.06-8.01 (m, 2H), 7.35 (d, J=7.9 Hz, 1H), 7.20 (bs, 2H), 7.01 (dd, J=5.9, 1.5 Hz, 1H), 6.99 (s, 1H), 3.68 (s, 4H), 3.56-3.49 (m, 2H), 3.19 (s, 2H), 2.35 (s, 3H); MS (ESI) m/z 439 [C$_{25}$H$_{22}$N$_6$O$_2$+H]$^+$

Example 93: (4-(3-((2-aminopyridin-4-yl)ethynyl)imidazo[1,2-a]pyrazin-6-yl)-2-chlorophenyl) (morpholino)methanone

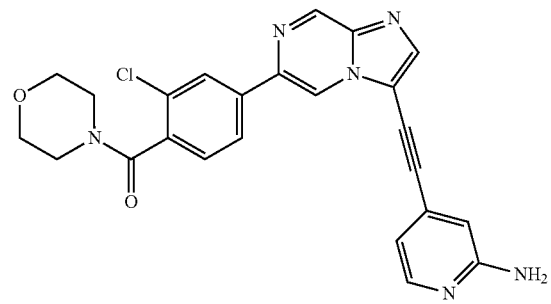 [SMILES: Nc1cc(C#Cc2cnc3cnc(-c4ccc(C(=O)N5CCOCC5)c(Cl)c4)cn23)ccn1]

The title compound was synthesized in a similar fashion as described for Example 91 starting from (4-(3-bromoimidazo[1,2-a]pyrazin-6-yl)-2-chlorophenyl)(morpholino) methanone (55 mg, 0.13 mmol) and 4-ethynylpyridin-2-amine (40.2 mg, 0.26 mmol). The reaction crude product was purified by flash column chromatography (silica gel, eluent DCM/Methanol 96:4) and was washed with NaHCO$_3$ (2×5 mL). The organic phase was dried over Na₂SO₄, filtered and concentrated to dryness under reduced pressure to afford (4-(3-((2-aminopyridin-4-yl)ethynyl)imidazo[1,2-a]pyrazin-6-yl)-2-chlorophenyl)(morpholino)methanone (11.6 mg, 0.025 mmol, 19.4%, AUC HPLC 95.42%) as yellow solid mp: 119.8-121.1° C. ¹H NMR (400 MHz, CDCl₃) δ (ppm): 9.15 (s, 1H), 8.49 (s, 1H), 8.07 (d, J=4.6 Hz, 1H), 8.02 (s, 2H), 7.87 (d, J=7.7 Hz, 1H), 7.38 (d, J=7.7 Hz, 1H) 6.77 (d, J=4.6 Hz, 1H), 6.63 (s, 1H), 4.52 (s, 2H), 3.90-3.80 (m, 1H), 3.79-3.70 (m, 3H), 3.69-3.50 (m, 2H), 3.35-3.15 (m, 2H); MS (ESI) m/z 459.10 [C₂₄H₁₉ClN₆O₂+H]⁺.

Example 94: morpholino(4-(3-(pyridin-4-ylethynyl) imidazo[1,2-a]pyridin-6-yl)phenyl)methanone

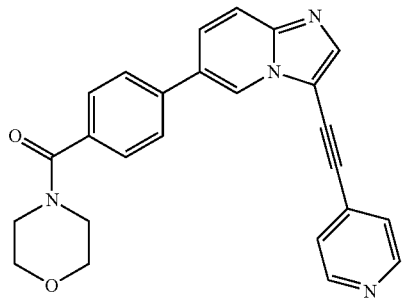 [SMILES: O=C(c1ccc(-c2ccc3ncc(C#Cc4ccncc4)n3c2)cc1)N1CCOCC1]

The title compound was synthesized from (4-(3-ethynylimidazo[1,2-a]pyridin-6-yl)phenyl)(morpholino)methanone and 4-iodopyridine in a similar method as described for Example 1. The crude product was purified by flash column chromatography (silica gel, eluent CHCl₃/CH₃OH 95:5) to afford morpholino(4-(3-(pyridin-4-ylethynyl)imidazo[1,2-a]pyridin-6-yl)phenyl)methanone (40 mg, 32.5%, AUC HPLC 97.33%) as a pale yellow solid. m.p: 165-166° C.; ¹H NMR (400 MHz, CDCl₃) δ (ppm): 8.66 (s, 2H), 8.49 (s, 1H), 8.03 (s, 1H), 7.82 (d, J=9.2 Hz, 1H), 7.73 (d, J=7.9 Hz, 2H), 7.51 (d, J=7.9 Hz, 3H), 7.42 (s, 2H), 3.74 (s; 8H); MS (ESI) m/z 409.06 [C₂₅H₂₀N₄O₂+H]⁺.

Example 95: (4-(3-((3-methylpyridin-4-yl)ethynyl) imidazo[1,2-a]pyridin-6-yl)phenyl) (morpholino) methanone

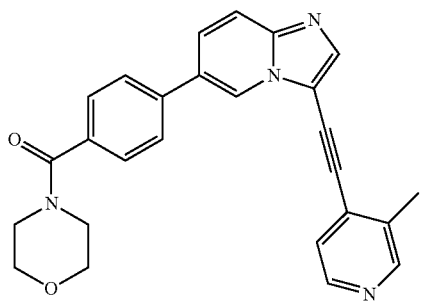 [SMILES: Cc1cnccc1C#Cc1cnc2ccc(-c3ccc(C(=O)N4CCOCC4)cc3)cn12]

The title compound was synthesized from (4-(3-ethynylimidazo[1,2-a]pyridin-6-yl)phenyl)(morpholino)methanone and 4-bromo-3-methylpyridine in a similar method as described for Example 32. The crude product was purified by flash chromatography (silica gel, eluent CH₂Cl₂/CH₃OH 95:5) to afford (4-(3-((3-methylpyridin-4-yl)ethynyl)imidazo[1,2-a]pyridin-6-yl)phenyl)(morpholino)methanone (80 mg, 41.8%, LC-MS 97%, AUC HPLC 98.23%) as an off-white solid; m.p: 99-104° C.; ¹H NMR (400 MHz, CDCl₃) δ (ppm): 8.55-8.53 (m, 3H), 8.02 (s, 1H), 7.82 (d, J=5.7 Hz, 1H), 7.71 (d, J=9.2 Hz, 2H), 7.52 (d, J=7.9 Hz, 3H), 7.31 (d, J=4.8 Hz, 1H), 3.73-3.71 (m, 8H), 2.54 (s, 3H); MS (ESI) m/z 423.04 [C₂₆H₂₂N₄O₂+H]⁺.

Example 96: (4-(3-((2-aminopyridin-4-yl)ethynyl) imidazo[1,2-a]pyridin-6-yl)phenyl)(morpholino) methanone

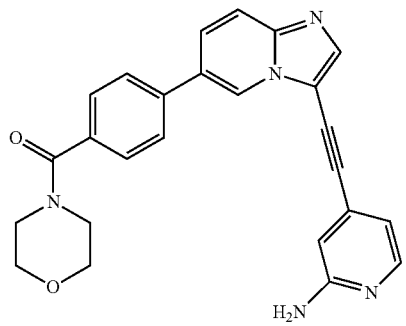 [SMILES: Nc1cc(C#Cc2cnc3ccc(-c4ccc(C(=O)N5CCOCC5)cc4)cn23)ccn1]

Step 1: Preparation of tert-butyl 4-((6-(4-(morpholine-4-carbonyl)phenyl)imidazo[1,2-a]pyridin-3-yl) ethynyl)pyridin-2-ylcarbamate The title compound was synthesized from (4-(3-ethynylimidazo[1,2-a]pyridin-6-yl)phenyl)(morpholino)methanone and tert-butyl 4-bromopyridin-2-ylcarbamate in a similar method to that described for Example 32. The crude product was purified by flash chromatography (silica gel, eluent CHCl₃/CH₃OH 95:5) to afford tert-butyl 4-((6-(4-(morpholine-4-carbonyl)phenyl)imidazo[1,2-a]pyridin-3-yl)ethynyl)pyridin-2-ylcarbamate (90 mg, 57%, LC-MS 61%) as a solid.

Step 2: Preparation of (4-(3-((2-aminopyridin-4-yl) ethynyl)imidazo[1,2-a]pyridin-6-yl)phenyl)(morpholino)methanone The title compound was synthesized from tert-butyl 4-((6-(4-(morpholine-4-carbonyl)phenyl)imidazo[1,2-a]pyridin-3-yl)ethynyl)pyridin-2-ylcarbamate in a similar method as described in step 2 of Example 31 synthesis. The crude product was purified by flash column chromatography (silica gel, eluent CH₂Cl₂/CH₃OH 90:10) to afford (4-(3-((2-aminopyridin-4-yl)ethynyl)imidazo[1,2-a]pyridin-6-yl)phenyl) (morpholino)methanone (50 mg, 51.5%, AUC HPLC 97.57%) as a solid. m.p: 133-138° C.; ¹H NMR (400 MHz, CDCl₃) δ (ppm): 8.46 (s, 1H), 8.12 (d, J=5.3 Hz, 1H), 8.02 (s, 1H), 7.79 (d, J=9.3 Hz, 1H), 7.61 (d, J=7.9 Hz, 2H), 7.56-7.54 (m, 3H), 6.80 (s, 1H), 6.79 (s, 1H), 4.53 (s, 2H), 3.75-3.73 (m, 8H); MS (ESI) m/z 424.11 [C₂₅H₂₁N₅O₂+H]⁺

Example 97: (4-(3-((1H-pyrazolo[3,4-b]pyridin-4-yl)ethynyl)imidazo[1,2-a]pyridin-6-yl)phenyl)(morpholino)methanone

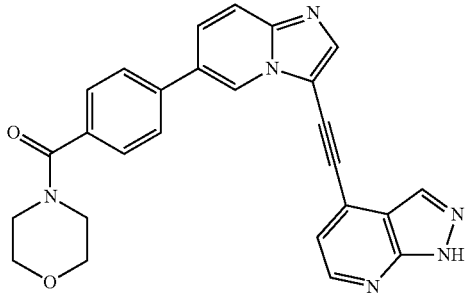 [SMILES: O=C(c1ccc(-c2ccc3ncc(C#Cc4ccnc5[nH]ncc45)n3c2)cc1)N1CCOCC1]

Step 1: Preparation of (4-(3-((1-(4-methoxybenzyl)-1H-pyrazolo[3,4-b]pyridin-4-yl)ethynyl)imidazo[1,2-a]pyridin-6-yl)phenyl)(morpholino)methanone The title compound was prepared from (4-(3-ethynylimidazo[1,2-a]pyridin-6-yl)phenyl)(morpholino)methanone and 4-iodo-1-(4-methoxybenzyl)-1H-pyrazolo[3,4-b]pyridine in a similar method to that described for Example 1. The crude product was purified by flash chromatography (silica gel, eluent $CHCl_3/CH_3OH$ 95:5) to afford (4-(3-((1-(4-methoxybenzyl)-1H-pyrazolo[3,4-b]pyridin-4-yl)ethynyl)imidazo[1,2-a]pyridin-6-yl)phenyl)(morpholino)methanone (470 mg, 97%, LC-MS 85.3%) as a light yellow solid; $^1$H NMR (400 MHz, $CDCl_3$) δ (ppm): 8.59 (d, J=4.8 Hz, 1H), 8.54 (s, 1H), 8.17 (s, 1H), 8.16 (s, 1H), 7.95 (bs, 1H), 7.68-7.57 (m, 6H), 7.34 (d, J=8.4 Hz, 2H), 6.84 (d, J=8.4 Hz, 2H), 5.68 (s, 2H), 3.82-3.50 (m, 8H), 3.76 (s, 3H); MS (ESI) m/z 569.17 $[C_{34}H_{28}N_6O_3+H]^+$

Step 2: Preparation of (4-(3-((1H-pyrazolo[3,4-b]pyridin-4-yl)ethynyl)imidazo[1,2-a]pyridin-6-yl)phenyl)(morpholino)methanone The title compound was synthesized from (4-(3-((1-(4-methoxybenzyl)-1H-pyrazolo[3,4-b]pyridin-4-yl)ethynyl)imidazo[1,2-a]pyridin-6-yl)phenyl)(morpholino)methanone by stirring with TFA at 100° C. for 4 h. The crude product (200 mg, LC-MS 78%) was purified by preparative HPLC to afford (4-(3-((1H-pyrazolo[3,4-b]pyridin-4-yl)ethynyl)imidazo[1,2-a]pyridin-6-yl)phenyl)(morpholino)methanone (25 mg, 9.6%, LC-MS 99%) as a pale yellow solid. $^1$H NMR (400 MHz, $CDCl_3$) δ (ppm): 10.97 (bs, 1H), 8.60 (d, J=4.9 Hz, 1H), 8.57 (s, 1H), 8.27 (s, 1H), 8.13 (s, 1H), 7.84 (d, J=9.2 Hz, 1H), 7.70 (d, J=7.9 Hz, 2H), 7.63-7.59 (m, 3H), 7.33 (d, J=4.9 Hz, 1H), 3.82-3.55 (m, 8H); MS (ESI) m/z 449.04 $[C_{26}H_{20}N_6O_2+H]^+$.

Example 98: (4-(3-((6-amino-1H-pyrrolo[2,3-b]pyridin-4-yl)ethynyl)imidazo[1,2-a]pyridin-6-yl)phenyl)(morpholino)methanone

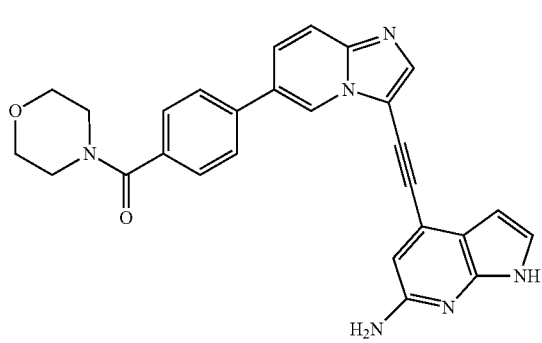 [SMILES: Nc1cc(C#Cc2cnc3ccc(-c4ccc(C(=O)N5CCOCC5)cc4)cn23)c2cc[nH]c2n1]

The title compound was synthesized from (4-(3-ethynylimidazo[1,2-a]pyridin-6-yl)phenyl)(morpholino)methanone and 4-iodo-1H-indol-6-amine in a similar procedure to that described for Example 1. The crude material was purified by preparative HPLC (C18, eluent $CH_3CN/H_2O$/HCOOH 0.1%) to afford (4-(3-((6-amino-1H-pyrrolo[2,3-b]pyridin-4-yl)ethynyl)imidazo[1,2-a]pyridin-6-yl)phenyl)(morpholino)methanone (5 mg, 12%, AUC HPLC 95%) as a brown solid. $^1$H NMR (400 MHz, $CDCl_3$) δ (ppm): 8.57 (s, 2H), 8.03 (s, 1H), 7.79 (d, J=9.3 Hz, 1H), 7.69 (d, J=8.0 Hz, 2H), 7.57 (d, J=8.1 Hz, 3H), 7.07 (s, 1H), 6.58-6.54 (m, 2H), 4.39-4.30 (bs, 2H), 4.01-3.30 (m, 8H); $^{13}$C NMR (100 MHz, $CDCl_3$) δ (ppm): 169.85, 154.56, 147.41, 145.33, 139.73, 138.72, 135.13, 128.20, 127.32, 127.20, 126.36, 124.39, 122.69, 121.29, 118.65, 113.24, 109.04, 104.86, 100.74, 96.98, 81.26, 66.92; MS (ESI) m/z 463 $[C_{27}H_{22}N_6O_2+H]^+$.

Example 99: (4-(3-((1H-pyrrolo[2,3-b]pyridin-4-yl)ethynyl)imidazo[1,2-a]pyridin-6-yl)phenyl)(morpholino)methanone

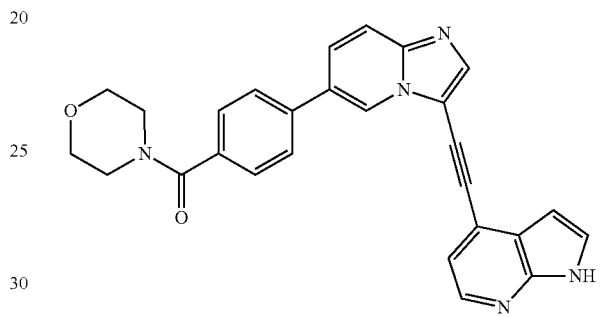

The title compound was synthesized from (4-(3-ethynylimidazo[1,2-a]pyridin-6-yl)phenyl)(morpholino)methanone and 4-iodo-1H-pyrrolo[2,3-b]pyridine in a similar method to that described for Example 1. The reaction crude product was purified by preparative HPLC (C18, eluent $CH_3CN/H_2O$/HCOOH 0.1%) to afford (4-(3-((1H-pyrrolo[2,3-b]pyridin-4-yl)ethynyl)imidazo[1,2-a]pyridin-6-yl)phenyl)(morpholino)methanone (8.8 mg, 22%, AUC HPLC. 97%) as brown solid. $^1$H NMR (400 MHz, $CDCl_3$) δ (ppm): 8.60 (s, 1H), 8.34 (d, J=4.96 Hz, 1H), 8.06 (s, 1H), 7.81 (d, J=9.3 Hz, 1H), 7.70 (d, J=8.3 Hz, 2H), 7.58 (q, J=3.6 Hz, 3H), 7.43 (t, J=2.8 Hz, 1H), 7.28-7.26 (m, 2H), 6.73-6.72 (m, 1H), 4.01-3.43 (m, 8H); $^{13}$C NMR (100 MHz, $CDCl_3$) δ (ppm): 169.84, 148.44, 145.40, 142.99, 139.88, 138.71, 135.16, 128.22, 127.32, 127.26, 126.44, 125.73, 122.69, 122.38, 120.37, 118.30, 117.95, 109.00, 100.65, 96.85, 82.39, 66.92; MS (ESI) m/z 488 $[C_{27}H_{21}N_5O_2+H]^+$.

Example 100: (4-(3-((1-methyl-1H-pyrrolo[2,3-b]pyridin-2-yl)ethynyl)imidazo[1,2-a]pyridin-6-yl)phenyl)(morpholino)methanone

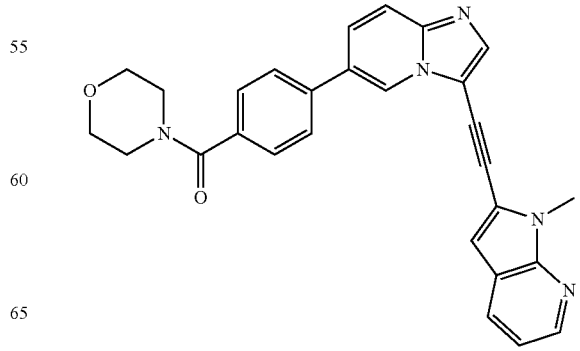

The title compound was synthesized from (4-(3-ethynylimidazo[1,2-a]pyridin-6-yl)phenyl)(morpholino)methanone and 2-iodo-1-methyl-1H-pyrrolo[2,3-b]pyridine in a similar method to that described for Example 1. The residue was purified by preparative HPLC (C18, eluent CH$_3$CN/ H$_2$O/HCOOH 0.1%) to afford (4-(3-((1-methyl-1H-pyrrolo[2,3-b]pyridin-2-yl)ethynyl)imidazo[1,2-a]pyridin-6-yl)phenyl)(morpholino)methanone (6.9 mg, AUC HPLC 95%) as a brown solid. $^1$H NMR (400 MHz, CH$_3$OD) δ (ppm): 8.74 (s, 1H), 8.35-8.32 (m, 1H), 8.05-8.00 (m, 2H), 7.87-7.77 (m, 4H), 7.59 (d, J=8.3 Hz, 2H), 7.17 (q, J=4.2 Hz, 1H), 6.99 (s, 1H), 3.99 (s, 3H), 3.89-3.48 (m, 8H); MS (ESI) m/z 462 [C$_{28}$H$_{23}$N$_5$O$_2$+H]$^+$.

Example 101: N-(4-((6-(4-(piperazine-1-carbonyl)phenyl)imidazo[1,2-a]pyridin-3-yl)ethynyl)pyridin-2-yl)acetamide

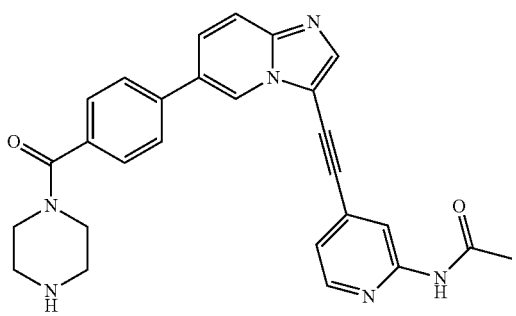 [SMILES: CC(=O)Nc1cc(C#Cc2cnc3ccc(-c4ccc(C(=O)N5CCNCC5)cc4)cn23)ccn1]

Step 1: Preparation of tert-butyl 4-(4-(3-((2-acetamidopyridin-4-yl)ethynyl)imidazo[1,2-a]pyridin-6-yl)benzoyl)piperazine-1-carboxylate The title compound was synthesized from tert-butyl 4-(4-(3-ethynylimidazo[1,2-a]pyridin-6-yl)benzoyl)piperazine-1-carboxylate and N-(4-bromopyridin-2-yl)acetamide in a similar method to that described for Example 32. The crude product was purified by flash chromatography (silica gel, eluent CHCl$_3$/CH$_3$OH 90:10) to afford tert-butyl 4-(4-(3-((2-acetamidopyridin-4-yl)ethynyl)imidazo[1,2-a]pyridin-6-yl)benzoyl)piperazine-1-carboxylate (220 mg, LC-MS 40%) as an off-white solid.

Step 2: Preparation of N-(4-((6-(4-(piperazine-1-carbonyl)phenyl)imidazo[1,2-a]pyridin-3-yl)ethynyl)pyridin-2-yl)acetamide The title compound was synthesized from tert-butyl 4-(4-(3-((2-acetamidopyridin-4-yl)ethynyl)imidazo[1,2-a]pyridin-6-yl)benzoyl)piperazine-1-carboxylate in a similar fashion to that described in step 2 of Example 45 synthesis. The crude product was purified by preparative HPLC to afford N-(4-((6-(4-(piperazine-1-carbonyl)phenyl)imidazo[1,2-a]pyridin-3-yl)ethynyl)pyridin-2-yl)acetamide (30 mg, AUC HPLC 96.5%) as a yellow solid. 1H NMR (400 MHz, DMSO-d$_6$) δ (ppm): 10.45 (s, 1H), 8.83 (s, 1H), 8.37 (d, J=5.6 Hz, 1H), 8.26 (s, 2H), 8.19 (s, 1H), 7.90-7.13 (m, 4H), 7.53 (d, J=8.0 Hz, 2H), 7.40 (d, J=5.2 Hz, 1H), 3.57 (bs, 4H), 2.72 (bs, 4H), 2.12 (s, 3H); MS (ESI) m/z 465.22 [C$_{27}$H$_{24}$N$_6$O$_2$+H]$^+$.

Example 102: (4-(3-((2-(3-amino-2-methylphenylamino)pyridin-4-yl)ethynyl)imidazo[1,2-a]pyridin-6-yl)phenyl) (piperazin-1-yl)methanone

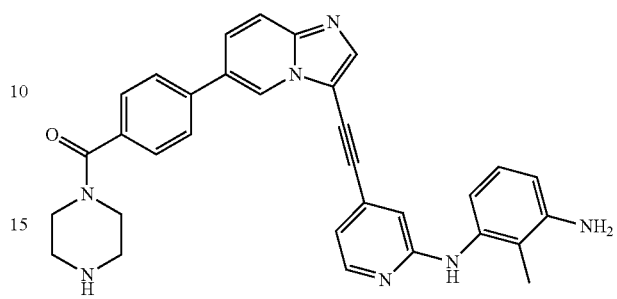

Step 1: Preparation of tert-butyl 4-(4-(3-((2-(3-amino-2-methylphenylamino)pyridin-4-yl)ethynyl)imidazo[1,2-a]pyridin-6-yl)benzoyl)piperazine-1-carboxylate The title compound was synthesized starting from tert-butyl 4-(4-(3-ethynylimidazo[1,2-a]pyridin-6-yl)benzoyl)piperazine-1-carboxylate and N-1-(4-iodopyridin-2-yl)-2-methylbenzene-1,3-diamine in a similar method to that described for Example 1. Water (2×100 mL) was added to the reaction mixture to induce the desired product precipitation which was filtered to give crude product. The crude product was washed with n-hexane and dried to afford tert-butyl 4-(4-(3-((2-(3-amino-2-methylphenylamino)pyridin-4-yl)ethynyl)imidazo[1,2-a]pyridin-6-yl)benzoyl)piperazine-1-carboxylate (230 mg, 78.8%) as a pale yellow solid. 1H NMR (400 MHz, CDCl$_3$) δ (ppm): 8.42 (s, 1H), 8.18 (d, J=5.3 Hz, 1H), 7.96 (s, 1H), 7.79 (d, J=9.2 Hz, 1H), 7.66-7.53 (m, 5H), 7.06 (t, J=7.9 Hz, 1H), 6.80-6.78 (m, 2H), 6.63 (d, J=7.9 Hz, 1H), 6.59 (s, 1H), 6.37 (s, 1H), 3.77 (bs, 4H), 3.48 (bs, 6H), 2.09 (s, 3H), 1.48 (s, 9H); MS (ESI) m/z 628 [C$_{37}$H$_{37}$N$_7$O$_3$+H]$^+$

Step 2: Preparation of (4-(3-((2-(3-amino-2-methylphenylamino)pyridin-4-yl)ethynyl)imidazo[1,2-a]pyridin-6-yl)phenyl)(piperazin-1-yl)methanone The title compound was synthesized from tert-butyl 4-(4-(3-((2-(3-amino-2-methylphenylamino)pyridin-4-yl)ethynyl)imidazo[1,2-a]pyridin-6-yl)benzoyl)piperazine-1-carboxylate in a similar fashion to that described for Example 45, step 2. The crude product was purified by preparative HPLC to afford (4-(3-((2-(3-amino-2-methylphenylamino)pyridin-4-yl)ethynyl)imidazo[1,2-a]pyridin-6-yl)phenyl)(piperazin-1-yl)methanone (80 mg, 41.4) as a pale yellow solid. $^1$H NMR (400 MHz, CDCl$_3$) δ (ppm): 8.43 (s, 1H), 8.18 (d, J=4.9 Hz, 1H), 7.95 (s, 1H), 7.75 (d, J=9.2 Hz, 1H), 7.65-7.52 (m, 5H), 7.06 (t, J=7.9 Hz, 1H), 6.81-6.78 (m, 2H), 6.63 (d, J=7.9 Hz, 1H), 6.59 (s, 1H), 6.36 (s, 1H), 3.76 (bs, 4H), 3.48 (bs, 2H), 2.96-2.88 (m, 4H), 2.09 (s, 3H); MS (ESI) m/z 528.24 [C$_{32}$H$_{29}$N$_7$O+H]$^+$.

Example 103: (N-(4-((6-(4-(piperazine-1-carbonyl)phenyl)imidazo[1,2-a]pyridin-3-yl)ethynyl)pyridin-2-yl)benzamide)

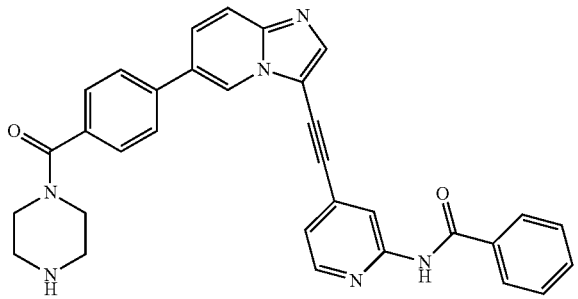 [SMILES: O=C(Nc1cc(C#Cc2cnc3ccc(-c4ccc(C(=O)N5CCNCC5)cc4)cn23)ccn1)c1ccccc1]

Step 1: Preparation of (tert-butyl 4-(4-(3-((2-benzamidopyridin-4-yl)ethynyl)imidazo[1,2-a]pyridin-6-yl)benzoyl)piperazine-1-carboxylate)

The title compound was prepared from tert-butyl 4-(4-(3-ethynylimidazo[1,2-a]pyridin-6-yl)benzoyl)piperazine-1-carboxylate and N-(4-bromopyridin-2-yl)benzamide in a similar fashion to that described for Example 32. The crude product was purified by column chromatography (silica gel, eluent CHCl$_3$/CH$_3$OH 98:2) to afford tert-butyl 4-(4-(3-((2-benzamidopyridin-4-yl)ethynyl)imidazo[1,2-a]pyridin-6-yl)benzoyl)piperazine-1-carboxylate (300 mg, 8.2%) as a pale yellow solid.

Step 2: Preparation of (N-(4-((6-(4-(piperazine-1-carbonyl)phenyl)imidazo[1,2-a]pyridin-3-yl)ethynyl)pyridin-2-yl)benzamide)

The title compound was prepared from (tert-butyl 4-(4-(3-((2-benzamidopyridin-4-yl)ethynyl)imidazo[1,2-a]pyridin-6-yl)benzoyl)piperazine-1-carboxylate) in a similar fashion to that described in step 2 of Example 45 synthesis. The crude product was purified by preparative HPLC to afford N-(4-((6-(4-(piperazine-1-carbonyl)phenyl)imidazo[1,2-a]pyridin-3-yl)ethynyl)pyridin-2-yl)benzamide (20 mg, LC-MS 98%) as a pale yellow solid. $^1$H NMR (400 MHz, CDCl$_3$) δ (ppm): 8.6 (s, 1H), 8.58 (s, 1H), 8.53 (s, 1H), 8.33 (d, J=5.3 Hz, 1H), 8.04 (d, J=0.8 Hz, 1H), 7.94 (d, J=8.3 Hz, 2H), 7.79 (d, J=9.2 Hz, 1H), 7.69 (d, J=7.4 Hz, 2H), 7.62-7.51 (m, 6H), 7.22 (d, J=5.3 Hz, 1H), 3.77-3.73 (bs, 2H), 3.5 (bs, 2H), 2.94 (bs, 4H); MS (ESI) m/z 527.18 [C$_{32}$H$_{26}$N$_6$O$_2$+H]$^+$.

Example 104: (4-(3-((1H-pyrazolo[3,4-b]pyridin-4-yl)ethynyl)imidazo[1,2-a]pyridin-6-yl)phenyl) (piperazin-1-yl)methanone

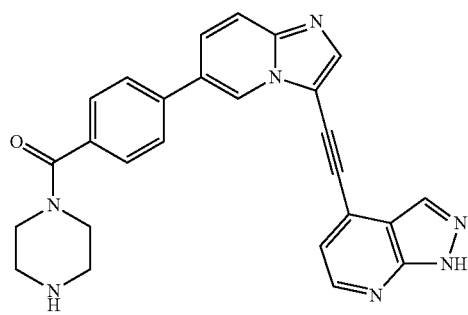 [SMILES: O=C(c1ccc(-c2ccc3ncc(C#Cc4ccnc5[nH]ncc45)n3c2)cc1)N1CCNCC1]

Step 1: Preparation of (tert-butyl 4-(4-(3-((1-(4-methoxybenzyl)-1H-pyrazolo[3,4-b]pyridin-4-yl)ethynyl)imidazo[1,2-a]pyridin-6-yl)benzoyl)piperazine-1-carboxylate)

The title compound was prepared starting from tert-butyl 4-(4-(3-ethynylimidazo[1,2-a]pyridin-6-yl)benzoyl)piperazine-1-carboxylate and 4-iodo-1-(4-methoxybenzyl)-1H-pyrazolo[3,4-b]pyridine in a similar fashion as described for Example 1. The crude product was washed with n-hexane and dried to afford tert-butyl 4-(4-(3-((1-(4-methoxybenzyl)-1H-pyrazolo[3,4-b]pyridin-4-yl)ethynyl)imidazo[1,2-a]pyridin-6-yl)benzoyl)piperazine-1-carboxylate (320 mg, 58.9%) as a yellow solid. $^1$H NMR (400 MHz, DMSO d$_6$) δ (ppm): 8.95 (s, 1H), 8.65 (d, J=4.9 Hz, 1H), 8.46 (s, 1H), 7.94-7.89 (m, 4H), 7.59-7.54 (m, 3H), 7.48-7.45 (m, 2H), 7.25 (d, J=8.3 Hz, 2H), 6.87 (d, J=8.3 Hz, 2H), 5.64 (s, 2H), 3.7 (s, 3H), 3.6-3.35 (m, 8H), 1.41 (s, 9H); MS (ESI) m/z 668.3 [C$_{39}$H$_{37}$N$_7$O$_4$+H]$^+$.

Step 2: Preparation of (N-(4-((6-(4-(piperazine-1-carbonyl)phenyl)imidazo[1,2-a]pyridin-3-yl)ethynyl)pyridin-2-yl)benzamide)

The title compound was prepared in a similar fashion as in step 2 of Example 97 synthesis. The crude product (180 mg, LC-MS 58%) was purified by preparative HPLC to afford (4-(3-((1H-pyrazolo[3,4-b]pyridin-4-yl)ethynyl)imidazo[1,2-a]pyridin-6-yl)phenyl)(piperazin-1-yl)methanone (30 mg, 37.3%, LC-MS 97.7%) as a pale yellow solid. $^1$H NMR (400 MHz, DMSO-d$_6$) δ (ppm): 13.91 (bs, 1H), 8.91 (s, 1H), 8.59 (d, J=4.8 Hz, 1H), 8.43 (s, 1H), 8.27 (s, 1H), 7.92-7.84 (m, 4H), 7.55-7.50 (m, 3H), 3.56 (bs, 2H), 3.4 (bs, 2H), 2.71-2.67 (m, 4H); MS (ESI) m/z 446.4 [C$_{26}$H$_{21}$N$_7$O+H]$^+$.

Example 105: piperazin-1-yl(4-(3-((2-(pyridin-3-ylamino)pyridin-4-yl)ethynyl)imidazo[1,2-a]pyridin-6-yl)phenyl)methanone

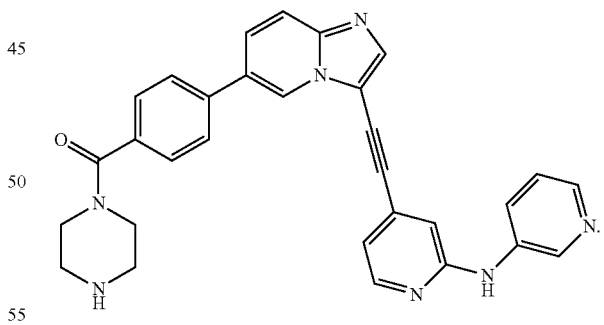

Step 1: Preparation of tert-butyl 4-(4-(3-((2-(pyridin-3-ylamino)pyridin-4-yl)ethynyl)imidazo[1,2-a]pyridin-6-yl)benzoyl)piperazine-1-carboxylate The title compound was prepared from tert-butyl 4-(4-(3-ethynylimidazo[1,2-a]pyridin-6-yl)benzoyl)piperazine-1-carboxylate and 4-bromo-N-(pyridin-3-yl)pyridin-2-amine in a similar fashion as described for Example 32. The crude product was purified by flash column chromatography (silica gel, eluent CHCl$_3$/CH$_3$OH 97:3) to afford tert-butyl 4-(4-(3-((2-(pyridin-3-ylamino)pyridin-4-yl)ethynyl)imidazo[1, 2-a]pyridin-6-yl)benzoyl)piperazine-1-carboxylate (200 mg, 14.7%) as a brown solid.

Step 2: Preparation of piperazin-1-yl(4-(3-((2-(pyridin-3-ylamino)pyridin-4-yl)ethynyl)imidazo[1,2-a]pyridin-6-yl)phenyl)methanone The title compound was prepared from tert-butyl 4-(4-(3-((2-(pyridin-3-ylamino)pyridin-4-yl)ethynyl)imidazo[1,2-a]pyridin-6-yl)benzoyl)piperazine-1-carboxylate (200 mg, 0.33 mmol) in a similar fashion as in step 2, of Example 45 synthesis. The crude product was purified by preparative HPLC to afford piperazin-1-yl(4-(3-((2-(pyridin-3-ylamino)pyridin-4-yl)ethynyl)imidazo[1,2-a]pyridin-6-yl)phenyl)methanone (25 mg, 15%, AUC HPLC 96.8%) as a light yellow solid. $^1$H NMR (400 MHz, DMSO-$d_6$) δ (ppm): 9.40 (s, 1H), 8.83 (s, 1H), 8.80 (s, 1H), 8.25-8.13 (m, 4H), 7.93-7.82 (m, 4H), 7.6 (d, J=7.9 Hz, 2H), 7.32-7.29 (m, 1H), 7.06 (s, 2H), 3.64-3.4 (bs, 4H), 3.05 (bs, 4H); MS (ESI) m/z 500.1 $[C_{30}H_{25}N_7O+H]^+$.

Example 106: piperazin-1-yl(4-(3-((2-(o-tolylamino)pyridin-4-yl)ethynyl)imidazo[1,2-a]pyridin-6-yl)phenyl)methanone

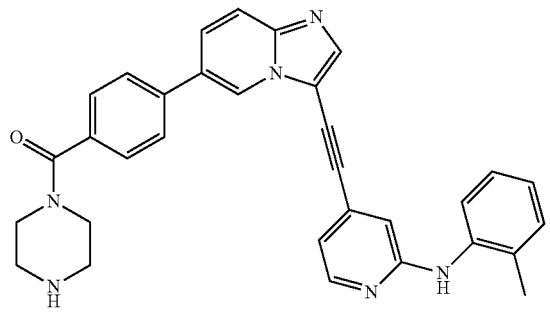 [SMILES: Cc1ccccc1Nc1cc(C#Cc2cnc3ccc(-c4ccc(C(=O)N5CCNCC5)cc4)cn23)ccn1]

Step 1: Preparation of (tert-butyl 4-(4-(3-((2-(o-tolylamino)pyridin-4-yl)ethynyl)imidazo[1,2-a]pyridin-6-yl)benzoyl)piperazine-1-carboxylate)

The title compound was prepared from tert-butyl 4-(4-(3-ethynylimidazo[1,2-a]pyridin-6-yl)benzoyl)piperazine-1-carboxylate and 4-iodo-N-(o-tolyl)pyridin-2-amine in a similar fashion as described for Example 1. The crude product was purified by flash column chromatography (silica gel, eluent CHCl$_3$/CH$_3$OH 98:2) to afford tert-butyl 4-(4-(3-((2-(o-tolylamino)pyridin-4-yl)ethynyl)imidazo[1,2-a]pyridin-6-yl)benzoyl)piperazine-1-carboxylate (190 mg, 68.5%, LC-MS 90%) as a pale yellow solid.

Step 2: Preparation of (piperazin-1-yl(4-(3-((2-(o-tolylamino)pyridin-4-yl)ethynyl)imidazo[1,2-a]pyridin-6-yl)phenyl)methanone)

The title compound was prepared from tert-butyl 4-(4-(3-((2-(o-tolylamino)pyridin-4-yl)ethynyl)imidazo[1,2-a]pyridin-6-yl)benzoyl)piperazine-1-carboxylate in a similar fashion as step 2, Example 45. The crude product was purified by column chromatography (silica gel, eluent MeOH/DCM 10:90) and by preparative HPLC to afford piperazin-1-yl(4-(3-((2-(o-tolylamino)pyridin-4-yl)ethynyl)imidazo[1,2-a]pyridin-6-yl)phenyl)methanone (50 mg, 33.3%, AUC HPLC 98%) as a pale yellow solid. $^1$H NMR (400 MHz, CDCl$_3$) δ (ppm): 8.44 (s, 1H), 8.20 (d, J=5.2 Hz, 1H), 7.96 (s, 1H), 7.76 (d, J=9.2 Hz, 1H), 7.65-7.53 (m, 5H), 7.44 (d, J=7.9 Hz, 1H), 7.29-7.23 (m, 2H), 7.15-7.13 (m, 1H), 6.84 (d, J=4.8 Hz, 1H), 6.74 (s, 1H), 6.37 (s, 1H), 3.8 (bs, 2H), 3.5 (bs, 2H), 2.94-2.84 (m, 4H), 2.30 (s, 3H); MS (ESI) m/z 513.13 $[C_{32}H_{28}N_6O+H]^+$.

Example 107: N-(4-((6-(4-(piperazine-1-carbonyl)phenyl)imidazo[1,2-a]pyridin-3-yl)ethynyl)pyridin-2-yl)acetamide

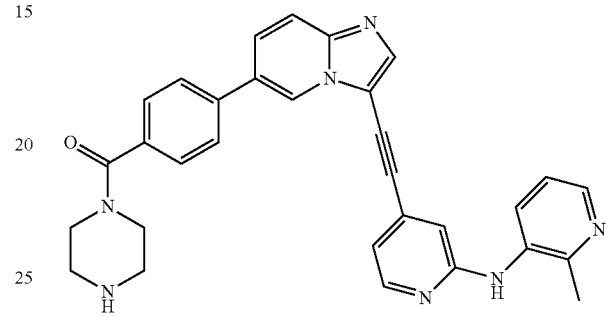

Step 1: Preparation of (tert-butyl 4-(4-(3-((2-(2-methylpyridin-3-ylamino)pyridin-4-yl)ethynyl)imidazo[1,2-a]pyridin-6-yl)benzoyl)piperazine-1-carboxylate)

The title compound was prepared from tert-butyl 4-(4-(3-ethynylimidazo[1,2-a]pyridin-6-yl)benzoyl)piperazine-1-carboxylate and 4-bromo-N-(2-methylpyridin-3-yl)pyridin-2-amine in a similar fashion as described for Example 32. The crude product was purified by column chromatography (silica gel, eluent CHCl$_3$/CH$_3$OH 97:3) to afford tert-butyl 4-(4-(3-((2-(2-methylpyridin-3-ylamino)pyridin-4-yl)ethynyl)imidazo[1,2-a]pyridin-6-yl)benzoyl)piperazine-1-carboxylate (160 mg, 74.8%, LC-MS 68%) as a yellow solid.

Step 2: Preparation of ((4-(3-((2-(2-methylpyridin-3-ylamino)pyridin-4-yl)ethynyl)imidazo[1,2-a]pyridin-6-yl)phenyl)(piperazin-1-yl)methanone)

The title compound was prepared from tert-butyl 4-(4-(3-((2-(2-methylpyridin-3-ylamino)pyridin-4-yl)ethynyl)imidazo[1,2-a]pyridin-6-yl)benzoyl)piperazine-1-carboxylate in a similar fashion as step 2, Example 45. The crude product (140 mg, LC-MS 70.7%) was purified by preparative HPLC to afford N-(4-((6-(4-(piperazine-1-carbonyl)phenyl)imidazo[1,2-a]pyridin-3-yl)ethynyl)pyridin-2-yl)acetamide (20 mg, 15.9%, AUC HPLC 98.51%) as a yellow solid. $^1$H NMR (400 MHz, CDCl$_3$) δ (ppm): 8.45 (s, 1H), 8.32 (d, J=3.9 Hz, 1H), 8.24 (d, J=5.2 Hz, 1H), 7.99 (s, 1H), 7.78 (d, J=9.7 Hz, 1H), 7.65 (d, J=8.3 Hz, 2H), 7.56-7.52 (m, 3H), 7.28-7.19 (m, 1H), 6.92 (d, J=5.3 Hz, 1H), 6.76 (s, 1H), 6.29 (s, 1H), 3.8 (bs, 2H), 3.48 (bs, 2H), 2.98-2.86 (m, 4H), 2.57 (s, 3H); MS (ESI) m/z 512.4 $[C_{31}H_{27}N_7O-H]^+$.

211

Example 108. (4-(3-((2-aminopyridin-4-yl)ethynyl)imidazo[1,2-a]pyridin-6-yl)phenyl)(piperazin-1-yl)methanone

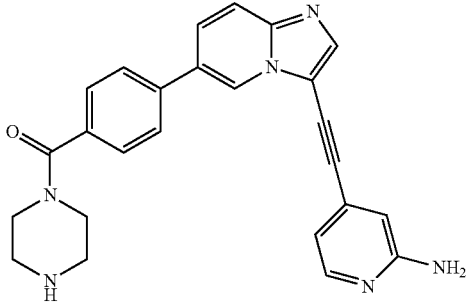 [SMILES: Nc1cc(C#Cc2cnc3ccc(-c4ccc(C(=O)N5CCNCC5)cc4)cn23)ccn1]

Step 1: Preparation of (tert-butyl 4-(4-(3-((2-(tert-butoxycarbonylamino)pyridin-4-yl)ethynyl)imidazo[1,2-a]pyridin-6-yl)benzoyl)piperazine-1-carboxylate)

The title compound was prepared from tert-butyl 4-(4-(3-ethynylimidazo[1,2-a]pyridin-6-yl)benzoyl)piperazine-1-carboxylate and tert-butyl (4-bromopyridin-2-yl)carbamate in a similar fashion Example 32. The crude product was purified by column chromatography (silica gel, eluent CHCl$_3$/CH$_3$OH 97:3) to afford tert-butyl 4-(4-(3-((2-(tert-butoxycarbonylamino)pyridin-4-yl)ethynyl)imidazo[1,2-a]pyridin-6-yl)benzoyl)piperazine-1-carboxylate (210 mg, 48%, LC-MS 55%) as a solid.

Step 2: Preparation of (4-(3-((2-aminopyridin-4-yl)ethynyl)imidazo[1,2-a]pyridin-6-yl)phenyl)(piperazin-1-yl)methanone)

The title compound was prepared from tert-butyl 4-(4-(3-((2-(tert-butoxycarbonylamino)pyridin-4-yl)ethynyl)imidazo[1,2-a]pyridin-6-yl)benzoyl)piperazine-1'-carboxylate in a similar fashion as step 2, Example 45. The crude product (130 mg, LC-MS 26%) was purified by preparative HPLC to afford (4-(3-((2-aminopyridin-4-yl)ethynyl)imidazo[1,2-a]pyridin-6-yl)phenyl)(piperazin-1-yl)methanone (20 mg, 14%, AUC HPLC 97%) as a yellow solid. $^1$H NMR (400 MHz, CDCl$_3$) δ (ppm): 8.46 (s, 1H), 8.11 (d, J=5.3 Hz, 1H), 7.99 (s, 1H), 7.78 (d, J=9.2 Hz, 1H), 7.67-7.65 (m, 2H), 7.57-7.52 (m, 3H), 6.80 (d, J=4 Hz, 1H), 6.65 (s, 1H), 4.50 (bs, 2H), 3.80 (bs, 2H), 3.48 (bs, 2H), 2.96-2.87 (m, 4H); MS (ESI) m/z 423.17 [C$_{25}$H$_{22}$N$_6$O+H]$^+$.

Example 109: piperazin-1-yl(4-(3-(pyridin-4-ylethynyl)imidazo[1,2-a]pyridin-6-yl)phenyl)methanone

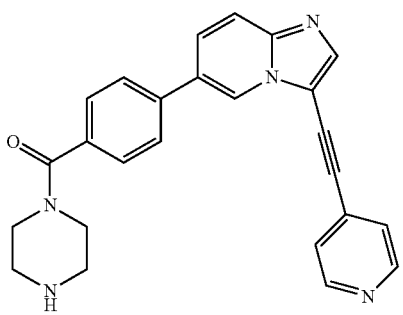 [SMILES: O=C(c1ccc(-c2ccc3ncc(C#Cc4ccncc4)n3c2)cc1)N1CCNCC1]

212

Step 1: Preparation of tert-butyl 4-(4-(3-(pyridin-4-ylethynyl)imidazo[1,2-a]pyridin-6-yl)benzoyl)piperazine-1-carboxylate The title compound was prepared from tert-butyl 4-(4-(3-ethynylimidazo[1,2-a]pyridin-6-yl)benzoyl)piperazine-1-carboxylate and 4-iodopyridine in a similar fashion as Example 1. The crude product was purified by flash chromatography (silica gel, eluent CHCl$_3$/CH$_3$OH 90:10) afforded tert-butyl 4-(4-(3-(pyridin-4-ylethynyl)imidazo[1,2-a]pyridin-6-yl)benzoyl)piperazine-1-carboxylate (80 mg, 68%, LC-MS 93%) as a solid.

Step 2: Preparation of piperazin-1-yl(4-(3-(pyridin-4-ylethynyl)imidazo[1,2-a]pyridin-6-yl)phenyl)methanone The title compound was prepared from tert-butyl 4-(4-(3-(pyridin-4-ylethynyl)imidazo[1,2-a]pyridin-6-yl)benzoyl)piperazine-1-carboxylate in a similar fashion as described in step 2 of Example 45 synthesis. The crude product was purified by flash column chromatography (silica gel, eluent CH$_2$Cl$_2$/CH$_3$OH 90:10) to afford piperazin-1-yl(4-(3-(pyridin-4-ylethynyl)imidazo[1,2-a]pyridin-6-yl)phenyl)methanone, (30 mg, 46.8%, AUC HPLC 97.88%) as a light brown solid; m.p: 125-130° C. H NMR (400 MHz, CDCl$_3$) δ (ppm): 8.60 (d, J=4.4 Hz, 2H), 8.48 (s, 1H), 8.02 (s, 1H), 7.82 (d, J=9.2 Hz, 1H), 7.61 (d, J=7.4 Hz, 2H), 7.50 (d, J=7.9 Hz, 3H), 7.42 (d, J=4.8 Hz, 2H), 3.79 (s, 2H), 3.48 (s, 2H), 2.88 (s, 4H); MS (ESI) m/z 408.25 [C$_{25}$H$_{21}$N$_5$O+H]$^+$.

Example 110: (4-(3-((1H-pyrrolo[2,3-b]pyridin-4-yl)ethynyl)imidazo[1,2-a]pyridin-6-yl)phenyl)(piperazin-1-yl)methanone

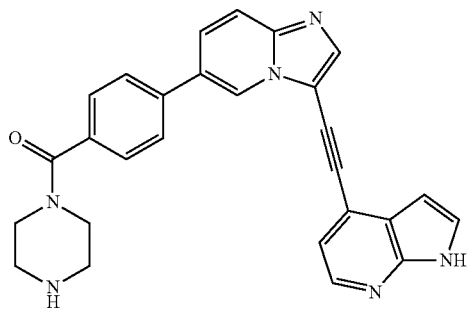 [SMILES: O=C(c1ccc(-c2ccc3ncc(C#Cc4ccnc5[nH]ccc45)n3c2)cc1)N1CCNCC1]

Step 1: Preparation of tert-butyl 4-((6-(4-(4-(tert-butoxycarbonyl)piperazine-1-carbonyl)phenyl)imidazo[1,2-a]pyridin-3-yl)ethynyl)-1H-pyrrolo[2,3-b]pyridine-1-carboxylate The title compound was prepared from tert-butyl 4-(4-(3-ethynylimidazo[1,2-a]pyridin-6-yl)benzoyl)piperazine-1-carboxylate and tert-butyl 4-bromo-1H-pyrrolo[2,3-b]pyridine-1-carboxylate in a similar fashion as described for Example 32. The crude product was purified by flash chromatography (silica gel, eluent CHCl$_3$/CH$_3$OH 90:10) to afford tert-butyl 4-((6-(4-(4-(tert-butoxycarbonyl)piperazine-1-carbonyl)phenyl)imidazo[1,2-a]pyridin-3-yl)ethynyl)-1H-pyrrolo[2,3-b]pyridine-1-carboxylate (350 mg, 51%, LC-MS 91.6%) as a pale yellow solid.

Step 2: Preparation of tert-butyl 4-((6-(4-(4-(tert-butoxycarbonyl)piperazine-1-carbonyl)phenyl)imidazo[1,2-a]pyridin-3-yl)ethynyl)-1H-pyrrolo[2,3-b]pyridine-1-carboxylate The title compound was prepared from tert-butyl 4-(4-(3-(pyridin-4-ylethynyl)imidazo[1,2-a]pyridin-6-yl)benzoyl)piperazine-1-carboxylate in a similar fashion as step 2 of Example 45 synthesis. The reaction mixture was concentrated and basified with NaHCO₃, diluted with EtOAc and washed in turn with water and brine solution. The organic layer was dried over anhydrous Na₂SO₄ and concentrated under reduced pressure to obtain crude product. The crude product was purified by flash column chromatography (silica gel, eluent CHCl₃/CH₃OH 90:10) and by preparative HPLC to afford to afford (4-(3-((1H-pyrrolo[2,3-b]pyridin-4-yl)ethynyl)imidazo[1,2-a]pyridin-6-yl)phenyl)(piperazin-1-yl)methanone (70 mg, 29%, AUC HPLC 98.53%) as a pale yellow solid; m.p: 242-245° C.; $^1$H NMR (400 MHz, DMSO d$_6$) δ (ppm): 11.94 (s, 1H), 8.82 (s, 1H), 8.27 (d, J=4.8 Hz, 2H), 8.20 (s, 1H), 7.90-7.82 (m, 4H), 7.64 (s, 1H), 7.53 (d, J=8.4 Hz, 2H), 7.38 (d, J=4.8 Hz, 1H), 6.71 (s, 1H), 3.75 (bs, 4H), 2.67 (bs, 4H); MS (ESI) m/z 447.08 [C$_{27}$H$_{22}$N$_6$O+H]$^+$.

Example 111: (4-(3-((6-amino-1H-pyrrolo[2,3-b]pyridin-4-yl)ethynyl)imidazo[1,2-a]pyridin-6-yl)phenyl)(piperazin-1-yl)methanone

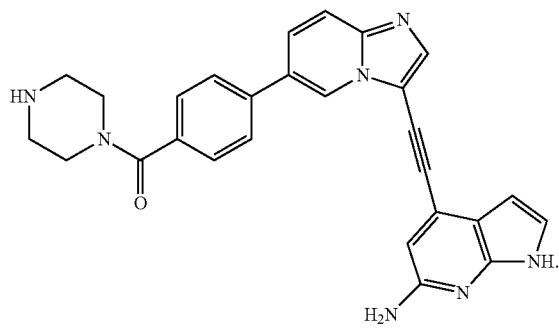 [SMILES: Nc1cc(C#Cc2cnc3ccc(-c4ccc(C(=O)N5CCNCC5)cc4)cn23)c2cc[nH]c2n1]

Step 1: Preparation of tert-butyl 4-(4-(3-((6-amino-1H-pyrrolo[2,3-b]pyridin-4-yl)ethynyl)imidazo[1,2-a]pyridin-6-yl)benzoyl)piperazine-1-carboxylate The title compound was prepared from (tert-butyl 4-(4-(3-ethynylimidazo[1,2-a]pyridin-6-yl)benzoyl)piperazine-1-carboxylate and 4-iodo-1H-indol-6-amine in a similar fashion as Example 1. The crude product was purified by preparative HPLC (C18, eluent CH₃CN/H₂O/HCOOH 0.1%) to afford tert-butyl 4-(4-(3-((6-amino-1H-pyrrolo[2,3-b]pyridin-4-yl)ethynyl)imidazo[1,2-a]pyridin-6-yl)benzoyl)piperazine-1-carboxylate (16 mg, 25%, AUC HPLC 99%) as a brown solid. $^1$H NMR (400 MHz, CH₃OD) δ (ppm): 8.74 (s, 1H), 8.03 (s, 1H), 7.91-7.60 (m, 4H), 7.61 (d, J=8.2 Hz, 2H), 7.07 (d, J=3.4 Hz, 1H), 6.63 (s, 1H), 6.45 (d, J=3.5 Hz, 1H), 4.54 (s, 1H), 3.81-3.51 (m, 8H), 1.47 (s, 9H); MS (ESI) m/z 562 [C$_{32}$H$_{31}$N$_7$O$_2$+H]$^+$.

Step 2: Preparation of (4-(3-((6-amino-1H-pyrrolo[2,3-b]pyridin-4-yl)ethynyl)imidazo[1,2-a]pyridin-6-yl)phenyl)(piperazin-1-yl)methanone The title compound was prepared from tert-butyl 4-(4-(3-((6-amino-1H-pyrrolo[2,3-b]pyridin-4-yl)ethynyl)imidazo[1,2-a]pyridin-6-yl)benzoyl)piperazine-1-carboxylate in a similar fashion as step 2 of Example 45. The reaction mixture was purified by preparative HPLC (C18, eluent CH₃CN/H₂O/HCOOH 0.1%) to afford (4-(3-((6-amino-1H-pyrrolo[2,3-b]pyridin-4-yl)ethynyl)imidazo[1,2-a]pyridin-6-yl)phenyl)(piperazin-1-yl)methanone (14 mg, 100%, AUC HPLC 99%) as brown solid. $^1$H NMR (400 MHz, DMSO-d$_6$) δ (ppm): 11.26 (s, 1H), 8.84 (s, 1H), 8.77 (s, 1H), 7.94-7.83 (m, 4H), 7.64 (d, J=8.2 Hz, 2H), 7.11 (s, 1H), 6.58 (s, 1H), 6.47 (s, 1H), 4.20-3.11 (m, 8H); $^{13}$C NMR (100 MHz, DMSO-d$_6$) δ (ppm): 168.72, 137.65, 134.41, 128.03, 127.01, 122.88, 117.51, 111.23, 103.95, 42.59; MS (ESI) m/z 462 [C$_{27}$H$_{23}$N$_7$O$_2$+H]$^+$.

Example 112: (4-(3-((1H-benzo[d]imidazol-5-yl)ethynyl)imidazo[1,2-a]pyridin-6-yl)phenyl)(morpholino)methanone

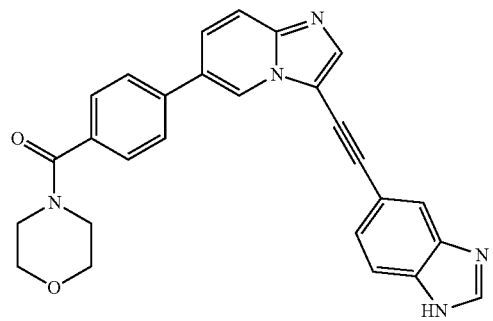 [SMILES: O=C(c1ccc(-c2ccc3ncc(C#Cc4ccc5[nH]cnc5c4)n3c2)cc1)N1CCOCC1]

To a solution of (4-(3-iodoimidazo[1,2-a]pyridin-6-yl)phenyl)(morpholino)methanone (500 mg, 1.15 mmol) and diisopropylethylamine (0.62 mL, 3.46 mmol) in DMF (15 mL) under argon were successively added Pd(PPh₃)₄ (66.6 mg, 0.0 mmol), PPh₃ (14.9 mg, 0.057 mmol), CuI (32.8 mg, 0.173 mmol) and 5-ethynyl-1H-benzo[d]imidazole (196 mg, 1.38 mmol), the reaction mixture was heated at 80° C. for 10 h. The reaction mixture was poured into ice-water, extracted with ethyl acetate. The organic layer was washed in turn with water and brine, was dried over Na₂SO₄, filtered and concentrated under reduced pressure. The residue was purified by preparative HPLC to afford (4-(3-((1H-benzo[d]imidazol-5-yl)ethynyl)imidazo[1,2-a]pyridin-6-yl)phenyl)(morpholino)methanone (300 mg, 58.8%, HPLC 98%) as an off-white solid. $^1$H NMR (400 MHz, (DMSO-d$_6$) δ (ppm): 12.68 (s, 1H), 8.80 (s, 1H), 8.33 (S, 1H), 8.05-7.84 (m, 4H), 7.82-7.49 (m, 6H), 3.62-3.28 (m, 8H); MS (ESI) m/z: 448.08 [C$_{27}$H$_{21}$N$_5$O$_2$+H]$^+$.

Example 113: (4-(3-((1H-benzo[d]imidazol-5-yl)ethynyl)imidazo[1,2-a]pyridin-6-yl)phenyl)(4-methylpiperazin-1-yl)methanone

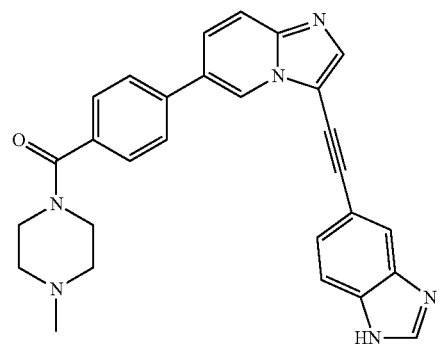 [SMILES: CN1CCN(C(=O)c2ccc(-c3ccc4ncc(C#Cc5ccc6[nH]cnc6c5)n4c3)cc2)CC1]

To a solution of (4-(3-iodo-3aH-pyrrolo[3,2-b]pyridin-5-yl)phenyl)(4-methylpiperazin-1-yl)methanone (800 mg, 1.79 mmol) and diisopropylethylamine (0.64 mL, 3.58 mmol) in DMF (05 mL) were successively added Pd(PPh$_3$)$_4$ (103 mg, 0.0896 mmol), PPh$_3$ (23.4 mg; 0.0896 mmol), CuI (51 mg, 0.268 mmol) and 5-ethynyl-1H-benzo[d]imidazole (254 mg, 1.79 mmol). The reaction mixture was heated at 80° C. for 10 h under argon. and was poured into ice water, extracted with ethyl acetate. The organic layer was washed in turn with water and brine, was was dried over Na$_2$SO$_4$, filtered and concentrated under reduced pressure. The residue was purified by preparative HPLC to afford (4-(3-((1H-benzo[d]imidazol-5-yl)ethynyl)imidazo[1,2-a]pyridin-6-yl)phenyl)(4-methylpiperazin-1-yl)methanone (220 mg, 26.6%, HPLC 98%) as pale yellow solid. $^1$H NMR (400 MHz, (DMSO-d$_6$) δ (ppm): 8.77 (s, 1H), 8.24 (s, 1H), 8.03 (S, 2H), 7.95 (s, 1H), 7.87 (d, J=14 Hz, 2H), 7.84-7.77 (m, 2H), 7.65 (d, J=8.4 Hz, 1H), 7.55 (d, J=8.4 Hz, 1H), 7.48 (d, J=8.4 Hz, 1H), 3.42-3.39 (m, 4H), 2.37-2.32 (m, 4H), 2.20 (s, 3H); MS (ESI) m/z: 461.45 [C$_{28}$H$_{24}$N$_6$O+H]$^+$.

Example 114: morpholino(4-(3-(pyridin-4-ylethynyl)pyrazolo[1,5-a]pyrimidin-5-yl)phenyl)methanone

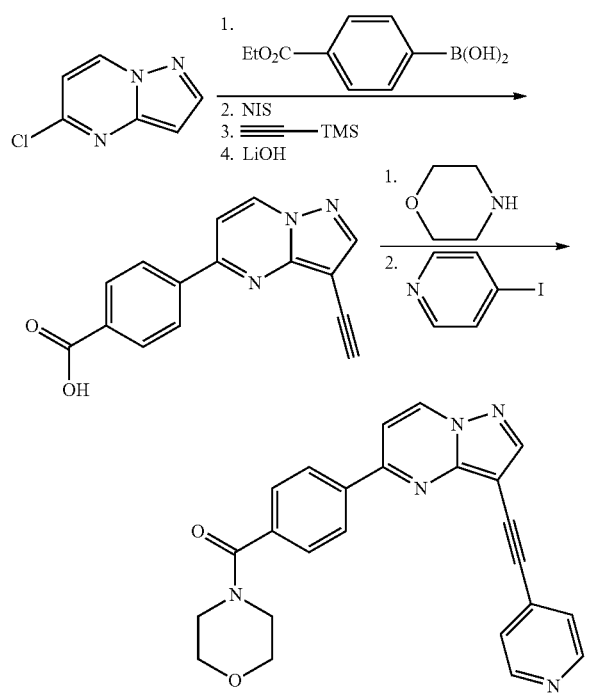

Step 1: Preparation of ethyl 4-(pyrazolo[1,5-a]pyrimidin-5-yl)benzoate

A mixture of 4-(ethoxycarbonyl)phenylboronic acid (6.08 g, 31.37 mmol), K$_3$PO$_4$ (11 g, 52.28 mmol), Pd(PPh$_3$)$_4$ (0.4 g) and 5-chloropyrazolo[1,5-a]pyrimidine (4 g, 26.14 mmol) in a mixture of 1,4-dioxane (250 mL) and H$_2$O (50 mL) was stirred at room temperature. The reaction mixture was refluxed overnight under argon and the reaction mixture was diluted with EtOAc and washed in turn with water and brine. The organic layer was dried over anhydrous Na$_2$SO$_4$ and concentrated under reduced pressure to give the crude product which was purified by flash column chromatography (silica gel, eluent petroleum ether/EtOAc 50:50) to afford ethyl 4-(pyrazolo[1,5-a]pyrimidin-5-yl)benzoate (3.6 g, 52%, LC-MS 95%) as a yellow solid.

Step 2: Preparation of ethyl 4-(3-iodopyrazolo[1,5-a]pyrimidin-5-yl)benzoate

To a solution of ethyl 4-(pyrazolo[1,5-a]pyrimidin-5-yl)benzoate 1 (3.6 g, 13.48 mmol) in ACN (60 mL) was added NIS (3.6 g, 16.17 mmol) at 0° C. to room temperature and stirred at the same temperature for 3 h. The restion mixture was diluted with water (100 mL) and filtered. The filtrate was washed with water to afford ethyl 4-(3-iodopyrazolo[1,5-a]pyrimidin-5-yl)benzoate (4.6 g, 88%, LC-MS 99%) as a yellow solid.

Step 3: Preparation of ethyl 4-(3-((trimethylsilyl)ethynyl)pyrazolo[1,5-a]pyrimidin-5-yl)benzoate A mixture of ethyl 4-(3-iodopyrazolo[1,5-a]pyrimidin-5-yl)benzoate (4.6 g, 11.7 mol), ethynyltrimethylsilane (1.37 g, 14.04 mmol), CuI (725 mg, 3.81 mmol), and DIPEA (2.26 g, 17.5 mol) was stirred under argon for 30 min prior to the addition of Pd(PPh$_3$)$_4$. The reaction mixture was heated at 80° C. for 4 h, was diluted with Water (100 mL). The precipitate was isolated by filtration and purified by flash chromatography (silica gel, eluent petroleum ether/EtOAc 50:50) to afford ethyl 4-(3-((trimethylsilyl)ethynyl)pyrazolo[1,5-a]pyrimidin-5-yl)benzoate (3.6 g, 85%, LC-MS 95%) as a yellow solid. $^1$H NMR (400 MHz, CDCl$_3$) δ (ppm): 8.25-8.23 (m, 5H), 7.38 (d, J=7.6 Hz, 2H), 4.4 (q, 2H), 1.43 (t, J=7.6 Hz, 3H), 0.31 (s, 9H); MS (ESI) m/z 364 [M+1]$^+$.

Step 4: Preparation of 4-(3-ethynylpyrazolo[1,5-a]pyrimidin-5-yl)benzoic acid

To a solution of ethyl-4-(3-(trimethylsilyl)ethynyl)pyrazolo[1,5-a]pyrimidin-5-yl)benzoate (1.8 g, 4.95 mmol) in THF (15 mL) was added LiOH (0.62 g, 14.87 mmol) in water (3 mL) and MeOH (5 mL) and stirred for 4 h at room temperature. The reaction mixture was concentrated under reduced pressure to afford 4-(3-ethynylpyrazolo[1,5-a]pyrimidin-5-yl)benzoic acid (1.2 g, 92%) as a light brown solid; $^1$H NMR (400 MHz, CDCl$_3$) δ (ppm): 13.20 (s, 1H), 9.32 (d, J=6.8 Hz, 1H), 8.45 (m, 3H), 8.12 (s, 2H), 7.83 (d, J=7.6 Hz, 1H), 4.32 (s, 1H); MS (ESI) m/z 264 [M+1].

Step 5: Preparation of (4-(3-ethynylpyrazolo[1,5-a]pyrimidin-5-yl)phenyl)(morpholino)methanone To a solution of 4-(3-ethynylpyrazolo[1,5-a]pyrimidin-5-yl)benzoic acid (0.6 g, 2.28 mmol) in DMF (6 mL) was added NMM (0.46 g, 4.56 mmol) followed by HATU (1.3 g, 3.42 mmol) and the mixture was stirred at room temperature for 30 min prior to the addition of morpholine (0.23 g, 2.73 mmol). The reaction mixture was stirred at room temperature for overnight, was diluted with EtOAc and washed in turn with water and brine solution. The organic layer was dried over anhydrous Na$_2$SO$_4$ and concentrated under reduced pressure. The residue was purified by column chromatography (silica gel, eluent CHCl$_3$/CH$_3$OH 96.5:3.5) to afford (4-(3-ethynylpyrazolo[1,5-a]pyrimidin-5-yl)phenyl)(morpholino)methanone (0.45 g, 51%) as a yellow solid. $^1$H NMR (400 MHz, CDCl$_3$) δ (ppm): 8.72 (d, J=7.2 Hz, 1H), 8.25-8.22 (m, 3H), 7.55 (d, J=8.0 Hz, 2H), 7.41 (d, J=7.6 Hz, 1H), 3.60 (s, 6H), δ 3.55 (s, 1H), 3.50 (s, 2H); MS (ESI) m/z 333 [M+1].

Step 6: Preparation of morpholino(4-(3-(pyridin-4-ylethynyl)pyrazolo[1,5-a]pyrimidin-5-yl)phenyl) methanone The title compound was synthesized from (4-(3-ethynylpyrazolo[1,5-a]pyrimidin-5-yl)phenyl)(morpholino) methanone and 4-iodopyridine in a similar fashion as described for Example 1. The crude product was purified by flash chromatography to afford morpholino(4-(3-(pyridin-4-ylethynyl)pyrazolo[1,5-a]pyrimidin-5-yl)phenyl)methanone (80 mg, 44%, AUC HPLC 96.38%) as an yellow solid: m.p. 206-209° C. $^1$H NMR (400 MHz, CDCl$_3$) δ (ppm): 8.75 (d, J=7.2 Hz, 1H), 8.62 (d, J=5.6 Hz, 2H), 8.34 (s, 1H), 8.26 (d, J=8.0 Hz, 2H), 7.60 (d, J=8.4 Hz, 2H), 7.47-7.40 (m, 3H), 3.82-3.65 (m, 8H); MS (ESI) m/z 410.07 [C$_{24}$H$_{19}$N$_5$O$_2$+H]$^+$.

Example 115: piperazin-1-yl(4-(3-(pyridin-4-ylethynyl)pyrazolo[1,5-a]pyrimidin-5-yl)phenyl)methanone

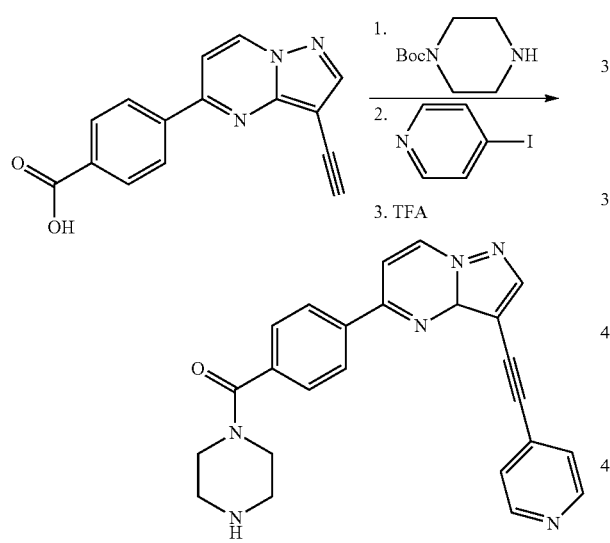

Step 1: Preparation of tert-butyl 4-(4-(3-ethynylpyrazolo[1,5-a]pyrimidin-5-yl)benzoyl)piperazine-1-carboxylate To a solution of 4-(3-ethynylpyrazolo[1,5-a]pyrimidin-5-yl)benzoic acid (0.3 g, 1.14 mmol) in DMF (6 mL) was added NMM (0.23 g, 2.28 mmol) followed by HATU (0.65 g, 1.71 mmol) at room temperature and stirred for 30 min prior to the addition of tert-butyl piperazine-1-carboxylate (0.25 g, 1.36 mmol). The reaction mixture was stirred at room temperature overnight, was diluted with EtOAc and washed in turn with water and brine. The organic layer was dried over anhydrous Na$_2$SO$_4$ and concentrated under reduced pressure. The crude product was purified by column chromatography (silica gel, eluent CHCl$_3$/CH$_3$OH 96.5:3.5) to afford tert-butyl 4-(4-(3-ethynylpyrazolo[1,5-a]pyrimidin-5-yl)benzoyl)piperazine-1-carboxylate (0.3 g, 61% as a yellow solid.

Step 2: Preparation of tert-butyl 4-(4-(3-(pyridin-4-ylethynyl)pyrazolo[1,5-a]pyrimidin-5-yl)benzoyl) piperazine-1-carboxylate The title compound was synthesized from tert-butyl 4-(4-(3-ethynylpyrazolo[1,5-a]pyrimidin-5-yl)benzoyl)piperazine-1-carboxylate and 4-iodopyridine in a similar fashion as Example 1. The crude product was purified by flash chromatography (silica gel, eluent CH$_2$Cl$_2$/CH$_3$OH 10:90) to afford tert-butyl 4-(4-(3-(pyridin-4-ylethynyl)pyrazolo[1,5-a]pyrimidin-5-yl)benzoyl)piperazine-1-carboxylate (200 mg, 57%) as a yellow solid.

Step 3: Preparation of piperazin-1-yl(4-(3-(pyridin-4-ylethynyl)pyrazolo[1,5-a]pyrimidin-5-yl)phenyl) methanone The title compound was synthesized from tert-butyl 4-(4-(3-(pyridin-4-ylethynyl)pyrazolo[1,5-a]pyrimidin-5-yl)benzoyl)piperazine-1-carboxylate in a similar fashion as step 2, Example 45. The crude product was purified by column chromatography (silica gel, eluent CH$_2$Cl$_2$/CH$_3$OH 90:10) to afford piperazin-1-yl(4-(3-(pyridin-4-ylethynyl)pyrazolo[1,5-a]pyrimidin-5-yl)phenyl)methanone (60 mg, 44%, AUC HPLC 98.4%) as a yellow solid. m.p. 120-136° C. $^1$H NMR (400 MHz, CDCl$_3$) δ (ppm): 8.74 (d, J=7.6 Hz, 1H), 8.62 (d, J=5.2 Hz, 2H), 8.33 (s, 1H), 8.25 (d, J=7.6 Hz, 2H), 7.59 (d, J=8.0 Hz, 2H), 7.46-7.40 (m, 3H), 3.80 (bs, 2H), 3.44 (bs, 2H), 2.86 (bs, 2H); MS (ESI) m/z 409.06 [C$_{24}$H$_2$N$_6$O+H]$^+$.

Example 116. (4-(3-((3-methylpyridin-4-yl)ethynyl) pyrazolo[1,5-a]pyrimidin-5-yl)phenyl)(morpholino) methanone

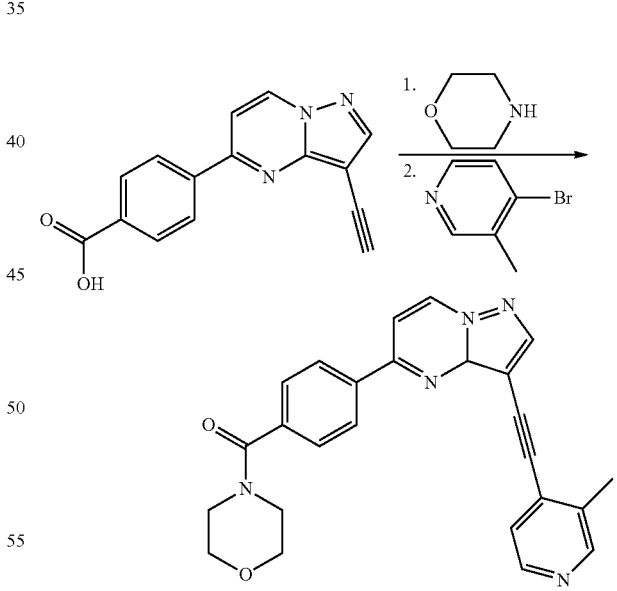

Step 1: Preparation of (4-(3-ethynylpyrazolo[1,5-a] pyrimidin-5-yl)phenyl)(morpholino)methanone To a solution of 4-(3-ethynylpyrazolo[1,5-a]pyrimidin-5-yl)benzoic acid (0.6 g, 2.28 mmol) in DMF (6 mL) was added NMM (0.46 g, 4.56 mmol) followed by HATU (1.3 g, 3.42 mmol) at room temperature and stirred for 30 min prior to the addition of morpholine (0.23 g, 2.73 mmol). The reaction mixture was stirred at room temperature overnight, was diluted with EtOAc and washed in turn with water and brine solution. The organic layer was dried over anhydrous Na₂SO₄ and concentrated under reduced pressure to give the crude product which was purified by column chromatography (silica gel, eluent CHCl₃/CH₃OH 96.5:3.5) to afford (4-(3-ethynylpyrazolo[1,5-a]pyrimidin-5-yl)phenyl)(morpholino)methanone (0.45 g, 51% as a yellow solid. ¹H NMR (400 MHz, CDCl₃) δ (ppm): 8.70 (d, J=7.2, 1H), 8.25-8.22 (m, 3H), 7.55 (d, J=8.0, 2H), 7.40 (d, J=7.6, 1H), 3.55 (s, 1H), 3.60-4.00 (m, 6H), 3.50 (bs, 2H); MS (ESI) m/z 333 $[C_{19}H_{16}N_4O_2+H]^+$.

Step 2: Preparation of (4-(3-((3-methylpyridin-4-yl)ethynyl)pyrazolo[1,5-a]pyrimidin-5-yl)phenyl)(morpholino)methanone The title compound was synthesized from (4-(3-ethynylpyrazolo[1,5-a]pyrimidin-5-yl)phenyl)(morpholino)methanone and 4-bromo-3-methyl pyridine in a similar fashion as Example 32. The crude product was purified by flash chromatography (silica gel, eluent CH₂Cl₂/CH₃OH 90:10) to afford (4-(3-((3-methylpyridin-4-yl)ethynyl)pyrazolo[1,5-a]pyrimidin-5-yl)phenyl)(morpholino)methanone (35 mg, 16%, AUC HPLC 98.63%) as a yellow solid. m.p. 233-236° C. ¹H NMR (400 MHz, CDCl₃) δ (ppm): 8.75 (d, J=7.2 Hz, 1H), 8.52 (s, 2H), 8.42 (s, 1H), 8.21-8.4 (m, 3H), 7.60 (d, J=7.6 Hz, 2H), 7.41 (d, J=6.8 Hz, 1H), 3.8-3.40 (m, 8H), 2.58 (s, 3H); MS (ESI) m/z 409.06 $[C_{24}H_{20}N_6O+H]^+$.

Example 117: (4-(3-((2-aminopyridin-4-yl)ethynyl)pyrazolo[1,5-a]pyrimidin-5 yl)phenyl)(morpholino)methanone

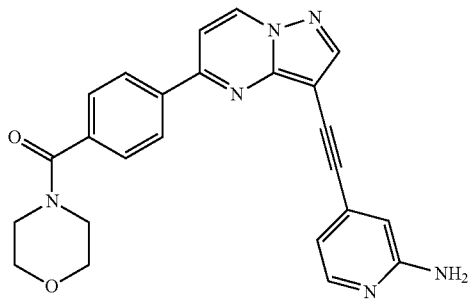 [SMILES: Nc1cc(C#Cc2cnn3ccc(-c4ccc(C(=O)N5CCOCC5)cc4)nc23)ccn1]

To a solution of (4-(3-iodopyrazolo[1,5-a]pyrimidin-5-yl)phenyl)(morpholino)methanone (150 mg, 0.35 mmol) in anhydrous acetonitrile (6 mL) was added 4-ethynylpyridin-2-amine (71.13 mg, 0.46 mmol), Pd(PPh₃)₄ (20.22 mg, 0.018 mmol), CuI (6.67 mg, 0.035 mmol) and 3 mL of DIPEA. The reaction mixture was heated at 75° C. under nitrogen overnight, was diluted with DCM (100 mL), filtered through celite and concentrated under reduced pressure. The residue was purified by flash column chromatography (silica gel, eluent DCM/Methanol 96:4) to afford (4-(3-((2-aminopyridin-4-yl)ethynyl)pyrazolo[1,5-a]pyrimidin-5 yl)phenyl)(morpholino)methanone (59.38 mg, 0.14 mmol, 40%, AUC HPLC 97.07%) as yellow solid mp: 129.8-130.6° C. ¹H NMR (400 MHz, CDCl₃) δ (ppm): 8.74 (d, J=7.3 Hz, 1H), 8.31 (s, 1H), 8.25 (d, J=8.2 Hz, 2H), 8.06 (d, J=5.2 Hz, 1H), 7.59 (d, J=8.2 Hz, 2H), 7.40 (d, J=7.3 Hz, 1H), 6.84 (d, J=5.2 Hz, 1H), 6.71 (s, 1H), 4.55 (bs, 2H), 4.00-3.30 (m, 8H); ¹³C NMR (400 MHz, CDCl₃) δ (ppm): 169.61, 158.25, 156.56, 148.67, 148.25, 147.88, 137.84, 137.70, 136.05, 133.29, 127.88, 116.08, 110.27, 106.45, 93.81, 91.43, 83.35, 66.88; MS (ESI) m/z 425.20 $[C_{24}H_{20}N_6O_2+H]^+$.

Example 118: (4-(3-((2-aminopyridin-4-yl)ethynyl)imidazo[1,2-a]pyrazin-6-yl)phenyl)(morpholino)methanone

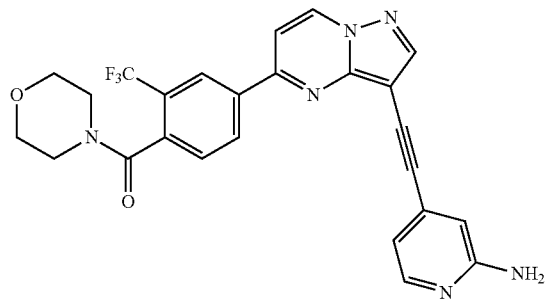 [SMILES: Nc1cc(C#Cc2cnn3ccc(-c4ccc(C(=O)N5CCOCC5)c(C(F)(F)F)c4)nc23)ccn1]

To a solution of (4-(3-iodopyrazolo[1,5-a]pyrimidin-5-yl)-2-(trifluoromethyl)phenyl)(morpholino)methanone (180 mg, 0.36 mmol) in anhydrous acetonitrile (3 mL) was added 4-ethynylpyridin-2-amine (83.5 mg, 0.54 mmol), Pd(PPh₃)₄ (20.80 mg, 0.018 mmol), CuI (6.86 mg, 0.036 mmol) and 1.5 mL of DIPEA. The reaction mixture was heated under nitrogen at 85° C. for 1.5 h, was then diluted with 100 mL of DCM, filtered through celite and concentrated under reduced pressure. The residue was purified by flash column chromatography (silica gel, eluent DCM/Methanol 96:4) to give (4-(3-((2-aminopyridin-4-yl)ethynyl)pyrazolo[1,5-a]pyrimidin-5-yl)-2-chlorophenyl)(morpholino)methanone (141.2 mg, 0.29 mmol, 79.7%, AUC HPLC 99.33%) as yellow-orange solid mp: 247.8-248.3° C. 1H NMR (400 MHz, CDCl₃) δ (ppm): 8.79 (d, J=7.4 Hz, 1H), 8.52 (s, 1H), 8.44 (d, J=8.0 Hz, 1H), 8.34 (s, 1H), 8.07 (d, J=5.2 Hz, 1H), 7.53 (d, J=8.0 Hz, 1H), 7.40 (d, J=7.4 Hz, 1H), 6.83 (d, J=5.2 Hz, 1H), 6.71 (s, 1H), 4.55 (bs, 2H), 4.00-3.85 (m, 1H), 3.84-3.70 (m, 3H), 3.69-3.50 (m, 2H), 3.30-3.15 (m, 2H); MS (ESI) m/z 493.10 $[C_{25}H_{19}F_3N_6O_2+H]^+$.

Example 119: (4-(3-((2-aminopyridin-4-yl)ethynyl)pyrazolo[1,5-a]pyrimidin-5-yl)-2-methylphenyl)(morpholino) methanone

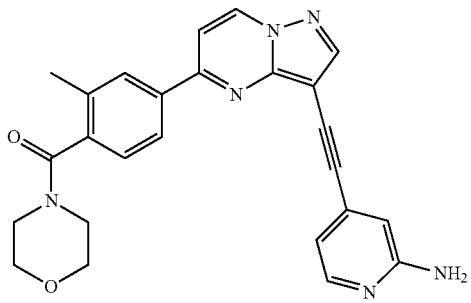 [SMILES: Cc1cc(-c2ccn3ncc(C#Cc4ccnc(N)c4)c3n2)ccc1C(=O)N1CCOCC1]

To a solution of (4-(3-iodopyrazolo[1,5-a]pyrimidin-5-yl)-2-methylphenyl)(morpholino) methanone (100 mg, 0.223 mmol), 4-ethynylpyridin-2-amine hydrochloride (42 mg, 0.268 mmol), PdCl$_2$(PPh$_3$)$_2$ (20 mg, 0.0290 mmol), CuI (4 mg, 0.0223 mmol) in a mixture of DMF and THF (1:3, 2.0 mL) was added Et$_3$N (2.0 mL). The resulting mixture was stirred at room temperature for 12 h. The solvents were removed in vacuo and the residue was purified by flash column chromatography (eluent EtOAc/CH$_3$OH 85:15) followed by preparative HPLC to afford (4-(3-((2-aminopyridin-4-yl)ethynyl)pyrazolo[1,5-a]pyrimidin-5-yl)-2-methylphenyl)(morpholino) methanone (29.9 mg, 31%, AUC HPLC 99.2%) as a yellow solid. $^1$H NMR (600 MHz, DMSO-d$_6$) δ 9.30 (d, J=7.4 Hz, 1H), 8.55 (s, 1H), 8.19 (d, J=1.8 Hz, 1H), 8.17-8.11 (m, 1H), 7.94 (d, J=5.3 Hz, 1H), 7.83 (d, J=7.4 Hz, 1H), 7.41 (d, J=8.0 Hz, 1H), 6.64-6.56 (m, 2H), 6.11 (s, 2H), 3.68 (m, 4H), 3.52 (m, 2H), 3.18 (m, 2H), 2.36 (s, 3H); $^{13}$C NMR (150 MHz, DMSO-d$_6$) δ 168.0, 159.8, 156.5, 148.1, 147.8, 138.5, 137.4, 136.2, 134.8, 131.3, 129.2, 126.6, 125.1, 113.1, 109.0, 107.1, 91.8, 91.1, 83.2, 66.2, 46.7, 18.7; MS (ESI) m/z 439 [C$_{25}$H$_{22}$N$_6$O$_2$+H]$^+$ Example 120: (4-(3-((2-aminopyridin-4-yl)ethynyl) pyrazolo[1,5-a]pyrimidin-5-yl)-2-chlorophenyl) (morpholino)methanone

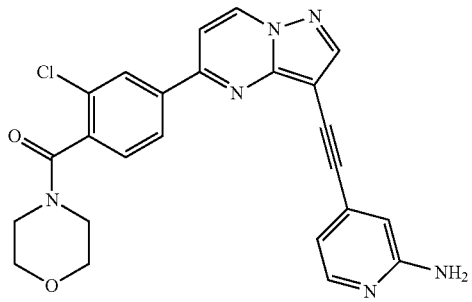 [SMILES: Nc1cc(C#Cc2cnn3ccc(-c4ccc(C(=O)N5CCOCC5)c(Cl)c4)nc23)ccn1]

To a solution of (2-chloro-4-(3-iodopyrazolo[1,5-a]pyrimidin-5-yl)phenyl)(morpholino)methanone (180 mg, 0.38 mmol) in anhydrous acetonitrile (3 mL) was added 4-ethynylpyridin-2-amine (89 mg, 0.58 mmol), Pd(PPh$_3$)$_4$ (21.96 mg, 0.019 mmol), CuI (7.24 mg, 0.038 mmol) and 1.5 mL of DIPEA. The reaction mixture was heated at 85° C. for 1.5 h under nitrogen. The reaction mixture was diluted with 100 mL of DCM, filtered through celite and concentrated under reduced pressure. The residue was purified by flash column chromatography (silica gel, eluent DCM/Methanol 96:4) to give (4-(3-((2-aminopyridin-4-yl)ethynyl)pyrazolo[1,5-a]pyrimidin-5-yl)-2-chlorophenyl)(morpholino)methanone (159.4 mg, 0.35 mmol, 91%, AUC HPLC 99.53%) as yellow solid mp: 218.5-219.6° C. $^1$H NMR (400 MHz, CDCl$_3$) δ (ppm): 8.77 (d, J=7.4 Hz, 1H), 8.35 (s, 1H), 8.29 (d, J=1.2 Hz, 1H), 8.14 (dd, J=8.0, 1.2 Hz, 1H), 8.10 (d, J=5.2 Hz, 1H), 7.50 (d, J=8.0 Hz, 1H), 7.37 (d, J=7.4 Hz, 1H), 6.86 (d, J=5.2 Hz, 1H), 6.73 (s, 1H), 4.52 (s, 2H), 4.00-3.85 (m, 1H), 3.84-3.80 (m, 3H), 3.79-3.55 (m, 2H), 3.45-3.15 (m, 2H); $^{13}$C NMR (400 MHz, CDCl$_3$) δ (ppm): 166.28, 158.32, 155.15, 148.45, 148.17, 138.79, 137.51, 136.24, 133.03, 131.47, 128.77, 128.56, 126.35, 116.11, 110.19, 106.20, 94.16, 91.64, 82.90, 66.79, 66.73, 47.17, 42.17; MS (ESI) m/z 459.10 [C$_{24}$H$_{19}$ClN$_6$O$_2$+H]$^+$ Example 121: (4-(3-((2-aminothiazol-5-yl)ethynyl) imidazo[1,2-b]pyridazin-6-yl)phenyl) (morpholino) methanone

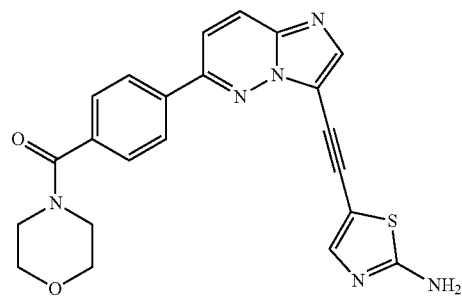 [SMILES: Nc1ncc(C#Cc2cnc3ccc(-c4ccc(C(=O)N5CCOCC5)cc4)nn23)s1]

Step 1: Preparation of tert-butyl 5-((6-(4-(morpholine-4-carbonyl)phenyl)imidazo[1,2-b]pyridazin-3-yl)ethynyl)thiazol-2-ylcarbamate To a solution of (4-(3-iodoimidazo[1,2-b]pyridazin-6-yl)phenyl)(morpholino)methanone (300 mg, 0.691 mmol) in DMF (10 mL) were successively added Pd(PPh$_3$)$_4$ (40 mg, 0.03 mmol), CuI (19.6 mg, 0.11 mmol), N,N-diisopropylethylamine (0.23 mL, 1.38 mmol) and tert-butyl 5-ethynylthiazol-2-ylcarbamate (185 mg, 0.82 mmol). The reaction mixture was heated at 80° C. for 5 h under argon, was filtered through celite and the filtrate was concentrated under reduced pressure. The residue was purified by column chromatography (Silica gel, eluent dichloromethane/MeOH 9:1) to afford tert-butyl 5-((6-(4-(morpholine-4-carbonyl) phenyl)imidazo[1,2-b]pyridazin-3-yl)ethynyl)thiazol-2-ylcarbamate (300 mg). $^1$H NMR (400 MHz, (DMSO-d$_6$) δ (ppm): 11.94 (s, 1H), 8.35 (d, J=9.2 Hz, 1H), 8.23-8.00 (m, 3H), 7.96 (d, J=12.8 Hz, 1H), 7.84 (s, 1H), 7.62 (d, J=8.0 Hz, 2H), 3.63-3.60 (bs, 8H), 1.52 (s, 9H). MS (ESI) m/z: 531.60 [C$_{27}$H$_{26}$N$_6$O$_4$S+H]$^+$.

Step 2: Preparation of (4-(3-((2-aminothiazol-5-yl) ethynyl)imidazo[1,2-b]pyridazin-6-yl)phenyl)(morpholino)methanone A solution of tert-butyl 5-((6-(4-(morpholine-4-carbonyl) phenyl)imidazo[1,2-b]pyridazin-3-yl) ethynyl)thiazol-2-ylcarbamate (300 mg, 0.56 mmol) in a mixture of trifluoroacetic acid (3 mL) and dichloromethane (10 mL) was stirred at room temperature for 3 h. The reaction mixture was concentrated under reduced pressure and the residue was basified with a saturated aqueous solution of NaHCO$_3$, extracted with a solution of 10% methanol in dichloromethane. The organic layer was washed with water and brine, dried over Na$_2$SO$_4$, filtered and concentrated under reduced pressure. The residue was purified by preparative HPLC to afford (4-(3-((2-aminothiazol-5-yl)ethynyl)imidazo[1,2-b]pyridazin-6-yl)phenyl)(morpholino)methanone (60 mg, 25%, AUC HPLC 98.69%) as a yellow solid. mp 245-254° C.; $^1$H NMR (400 MHz, (DMSO-d$_6$) δ (ppm): 8.33 (d, J=9.6 Hz, 1H), 8.18-8.17 (m, 3H), 7.97 (d, J=9.2 Hz, 1H), 7.62-7.61 (m, 4H), 7.44 (s, 1H), 3.64-3.62 (m, 8H); MS (ESI) m/z: 431.11 [C$_{22}$H$_{18}$N$_6$O$_2$S+H]$^+$.

Example 122: (4-(3-((2-aminopyridin-4-yl)ethynyl)imidazo[1,2-b]pyridazin-6-yl)-3-fluorophenyl)(morpholino)methanone formate salt

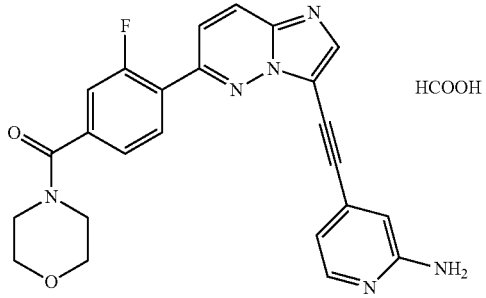 [SMILES: Nc1cc(C#Cc2cnc3ccc(-c4ccc(C(=O)N5CCOCC5)cc4F)nn23)ccn1 ; "HCOOH"]

A solution of (3-fluoro-4-(3-iodoimidazo[1,2-b]pyridazin-6-yl)phenyl)(morpholino)methanone (92 mg, 0.203 mmol), 4-ethynylpyridin-2-amine (36 mg, 0.305 mmol), $PdCl_2(PPh_3)_2$ (19 mg, 0.0264 mmol), CuI (4 mg, 0.0203 mmol) in a mixture of DMF (1.0 mL) and (1.0 mL). The mixture was blanketed with argon and heated at 90° C. for 2 h. The solvents were removed in vacuo and the crude residue was purified by column chromatography (silica gel, eluent $EtOAc/CH_3OH$ 90:10) and preparative HPLC to afford (4-(3-((2-aminopyridin-4-yl)ethynyl)imidazo[1,2-b]pyridazin-6-yl)-3-fluorophenyl)(morpholino)methanoneformate salt (40.0 mg, 40%, AUC HPLC: 97.2%) as a green-brown solid mp: 78.2-79.4° C.); $^1H$ NMR (600 MHz, DMSO-$d_6$) δ 8.37 (d, J=9.5 Hz, 1H), 8.31 (s, 1H), 8.13 (s, 1H), 8.00-7.93 (m, 2H), 7.75 (dd, J=9.4, 2.1 Hz, 1H), 7.54 (dd, J=10.9, 1.5 Hz, 1H), 7.47 (dd, J=7.9, 1.6 Hz, 1H), 6.64 (d, J=4.9 Hz, 2H), 6.33 (s, 2H), 3.71-3.62 (m, 4H), 3.62-3.52 (m, 4H); $^{13}C$ NMR (150 MHz, DMSO-$d_6$) δ 167.00, 163.06, 160.36, 159.40, 158.69, 149.05, 147.57, 139.76, 138.97, 131.27, 130.48, 126.22, 124.29, 123.72, 115.46, 112.80, 111.70, 109.41, 96.90, 79.05, 66.01, 47.62, 42.06; MS (ESI) m/z 443 $[C_{24}H_{19}FN_6O_2+H]^+$.

Example 123: (4-(3-((2-aminopyridin-4-yl)ethynyl)pyrazolo[1,5-a]pyrimidin-5-yl)-3-fluorophenyl)(morpholino) methanone formic acid salt

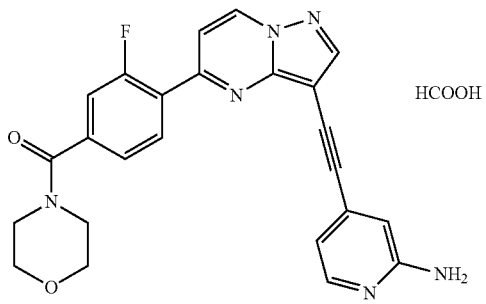 [SMILES: Nc1cc(C#Cc2cnn3ccc(-c4ccc(C(=O)N5CCOCC5)cc4F)nc23)ccn1 ; "HCOOH"]

A solution of (3-fluoro-4-(3-iodopyrazolo[1,5-a]pyrimidin-5-yl)phenyl)(morpholino)methanone (89 mg, 0.197 mmol), 4-ethynylpyridin-2-amine (35 mg, 0.295 mmol), $PdCl_2(PPh_3)_2$ (20 mg, 0.0256 mmol), CuI (4 mg, 0.0197 mmol) in a mixture of DMF (1.0 mL) and DIPEA (1.0 mL) was heated at 90° C. for 2 h. The solvents were removed in vacuo and the crude residue was purified by column chromatography (silica gel, eluent $EtOAc/CH_3OH$ 95:5) and by preparative HPLC to afford (4-(3-((2-aminopyridin-4-yl)ethynyl)pyrazolo[1,5-a]pyrimidin-5-yl)-3-fluorophenyl)(morpholino) methanoneformic acid salt (54.8 mg, 57%, AUC HPLC: 98.0%) as a brown solid (mp: 57.6-58.9° C.); $^1H$ NMR (600 MHz, DMSO-$d_6$) δ 9.33 (d, J=7.3 Hz, 1H), 8.62 (s, 1H), 8.17-8.10 (m, 2H), 7.93 (d, J=5.5 Hz, 1H), 7.59 (dd, J=7.4, 1.8 Hz, 1H), 7.52 (d, J=11.2 Hz, 1H), 7.46 (d, J=7.8 Hz, 1H), 6.69-6.62 (m, 2H), 6.50 (s, 2H), 3.74-3.62 (m, 4H), 3.62-3.53 (m, 4H); $^{13}C$ NMR (150 MHz, DMSO-$d_6$) δ 166.98, 163.06, 160.80, 159.13, 158.55, 153.76, 148.19, 145.75, 139.95, 137.31, 132.55, 131.33, 125.69, 123.66, 115.54, 113.11, 110.36, 110.05, 91.98, 91.00, 66.01, 47.56, 42.06; MS (ESI) m/z 443 $[C_{24}H_{19}FN_6O_2+H]^+$.

The following examples serve to illustrate the invention without limiting the scope thereof.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

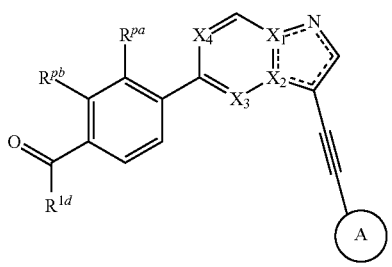

(I)

or a pharmaceutically acceptable salt thereof,
wherein
  $X_1$ and $X_2$ are independently N or C;
  $X_3$ and $X_4$ are independently N or $CR^2$;
  provided that two of $X_1$, $X_2$, $X_3$, and $X_4$ are N;
  ⎓ is a single or double bond, as valency allows;
  $R^{pa}$ is hydrogen, halogen, CN, optionally substituted $C_{1-6}$ alkyl, —$OR^A$, —$N(R^B)_2$;
  $R^C$ is optionally substituted $C_{1-6}$ alkyl;
  $R^{pb}$ is independently hydrogen, halogen, CN, —$OR^A$, —$N(R^B)_2$, optionally substituted $C_{1-6}$ alkyl, optionally substituted $C_{3-6}$ carbocyclyl, optionally substituted aryl, optionally substituted heterocyclyl, or optionally substituted heteroaryl;
  $R^{1d}$ is optionally substituted six-membered heterocyclyl, —$OR^A$, or —$N(R^B)_2$;
  each instance of $R^2$ is independently hydrogen, halogen, optionally substituted $C_{1-6}$ alkyl, optionally substituted $C_{3-6}$ carbocyclyl, —$OR^A$, or —$N(R^B)_2$,
  Ring A is optionally substituted phenyl, optionally substituted five-membered heteroaryl, optionally substituted six-membered heteroaryl, or optionally substituted 5,6-bicyclic heteroaryl;
  each instance of $R^A$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, or an oxygen protecting group; and
  each instance of $R^B$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, optionally substituted acyl, or a nitrogen protecting group.

2. The compound of claim 1, wherein the compound is of Formula (IX-a):

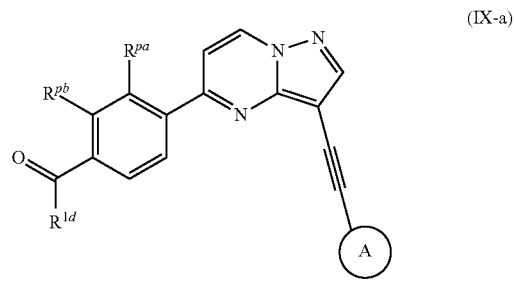

(IX-a)

or a pharmaceutically acceptable salt thereof.

3. The compound of claim 1, or a pharmaceutically acceptable salt thereof, wherein $R^{1d}$ is optionally substituted six-membered heterocyclyl.

4. The compound of claim 1, wherein the compound is of Formula (IX-b):

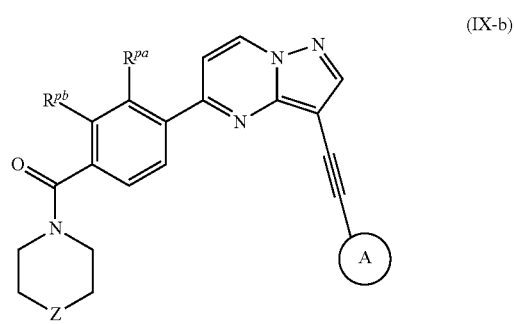

(IX-b)

or a pharmaceutically acceptable salt thereof,
wherein
  Z is —O— or —$NR^{NZ}$—; and
  each instance of $R^{NZ}$ is independently hydrogen, optionally substituted $C_{1-6}$ alkyl, or a nitrogen protecting group.

5. The compound of claim 4, or a pharmaceutically acceptable salt thereof, wherein Z is —O—.

6. The compound of claim 4, or a pharmaceutically acceptable salt thereof, wherein Z is —$NR^{NZ}$—, wherein $R^{NZ}$ is hydrogen or optionally substituted $C_{1-6}$ alkyl.

7. The compound of claim 1, or a pharmaceutically acceptable salt thereof, wherein $R^{pa}$ and $R^{pb}$ are hydrogen.

8. The compound of claim 1, or a pharmaceutically acceptable salt thereof, wherein Ring A is optionally substituted five-membered heteroaryl with two heteroatoms selected from the group consisting of O, S, and N; or Ring A is optionally substituted six-membered heteroaryl with one or two N.

9. The compound of claim 8, or a pharmaceutically acceptable salt thereof, wherein Ring A is one of the following formulae:

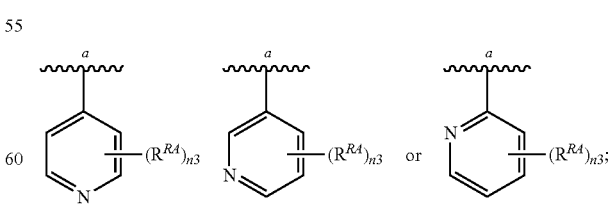

wherein
  a indicates the point of attachment to the alkyne;
  each instance of $R^{RA}$ is independently hydrogen, halogen, optionally substituted $C_{1-6}$ alkyl, optionally substituted acyl, —CN, —$OR^{AO}$, or —$N(R^{AN})_2$;

each instance of $R^{AO}$ is independently hydrogen, optionally substituted alkyl, optionally substituted carbocyclyl, optionally substituted aryl, optionally substituted heterocyclyl, optionally substituted heteroaryl, or an oxygen protecting group; and each instance of $R^{AN}$ is independently hydrogen, optionally substituted alkyl, optionally substituted carbocyclyl, optionally substituted aryl, optionally substituted heterocyclyl, optionally substituted heteroaryl, optionally substituted acyl, or a nitrogen protecting group; and each instance of n3 is independently an integer of 1 to 4, inclusive.

10. The compound of claim 9, or a pharmaceutically acceptable salt thereof, wherein $R^{RA}$ is $-N(R^{AN})_2$, $-NHR^{AN}$, or $-N(CH_3)R^{AN}$, wherein $R^{AN}$ is optionally substituted $C_{1-6}$ alkyl, or unsubstituted $C_{1-6}$ alkyl.

11. The compound of claim 10, or a pharmaceutically acceptable salt thereof, wherein $R^{RA}$ is $-N(Me)_2$.

12. The compound of claim 3, or a pharmaceutically acceptable salt thereof, wherein Z is $-O-$, and Ring A is wherein a indicates the point of attachment to the alkyne;

each instance of $R^{RA}$ is $-N(R^{AN})_2$;

each instance of $R^{AN}$ is independently hydrogen, optionally substituted alkyl, optionally substituted carbocyclyl, optionally substituted aryl, optionally substituted heterocyclyl, optionally substituted heteroaryl, optionally substituted acyl, or a nitrogen protecting group; and each instance of n3 is independently an integer of 1 to 4, inclusive.

13. The compound of claim 4, or a pharmaceutically acceptable salt thereof, wherein Z is $-O-$, and Ring A is
wherein a indicates the point of attachment to the alkyne;

each instance of $R^{RA}$ is $-N(Me)_2$; and each instance of n3 is independently an integer of 1 to 4, inclusive.

14. A compound of Formula (VII-a):

or a pharmaceutically acceptable salt thereof,
wherein
  $R^{1d}$ is optionally substituted six-membered heterocyclyl;
wherein
  $R^{pa}$ is hydrogen, halogen, CN, optionally substituted $C_{1-6}$ alkyl, $-OR^A$, $-N(R^B)_2$, $-NH-CO-R^C$;
  $R^C$ is optionally substituted $C_{1-6}$ alkyl;
  $R^{pb}$ is independently hydrogen, halogen, CN, $-OR^A$, $-N(R^B)_2$, optionally substituted $C_{1-6}$ alkyl, optionally substituted $C_{3-6}$ carbocyclyl, optionally substituted aryl, optionally substituted heterocyclyl, or optionally substituted heteroaryl;
  each instance of $R^A$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, or an oxygen protecting group;
  each instance of $R^B$ is independently hydrogen, optionally substituted $C_{1-6}$ alkyl, optionally substituted $C_{3-6}$ carbocyclyl, optionally substituted aryl, optionally substituted heterocyclyl, optionally substituted heteroaryl, optionally substituted acyl, or a nitrogen protecting group; and
  Ring A is optionally substituted phenyl, optionally substituted five-membered heteroaryl, optionally substituted six-membered heteroaryl, or optionally substituted 5,6-bicyclic heteroaryl.

15. The compound of claim 14, wherein the compound is of Formula (VII-b):

or a pharmaceutically acceptable salt thereof,
wherein
  Z is $-O-$ or $-NR^{Nz}-$; and
  each instance of $R^{Nz}$ is independently hydrogen, optionally substituted $C_{1-6}$ alkyl, or a nitrogen protecting group.

16. A pharmaceutical composition comprising a compound of claim 1, or a pharmaceutically acceptable salt thereof, and a pharmaceutically acceptable excipient.

17. A method of treating a disease in a subject in need thereof, the method comprising administering to the subject an effective amount of a compound of claim 14, or a pharmaceutically acceptable salt thereof, the disease comprising a MNK-related disorder, an mTOR-related disorder, a PI3K-related disorder, a HER-related disorder, or a JAK-related disorder, wherein the PI3K-related disorder is a PIK3 α-related disorder, PIK3 β-related disorder, PIK3γ-related disorder, or PIK3 δ-related disorder; wherein the HER-related disorder is a HER2-related disorder or a HER3-related disorder; wherein the JAK-related disorder is a JAK1-related disorder, a JAK2-related disorder, or a JAK3-related disorder; and wherein the MNK-related disorder is MNK1-related disorder or MNK2-related disorder.

18. A method of treating a MNK-related disorder in a subject, treating an mTOR-related disorder in a subject, treating a PI3K-related disorder in a subject, or treating a JAK-related disorder in a subject, comprising administering an effective amount of a compound of claim 14 to the subject, wherein the PI3K-related disorder is a PI3K α-related disorder, a PI3K β-related disorder, a PI3K γ-related disorder, or a PI3K δ-related disorder; wherein the JAK-related disorder is a JAK1-related disorder, a JAK2-related disorder, or a JAK3-related disorder.

19. A kit comprising a compound of claim 1, or a pharmaceutically acceptable salt thereof; and instructions for administering the compound to a subject.

20. The compound or pharmaceutically acceptable salt thereof of claim 14, wherein Z is —O— and Ring A is optionally substituted 5-membered monocyclic heteroaryl, 6-membered monocyclic heteroaryl, or 5,6-bicyclic heteroaryl.

21. The compound or pharmaceutically acceptable salt thereof of claim 20, wherein Ring A is one of the following formulae:

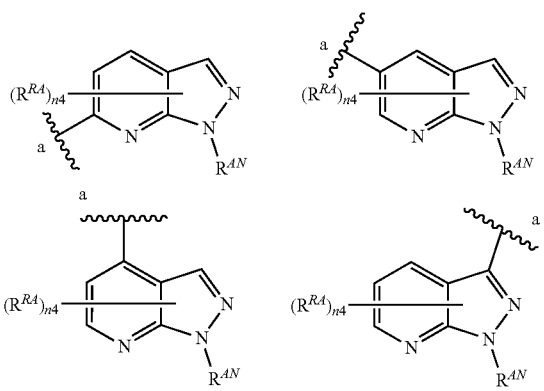

-continued

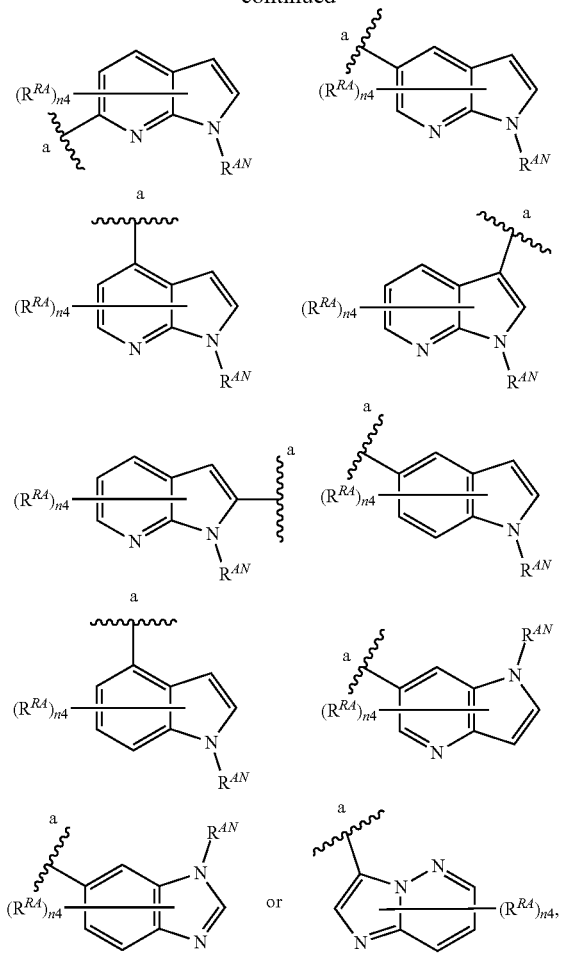

wherein:
a indicates the point of attachment to the alkyne;
each instance of $R^{RA}$ is independently hydrogen, halogen, optionally substituted $C_{1-6}$ alkyl, optionally substituted acyl, —CN, —OR$^{AO}$, or —N(R$^{AN}$)$_2$;
each instance of $R^{AO}$ is independently hydrogen, optionally substituted alkyl, optionally substituted carbocyclyl, optionally substituted aryl, optionally substituted heterocyclyl, optionally substituted heteroaryl, or an oxygen protecting group;
$R^{AN}$ is hydrogen, optionally substituted alkyl, optionally substituted carbocyclyl, optionally substituted aryl, optionally substituted heterocyclyl, optionally substituted heteroaryl, optionally substituted acyl, or a nitrogen protecting group;
each instance of n2 is independently an integer of 1 or 2;
each instance of n3 is independently an integer of 1 to 4, inclusive; and
each instance of n4 is independently an integer of 1 to 5, inclusive.

* * * * *